US011400019B2

(12) United States Patent
Miksztal et al.

(10) Patent No.: US 11,400,019 B2
(45) Date of Patent: *Aug. 2, 2022

(54) SUSTAINED RELEASE DRUG DELIVERY SYSTEMS WITH REDUCED IMPURITIES AND RELATED METHODS

(71) Applicant: DURECT CORPORATION, Cupertino, CA (US)

(72) Inventors: Andrew R. Miksztal, Palo Alto, CA (US); Judy Joice, San Jose, CA (US); Susan Autio, San Jose, CA (US); Mark P. Davis, Middleton, WI (US)

(73) Assignee: DURECT CORPORATION, Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/504,913

(22) Filed: Oct. 19, 2021

(65) Prior Publication Data

US 2022/0133595 A1   May 5, 2022

Related U.S. Application Data

(63) Continuation of application No. PCT/US2021/013132, filed on Jan. 12, 2021.

(60) Provisional application No. 62/960,565, filed on Jan. 13, 2020.

(51) Int. Cl.
| | | |
|---|---|---|
| *A61J 1/20* | (2006.01) | |
| *A61K 31/445* | (2006.01) | |
| *A61K 47/10* | (2017.01) | |
| *A61K 47/26* | (2006.01) | |

(52) U.S. Cl.
CPC .......... *A61J 1/2089* (2013.01); *A61K 31/445* (2013.01); *A61K 47/10* (2013.01); *A61K 47/26* (2013.01)

(58) Field of Classification Search
CPC ..... A61J 1/2089; A61K 31/445; A61K 47/10; A61K 47/26
See application file for complete search history.

(56) References Cited

U.S. PATENT DOCUMENTS

| | | | |
|---|---|---|---|
| 2,931,802 A | 4/1960 | Touey et al. |
| 3,215,137 A | 11/1965 | Laakso |
| 3,346,381 A | 10/1967 | Grieg |
| 3,412,890 A | 11/1968 | Rich |
| 3,473,949 A | 10/1969 | Eldred et al. |
| 3,743,398 A | 7/1973 | Johnson et al. |
| 3,755,466 A | 8/1973 | ReuterK et al. |
| 3,763,018 A | 10/1973 | Raff et al. |
| 3,797,492 A | 3/1974 | Place |
| 3,828,389 A | 8/1974 | Heisler |
| 3,853,837 A | 12/1974 | Fujino et al. |
| 3,923,939 A | 12/1975 | Baker et al. |
| 3,962,162 A | 6/1976 | Sclunank |
| 3,987,790 A | 10/1976 | Eckenhoff et al. |
| 3,992,365 A | 11/1976 | Beddell et al. |
| 4,008,719 A | 2/1977 | Theeuwes et al. |
| 4,024,248 A | 5/1977 | Konig et al. |
| 4,069,251 A | 1/1978 | Mannsfield et al. |
| 4,079,038 A | 3/1978 | Choi et al. |
| 4,093,709 A | 6/1978 | Choi et al. |
| 4,100,274 A | 7/1978 | Dutta et al. |
| 4,131,648 A | 12/1978 | Choi et al. |
| 4,180,646 A | 2/1979 | Choi et al. |
| 4,138,344 A | 6/1979 | Choi et al. |
| 4,304,767 A | 8/1981 | Heller et al. |
| 4,305,927 A | 12/1981 | Theeuwes et al. |
| 4,322,323 A | 3/1982 | Capoza |
| 4,360,019 A | 11/1982 | Portner et al. |
| 4,395,405 A | 7/1983 | Noda et al. |
| 4,395,495 A | 7/1983 | Cummings |
| 4,411,890 A | 10/1983 | Momany |
| 4,443,340 A | 4/1984 | May et al. |
| 4,487,603 A | 12/1984 | Harris |
| 4,530,840 A | 7/1985 | Tice et al. |
| 4,549,010 A | 10/1985 | Sparer et al. |
| 4,562,024 A | 12/1985 | Rogerson |
| 4,568,559 A | 2/1986 | Nuwayser et al. |
| 4,622,219 A | 11/1986 | Haynes |

(Continued)

FOREIGN PATENT DOCUMENTS

| | | |
|---|---|---|
| AU | 8374575 | 8/1975 |
| CA | 2222567 | 12/1996 |

(Continued)

OTHER PUBLICATIONS

Patel et al. International Journal of Current Research, vol. 9, Issue 6, pp. 53036-53043, Jun. 2017. (Year: 2017).*
"New Drugs/Programs", *Current Drug Discovery*, (Nov. 2004) pp. 7-10.
"Polycaprolactone" https://en.wikipedia.org/wiki/Polycaprolactone 1 page, Jun. 16, 2008.
"Polyglycolide" https://en.wikipedia.org/wiki/Polyglycolide 3 pages, printed Jun. 16, 2008.
"Polylactic Acid" https://en.wikipedia.org/wiki/Polylactic_acid, 1 page, printed Jun. 16, 2008.

(Continued)

*Primary Examiner* — Doan T Phan
(74) *Attorney, Agent, or Firm* — Bozicevic, Field & Francis LLP; Khin Chin

(57) ABSTRACT

The present disclosure relates to sustained release drug delivery systems. In some cases, a composition comprises an active pharmaceutical agent; at least one of sucrose acetate isobutyrate and a polyorthoester; an organic solvent; and 2,6-dimethylaniline, wherein the 2,6-dimethylaniline is present at a level less than 500 ppm. In some cases, a composition comprises N-oxide of active pharmaceutical agent at a level less than 1 wt %, based on weight of the composition. In some case, a composition comprises metal present at a level less than 5 ppm. Dosage forms and methods are also provided.

27 Claims, 32 Drawing Sheets

(56) References Cited

U.S. PATENT DOCUMENTS

| | | |
|---|---|---|
| 4,623,588 A | 11/1986 | Nuwayser et al. |
| 4,630,019 A | 12/1986 | Portner et al. |
| 4,668,506 A | 5/1987 | Bawa |
| 4,692,147 A | 9/1987 | Duggan |
| 4,708,861 A | 11/1987 | Popescu et al. |
| 4,711,782 A | 12/1987 | Okada et al. |
| 4,713,244 A | 12/1987 | Bawa et al. |
| 4,725,442 A | 2/1988 | Haynes |
| 4,725,852 A | 2/1988 | Gamblin et al. |
| 4,745,160 A | 5/1988 | Churchill et al. |
| 4,767,628 A | 8/1988 | Hutchinson |
| 4,780,319 A | 10/1988 | Zentner et al. |
| 4,782,104 A | 11/1988 | Nakanishi |
| 4,795,641 A | 1/1989 | Kashdan |
| 4,834,984 A | 5/1989 | Goldie et al. |
| 4,844,909 A | 7/1989 | Goldie et al. |
| 4,853,218 A | 8/1989 | Yim et al. |
| 4,861,598 A | 8/1989 | Oshlack |
| 4,865,845 A | 9/1989 | Eckenhoff et al. |
| 4,866,050 A | 9/1989 | Ben-Amoz |
| 4,874,388 A | 10/1989 | Wong et al. |
| 4,891,225 A | 1/1990 | Langer et al. |
| 4,906,474 A | 3/1990 | Langer et al. |
| 4,931,279 A | 6/1990 | Bawa et al. |
| 4,938,763 A | 7/1990 | Dunn et al. |
| 4,946,931 A | 8/1990 | Heller et al. |
| 4,957,744 A | 9/1990 | Della Valle et al. |
| 4,957,998 A | 9/1990 | Heller et al. |
| 4,970,075 A | 11/1990 | Oshlack |
| 4,985,404 A | 1/1991 | Mitchell et al. |
| 4,990,341 A | 2/1991 | Goldie et al. |
| 5,019,400 A | 5/1991 | Gombotz et al. |
| 5,034,229 A | 7/1991 | Magruder et al. |
| 5,057,318 A | 10/1991 | Magruder et al. |
| 5,059,423 A | 10/1991 | Magruder et al. |
| 5,061,492 A | 10/1991 | Okada et al. |
| 5,077,033 A | 12/1991 | Viegas et al. |
| 5,085,866 A | 2/1992 | Cowsar et al. |
| 5,110,596 A | 5/1992 | Magruder et al. |
| 5,112,614 A | 5/1992 | Magruder et al. |
| 5,137,727 A | 8/1992 | Eckenhoff et al. |
| 5,149,543 A | 9/1992 | Cohen et al. |
| 5,151,093 A | 9/1992 | Theeuwes et al. |
| 5,181,914 A | 1/1993 | Zook |
| 5,188,837 A | 2/1993 | Domb |
| 5,192,743 A | 3/1993 | Hsu et al. |
| 5,209,746 A | 5/1993 | Balaban et al. |
| 5,211,951 A | 5/1993 | Sparer et al. |
| 5,219,572 A | 6/1993 | Sivaramakinshnan et al. |
| 5,234,692 A | 8/1993 | Magruder et al. |
| 5,234,693 A | 8/1993 | Magruder et al. |
| 5,242,910 A | 9/1993 | Damnj |
| 5,252,318 A | 10/1993 | Joshi et al. |
| 5,266,331 A | 11/1993 | Oshlack et al. |
| 5,278,201 A | 1/1994 | Dunn et al. |
| 5,278,202 A | 1/1994 | Dunn et al. |
| 5,279,608 A | 1/1994 | Cheikh |
| 5,286,496 A | 2/1994 | Stapler et al. |
| 5,308,348 A | 5/1994 | Bakaban et al. |
| 5,310,865 A | 5/1994 | Enomoto et al. |
| 5,312,389 A | 5/1994 | Theeuwes et al. |
| 5,324,519 A | 6/1994 | Dunn et al. |
| 5,324,520 A | 6/1994 | Dunn et al. |
| 5,330,452 A | 7/1994 | Zook |
| 5,330,835 A | 7/1994 | Kikuchi et al. |
| 5,300,295 A | 8/1994 | Viegas et al. |
| 5,336,057 A | 8/1994 | Fukuda et al. |
| 5,340,572 A | 8/1994 | Patel et al. |
| 5,340,614 A | 8/1994 | Perman et al. |
| 5,340,849 A | 8/1994 | Dunn et al. |
| 5,342,627 A | 8/1994 | Chopra et al. |
| 5,350,741 A | 9/1994 | Takada |
| 5,352,662 A | 10/1994 | Brooks et al. |
| 5,356,635 A | 10/1994 | Raman et al. |
| 5,368,588 A | 11/1994 | Bettinger |
| 5,370,864 A | 12/1994 | Peterson et al. |
| 5,382,424 A | 1/1995 | Stapler et al. |
| 5,391,381 A | 2/1995 | Wong et al. |
| 5,399,353 A | 3/1995 | Bartnik et al. |
| 5,399,363 A | 3/1995 | Liversidge et al. |
| 5,415,866 A | 5/1995 | Zook |
| 5,441,732 A | 8/1995 | Hoeg et al. |
| 5,442,033 A | 8/1995 | Bezwada |
| 5,447,725 A | 9/1995 | Damani et al. |
| 5,456,679 A | 10/1995 | Balaban et al. |
| 5,478,577 A | 12/1995 | Sackler et al. |
| 5,487,898 A | 1/1996 | Lu et al. |
| 5,492,253 A | 2/1996 | Proshan |
| 5,505,922 A | 4/1996 | Thut |
| 5,511,355 A | 4/1996 | Dingier |
| 5,540,912 A | 7/1996 | Roorda et al. |
| 5,545,408 A | 8/1996 | Trigg et al. |
| 5,549,912 A | 8/1996 | Oshiack et al. |
| 5,556,905 A | 9/1996 | Frappier et al. |
| 5,557,318 A | 9/1996 | Gabriel |
| 5,569,450 A | 10/1996 | Duan et al. |
| 5,571,525 A | 11/1996 | Roorda et al. |
| 5,587,175 A | 12/1996 | Viegas et al. |
| 5,599,534 A | 2/1997 | Himmelstein et al. |
| 5,599,552 A | 2/1997 | Dunn et al. |
| 5,599,852 A | 2/1997 | Scopelianos |
| 5,607,686 A | 3/1997 | Totakura et al. |
| 5,610,184 A | 3/1997 | Shahinian, Jr. |
| 5,614,206 A | 3/1997 | Randolph et al. |
| 5,618,563 A | 4/1997 | Berde et al. |
| 5,620,700 A | 4/1997 | Berggen et al. |
| 5,628,993 A | 5/1997 | Yamagata |
| 5,632,727 A | 5/1997 | Tipton et al. |
| 5,633,000 A | 5/1997 | Grossman et al. |
| 5,651,986 A | 7/1997 | Brem et al. |
| 5,654,010 A | 8/1997 | Johnson et al. |
| 5,656,295 A | 8/1997 | Oshlack et al. |
| 5,656,297 A | 8/1997 | Bernstein et al. |
| 5,660,817 A | 8/1997 | Masterman et al. |
| 5,661,104 A * | 8/1997 | Virgilio ............... C02F 1/50 514/741 |
| 5,672,360 A | 9/1997 | Sackler et al. |
| 5,681,873 A | 10/1997 | Norton et al. |
| 5,700,485 A | 12/1997 | Berde et al. |
| 5,702,716 A | 12/1997 | Dunn et al. |
| 5,707,647 A | 1/1998 | Dunn et al. |
| 5,707,664 A | 1/1998 | Illum |
| 5,708,011 A | 1/1998 | Bardsley et al. |
| 5,713,847 A | 2/1998 | Howard, III et al. |
| 5,717,030 A | 2/1998 | Dunn et al. |
| 5,725,491 A | 3/1998 | Tipton et al. |
| 5,725,841 A | 3/1998 | Dunn et al. |
| 5,728,396 A | 3/1998 | Peery et al. |
| 5,733,950 A | 3/1998 | Dunn et al. |
| 5,736,152 A | 4/1998 | Dunn |
| 5,739,176 A | 4/1998 | Dunn et al. |
| 5,744,153 A | 4/1998 | Yewey et al. |
| 5,747,051 A | 5/1998 | Granger et al. |
| 5,747,058 A | 5/1998 | Tipton et al. |
| 5,747,060 A | 5/1998 | Sackler et al. |
| 5,750,100 A | 5/1998 | Yamagata et al. |
| 5,759,563 A | 6/1998 | Yewey et al. |
| 5,760,077 A | 6/1998 | Shahinian, Jr. |
| 5,766,637 A | 6/1998 | Shine et al. |
| 5,777,124 A | 7/1998 | Zavareh et al. |
| 5,780,044 A | 7/1998 | Yewey et al. |
| 5,783,205 A | 7/1998 | Berggren et al. |
| 5,786,484 A | 7/1998 | Dyer et al. |
| 5,787,175 A | 7/1998 | Carter |
| 5,792,469 A | 8/1998 | Tipton et al. |
| 5,801,012 A | 9/1998 | Soff et al. |
| 5,804,212 A | 9/1998 | Illum |
| 5,836,935 A | 11/1998 | Ashton et al. |
| 5,837,228 A | 11/1998 | Shih et al. |
| 5,840,329 A | 11/1998 | Bai |
| 5,849,763 A | 12/1998 | Bardsley et al. |
| 5,874,388 A | 2/1999 | Hsu |
| 5,879,705 A | 3/1999 | Heafield et al. |
| 5,910,502 A | 6/1999 | Gennery |

(56) References Cited

U.S. PATENT DOCUMENTS

| | | |
|---|---|---|
| 5,919,473 A | 7/1999 | Elkhomy |
| 5,919,835 A | 7/1999 | Domb et al. |
| 5,922,340 A | 7/1999 | Berde et al. |
| 5,932,597 A | 8/1999 | Brown |
| 5,939,453 A | 8/1999 | Heller et al. |
| 5,942,241 A | 8/1999 | Chasin et al. |
| 5,942,253 A | 8/1999 | Gombotz et al. |
| 5,945,115 A | 8/1999 | Dunn et al. |
| 5,958,443 A | 9/1999 | Viegas et al. |
| 5,968,542 A | 10/1999 | Tipton |
| 5,968,543 A | 10/1999 | Heller et al. |
| 5,972,326 A | 10/1999 | Galin et al. |
| 5,972,366 A | 10/1999 | Haynes et al. |
| 5,976,109 A | 11/1999 | Hemth |
| 5,985,305 A | 11/1999 | Peery et al. |
| 5,990,194 A | 11/1999 | Dunn et al. |
| 5,993,856 A | 11/1999 | Ragavan et al. |
| 5,994,548 A | 11/1999 | Langston et al. |
| 5,997,527 A | 12/1999 | Gumucio et al. |
| 5,997,902 A | 12/1999 | Maruyama et al. |
| 6,004,295 A | 12/1999 | Langer et al. |
| 6,007,845 A | 12/1999 | Domb et al. |
| 6,008,355 A | 12/1999 | Huang et al. |
| 6,042,811 A | 3/2000 | Duan et al. |
| 6,046,187 A | 4/2000 | Berde et al. |
| 6,050,986 A | 4/2000 | Hektner |
| 6,051,558 A | 4/2000 | Burns et al. |
| 6,086,909 A | 7/2000 | Harrison et al. |
| 6,093,420 A | 7/2000 | Baichwal |
| 6,102,235 A | 8/2000 | Stern et al. |
| 6,103,266 A | 8/2000 | Tapolski et al. |
| 6,106,301 A | 8/2000 | Merril |
| 6,113,938 A | 9/2000 | Chen et al. |
| 6,117,425 A | 9/2000 | McPhee et al. |
| 6,119,890 A | 9/2000 | Kawamata |
| 6,120,789 A | 9/2000 | Dunn |
| 6,120,804 A | 9/2000 | Drizen et al. |
| 6,126,919 A | 10/2000 | Stefely et al. |
| 6,129,933 A | 10/2000 | Oshlack et al. |
| 6,130,200 A | 10/2000 | Brodbeck et al. |
| 6,132,420 A | 10/2000 | Dionne et al. |
| 6,132,766 A | 10/2000 | Sankaram et al. |
| 6,136,334 A | 10/2000 | Viegas et al. |
| 6,143,314 A | 11/2000 | Chandeashekar et al. |
| 6,143,322 A | 11/2000 | Sackler et al. |
| 6,156,331 A | 12/2000 | Peery et al. |
| 6,193,991 B1 | 2/2001 | Shukla |
| 6,193,994 B1 | 2/2001 | Lee et al. |
| 6,197,327 B1 | 3/2001 | Harrison et al. |
| 6,203,813 B1 | 3/2001 | Gooberman |
| 6,214,387 B1 | 4/2001 | Berde et al. |
| 6,217,906 B1 | 4/2001 | Gumucio et al. |
| 6,217,911 B1 | 4/2001 | Vaung et al. |
| 6,238,702 B1 | 5/2001 | Berde et al. |
| 6,245,351 B1 | 6/2001 | Nara et al. |
| 6,248,112 B1 | 6/2001 | Gambale et al. |
| 6,248,345 B1 | 6/2001 | Goldenheim et al. |
| 6,255,502 B1 | 7/2001 | Penkler et al. |
| 6,261,547 B1 | 7/2001 | Bawa et al. |
| 6,261,584 B1 | 7/2001 | Peery et al. |
| 6,270,787 B1 | 8/2001 | Ayer |
| 6,283,948 B1 | 9/2001 | Roorda |
| 6,291,013 B1 | 9/2001 | Gibson et al. |
| 6,309,375 B1 | 10/2001 | Glines et al. |
| 6,312,717 B1 | 11/2001 | Molinoff et al. |
| 6,322,548 B1 | 11/2001 | Payne et al. |
| 6,331,311 B1 | 12/2001 | Brodbeck et al. |
| 6,352,667 B1 | 3/2002 | English |
| 6,355,273 B1 | 3/2002 | Carli et al. |
| 6,372,245 B1 | 4/2002 | Bowman et al. |
| 6,375,659 B1 | 4/2002 | Erbe et al. |
| 6,375,978 B1 | 4/2002 | Kleiner et al. |
| 6,384,227 B2 | 5/2002 | Dyer et al. |
| 6,395,292 B2 | 5/2002 | Peery et al. |
| 6,395,293 B2 | 5/2002 | Polson et al. |
| 6,403,057 B1 | 6/2002 | Schneider et al. |
| 6,403,609 B1 | 6/2002 | Asgharian |
| 6,413,536 B1 | 7/2002 | Gibson et al. |
| 6,417,201 B1 | 7/2002 | Bardsley et al. |
| 6,420,454 B1 | 7/2002 | Wenz et al. |
| 6,423,818 B1 | 7/2002 | Matsuda et al. |
| 6,426,339 B1 | 7/2002 | Berde et al. |
| 6,432,415 B1 | 8/2002 | Osborne et al. |
| 6,436,091 B1 | 8/2002 | Harper et al. |
| 6,440,493 B1 | 8/2002 | Gibson et al. |
| 6,447,522 B2 | 9/2002 | Gambale et al. |
| 6,451,346 B1 | 9/2002 | Shah |
| 6,468,961 B1 | 10/2002 | Brodbeck et al. |
| 6,479,074 B2 | 11/2002 | Murdock et al. |
| 6,486,138 B1 | 11/2002 | Asgharian et al. |
| 6,498,153 B1 | 12/2002 | Cady et al. |
| 6,508,808 B1 | 1/2003 | Carr et al. |
| 6,514,516 B1 | 2/2003 | Chasin et al. |
| 6,521,259 B1 | 2/2003 | Chasin et al. |
| 6,524,606 B1 | 2/2003 | Ng et al. |
| 6,524,607 B1 | 2/2003 | Goldenheim et al. |
| 6,525,102 B1 | 2/2003 | Chen et al. |
| 6,543,081 B1 | 3/2003 | Goldenheim et al. |
| 6,590,059 B2 | 7/2003 | Ng et al. |
| 6,613,335 B1 | 9/2003 | Ruelle |
| 6,673,767 B1 | 1/2004 | Brodbeck et al. |
| 6,699,908 B2 | 3/2004 | Sackler et al. |
| 6,733,783 B2 | 5/2004 | Oshlack et al. |
| 6,840,931 B2 | 1/2005 | Peterson et al. |
| 6,863,782 B2 | 3/2005 | Newsome et al. |
| 6,921,541 B2 | 7/2005 | Chasin et al. |
| 6,992,065 B2 | 1/2006 | Okumu |
| 7,053,209 B1 | 5/2006 | Gibson et al. |
| 7,128,927 B1 | 10/2006 | Dunn |
| 7,368,126 B2 | 5/2008 | Chen et al. |
| 7,829,109 B2 | 11/2010 | Chen et al. |
| 7,833,543 B2 | 11/2010 | Gibson et al. |
| 8,110,209 B2 | 2/2012 | Prestrelski et al. |
| 8,133,507 B2 | 3/2012 | Yum et al. |
| 8,147,870 B2 | 4/2012 | Yum et al. |
| 8,153,149 B2 | 4/2012 | Verity |
| 8,153,152 B2 | 4/2012 | Yum et al. |
| 8,153,661 B2 | 4/2012 | Verity |
| 8,168,217 B2 | 5/2012 | Yum et al. |
| 8,182,835 B2 | 5/2012 | Kim et al. |
| 8,231,903 B2 | 7/2012 | Fraatz et al. |
| 8,252,303 B2 | 8/2012 | Chen et al. |
| 8,252,304 B2 | 8/2012 | Ng et al. |
| 8,278,330 B2 | 10/2012 | Chen et al. |
| 8,337,883 B2 | 12/2012 | Yum et al. |
| 8,354,124 B2 | 1/2013 | Yum et al. |
| 8,415,401 B2 | 4/2013 | Yum et al. |
| 8,420,120 B2 | 4/2013 | Yum et al. |
| 8,496,943 B2 | 7/2013 | Fereira et al. |
| 8,501,215 B2 | 8/2013 | Chen et al. |
| 8,753,665 B2 | 6/2014 | Verity |
| 8,834,921 B2 | 9/2014 | Kim et al. |
| 8,846,072 B2 | 9/2014 | Verity |
| 8,945,614 B2 | 2/2015 | Yum et al. |
| 8,951,556 B2 | 2/2015 | Yum et al. |
| 9,192,575 B2 | 11/2015 | Kim et al. |
| 9,205,052 B2 | 12/2015 | Kim et al. |
| 9,446,036 B2 | 9/2016 | Ottoboni et al. |
| 9,585,838 B2 | 3/2017 | Hartounian et al. |
| 10,201,496 B2 | 2/2019 | Chen et al. |
| 10,471,001 B2 | 11/2019 | Chen et al. |
| 10,471,002 B2 | 11/2019 | Chen et al. |
| 11,083,796 B2 | 8/2021 | Junnarkar et al. |
| 2001/0000522 A1 | 4/2001 | Dyer et al. |
| 2001/0004644 A1 | 6/2001 | Levin |
| 2001/0013518 A1 | 8/2001 | Lallement et al. |
| 2001/0029257 A1 | 10/2001 | Murdock et al. |
| 2001/0046518 A1 | 11/2001 | Sawhney |
| 2001/0055607 A1 | 12/2001 | Levin |
| 2002/0001608 A1 | 1/2002 | Polson et al. |
| 2002/0001631 A1 | 1/2002 | Okumu |
| 2002/0004063 A1 | 1/2002 | Zhang |
| 2002/0006443 A1 | 1/2002 | Curatolo |
| 2002/0010150 A1 | 1/2002 | Cortese et al. |

(56) References Cited

U.S. PATENT DOCUMENTS

| | | |
|---|---|---|
| 2002/0016338 A1 | 2/2002 | Mather et al. |
| 2002/0028181 A1 | 3/2002 | Miller et al. |
| 2002/0028243 A1 | 3/2002 | Masters |
| 2002/0037104 A1 | 3/2002 | Myers et al. |
| 2002/0037300 A1 | 3/2002 | Ng et al. |
| 2002/0037358 A1 | 3/2002 | Barry et al. |
| 2002/0037904 A1 | 3/2002 | Zhang et al. |
| 2002/0141966 A1 | 3/2002 | Dang |
| 2002/0039594 A1 | 4/2002 | Unger |
| 2002/0045668 A1 | 4/2002 | Dang et al. |
| 2002/0061326 A1 | 5/2002 | Li et al. |
| 2002/0064536 A1 | 5/2002 | Hunt |
| 2002/0086971 A1 | 7/2002 | Pham |
| 2002/0114835 A1 | 8/2002 | Sackler et al. |
| 2002/0054915 A1 | 9/2002 | Goldenheim et al. |
| 2002/0168336 A1 | 11/2002 | Ng et al. |
| 2002/0173552 A1 | 11/2002 | Cleland et al. |
| 2002/0176844 A1 | 11/2002 | Ng et al. |
| 2003/0044467 A1 | 3/2003 | Brodbeck et al. |
| 2003/0045454 A1 | 3/2003 | Okumu et al. |
| 2003/0059376 A1 | 3/2003 | Libbey et al. |
| 2003/0108609 A1 | 6/2003 | Berry et al. |
| 2003/0114430 A1 | 6/2003 | MacLeod et al. |
| 2003/0152630 A1 | 8/2003 | Ng et al. |
| 2003/0152634 A1 | 8/2003 | Bodmeier |
| 2003/0152637 A1 | 8/2003 | Chasin et al. |
| 2003/0180364 A1 | 9/2003 | Chen et al. |
| 2003/0185873 A1 | 10/2003 | Chasin et al. |
| 2003/0170289 A1 | 11/2003 | Chen et al. |
| 2003/0211140 A1 | 11/2003 | Mantripragada et al. |
| 2003/0215515 A1 | 11/2003 | Truong-le et al. |
| 2004/0001889 A1 | 1/2004 | Chen et al. |
| 2004/0018238 A1 | 1/2004 | Shukla |
| 2004/0024021 A1 | 2/2004 | Sudo et al. |
| 2004/0037885 A1 | 2/2004 | Seo et al. |
| 2004/0042194 A1 | 3/2004 | Hsieh |
| 2004/0052336 A1 | 3/2004 | Langlet et al. |
| 2004/0106987 A1 | 3/2004 | Palasis et al. |
| 2004/0022859 A1 | 5/2004 | Chen et al. |
| 2004/0024069 A1 | 5/2004 | Chen et al. |
| 2004/0101557 A1 | 5/2004 | Gibson et al. |
| 2004/0151753 A1 | 5/2004 | Chen et al. |
| 2004/0151774 A1 | 5/2004 | Pauletti et al. |
| 2004/0109893 A1 | 6/2004 | Chen et al. |
| 2001/0138237 | 7/2004 | Shah |
| 2004/0138237 A1 | 7/2004 | Shah |
| 2004/0142902 A1 | 7/2004 | Struijker-Boudier |
| 2004/0146562 A1 | 7/2004 | Shah |
| 2004/0161382 A1 | 8/2004 | Tum et al. |
| 2004/0208845 A1 | 10/2004 | Michal et al. |
| 2004/0224019 A1 | 11/2004 | Zale et al. |
| 2004/0224903 A1 | 11/2004 | Berry et al. |
| 2005/0008661 A1 | 1/2005 | Fereira et al. |
| 2005/0042194 A1 | 2/2005 | Ng et al. |
| 2005/0095284 A1 | 5/2005 | Trautman |
| 2005/0106214 A1 | 5/2005 | Chen |
| 2005/0106304 A1 | 5/2005 | Cook et al. |
| 2005/0171052 A1 | 8/2005 | Cook et al. |
| 2005/0232876 A1 | 10/2005 | Minga et al. |
| 2005/0244489 A1 | 11/2005 | Paris |
| 2005/0266087 A1 | 12/2005 | Junnarkar et al. |
| 2005/0276856 A1 | 12/2005 | Fereira et al. |
| 2005/0281879 A1 | 12/2005 | Chen et al. |
| 2006/0034926 A1 | 2/2006 | Fraatz et al. |
| 2006/0058401 A1 | 3/2006 | Ishikawa et al. |
| 2006/0155101 A1 | 7/2006 | Heller et al. |
| 2006/0165800 A1 | 7/2006 | Chen et al. |
| 2006/0121085 A1 | 8/2006 | Warren et al. |
| 2006/0210599 A1 | 9/2006 | Gibson et al. |
| 2008/0023261 A1 | 1/2008 | Kaneko et al. |
| 2008/0145419 A1 | 6/2008 | Gibson et al. |
| 2008/0152708 A1 | 6/2008 | Gibson et al. |
| 2008/0167630 A1 | 7/2008 | Verity |
| 2008/0206321 A1 | 8/2008 | Yum et al. |
| 2008/0287464 A1 | 11/2008 | Wright et al. |
| 2009/0023689 A1 | 1/2009 | Yum et al. |
| 2009/0023690 A1 | 1/2009 | Yum et al. |
| 2009/0036490 A1 | 2/2009 | Verity |
| 2009/0037490 A1 | 2/2009 | Ohira |
| 2009/0215808 A1 | 8/2009 | Yum et al. |
| 2009/0298862 A1 | 12/2009 | Yum et al. |
| 2010/0160375 A1 | 6/2010 | King |
| 2011/0009451 A1 | 1/2011 | Verity |
| 2011/0046181 A1 | 2/2011 | Chen et al. |
| 2012/0135072 A1 | 5/2012 | Yum et al. |
| 2012/0135073 A1 | 5/2012 | Yum et al. |
| 2012/0177697 A1 | 7/2012 | Chen |
| 2013/0251674 A1 | 9/2013 | Fereira et al. |
| 2013/0281480 A1 | 10/2013 | Yum et al. |
| 2013/0287845 A1 | 10/2013 | Yum et al. |
| 2013/0289053 A1 | 10/2013 | Wright et al. |
| 2013/0289069 A1 | 10/2013 | Verity |
| 2013/0295168 A1 | 11/2013 | Yum et al. |
| 2013/0317049 A1 | 11/2013 | Yum et al. |
| 2013/0337059 A1 | 12/2013 | Yum et al. |
| 2013/0337060 A1 | 12/2013 | Yum et al. |
| 2013/0345260 A1 | 12/2013 | Gibson et al. |
| 2014/0275147 A1 | 9/2014 | Yum et al. |
| 2014/0308352 A1 | 10/2014 | Wright et al. |
| 2015/0111924 A1 | 4/2015 | Verity |
| 2016/0235726 A1 | 8/2016 | Verity |
| 2017/0087086 A1 | 3/2017 | Chen et al. |
| 2017/0216267 A1 | 8/2017 | Verity |
| 2018/0256553 A1 | 9/2018 | Verity |
| 2019/0231762 A1 | 8/2019 | Verity |
| 2022/0023424 A1 | 1/2022 | Junnarkar et al. |

FOREIGN PATENT DOCUMENTS

| | | |
|---|---|---|
| CA | 2283517 | 4/1998 |
| CA | 2291087 | 12/1998 |
| CA | 2303442 | 3/1999 |
| CA | 2379436 | 10/2002 |
| DE | 2213717 | 11/1972 |
| DE | 2321174 | 11/1973 |
| DE | 2438352 | 2/1976 |
| DE | 2720245 | 11/1977 |
| DE | 19520237 | 12/1996 |
| DE | 19714765 | 10/1998 |
| EP | 0244118 | 11/1987 |
| EP | 0413528 | 2/1991 |
| EP | 0535899 | 4/1993 |
| EP | 0537559 | 4/1993 |
| EP | 0539559 | 5/1993 |
| EP | 0539751 | 5/1993 |
| EP | 0621042 | 10/1994 |
| EP | 0635531 | 1/1995 |
| EP | 0640336 | 3/1995 |
| EP | 0671162 | 9/1995 |
| EP | 0711548 | 5/1996 |
| EP | 0773034 | 5/1997 |
| EP | 0795329 | 9/1997 |
| EP | 0999825 | 5/2000 |
| EP | 1010436 | 6/2000 |
| EP | 0782569 | 3/2002 |
| EP | 0862416 | 9/2002 |
| EP | 0804417 | 6/2003 |
| EP | 0788480 | 7/2003 |
| EP | 0788481 | 8/2003 |
| EP | 1348427 | 10/2003 |
| EP | 1032390 | 11/2003 |
| EP | 0778768 | 5/2004 |
| EP | 1515697 | 3/2005 |
| EP | 1548093 | 6/2005 |
| EP | 1212092 | 10/2005 |
| EP | 1100460 | 4/2008 |
| EP | 2238478 | 10/2010 |
| EP | 1809329 | 12/2011 |
| GB | 1088992 | 10/1967 |
| GB | 1218430 | 1/1971 |
| GB | 2238478 | 6/1991 |
| JP | 59210024 | 11/1984 |
| JP | S 62000419 | 1/1987 |
| JP | 63302858 | 12/1988 |

(56) References Cited

FOREIGN PATENT DOCUMENTS

| | | |
|---|---:|---|
| JP | 2096516 | 4/1990 |
| JP | H 0296516 | 4/1990 |
| JP | 5194273 | 8/1993 |
| JP | 7053356 | 2/1995 |
| JP | 07070297 | 3/1995 |
| JP | 7115901 | 5/1995 |
| JP | 7124196 | 5/1995 |
| JP | H 7112940 | 5/1995 |
| JP | 8501064 | 2/1996 |
| JP | 8505395 | 6/1996 |
| JP | 08206191 | 8/1996 |
| JP | 8512303 | 12/1996 |
| JP | 9502181 | 3/1997 |
| JP | 2000185091 | 7/2000 |
| JP | 2001509146 | 7/2001 |
| JP | 2002512597 | 4/2002 |
| JP | 2004536036 | 12/2004 |
| JP | 2005514349 | 5/2005 |
| JP | 2005519873 | 7/2005 |
| JP | 2008513467 | 3/2006 |
| JP | 2008512597 | 4/2008 |
| JP | 4330175 | 6/2009 |
| JP | 4501076 | 7/2010 |
| NZ | 533435 | 10/2007 |
| NZ | 533436 | 10/2007 |
| NZ | 537955 | 10/2007 |
| WO | WO 1990003768 | 4/1990 |
| WO | WO 1990003809 | 4/1990 |
| WO | WO 1991016929 | 11/1991 |
| WO | WO 1991017900 | 11/1991 |
| WO | WO 1991018016 | 11/1991 |
| WO | WO 1992011843 | 7/1992 |
| WO | WO 1992017900 | 10/1992 |
| WO | WO 1993000006 | 1/1993 |
| WO | WO 1993003751 | 3/1993 |
| WO | WO 1993007833 | 4/1993 |
| WO | WO 1993020134 | 10/1993 |
| WO | WO 1993024150 | 12/1993 |
| WO | WO 1994005265 | 3/1994 |
| WO | WO 1994014416 | 7/1994 |
| WO | WO 1994014417 | 7/1994 |
| WO | WO 1994015587 | 7/1994 |
| WO | WO 1994028935 | 12/1994 |
| WO | WO 1995001786 | 1/1995 |
| WO | WO 1995006693 | 3/1995 |
| WO | WO 1995009613 | 4/1995 |
| WO | WO 1995001379 | 5/1995 |
| WO | WO 1995017901 | 7/1995 |
| WO | WO 1996009290 | 3/1996 |
| WO | WO 1996012699 | 5/1996 |
| WO | WO 1996012700 | 5/1996 |
| WO | WO 1996021427 | 7/1996 |
| WO | WO 1996022281 | 7/1996 |
| WO | WO 1996039995 | 12/1996 |
| WO | WO 1996041616 | 12/1996 |
| WO | WO 1997015285 | 5/1997 |
| WO | WO 1997027840 | 8/1997 |
| WO | WO 1997049391 | 12/1997 |
| WO | WO 1998027962 | 7/1998 |
| WO | WO 1998027963 | 7/1998 |
| WO | WO 1998034596 | 8/1998 |
| WO | WO 1998044903 | 10/1998 |
| WO | WO 1998051246 | 11/1998 |
| WO | WO 1998053837 | 12/1998 |
| WO | WO 1999006023 | 2/1999 |
| WO | WO 1999013913 | 3/1999 |
| WO | WO 1999025349 | 5/1999 |
| WO | WO 1999033446 | 7/1999 |
| WO | WO 1999047073 | 9/1999 |
| WO | WO 1999062983 | 9/1999 |
| WO | WO 2000000120 | 1/2000 |
| WO | WO 2000000181 | 1/2000 |
| WO | WO 2000033866 | 6/2000 |
| WO | WO 2000045790 | 8/2000 |
| WO | WO 2000054745 | 9/2000 |
| WO | WO 2000074650 | 12/2000 |
| WO | WO 2000078335 | 12/2000 |
| WO | WO 2001042518 | 12/2000 |
| WO | WO 2001043528 | 12/2000 |
| WO | WO 2001003670 | 1/2001 |
| WO | WO 2001015734 | 3/2001 |
| WO | WO 2001051024 | 7/2001 |
| WO | WO 2001051041 | 7/2001 |
| WO | WO 2001076599 | 10/2001 |
| WO | WO 2001078983 | 10/2001 |
| WO | WO 2001085139 | 11/2001 |
| WO | WO 2001049336 | 12/2001 |
| WO | WO 2002000137 | 1/2002 |
| WO | WO 2002001608 | 1/2002 |
| WO | WO 2002010436 | 2/2002 |
| WO | WO 2002028366 | 4/2002 |
| WO | WO 1992007555 | 5/2002 |
| WO | WO 2002038185 | 5/2002 |
| WO | WO 2002043800 | 6/2002 |
| WO | WO 2002053187 | 7/2002 |
| WO | WO 2002058670 | 8/2002 |
| WO | WO 2002067895 | 9/2002 |
| WO | WO 2002067991 | 9/2002 |
| WO | WO 2003000282 | 1/2003 |
| WO | WO 2003041684 | 5/2003 |
| WO | WO 2003041685 | 5/2003 |
| WO | WO 2003041757 | 5/2003 |
| WO | WO 2003059320 | 7/2003 |
| WO | WO 2003072113 | 9/2003 |
| WO | WO 2003082188 | 10/2003 |
| WO | WO 2003086368 | 10/2003 |
| WO | WO 2003101358 | 12/2003 |
| WO | WO 2003101961 | 12/2003 |
| WO | WO 2004000269 | 12/2003 |
| WO | WO 2004007451 | 1/2004 |
| WO | WO 2004011032 | 2/2004 |
| WO | WO 2004012703 | 2/2004 |
| WO | WO 2004014466 | 2/2004 |
| WO | WO 2004037224 | 5/2004 |
| WO | WO 2004037289 | 5/2004 |
| WO | WO 2004043432 | 5/2004 |
| WO | WO 2004052336 | 6/2004 |
| WO | WO 2004056338 | 7/2004 |
| WO | WO 2004082658 | 9/2004 |
| WO | WO 2004089335 | 10/2004 |
| WO | WO 2004101557 | 11/2004 |
| WO | WO 2004108111 | 12/2004 |
| WO | WO 2005009408 | 2/2005 |
| WO | WO 2005048744 | 6/2005 |
| WO | WO 2005048930 | 6/2005 |
| WO | WO 2005049069 | 6/2005 |
| WO | WO 2005105031 | 11/2005 |
| WO | WO 2005115333 | 12/2005 |
| WO | WO 2006033948 | 3/2006 |
| WO | WO 2006083950 | 8/2006 |
| WO | WO 2006084139 | 8/2006 |
| WO | WO 2006084140 | 8/2006 |
| WO | WO 2006084141 | 8/2006 |
| WO | WO 2008023261 | 2/2008 |
| WO | WO 2014144984 | 9/2014 |
| WO | 2015164272 | 10/2015 |
| WO | WO-2018191412 A1 * | 10/2018 ........... A61K 31/167 |

OTHER PUBLICATIONS

"3M DDS Announces Development of New HFA-Compatible Excipients: Novel Oligomeric Acids as MDI Suspension Aids and Solubilizers", 3M Delivery Newsletter, 3M Drug Delivery Systems, vol. 15, Jun. 2000.

Adams EG, et al. "A comparison of the abuse liability of tramadol, NSAIDS, and hydrocodone in patients with chronic pain", *Journal of Pain and Symptom Management*. 31(5), (2006) pp. 465-476.

Ahuja et al. (1995) "Intra-Articular Morphine Versus Bupivacaine for Postoperative Analgesia Following Knee Arthroscopy" *The Knee* 2(4): pp. 227-231.

Ajayaghosh, A., et al. (1990) "Solid-Phase Synthesis of N-Methyl and N-Ethylamides of Peptides Using Photolytically Detachable

(56) References Cited

OTHER PUBLICATIONS ((3-Nitro-4-((alkylamino)methyl)benzamido)methyl)polystrene Resin", *J. Org. Chem.*, 55:2826-2829.

Allahham A, et al. (2004) "Flow and injection characteristics of pharmaceutical parenteral formulations using a micro-capillary rheometer", *Int J Pharm.*;270(1-2):139-148.

Ansel, H.C. et al., Pharmaceutical Dosage Forms and Drug Delivery System, sixth ed., (1995).

Baker, M., et al., "Sulfite supported lipid peroxidation in propofol emulsions," Anesthesiology 2002; 97: 1162-7.

Barb, R. et al., "Evaluation of the Saber Delivery System for the Controlled Release of Deslorelin: Effect of Dose in Estrogen Primed Ovarectomized Gilts," Proceed. Int'l Symp. Control. Rel. Bioact. Mater., 26 (1999).

Barr, J., et al., Post surgical pain management with poly(ortho esters), *Adv. Drug Del. Rev.*, 54 (2002) 1041-1048.

Bartfield et al. (1998) "Randomized Trial of Diphenhydramine Versus Benzyl Alcohol with Epinephrine as an Alternative to Lidocaine Local Anesthesia" *Ann Emerg Med* 32(6):650-654.

Bartfield et al. (2001) "Benzyl Alcohol with Epinephrine as an Alternative To Lidocaine With Epinephrine" *J Emerg Med* 21(4):375-379.

Bartosz, et al., (1997) "Antioxidant and Prooxidant Properties Of Captopril And Enalapril",Free Radical Biology & Medicine, 23(5):729-735.

Becker, S.E., et al. "Effects of Gonadotropin-Releasing Hormone Infused in a Pulsatile or Continuous Fashion on Serum Gonadotropin Concentrations and Ovulation in the Mare," J. Anim. Sci. (1992) 70:1208-1215.

Bekersky I, et al. "Effect of low- and high-fat meals on tacrolimus absorption following 5 mg single oral doses to healthy human subjects." J Clin Pharmacol 2001 ; 4 1 (2): 176-82.

Betschart, R., et al., "Evaluation of the Saber™ Delivery System for the Controlled Release of the GnRH Analogue Deslorelin for Advancing Ovulation in Mares: Effect of Gamma Radiation," Proceed. Int'l Symp, Control, Rel. Bioact. Mater. 25 (1998) Controlled Release Society, Inc, pp. 655-656.

Bhatia & Singh "Percutaneous Absorption of LHRH Through Porcine Skin: Effect of N-Methyl 2-Pyrrolidone and Isopropyl Myristate"; *Drug Development & Industrial Pharmacy* 23(11): 1113-1114 (1997).

Blanco, M.D. et al. "Bupivacaine-loaded comatrix formed by alumin microspheres included in a poly(lactide-coglycolide) film: in vivo biocompatibility and drug release studies," *Biomaterials*, vol. 20, pp. 1919-1924, 1999.

Brannan, Robert G., "Reactive sulfur species act as prooxidants in liposomal and skeletal muscle model systems," J Agric. Food Chern., 2010, 58,3767-3771.

Brevard J, et al. "Pain and opioid abuse in a population of substance abuse patients: data from the NAVIPPRO system." Conference paper presented at the 42nd American Pain Society (APS) Annual Scientific Meeting, Washington D.C., 2007.

Buhler, K. GnRH Agonists and Safety, In GnRH Analogues The State of the Art 1993, A Summary of the 3rd International Symposium on GnRH Analogues in Cancer and Human Reproduction, Geneva, Feb. 1993.

Burns, P. et al., "Pharmacodynamic Evaluation of the Saber.™. Delivery System for the Controlled Release of the GnRH Analogue Deslorelin Acetate for Advancing Ovulation in Cyclic Mares," Proceed. Int'l. Symp. Control. Rel. Bioact. Mater., 24 (1997), Controlled Release Society, Inc.

Castillo, J. et al., Glucocorticoids Prolong Rat Sciatic Nerve Blockade In Vivo from Bupivacaine Microspheres, *Anesthesiology*, 85, 1157-1166, 1996.

Cellulose Acetate Butyrate. In: European pharmacopoeia. 4 edn Strasbourg Cedex, France: Council of Europe; 2001; p. 853-854.

Chia, H., et al., "Auto-Catalyzed poly(ortho ester) microspheres: a study of their erosion and drug release mechanism", *J. Control. Rel.* 75 (2001) 11-25.

Cleland, J.L. "Injectable Gels for Local and Systemic Delivery of Proteins," *Proceed. Int'l. Symp. Control. Rel. Bioact. Mater.*, vol. 28, 2001.

Cornelli, U., et al., "Bioavailability and antioxidant activity of some food supplements in men and women using the D-Roms test as a marker of oxidative stress," J Nutr., 131, 3208-3211 (2011).

Coy, et al., "Solid Phase Synthesis of Luteinizing Hormone-Releasing Hormone and Its Analogs," Methods Enzymol, 37, 416 (1975).

D 2857-95 (2001) "Standard Practice for Dilute Solution Viscosity of Polymers" Copyright by ASTM Int'l.

De, Asim K. and DE, Avik, (2014), "Reaction Rate Constants for Hydrogen Peroxide Oxidation of Phenol and Chlorinated Phenols in a Continuous Stirred Tank Reactor", International Journal of Engineering Research & Technology (IJERT), 3(6):222-226.

Deng, J.; Li, L.; et al., "In vitro characterization of polyorthoester microparticles containing bupivacaine", *Pharmaceutical Development and Technology*, vol. 8, No. 1, pp. 31-38, 2003.

Desai, Neil P., et al. "Surface Modifications of Polymeric Biomaterials for Reduced Thrombogenicity," Polymeric Materials Science and Engineering, vol. 62, 1990 by ACS.

Dodson, K.M., et al. "Oral Controlled Release of Antiretrovirals Using the SABER Delivery System Incorporated into Soft Gelatin Capsules", AAPS Meeting, 1999, New Orleans, LA.

Duan, D. et al., "Novel Dispersing Aids for Hydrofluoroalkane-Based Metered Dose Inhalers," 1998 Conference of the American Association of Pharmaceutical Scientists, San Francisco, California, Nov. 1998.

Duan, D. et al., "Oligomeric Lactic Acids as Solubilizing Aids for HFA-Based Metered Dose Inhalers," 1998 Conference of the American Association of Pharmaceutical Scientists, San Francisco, California, Nov. 1998.

Duenas, E. et al. "Sustained Delivery of rhVEGF from a Novel Injectable Liquid, Plad" *Proceed. Int'l. Symp. Control. Rel. Bioact. Mater.*, vol. 28, 2001.

Dunbar SA, Katz NP "Chronic opioid therapy for nonmalignant pain in patients with a history of substance abuse: report of 20 cases." Journal of Pain and Symptom Management. 1 1 (3), 163-1 7 1. 1996.

Einmahl, S., et al., "Therapeutic applications of viscous and injectable poly(ortho esters)", *Adv. Drug Del. Rev* 53 (2001)45-73.

Ekelund, A., et al., "Treatment of Postoperative Pain in Shoulder Surgery with SABER-Bupivacaine" Poster, Meeting: American Society of Regional Anesthesia and Pain Medicine (ASRA) Apr. 3-6, 2014.

Ellis, D., et al., "Treatment of Postoperative Pain in Shoulder Surgery with SABER-Bupivacaine," Poster, American Pain Society 32nd Annual Scientific Meeting, New Orleans, LA May 8, 2013.

Elmas, O., et al., "The prooxidant effect of sodium metabisulfite in rat liver and kidney," Reg. Tax. Pharm., 42:77-82 (2005).

English Translation of Japanese Office Action dated Mar. 6, 2012 for Japanese Patent Application No. 2009-108881.

English Translation of Japanese Office Action dated Mar. 6, 2012 for Japanese Patent Application No. 2009-2735.

English translation of Office Action, dated Jan. 12, 2010, from Japanese Application No. 504650/05, which is a family member of the present annlication.

English translation of Office Action, dated Oct. 29, 2009, from Japanese Application No. 516150/04, which is a family member of the present annlication.

Fitzgerald, B.P, et al., (1993) "Effect of Constant Administration of a Gonadotropin-Releasing Hormone Agonist on Reproductive Activity in Mares: Preliminary Evidence on Suppression of Ovulation During the Breeding Season," Am. J. Vet. Res., 54:10 1746-1751.

Fleury, J., et al., "Evaluation of the Saber™. Delivery System for the Controlled Release of the Deslorelin for Advancing Ovulation in the Mare: Effects of Formulation & Dose," Proceed. Int'l. Symp. Control. Rel. Bioact. Mater. 25 (1998) Controlled Release Society, Inc. pp. 657-658.

Gan, T., et al., "SABER-Bupivacaine Reduced Pain Intensity for 72 Hours Following Abdominal Surgery Relative to Bupivacaine-HCl" Abstract, American Society of Anesthesiologists, 2014.

(56) References Cited

OTHER PUBLICATIONS

Gan, T., et al., "The Cardiac Safety of SABER-Bupivacaine in Patients Undergoing Abdominal Surgery: An assessment of Holter Monitoring Data from the BESST Trial", Poster & Abstract, International Anesthesia Research Society Annual Meeting, Fairmont Queen Elizabeth, Montreal, Canada, May 17-20, 2014.

Gan, T., et al., "Treatment of Postoperative Pain in Major AbdominalSurgery with SABER-Bupivacaine: Results of the BESST Trial", AmericanSociety of Regional Anesthesia and Pain Medicine (ASRA) Apr. 3-6, 2014.

Garry, M.G. et al. "Evaluation of the efficiency of a bioerodible bupivacaine polymer system on antinociception and inflammatory mediator release," Pain, vol. 82, pp. 49-55, 1999.

Gilderman L., et al. "Remoxy™: A New Opioid Drug With Effective Analgesia and Abuse-Resistance." American Pain Society Annual Meeting, San Antonio, TX, May 2006.

Ginther, O.J. et al. "Effect of a Synthetic Gonadotropin-Releasing Hormone on Plasma Concentrations of Luteinizing Hormone in Ponies," Am. J. Vet. Res., 35: 79-81 (1974).

Ginther, O.J., "Ultrasonic Imaging and Reproductive Events in the Mare," Equiservices, Cross Plains, WI Chapter 4:43-72 (1986).

Ginther, O.J., Reproductive Biology of the Mare: Basic and Applied Aspects, EquiServices, Chapter 12, 499-508 Cross Plains, Wisconsin (1992).

Glajchen, M. "Chronic Pain: Treatment Barriers and Strategies for Clinical Practice." J AM Board Fam Pract. 2001; 14(3): 178-183.

Gomoll, A.H., et al., "Chondrolysis after continuous intra-articular bupivacaine infusion: an experimental model investigating chondrotoxicity in the rabbit shoulder", Arthroscopy: The Journal of Arthroscopic and Related Surgery, vol. 22., No. 8 (Aug), 2006, pp. 813-819.

Gorman, G., et al., "Quantitative determination of bupivacaine in plasma from multiple species using LC/MS/MS", slide, ASMS presentation; 53$^{rd}$ ASMS Conference, Jun. 5-9, 2005, San Antonio, TX.

Grant et al. (2001) "DRV Liposomal Bupivacaine Preparation, Characterization, and In Vivo Evaluation in Mice"; Pharm Res. 18(3):336-43.

Guevello, P. Le et al. "High-performance liquid chromatographic determination of bupivacaine in plasma samples for biopharmaceutical studies and application to seven other local anaesthetics," Journal of Chromatography, vol. 622, pp. 284-290, 1993.

Gunatillake, P.; Adhikari, R., "Biodegradable synthetic polymers fortissue engineering", European Cells and Materials vol. 5, (2003), pp. 1-16.

Hadj, A., et al., "SABER™ Bupivacaine, a novel extended-release formulation of bupivacaine for postoperative pain control demonstrates dose-response, safely and no impact on surgical wound healing following inguinal herniorrhaphy" American College of Surgeons 95$^{th}$ Annual Clinical Congress, Oct. 12, 2009.

Hadj, A., et al., "Safety and efficacy of extended-release bupivacaine local anaesthetic in open hernia repair: a randomized controlled trial", ANZ Journal of Surgery, Mar. 11, 2011, pp. 1-7.

Halladay, S., et al., "Pharmacokinetic Evaluation of subcutaneously administered SABER™-bupivacaine (Posidur™) following open inguinal hernia repair", presentation slide, CRS 2006.

Halladay, S., et al., (2006) "Pharmacokinetic evaluation of the SABER™ Delivery system for controlled release of bupivacaine in healthy volunteers", CRS poster.

Harrison, L., et al. "Comparison of HCG, Buserelin and Luprostiol for Induction of Ovulation in Cyclling Mares," J. Eq. Vet. Sci., 11:163-166 (1991).

Hassan, H.G. et al., "Effects of Adjuvants to Local Anaesthetics on their Duration", Acta Anaesthesial Scand., 29, 384-388, 1985.

Hatakeyama et al., "Synthesis and physical properties of polyurethanes from saccharide-based polycaprolactones." Macromolecular Symposia, vol. 130, pp. 127-138, 1998.

Hays LR. "A profile of OxyContin addiction. Journal of Addictive Diseases"; 23 (4), 1-9, 2004.

Heller et al., "Development of poly(ortho esters) and their application for bovine serum albumin and bupivacaine delivery", J. Contr. Rel., vol. 78, No. 1-3, pp. 133-141 (2002).

Heller, J et al., "Preparation Of Polyacetals By The Reaction Of Divinyl Ethers and Polyols", Journal of Polymer Science: Polymer Letters Edition, vol. 18, 293-297 (1980), pp. 293-297.

Heller, J, "Poly(ortho esters)", Adv. in Polymer Sci., 107, 41-92 (1993).

Heller, J, et al., "Development of a Tetracycline Delivery System for the Treatment of Periodontal Disease Using a Semisolid Poly(Ortho Ester)", APS Research Institute Conference, 5th meeting, 106-110 (1996).

Heller, J., Barr, J., et al., "Poly(ortho esters): Synthesis, characterization, properties and uses", Adv. Drug Del. Rev. 54 (2002) 1015-1039.

Heller, J., et al., "Injectable semi-solid poly (ortho esters) for the controlled delivery of therapeutic agents: Synthesis and Applications", Drug Development & Delivery, vol. 2, No. 1, Jan./Feb. 2002, Posted Mar. 27, 2008.

Heller, J., et al., "Poly(ortho esters)—their development and some recent applications", Eur J. Pharm Biopharm, Jul. 2000; 50(1): 121-128.

Henry, C. (1995) "Sucrose Acetate Isobutyrate Special Grade for Beverage Applications" International Food Ingred. pp. 47-49.

Hoffmann, M.R. and Edwards, J.O., (1975) "Kinetics of the Oxidation of Sulfite by Hydrogen Peroxide in Acidic Solution", The Journal of Physical Chemistry, 79(20):2096-2098.

Hoskin PJ et al. "The bioavailability and pharmacokinetics of morphine after intravenous, oral and buccal administration in healthy volunteers." Br J Clin Pharmacol 1989; 27 (4):499-505.

Hyland, J.H., et al. "Infusion of Gonadotrophin-Releasing Hormone (GnRH) Induces of Ovulation and Fertile Oestrus in Mares During Seasonal Anoestrus," J. Reprod. Fert., Suppl. 35 (1987), 211-220.

Inciardi et al. (2007) "Mechanisms of prescription drug diversion among drug-involved club- and street-based populations" Pain Medicine. 8(2), 17 1-183.

Irvine, C.H.G., "GnRH Clinical Application," In Equine Reproduction, (eds) McKinon, A.O. and Voss, J.L., Chapter 36, pp. 41-45, Lea & Febiger (1993).

Irvine, D.S., "Duration of Oestrus and Time of Ovulation in Mares Treated with Synthetic GnRH (Ay24,031)," J. Reprod. Fert. Supp. 23:279-283 (1975).

Ishida T, Oguri K, et al. "Isolation and identitication of urinary metabolites of oxycodone in rabbits." Drug Metab Dispos 1979; 7 (3): 162-5.

Ishida T, Oguri K, Yoshimura H. "Determination of oxycodone metabolites in urines and feces of several mammalian species." J Pharmacobiodyn 1982; 5 (7):52 1-5.

Iyakuhn Tenkabutsu Kenkyykai Ed. "Jitsuyo Iyakuhin Tenkabutsu (Practical Medical Additives)" pub. Kagaku Kogyo-sha Mar. 5, 1974, Tokyo.

Japanese Office Action for Japanese Patent Application No. 2007-532447 dated Nov. 15, 2011.

Jochle, W., et al., Control of Ovulation in the Mare with Ovuplant. TM., a Short-Term Release Implant (STI) Containing the GNRH Analogue Deslorelin Acetate: J. Eq. Vet. Sci., 44:632 (1994).

Johnson & Verity (2002) "Applications of Continuous Site-Directed Drug Delivery" Proc West Pharmacol Soc 45:219-222.

Johnston LD, O'Malley PM, Bachman JG, Schulenberg, JE. "Monitoring the future. National results on adolescent drug use: overview of key findings" (NIH Publication No. 05-5726). Bethesda, MD: National Institute on Drug Abuse 2004.

Kasraian et al. (1999) "Developing an Injectable Formula Containing an Oxygen-Sensitive Drug: A Case Study of Danofloxacin Injectable" Pharm Dev Technol 4(4):475-480.

Katz NP, et al. "Behavioral monitoring and urine toxicology testing in patients receiving long-term opioid therapy." Anesth Analg. 97(4), 1097-102.2003.

Katz NP, et al. "Challenges in the development of prescription opioid abuse-deterrent formulations." Clin J Pain, 2007;23(8):648-60.

(56) References Cited

OTHER PUBLICATIONS

Katz NP, et al. "Development and preliminary experience with an ease of extractability rating system for prescription opioids." Drug Development and Industrial Pharmacy. 32(6) 727-746(20), 2006.
Katz NP, et al. "Prescription monitoring of medical and non-medical Schedule II opioid abuse in Massachusetts: 1996-2005." Conference paper presented at the 69th College on Problems of Drug Dependence (CPDD), Quebec, Canada, 2007.
Kim et al. (2001) "Comparing the Effect on Protein Stability of Methionine Oxidation Versus Mutagenesis: Steps Toward Engineering Oxidative Resistance in Proteins" Protein Enqineerinq 14(5):343-347.
Kulkarni et al., "Polyactic Acid for Surgical Implants," Arch. Surg., 93:389 (1966).
Lacoste, D., et al., "Reversible inhibition of testicular androgen secretion by 3-, 5- and 6-month controlled-release microsphere formulations of the LH-RH agonist [D-Trp$^6$, des-Gly-NH$_2^{10}$] LH-RH ethylamide in the dog"; *J. Steroid Biochem.* 33:5, 1007-1011 (1989).
Laggner, H., et al., "Sulfite facilitates LDL lipid oxidation by transition metal ions: A pro-oxidant in wine?" FEES Letters, 579 (2005) 6486-6492.
Lalovic B, et al. "Pharmacokinetics and pharmacodynamics of oral oxycodone in healthy human subjects: role of circulating active metabolites" Clin Pharmacol Ther 2006; 79 (5):461-79.
Lambert, W.J. et al. "Development of an in situ forming biodegradable poly-lactide-co-glycolide system for controlled release of proteins," *Journal of Controlled Release*, vol. 33, pp. 189-195, 1995.
Lapenna et al., (1995) "The Prooxidant Properties of Captopril," Biochemical Pharmacology, 50(1): pp. 27-32.
Li et al., (1993) "Chemical Pathways of Peptide Degradation. V. Ascorbic Acid Promotes Rather than Inhibits the Opxidation of Methionine to Methionine Sulfoxide in Small Model Peptides"; *Pharmaceutical Research*, 10(11):1572-1579.
Loy, R.G. et al. "The Effects of Human Chorionic Gonadotrophin on Ovulation, Length of Estrus, and Fertility in the Mare," Cornell Vet. 56:41-50 (1966).
Lu, Jian-Ming, et al., (2010) "Chemical and molecular mechanisms of antioxidants: experimental approaches and model systems", J. Cell. Mol. Med., 14(4):840-860.
Mank, R. et al., "Parenterale Depotarzneiformen auf der Basis von biologisch abbaubaren Polymeren", Die Pharmazie, 46(1), 9-18, XP-000208772, 1991.
Material Safety Data Sheet of Eastman Chemical Products, "SAIB" Sucrose Acetate Isobutyrate, (Jun. 2004) pp. 2-18.
Material Safety Data Sheet of Eastman Fine Chemical Pharmaceutical Ingredients, Sucrose Acetate Isobutyrate Special Grade (SAIB-SG), Publication No. EFC-211, (May 1991).
Material Safety Data Sheet of Eastman Products for the Food Industry, "Sucrose Acetate Isobutyrate (SAIB-SB) for Use in Fruit-Flavored Beverages," Publication No. ZM-90, pp. 2-7 (Sep. 1989).
McCabe et al. "Motives, diversion and routes of administration associated with nonmedical use of prescription opioids." Addictive Behaviors. 32, 562-575, 2007.
McCarthy, P. et al., "Management of Stallions on Large Breeding Farms," Stallion Management, vol. 8, No. 1, Apr. 1992, pp. 219-235.
McKinnon, A.O., et al. "Effect of a GnRH Analogue (Ovuplant), hCG and Dexamethasone on Time to Ovulation in Cycling Mares." World Equine Veterinary Review, (1997) 2:3 16-18.
McKinnon, A.O., et al. "Repeated Use of a GnRH Analogue Deslorelin (Ovuplant) for Hastening Ovulation in the Transitional Mare," Equine Vet. J., (1996) 29:2 153-155.
McLellan AT, Luborsky L, Woody GE, O'Brien CP. "An improved diagnostic instrument for substance abuse patients." The Addiction Severity Index. J Nerv Ment Dis. 1980; 168:26-33.
Mearns, "Changing Seasons," The Blood-Horse, Sep. 28, 1996, p. 4794-4795.

Merkli et al (1995) "The use of acidic and basic excipients in the release of 5-fluorouracil and mitomycin C from a semi-solid bioerodible poly (ortho ester)"; Journal of Controlled Release, vol. 33, Issue 3; pp. 415-421.
Merkli et al., "Purity and stability assessment of a semi-solid poly(ortho ester) used in drug delivery systems", *Biomaterials*, vol. 17, No. 9, pp. 897-902 (1996).
Merrifield, B., "Solid Phase Synthesis" Science 232:342 (1986).
Meyer RJ, et al. Awareness topic: mitigating the risk of ethanol induced dose dumping from oral sustained controlled release dosage forms. In: FDA's Advisory Committee for Pharmaceutical Science Meeting, Oct. 2005.
Montovan, S.M., et al., "The Effect of a Potent GnRH Agonist on Gonadal and Sexual Activity in the Horse," Theriogenology, 33:6, 1305-1321 (1990).
Moodie, J., et al., "SABER-Bupivacaine Reduces Postoperative Pain Intensity and Opioid Use for 72 Hours in Soft-Tissue and Bony Surgeries", Abstract, American Society of Anesthesiologists, 2014.
Moore, P. A., "Long Acting Local Anesthetic: A Review of Clinical Efficacy in Dentistry," Compend. Cont. Ed. Dent., 11, 22-30, 1990.
Mumford, E.L. et al., "Use of Deslorelin Short-Term Implants to Induce Ovulation in Cycling Mares During Three Consecutive Estrov Cycles," Animal Reproduction Science, 139 (1995) 129-140.
Murray S, et al. "Alcohol-associated rapid release of a long-acting opioid" CMAJ 2005; 173(7):756.
Nakagaki "Seizai Butsuri Kagaku (Physical Chemistry of Medical Preparations)", pub. Asakura Shoten, Nov. 5, 1968, Tokyo.
Nally, J., et al., "Induction of Mucosal IgA Specific for SeMF3 for *Streptococcus equi* with Intranasal Vaccination Using A Sucrose Acetate Isobutyrate Based Delivery System", Proceed. Int'l. Symp. Control. Rel. Bioact. Mater., 26 (1999) Controlled Release Society, Inc.
Nett et al., "Further Studies on the Radioimmunoassay of Gonadotropin-Releasing Hormone: Effect of Radioiodination, Antiserum and Unextracted Serum on Levels of Immunoreactivity in Serum," Endocrinology 101:1135 (1977).
Ng, S.Y.; et al., "Synthesis and erosion studies of self-catalyzed poly(ortho ester)s", *Macromolecules* 1997, 30 770-772.
Nguyen, et al. (1984) "Hydrolysis of some poly(ortho-ester)s in homogeneous solutions"; *J Pharm Sci.* 73(11); pp. 1563-1568.
Nicholson D., et al., "Post-Operative Pain Control with Extended-Release Bupivacaine Formulation. Clinical Trial Results in Inguinal Hernia Repair," American Hernia Society, Mar. 15, 2008.
Okumu, F.W. et al. "Evaluation of the Saber™ Delivery System for Sustained Release of Growth Hormone—Formulation Design and In Vivo Assessment," *Proceed. Int 'l. Symp. Control. Rel. Bioact. Mater.*, vol. 28, 2001.
Okumu, F.W. et al. "Sustained Delivery of Growth Hormone from a Novel Injectable Liquid, Plad," *Proceed. Int'l. Symp. Control. Rel. Bioact. Mater.*, vol. 28, 2001.
Papaconstantinou, H., et al., "Intra-incisional depot bupivacaine reduces pain intensity and opioid consumption for 72 hours following openlaparotomy, compared with bupivacaine HCl", Poster, ASCRS conference May 30, 2015-Jun. 3, 2015.
Philip, B.K. et al. "The Economic Impact of Opioids on Postoverative Pain Management," *Journal of Clinical Anesthesia*, vol. 14, pp. 354-364, 2002.
Pulido et al., "Enzymatic Regioselective Acylation of Hexoses and Pentoses Using Oxime Esters.", J. Chem. Soc. Perkin Trans. 1, (21), 2891-2898, 1992.
Rabb et al., "Effects of Active Immunisation Against GnRH on LH, FSH and Prolactin Storage, Sectretion and Response to Their Secretagogues in Pony Geldings," J. Anim. Sci., 68:3322-3329 (1990).
Reynolds, R.C. et al., "Sucrose acetate isobutyrate (SAIB): historical aspects of its use in beverages and a review of toxicity studies prior to 1988," Food Chem. Toxicol., 1998,36 (2), pp. 8 1-93.
Reynolds, R.C., "Metabolism and pharmacokinetics of sucrose acetate isobutyrate (SAIB) and sucrose octaisobutyrate (SOIB) in rats, dogs, monkeys or humans: a review," Food Chem. Toxicol. , 1998,36 (2), pp. 95-99.

(56) References Cited

OTHER PUBLICATIONS

Roser, J.J., et al., "The Development of Antibodies to Human Chorionic Gonadotrpins Following its Repeated Injection in the Cyclic Mare," J. Reprod. Fert. Suppl., 173-179 (1979).

Sakagami and Satoh, (1997) "Prooxidant action of two antioxidants: ascorbic acid and gallic acid", Anticancer Res., 17:221-224.

Schreier, J., DeLuca, P., "Porous Bone morphogenetic Protein-2 Microspheres: Polymer Binding and In Vitro Release", *AAPS PharmsciTech* 2001; 2(3) art. 17, pp. 1-7.

Schwach-Abdellaoui, K., et al., "Controlled delivery of metoclopramide using an injectable semi-solid poly(ortho ester) for veterinary application" *International Journal of Pharmaceutics*, 2002, 248: 31-37.

Sekar, M., et al., "SABER™ Formulation for Intra-Articular Delivery of rhGH", The American Association of Pharmaceutical Scientists 2009 National Biotechnology Meeting, Jun. 21-25, 2009.

Seymour L. et al., "Poly(ortho ester) matrices for controlled release of the antitumor agent 5-fluorouracil", *J. Controlled Release*, 31, 201-206 (1994).

Shah, J., et al., "Pharmacokinetic Characteristics of SABER-Bupivacaine in Humans Demonstrate Sustained Drug Delivery for up to 72 Hours in a Variety of Surgical Models", American Society of Regional Anesthesia and Pain Medicine (ASRA) Apr. 3-6, 2014.

Shah, J., et al., "Pharmacokinetic characteristics of SABER™-bupivacaine (Posidur™) formulation in humans", APS slide, 2007.

Shah, J., et al., "The PK Profile of SABER-Bupivacaine in Humans Across Surgical Models Demonstrates Sustained 72-Hour Drug Delivery," Abstract, American Society of Anesthesiologists, 2014.

Shih C. et al. (1984) "Drug delivery from catalysed erodible polymeric matrices of poly (ortho ester)s"; *Biomaterials*. 5(4); pp. 237-240.

Sintzel, M., et al., Synthesis and characterization of self-catalyzed poly (ortho ester), *Biomaterials* 19, 1998, 791-800.

Sparer R., "Controlled release from erodible poly(ortho ester) drug delivery systems", *J. Contr. Rel.*, 1, 23-32 (1984).

Sullivan, J., "Duration of Estrus and Ovulation Time in Nonlactating Mares Given Human Chorionic Gonadotropin During Three Successive Estrous Periods," J. Am. Vet. Med. Assoc., 63:895 (1973).

Sullivan, S. A. (1998), "Sustained Release of Orally Administered Active Using SABER™ Delivery System Incorporated into Soft Gelatin Capsules" Proceed. Int'l Symp. Control. Rel. Bioact. Mater . . . , 25:918-919.

Sullivan, S., et al., "Delivery of Taxol and other antineoplastic agents from a novel system based on sucrose acetate isobutyrate", AAPS, Boston, 1997.

Swiderski et al., "Application of 14C Isotope in Studies on the Lability of Sugar Substituents" Nukleonika, Supl., vol. 10, pp. 347-352, 1966.

Tafazoli et al., (2005) "Prooxidant and Antioxidant Activity of Vitamin E Analogues and Troglitazone," Chern. Res. Toxicol., 18:1567-1574_.

Thompson, Jr., D.L., et al., "Effects of Melatonin and Thyrotropin Releasing Hormone of Mares Durignthe Nonbreeding Season," J. Anim. Sci., 58:3, 668-677(1983).

Thompson, Jr., D.L., et al., "Testosterone Effects on Mares During Synchronization with Altrenogest: FSH, LH, Estrous, Duration and Pregnancy Rate" J. Anim. Sci., 56:3, 678-686 (1983).

Trescot Am, et al. "Opioid Guidelines in the Management of Chronic Non-Cancer Pain." Pain Physician, 2006;9: 1-40.

Trieger, N. et al., "Bupivacaine and Post-Operative Analgesics in Oral Surgery," *Anesthesia Progress*, 20-2, 1979.

Troen et al. (2003) "The Atherogenic Effect of Excess Methionine Intake" PNAS 100(5):15089-15094.

University of Utah, Department of Chemical Engineering (2006) "A Viscosity: Viscosity Definitions" http://www.che.utah.edu/department_equipment/Projects_lab/A_ Viscometers/ViscosityDefinitions.pdf.

USP XXII, *The United States Pharmacopeial Convention, Inc., Bupivacaine*, 193-196, 1990.

Vega-Rios A, Villalobos H, Mata-Segreda JF. "Acid-catalyzed hydrolysis of triacylglycerols obeys monoexponential kinetics." Int J Chem Kinet. 1992; 24:887-94.

Voss, J.L. et al. "The Effect of HCG on Duration of Oestrus, Ovulation Time and Fertility in Mares," J. Reprod. Fert., Suppl. 23 (1975) 297-301.

Watts, R., et al., "Efficacy and Safety of SABER-Bupivacaine Local Anesthetic in Open Hernia Repair," American Society of Regional Anesthesia and Pain Medicine (ASRA) Apr. 3-6, 2014.

Watts, R., et al., "SABER-Bupivacaine Concurrently Reduces Postoperative Pain Intensity and Opioid Use for 72 Hours: Evaluation of CROPIRS Scores," Abstract, American Society of Anesthesiologists, 2014.

Wilson et al. (1999) "Benzyl Alcohol as an Alternative Local Anesthetic" *Ann Emerg Med* 33(5):495-499.

Baczyński, et al., (2002) "Determination of 2,6-dimethylaniline and o-toluidine impurities in preparations for local anaesthesia by the HPLC method with amperometric detection"; *Acta Poloniae Pharmaceutica* 59(5); pp. 333-339.

Damian and Miclăuş (2005) "Study of Free Radicals in Gamma-Irradiated Metoclopramid Using Spin Trapping ESR Spectroscopy": *Romanian J. Biophys.*, vol. 15, Nos. 1-4; pp. 121-126.

Difazio, C.A. (1979) "Metabolism of Local Anaesthetics in the Fetus, Newborn and Adult"; *British Journal of Anaesthesia* vol. 51, Supplement 1; pp. 29S-33S.

European Pharmacopoeia 10.0; "Bupivacaine hydrochloride"; (Jul. 2019) pp. 2015-2017.

European Pharmacopoeia et al; Pharmacopoeial Discussion Group Q11: Sterility Rev. 1, sign off; (Oct. 30, 2007). 1 page.

European Pharmacopoeia et al; Pharmacopoeial Discussion Group, Correction Code: Q11: Sterility: REV 1 CORR 1 Stage 5B; (Jun. 3, 2008). 1 page.

European Pharmacopoeia et al; Pharmacopoeial Discussion Group, Correction Code: Q11: Sterility: REV 1 CORR 2; (Nov. 11, 2008). 1 page.

European Pharmacopoeia et al; Pharmacopoeial Discussion Group, Correction Code: Q11: Sterility: REV 1 CORR 3 Stage 5B; (Jun. 10, 2009). 1 page.

European Pharmacopoeia; Pharmacopoeial Discussion Group, Sign-off Document, Name: Test for Sterility; (Sep. 10, 2002). 1 page.

Lavallée, R., et al.; "A Novel Strategy for the In-ProcessStabilization of N-Oxide Metabolites in Hemolyzed Plasma Determined by LC-MS/MS"; *Altasciences Clinical Research, Algorithme Pharma*; (Jun. 8, 2017); 1 page.

Pharmacopeial Forum (PF); "(71) Sterility Tests"; 29(4) Fourth Interim Revision Announcement; (Apr. 29, 2003) pp. 1-11.

Pharmacopeial Forum (PF); "(71) Sterility Tests"; 34(6) Sixth Interim Revision Announcement; (Jun. 2008) pp. 1-12.

Testa and Mayer (2003) "Chapter 4: The Hydrolysis of Amides"; *Hydrolysis in Drug and Prodrug Metabolism: Verlag Helvetica Chimica Acta*; Wiley-WCH; pp. 82-162.

Uddin, et al. (2016) "Stability determination and evaluation of gamma-irradiated nuclear factor-κβ antisense microsphere"; *MOJ Drug Design Development &Therapy* 1(1); pp. 1-6.

Wu, et al. (2014) "Reactive oxygen species-related activities of nano-iron metal and nano-iron oxides"; *Journal of Food and Drug Analysis* vol. 22, Issue 1; pp. 86-94.

ClinicalTrials.gov: NCT00818363; "A Safety and Effectiveness Study of SABER®-Bupivacaine for Pain Following Shoulder Surgery"; Durect Corporation; Jan. 7, 2009; 8 pages.

ClinicalTrials.gov: NCT00818363; "A Safety and Effectiveness Study of SABER®-Bupivacaine for Pain Following Shoulder Surgery"; Study Results; Durect Corporation; Jan. 7, 2009; 13 pages.

ClinicalTrials.gov: NCT00818363; "A Safety and Effectiveness Study of SABER®-Bupivacaine for Pain Following Shoulder Surgery"; Tabular View; Durect Corporation; Jan. 7, 2009; 13 pages.

ClinicalTrials.gov: NCT00974350; "A Safety and Efficacy Study of SABER®-Bupivacaine for Pain Following Hernia Repair"; Durect Corporation; Sep. 10, 2009; 7 pages.

ClinicalTrials.gov: NCT00974350; "A Safety and Efficacy Study of SABER®-Bupivacaine for Pain Following Hernia Repair"; Study Results; Durect Corporation; Sep. 10, 2009; 15 pages.

(56) References Cited

OTHER PUBLICATIONS

ClinicalTrials.gov: NCT00974350; "A Safety and Efficacy Study of SABER®-Bupivacaine for Pain Following Hernia Repair"; Tabular View; Durect Corporation; Sep. 10, 2009; 8 pages.
ClinicalTrials.gov: NCT00993798; "An International Trial to Evaluate the Efficacy and Safety of SABER®-Bupivacaine for Postoperative Pain Control in Patients Following Arthroscopic Shoulder Surgery"; Durect Corporation; Oct. 12, 2009; 8 pages.
ClinicalTrials.gov: NCT00993798; "An International Trial to Evaluate the Efficacy and Safety of SABER®-Bupivacaine for Postoperative Pain Control in Patients Following Arthroscopic Shoulder Surgery"; Study Results; Durect Corporation; Oct. 12, 2009; 10 pages.
ClinicalTrials.gov: NCT00993798; "An International Trial to Evaluate the Efficacy and Safety of SABER®-Bupivacaine for Postoperative Pain Control in Patients Following Arthroscopic Shoulder Surgery"; Tabular View; Durect Corporation; Oct. 12, 2009; 8 pages.
ClinicalTrials.gov: NCT00993226; "An International Trial to Evaluate the Efficacy and Safety of SABER®-Bupivacaine for Postoperative Pain Control in Patients Undergoing Hysterectomy"; Durect Corporation; Oct. 12, 2009; 8 pages.
ClinicalTrials.gov: NCT00993226; "An International Trial to Evaluate the Efficacy and Safety of SABER®-Bupivacaine for Postoperative Pain Control in Patients Undergoing Hysterectomy"; Study Results; Durect Corporation; Oct. 12, 2009; 10 pages.
ClinicalTrials.gov: NCT00993226; "An International Trial to Evaluate the Efficacy and Safety of SABER®-Bupivacaine for Postoperative Pain Control in Patients Undergoing Hysterectomy"; Tabular View; Durect Corporation; Oct. 12, 2009; 8 pages.
ClinicalTrials.gov: NCT01052012; "Bupivacaine Effectiveness and Safety in SABER® Trial (BESST)"; Durect Corporation; Jan. 20, 2010; 10 pages.
ClinicalTrials.gov: NCT01052012; "Bupivacaine Effectiveness and Safety in SABER® Trial (BESST)"; Study Results; Durect Corporation; Jan. 20, 2010; 22 pages.
ClinicalTrials.gov: NCT01052012; "Bupivacaine Effectiveness and Safety in SABER® Trial (BESST)"; Tabular View; Durect Corporation; Jan. 20, 2010; 9 pages.
ClinicalTrials.gov: NCT02574520; "Trial of Extended Release Bupivacaine for Pain Relief After Surgery (PERSIST)"; Durect Corporation; Oct. 14, 2015; 8 pages.
ClinicalTrials.gov: NCT02574520; "Trial of Extended Release Bupivacaine for Pain Relief After Surgery (PERSIST)"; Study Results; Durect Corporation; Oct. 14, 2015; 8 pages.
ClinicalTrials.gov: NCT02574520; "Trial of Extended Release Bupivacaine for Pain Relief After Surgery (PERSIST)"; Tabular View; Durect Corporation; Oct. 14, 2015; 8 pages.
AADPAC: FDA Briefing Document: Meeting of Anesthetic and Analgesic Drug Products Advisory Committee, Jan. 16, 2020; 388 pages.
AADPAC; Errata to the FDA Briefing Document Anesthetic and Analgesic Drug Products Advisory Committee Meeting (AADPAC) Jan. 16, 2020; 2 pages.
AADPAC; FDA Introductory Remarks: Anesthetic and Analgesic Drug Products Advisory Committee Meeting, Jan. 16, 2020; U.S. Food & Drug Administration; Slides; 71 pages.
AADPAC; Food and Drug Administration Center For Drug Evaluation and Research: Anesthetic And Analgesic Drug Products Advisory Committee (AADPAC) Meeting, Jan. 16, 2020; Transcript; 294 pages.
AADPAC; Meeting of the Anesthetic and Analgesic Drug Products Advisory Committee (Jan. 16, 2020); NDA 204803; DURECT Corporation; 465 pages.
AADPAC; SABER®-Bupivacaine: Meeting of the Anesthetic and Analgesic Drug Products Advisory Committee, Jan. 16, 2020; Durect Corporation; Slidse, 141 pages.
Doraiswamy, et al (2016) "A new method for treating postoperative pain associated with laparoscopic surgery"; Society of American Gastrointestinal and Endoscopic Surgeons Annual Meeting; Poster 1 page.
Ekelund, et al (2016) "SABER®-Bupivacaine Reduces Postoperative Pain and Opioid Consumption Following Arthroscopic Subacromial Decompression"; Presented at the 17th Annual European Federation of National Associations of Orthopaedics and Traumatology (EFORT) Congress; Poster #2168; 1 page.
Hadj, A. et al. (2008) "Postoperative pain control with extended-release bupivacaine formulation.Clinical Trial Results"; Royal Australasian College of Surgeons Annual Scientific Congress Hong Kong; pp. 1-10.
Meisner, Jon; "Consumption of opioid analgesics after surgery is inconsistently correlated with postoperative pain intensity"; ASRA $42^{nd}$ Annual Regional Anesthesiology & Acute Pain Medicine Meeting, Apr. 6-8, 2017; Poster; 1 page.
Page, et al (2016) "Long-Term Safety of SABER®-Bupivacaine in Arthroscopic Subacromial Decompression"; Presented at the 17th Annual European Federation of National Associations of Orthopaedics and Traumatology (EFORT) Congress; Poster #1831; 1 page.
Skolnik and Gan (2014) "New formulations of bupivacaine for the treatment of postoperative pain: liposomal bupivacaine and SABER-Bupivacaine"; Expert Opin. Pharmacother. 15(11); pp. 1535-1542.
Verity, et al; "Pharmacokinetic and Pharmacodynamic Study with Subcutaneous Administered SABER™ Bupivacaine Following Open Inguinal Hernia Repair" DURECT Corporation; (Aug. 2005) Poster,1 page.
Pramanick, et al. (2013) "Excipient Selection In Parenteral Formulation Development"; Pharma Times, vol. 45, No. 3; pp. 65-77.

\* cited by examiner

Figure 1

SUSTAINED RELEASE DRUG DELIVERY SYSTEMS WITH REDUCED IMPURITIES AND RELATED METHODS

CROSS-REFERENCE TO RELATED APPLICATIONS

This application claims the benefit of priority to U.S. Provisional Patent Application Ser. No. 62/960,565 filed on Jan. 13, 2020, the disclosure of which application is herein incorporated by reference.

TECHNICAL FIELD

The present disclosure relates generally to sustained release drug delivery systems.

BACKGROUND

Biodegradable carriers for drug delivery are useful because they obviate the need to remove the drug-depleted device. Examples of biodegradable drug delivery systems include systems for controlled delivery of active pharmaceutical agents, e.g., local anesthetics, disclosed in U.S. Pat. Nos. 8,846,072 and 10,213,510, which are herein incorporated by reference in their entireties.

There remains, however, a need for improved drug delivery systems and methods of administration and storage. For instance, there remains a need for drug delivery systems having improved storage stability and safety in use.

SUMMARY OF THE INVENTION

The inventors have determined that there also remains a need for sustained release delivery systems containing low amounts of impurities, such as 2,6-dimethylaniline, bupivacaine N-oxide, water, peroxide, benzyl acetate, benzyl isobutyrate, and/or low amounts of metal.

The present disclosure provides improved drug delivery systems having reduced impurities. The present disclosure provides improved drug delivery systems having improved stability and/or safety. Other features and advantages of the present invention will be set forth in the description of invention that follows, and in part will be apparent from the description or may be learned by practice of the invention. The invention will be realized and attained by the compositions and methods particularly pointed out in the written description and claims hereof.

The following numbered aspects, while non-limiting, are exemplary of certain aspects of the present disclosure:
1. A composition comprising:
   an active pharmaceutical agent;
   at least one of a high viscosity liquid carrier material (HVLCM) and a polyorthoester;
   an organic solvent; and
   2,6-dimethylaniline,
   wherein the 2,6-dimethylaniline is present in the composition at a level less than 500 ppm.
2. The composition of aspect 1, wherein the 2,6-dimethylaniline is present in the composition at a level less than 300 ppm.
3. The composition of aspect 1, wherein the 2,6-dimethylaniline is present in the composition at a level less than 200 ppm.
4. The composition of aspect 1, wherein the 2,6-dimethylaniline is present in the composition at a level less than 100 ppm.
5. The composition of aspect 1, wherein the 2,6-dimethylaniline is present in the composition at a level less than 15 ppm, less than 12 ppm, less than 10 ppm, or less than 5 ppm.
6. The composition of aspect 1, wherein the 2,6-dimethylaniline is present in the composition at a level ranging from 0.2 ppm to 500 ppm.
7. The composition of aspect 1, wherein the 2,6-dimethylaniline is present in the composition at a level ranging from 0.3 ppm to 200 ppm.
8. The composition of aspect 1, wherein the 2,6-dimethylaniline is present in the composition at a level ranging from 0.4 ppm to 100 ppm.
9. The composition of aspect 1, wherein the 2,6-dimethylaniline is present in the composition at a level ranging from 0.5 ppm to 10 ppm or 2 ppm to 8 ppm.
10. A composition comprising:
    an active pharmaceutical agent;
    at least one of a high viscosity liquid carrier material (HVLCM) and a polyorthoester;
    an organic solvent; and
    N-oxide of the active pharmaceutical agent,
    wherein the N-oxide of the active pharmaceutical agent is present in the composition at a level less than 1 wt %, based on weight of the composition.
11. The composition of aspect 10, wherein the N-oxide of the active pharmaceutical agent is present in the composition at a level less than 0.7 wt % or less than 0.5 wt %, based on weight of the composition.
12. The composition of aspect 10, wherein the N-oxide of the active pharmaceutical agent is present in the composition at a level less than 0.4 wt %, based on weight of the composition.
13. The composition of aspect 10, wherein the N-oxide of the active pharmaceutical agent is present in the composition at a level ranging from 0.01 wt % to 1 wt %, based on weight of the composition.
14. The composition of aspect 10, wherein the N-oxide of the active pharmaceutical agent is present in the composition at a level ranging from 0.05 wt % to 0.4 wt % or 0.1 wt % to 0.4 wt %, based on weight of the composition.
15. The composition of aspect 10, wherein the N-oxide of the active pharmaceutical agent is present in the composition at a level ranging from 0.1 wt % to 0.2 wt %, based on weight of the composition.
16. A composition comprising:
    an active pharmaceutical agent;
    at least one of a high viscosity liquid carrier material (HVLCM) and a polyorthoester;
    an organic solvent; and
    a metal,
    wherein the metal is present in the composition at a level less than 5 ppm.
17. The composition of aspect 16, wherein the metal is present in the composition at a level less than 4 ppm.
18. The composition of aspect 16, wherein the metal is present in the composition at a level less than 3 ppm.
19. The composition of aspect 16, wherein the metal is present in the composition at a level ranging from 0.01 ppm to 4 ppm.
20. The composition of aspect 16, wherein the metal is present in the composition at a level ranging from 0.05 ppm to 3 ppm.
21. The composition of aspect 16, wherein the metal is present in the composition at a level ranging from 0.1 ppm to 2 ppm.

22. A composition comprising:
   an active pharmaceutical agent;
   at least one of a high viscosity liquid carrier material (HVLCM) and a polyorthoester;
   an organic solvent; and
   water,
   wherein the water is present at a level less than 0.5 wt %, based on weight of the composition.
23. The composition of aspect 22, wherein the water is present in the composition at a level less than 0.4 wt %, based on weight of the composition.
24. The composition of aspect 22, wherein the water is present in the composition at a level less than 0.3 wt %, based on weight of the composition.
25. The composition of aspect 22, wherein the water is present in the composition at a level ranging from 0.03 wt % to 0.4 wt %, based on weight of the composition.
26. The composition of aspect 22, wherein the water is present in the composition at a level ranging from 0.05 wt % to 0.35 wt %, based on weight of the composition.
27. The composition of aspect 22, wherein the water is present in the composition at a level ranging from 0.08 wt % to 0.3 wt %, based on weight of the composition.
28. A composition comprising:
   an active pharmaceutical agent;
   a high viscosity liquid carrier material (HVLCM) comprising sucrose acetate isobutyrate;
   an organic solvent comprising benzyl alcohol; and
   benzyl acetate,
   wherein the benzyl acetate is present in the composition at a level less than 100 mg/mL.
29. The composition of aspect 28, wherein the benzyl acetate is present in the composition at a level less than 50 mg/mL.
30. The composition of aspect 28, wherein the benzyl acetate is present in the composition at a level less than 20 mg/mL or less than 15 mg/mL.
31. The composition of aspect 28, wherein the benzyl acetate is present in the composition at a level ranging from 0.1 mg/mL to 80 mg/mL.
32. The composition of aspect 28, wherein the benzyl acetate is present in the composition at a level ranging from 0.5 mg/mL to 40 mg/mL.
33. The composition of aspect 28, wherein the benzyl acetate is present in the composition at a level ranging from 1 mg/mL to 20 mg/mL or 1 mg/mL to 15 mg/mL.
34. A composition comprising:
   an active pharmaceutical agent;
   a high viscosity liquid carrier material (HVLCM) comprising sucrose acetate isobutyrate;
   an organic solvent comprising benzyl alcohol; and
   benzyl isobutyrate,
   wherein the benzyl isobutyrate is present in the composition at a level less than 50 mg/mL.
35. The composition of aspect 34, wherein the benzyl isobutyrate is present in the composition at a level less than 30 mg/mL.
36. The composition of aspect 34, wherein the benzyl isobutyrate is present in the composition at a level less than 10 mg/mL or less than 8 mg/mL.
37. The composition of aspect 34, wherein the benzyl isobutyrate is present in the composition at a level ranging from 0.1 mg/mL to 40 mg/mL.
38. The composition of aspect 34, wherein the benzyl isobutyrate is present in the composition at a level ranging from 0.5 mg/mL to 30 mg/mL.
39. The composition of aspect 34, wherein the benzyl isobutyrate is present in the composition at a level ranging from 1 mg/mL to 10 mg/mL or 1 mg/mL to 8 mg/mL.
40. A composition made by combining:
   an active pharmaceutical agent;
   a high viscosity liquid carrier material (HVLCM) comprising sucrose acetate isobutyrate having peroxide that is present at a level less than 200 ppm; and
   an organic solvent.
41. The composition of aspect 40, wherein the sucrose acetate isobutyrate has peroxide that is present at a level less than 100 ppm.
42. The composition of aspect 40, wherein the sucrose acetate isobutyrate has peroxide that is present at a level less than 80 ppm or less than 60 ppm.
43. The composition of aspect 40, wherein the sucrose acetate isobutyrate has peroxide that is present at a level ranging from 1 ppm to 100 ppm.
44. The composition of aspect 40, wherein the sucrose acetate isobutyrate has peroxide that is present at a level ranging from 2 ppm to 80 ppm.
45. The composition of aspect 40, wherein the sucrose acetate isobutyrate has peroxide that is present at a level ranging from 3 ppm to 60 ppm.
46. A composition made by combining:
   an active pharmaceutical agent;
   at least one of a high viscosity liquid carrier material (HVLCM) and a polyorthoester; and
   an organic solvent having peroxide that is present at a level less than 100 ppm, the organic solvent optionally comprising at least one of benzyl alcohol, dimethyl sulfoxide, and triacetin.
47. The composition of aspect 46, wherein the organic solvent has peroxide that is present at a level less than 85 ppm.
48. The composition of aspect 46, wherein the organic solvent has peroxide that is present at a level less than 10 ppm.
49. The composition of aspect 46, wherein the organic solvent has peroxide that is present at a level ranging from 1 ppm to 90 ppm.
50. The composition of aspect 46, wherein the organic solvent has peroxide that is present at a level ranging from 2 ppm to 85 ppm.
51. The composition of aspect 46, wherein the organic solvent has peroxide present at a level ranging from 3 ppm to 10 ppm.
52. A composition comprising:
   an active pharmaceutical agent;
   a high viscosity liquid carrier material (HVLCM) comprising sucrose acetate isobutyrate present at a level ranging from 30 wt % to 80 wt %, based on weight of the composition; and
   an organic solvent.
53. The composition of aspect 52, wherein the sucrose acetate isobutyrate is present in the composition at a level ranging from 40 wt % to 70 wt %, 50 wt % to 70 wt %, 60 wt % to 70 wt %, 61 wt % to 69 wt %, based on weight of the composition.
54. The composition of aspect 52, wherein the sucrose acetate isobutyrate is present in the composition at a level ranging from 62 wt % to 68 wt %, based on weight of the composition.
55. The composition of aspect 52, wherein the sucrose acetate isobutyrate is present in the composition at a level ranging from 63 wt % to 67 wt %, based on weight of the composition.

56. A composition comprising:
   an active pharmaceutical agent;
   at least one of a high viscosity liquid carrier material (HVLCM) and a polyorthoester, the HVLCM optionally comprising sucrose acetate isobutyrate present at a level ranging from 30 wt % to 80 wt %, based on weight of the composition, and optionally the composition is prepared using sucrose acetate isobutyrate having peroxide that is present at a level less than 200 ppm;
   an organic solvent, the organic solvent optionally comprising at least one of benzyl alcohol, dimethyl sulfoxide, and triacetin, and optionally the composition is prepared using organic solvent having peroxide that is present at a level less than 100 ppm; and
   at least one of:
      2,6-dimethylaniline, wherein the 2,6-dimethylaniline is present in the composition at a level less than 500 ppm,
      N-oxide of the active pharmaceutical agent, wherein the N-oxide of the active pharmaceutical agent is present in the composition at a level less than 1 wt %, based on weight of the composition,
      a metal, wherein the metal is present in the composition at a level less than 5 ppm,
      water, wherein the water is present at a level less than 0.5 wt %, based on weight of the composition,
      benzyl acetate, wherein the benzyl acetate is present in the composition at a level less than 100 mg/mL, and
      benzyl isobutyrate, wherein the benzyl isobutyrate is present in the composition at a level less than 50 mg/mL.

57. The composition of any one of aspects 1 to 56, wherein the active pharmaceutical agent comprises a local anesthetic.

58. The composition of any one of aspects 1 to 56, wherein the active pharmaceutical agent comprises at least one member selected from bupivacaine, lidocaine, ropivacaine, etidocaine, mepivacaine, pyrrocaine, and salts thereof.

59. The composition of any one of aspects 1 to 56, wherein the active pharmaceutical agent comprises bupivacaine or a salt thereof.

60. The composition of any one of aspects 1 to 59, wherein the active pharmaceutical agent is present in the composition in an amount ranging from 1 wt % to 25 wt %, based on weight of the composition.

61. The composition of any one of aspects 1 to 59, wherein the active pharmaceutical agent is present in the composition in an amount ranging from 5 wt % to 20 wt %, based on weight of the composition.

62. The composition of any one of aspects 1 to 59, wherein the active pharmaceutical agent is present in the composition in an amount ranging from 10 wt % to 15 wt %, based on weight of the composition.

63. The composition of any one of aspects 1 to 59, wherein the active pharmaceutical agent is present in the composition in an amount of about 12 wt %, based on weight of the composition.

64. The composition of any one of aspects 1 to 63, wherein the organic solvent comprises at least one member selected from benzyl alcohol, benzyl benzoate, dimethylsulfoxide, ethanol, N-methylpyrrolidone, and triacetin.

65. The composition of any one of aspects 1 to 63, wherein the organic solvent comprises benzyl alcohol.

66. The composition of any one of aspects 1 to 63, wherein the organic solvent comprises triacetin.

67. The composition of any one of aspects 1 to 63, wherein the organic solvent comprises dimethylsulfoxide.

68. The composition of any one of aspects 1 to 67, wherein the organic solvent is present in the composition in an amount sufficient to dissolve the active pharmaceutical agent in the composition, or the organic solvent is present in the composition in an amount of at least 5 wt %, based on weight of the composition.

69. The composition of any one of aspects 1 to 68, wherein the organic solvent is present in the composition in an amount of at least 10 wt %, based on weight of the composition.

70. The composition of any one of aspects 1 to 68, wherein the organic solvent is present in the composition in an amount of at least 15 wt %, based on weight of the composition.

71. The composition of any one of aspects 1 to 68, wherein the organic solvent is present in the composition in an amount of at least 20 wt %, based on weight of the composition.

72. The composition of any one of aspects 1 to 68, wherein the organic solvent is present in the composition in an amount ranging from 5 wt % to 45 wt %, based on weight of the composition.

73. The composition of any one of aspects 1 to 68, wherein the organic solvent is present in the composition in an amount ranging from 10 wt % to 35 wt %, based on weight of the composition.

74. The composition of any one of aspects 1 to 68, wherein the organic solvent is present in the composition in an amount ranging from 15 wt % to 30 wt %, based on weight of the composition.

75. The composition of any one of aspects 1 to 68, wherein the organic solvent is present in the composition in an amount ranging from 20 wt % to 25 wt %, based on weight of the composition.

76. The composition of any one of aspects 1 to 68, wherein the organic solvent is present in the composition in an amount of about 22 wt %, based on weight of the composition.

77. The composition of any one of aspects 1 to 76, wherein the composition comprises HVLCM comprising sucrose acetate isobutyrate.

78. The composition of any one of aspects 1 to 76, wherein the composition comprises HVLCM present in the composition in an amount sufficient to provide sustained release of the active pharmaceutical agent from the composition, such as sustained release of about 72 hours, or the composition comprises HVLCM present in the composition in an amount ranging from 50 wt % to 80 wt %, based on weight of the composition.

79. The composition of any one of aspects 1 to 76, wherein the composition comprises HVLCM present in the composition in an amount ranging from 55 wt % to 75 wt %, based on weight of the composition.

80. The composition of any one of aspects 1 to 76, wherein the composition comprises HVLCM present in the composition in an amount ranging from 60 wt % to 70 wt %, based on weight of the composition.

81. The composition of any one of aspects 1 to 76, wherein the composition comprises HVLCM present in the composition in an amount of about 66 wt %, based on weight of the composition.

82. The composition of any one of aspects 1 to 81, wherein the composition comprises polyorthoester.

83. The composition of any one of aspects 1 to 81, wherein the composition comprises polyorthoester having a weight average molecular weight ranging from 1000 Daltons to 10,000 Daltons.

84. The composition of any one of aspects 1 to 81, wherein the composition comprises polyorthoester present in an amount ranging from 40 wt % to 70 wt %, based on weight of the composition.

85. The composition of any one of aspects 1 to 84, further comprising meloxicam.

86. The composition of any one of aspects 1 to 85, wherein the composition has been stored at a temperature ranging from 15° C. to 30° C.

87. The composition of any one of aspects 1 to 85, wherein the composition has been stored at a temperature ranging from 20° C. to 25° C.

88. The composition of any one of aspects 1 to 9 and 56 to 87, wherein when the composition is stored in a sealed, upright, clear glass vial at 25° C./60% RH for 20 months, the 2,6-dimethylaniline is present at the level, e.g., when the composition is stored in a sealed, upright, clear glass vial at 25° C./60% RH for 20 months, the 2,6-dimethylaniline may be present at a level less than 500 ppm.

89. The composition of any one of aspects 1 to 9 and 56 to 87, wherein when the composition is stored in a sealed, upright, clear glass vial at 25° C./60% RH for 36 months, the 2,6-dimethylaniline is present at the level.

90. The composition of any one of aspects 1 to 9 and 56 to 87, wherein when the composition is stored in a sealed, upright, clear glass vial at 40° C./75% RH for 20 months, the 2,6-dimethylaniline is present at the level.

91. The composition of any one of aspects 1 to 9 and 56 to 87, wherein when the composition is stored in a sealed, upright, clear glass vial at 40° C./75% RH for 36 months, the 2,6-dimethylaniline is present at the level.

92. The composition of any one of aspects 10 to 15 and 56 to 87, wherein when the composition is stored in a sealed, upright, clear glass vial at 25° C./60% RH for 20 months, the N-oxide of the active pharmaceutical agent is present at the level.

93. The composition of any one of aspects 10 to 15 and 56 to 87, wherein when the composition is stored in a sealed, upright, clear glass vial at 25° C./60% RH for 36 months, the N-oxide of the active pharmaceutical agent is present at the level.

94. The composition of any one of aspects 10 to 15 and 56 to 87, wherein when the composition is stored in a sealed, upright, clear glass vial at 40° C./75% RH for 20 months, the N-oxide of the active pharmaceutical agent is present at the level.

95. The composition of any one of aspects 10 to 15 and 56 to 87, wherein when the composition is stored in a sealed, upright, clear glass vial at 40° C./75% RH for 36 months, the N-oxide of the active pharmaceutical agent is present at the level.

96. The composition of any one of aspects 16 to 21 and 56 to 87, wherein when the composition is stored in a sealed, upright, clear glass vial at 25° C./60% RH for 20 months, the metal is present at the level.

97. The composition of any one of aspects 16 to 21 and 56 to 87, wherein when the composition is stored in a sealed, upright, clear glass vial at 25° C./60% RH for 36 months, the metal is present at the level.

98. The composition of any one of aspects 16 to 21 and 56 to 87, wherein when the composition is stored in a sealed, upright, clear glass vial at 40° C./75% RH for 20 months, the metal is present at the level.

99. The composition of any one of aspects 16 to 21 and 56 to 87, wherein when the composition is stored in a sealed, upright, clear glass vial at 40° C./75% RH for 36 months, the metal is present at the level.

100. The composition of any one of aspects 22 to 27 and 56 to 87, wherein when the composition is stored in a sealed, upright, clear glass vial at 25° C./60% RH for 20 months, the water is present at the level.

101. The composition of any one of aspects 22 to 27 and 56 to 87, wherein when the composition is stored in a sealed, upright, clear glass vial at 25° C./60% RH for 36 months, the water is present at the level.

102. The composition of any one of aspects 22 to 27 and 56 to 87, wherein when the composition is stored in a sealed, upright, clear glass vial at 40° C./75% RH for 20 months, the water is present at the level.

103. The composition of any one of aspects 22 to 27 and 56 to 87, wherein when the composition is stored in a sealed, upright, clear glass vial at 40° C./75% RH for 36 months, the water is present at the level.

104. The composition of any one of aspects 28 to 33 and 56 to 87, wherein when the composition is stored in a sealed, upright, clear glass vial at 25° C./60% RH for 20 months, the benzyl acetate is present at the level.

105. The composition of any one of aspects 28 to 33 and 56 to 87, wherein when the composition is stored in a sealed, upright, clear glass vial at 25° C./60% RH for 36 months, the benzyl acetate is present at the level.

106. The composition of any one of aspects 28 to 33 and 56 to 87, wherein when the composition is stored in a sealed, upright, clear glass vial at 40° C./75% RH for 20 months, the benzyl acetate is present at the level.

107. The composition of any one of aspects 28 to 33 and 56 to 87, wherein when the composition is stored in a sealed, upright, clear glass vial at 40° C./75% RH for 36 months, the benzyl acetate is present at the level.

108. The composition of any one of aspects 34 to 39 and 56 to 87, wherein when the composition is stored in a sealed, upright, clear glass vial at 25° C./60% RH for 20 months, the benzyl isobutyrate is present at the level.

109. The composition of any one of aspects 34 to 39 and 56 to 87, wherein when the composition is stored in a sealed, upright, clear glass vial at 25° C./60% RH for 36 months, the benzyl isobutyrate is present at the level.

110. The composition of any one of aspects 34 to 39 and 56 to 87, wherein when the composition is stored in a sealed, upright, clear glass vial at 40° C./75% RH for 20 months, the benzyl isobutyrate is present at the level.

111. The composition of any one of aspects 34 to 39 and 56 to 87, wherein when the composition is stored in a sealed, upright, clear glass vial at 40° C./75% RH for 36 months, the benzyl isobutyrate is present at the level.

112. The composition of any one of aspects 52 to 87, wherein when the composition is stored in a sealed, upright, clear glass vial at 25° C./60% RH for 20 months, the sucrose acetate isobutyrate is present at the level.

113. The composition of any one of aspects 52 to 87, wherein when the composition is stored in a sealed, upright, clear glass vial at 25° C./60% RH for 36 months, the sucrose acetate isobutyrate is present at the level.

114. The composition of any one of aspects 52 to 87, wherein when the composition is stored in a sealed, upright, clear glass vial at 40° C./75% RH for 20 months, the sucrose acetate isobutyrate is present at the level.

115. The composition of any one of aspects 52 to 87, wherein when the composition is stored in a sealed, upright, clear glass vial at 40° C./75% RH for 36 months, the sucrose acetate isobutyrate is present at the level.

116. A dosage system comprising:
a container comprising a first inert material;
a closure capable of closing the container, the closure comprising a second inert material; and
the composition of any one of aspects 1 to 115 contained within the container.

117. The dosage system of aspect 116, wherein the dosage system does not include silicone oil.

118. The dosage system of any one of aspects 116 and 117, wherein the second inert material comprises a fluorocarbon.

119. The dosage system of any one of aspects 116 to 118, wherein the second inert material comprises tetrafluoroethylene.

120. The dosage system of any one of aspects 116 to 119, wherein the second inert material comprises a fluorinated polymer.

121. The dosage system of any one of aspects 116 to 120, wherein the closure comprises a fluorocarbon-coated stopper.

122. The dosage system of any one of aspects 110 to 121, wherein the first inert material comprises glass.

123. The dosage system of aspect 122, wherein the glass comprises clear glass.

124. The dosage system of any one of aspects 122 and 123, wherein the glass is transparent to visible light.

125. The dosage system of any one of aspects 122 to 124, wherein the glass has an optical density of 1 or less to wavelengths of light of from 400 nm to 600 nm.

126. The dosage system of any one of aspects 122 to 125, wherein the glass has an optical density of greater than 1 to wavelengths of light of from 100 nm to 250 nm.

127. The dosage system of any one of aspects 122 to 126, wherein the glass does not contain iron.

128. The dosage system of any one of aspects 122 to 126, wherein the glass comprises borosilicate glass that does not contain iron.

129. The dosage system of any one of aspects 122 to 128, wherein the glass comprises pyrex glass that does not contain iron.

130. The dosage system of any one of aspects 116 to 129, wherein the container comprises a vial.

131. A dosage system comprising:
 a first container;
 a second container within the first container, the second container comprising a first inert material and the first container reduces ambient visible light from irradiating onto the second container; and
 the composition of any one of aspects 1 to 115 within the second container.

132. The dosage system of aspect 131, wherein the first container comprises a box or a carton, optionally the first container is a 1-unit to 25-unit box or carton, such as a 10-unit box or carton, optionally ten of the second containers are in the first container, optionally the first container is in a second box.

133. The dosage system of any one of aspects 131 and 132, wherein the first container comprises a polymer.

134. The dosage system of any one of aspects 131 to 133, wherein the first container comprises a thermoplastic.

135. The dosage system of any one of aspects 131 to 134, wherein the first container comprises cellulose.

136. The dosage system of any one of aspects 131 to 135, wherein the first container comprises clay.

137. The dosage system of any one of aspects 131 to 136, wherein the first container comprises a material having a thickness of at least 0.5 mm or ranging from 0.4 mm to 3 mm, such as 0.5 mm to 2.5 mm, 0.5 mm to 1 mm, 0.6 mm to 0.9 mm, or 0.7 mm to 0.8 mm.

138. The dosage system of any one of aspects 116 to 137, further comprising a gas contained within the container that contains the composition, the gas having an oxygen content of less than 10 mol % or less than 10 wt %.

139. The dosage system of aspect 138, wherein the gas has an oxygen content ranging from 1 mol % to 10 mol % or 1 wt % to 10 wt %.

140. The dosage system of aspect 138, wherein the gas fills a headspace within the container that contains the composition.

141. The dosage system of any one of aspects 116 to 140, wherein the container that contains the composition comprises a layer that reduces light transmission.

142. A process comprising:
 filtering the composition of any one of aspects 1 to 115; and
 aseptically processing the composition.

143. The process of aspect 142, wherein the filtering comprises heating the composition to 25° C. to 50° C.

144. The process of aspect 142, wherein the filtering comprises heating the composition to 25° C. to 45° C.

145. The process of aspect 142, wherein the filtering comprises heating the composition to 30° C. to 35° C.

146. The process of any one of aspects 142 to 145, wherein the aseptically processing comprises filling the composition into a container.

147. The process of any one of aspects 146, wherein the filling is conducted under an atmosphere comprising an inert gas.

148. The process of aspect 147, wherein the inert gas comprises at least one member selected from nitrogen, helium, neon, argon, krypton, xenon, and carbon dioxide.

149. The process of aspect 147, wherein the inert gas comprises nitrogen.

150. The process of any one of aspect 142 to 149, wherein aseptically processing the composition comprises preparing a dosage system comprising: a container comprising a first inert material; a closure for closing the container, the closure comprising a second inert material; and the composition contained within the container; the process comprising filling the composition into the container.

151. The process of aspect 150, wherein the dosage system does not include silicone oil.

152. The process of any one of aspects 150 and 151, wherein the second inert material comprises a fluorocarbon.

153. The process of any one of aspects 150 to 152, wherein the second inert material comprises tetrafluoroethylene.

154. The process of any one of aspects 150 to 153, wherein the second inert material comprises a fluorinated polymer.

155. The process of any one of aspects 150 to 154, wherein the closure comprises a fluorocarbon-coated stopper.

156. The process of any one of aspects 150 to 155, wherein the first inert material comprises glass.

157. The process of aspect 156, wherein the glass comprises clear glass.

158. The process of any one of aspects 156 and 157, wherein the glass is transparent to visible light.

159. The process of any one of aspects 156 to 158, wherein the glass has an optical density of 1 or less to wavelengths of light of from 400 nm to 600 nm.

160. The process of any one of aspects 156 to 159, wherein the glass has an optical density of greater than 1 to wavelengths of light of from 100 nm to 250 nm.

161. The process of any one of aspects 156 to 160, wherein the glass does not contain iron.

162. The process of any one of aspects 156 to 161, wherein the glass comprises borosilicate glass that does not contain iron.

163. The process of any one of aspects 156 to 162, wherein the glass comprises pyrex glass that does not contain iron.

164. The process of any one of aspects 150 to 163, wherein the container comprises a vial.

165. The process of any one of aspect 142 to 149, wherein aseptically processing the composition comprises preparing a dosage system comprising: a first container; a second container within the first container, the second container comprising a first inert material and the first container preventing ambient visible light from irradiating onto the second container; and the composition within the second container; the process comprising filling the composition into the second container.

166. The process of aspect 165, wherein the first container comprises a box.

167. The process of any one of aspects 165 and 166, wherein the first container comprises a polymer.

168. The process of any one of aspects 165 to 167, wherein the first container comprises a thermoplastic.

169. The process of any one of aspects 165 to 168, wherein the first container comprises cellulose.

170. The process of any one of aspects 165 to 168, wherein the first container comprises clay.

171. The process of any one of aspects 165 to 170, wherein the first container has a thickness of at least 0.5 mm.

172. The process of any one of aspects 150 to 171, further comprising a gas contained within the container that contains the composition, the gas having an oxygen content of less than 10 mol % or less than 10 wt %.

173. The process of aspect 172, wherein the gas has an oxygen content ranging from 1 mol % to 10 mol % or 1 wt % to 10 wt %.

174. The process of aspect 172, wherein the gas fills a headspace within the container that contains the composition.

175. The process of any one of aspects 150 to 172, wherein the container that contains the composition comprises a layer that reduces light transmission.

176. A method of treating or prophylactically treating pain, comprising administering an effective amount of the composition of any one of aspects 1 to 175 to a subject in need thereof.

BRIEF DESCRIPTION OF THE DRAWINGS

FIG. 1 shows the water content and coloration of Formulation A samples.

DETAILED DESCRIPTION

Figure 2:
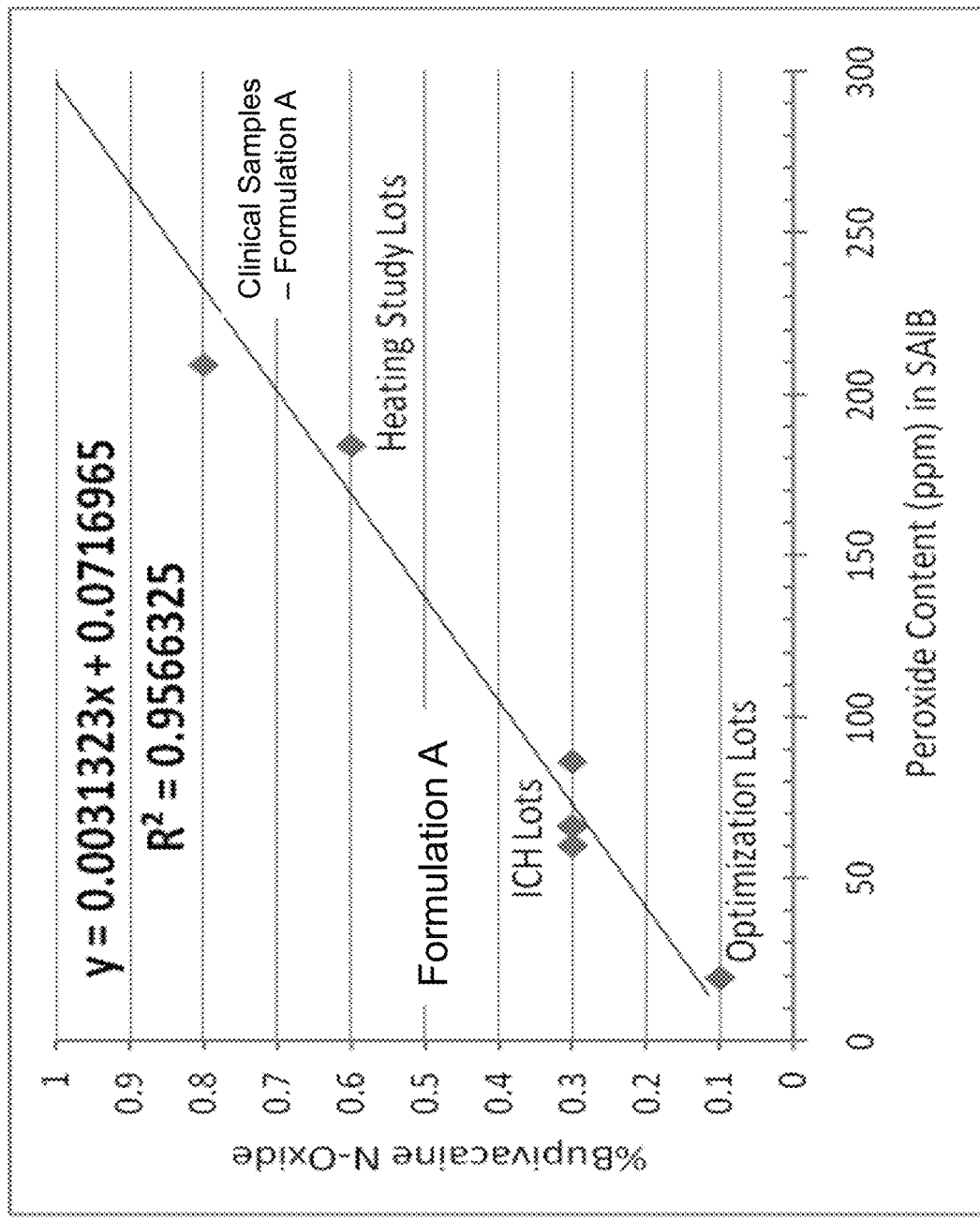
FIG. 2 shows a linear regression line fitted to the SAIB peroxide content data versus bupivacaine N-oxide levels.

Before describing the present invention in detail, it is to be understood that this invention is not limited to particularly exemplified carrier materials or process parameters as such may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entirety.

It must be noted that, as used in this specification and the appended claims, the singular forms "a," "an" and "the" include plural referents unless the content clearly dictates otherwise. Thus, for example, "a solvent" includes a mixture of two or more such carriers, reference to "an anesthetic" includes mixtures of two or more such agents, and the like.

As used herein, "present" at a level means that a given component, e.g., 2,6-dimethylaniline, is present at a level greater than zero.

The present disclosure relates to a plurality of strategies to improve stability and safety of sustained release drug delivery formulations. The strategies include improved sterilization, prevention of light induced degradation, and inert container closures, and low metal content.

In some aspects, the present disclosure relates to sustained release drug delivery formulations having low amounts of 2,6-dimethylaniline (Formula I):

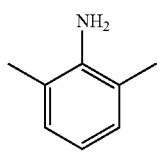

(Formula I)

In some cases, the 2,6-dimethylaniline is present in the drug delivery formulation at a level less than 500 ppm, such as less than 300 ppm, less than 200 ppm, less than 100 ppm, less than 15 ppm, less than 12 ppm, less than 10 ppm, or less than 5 ppm. In some cases, the 2,6-dimethylaniline is present in the drug delivery formulation at a level ranging from 0.2 ppm to 500 ppm, such as from 0.3 ppm to 200 ppm, from 0.4 ppm to 100 ppm, from 0.5 ppm to 10 ppm, or 2 ppm to 8 ppm.

In some cases, the present disclosure relates to compositions having low amounts of N-oxide of the active pharmaceutical agent. For instance, the N-oxide of the active pharmaceutical agent may be present in the composition at a level less than 1 wt %, such as less than 0.7 wt %, less than 0.5 wt %, or less than 0.4 wt %, based on weight of the composition. In some cases, the N-oxide of the active pharmaceutical agent is present in the composition at a level ranging from 0.01 wt % to 1 wt %, such as from 0.05 wt % to 0.4 wt %, 0.1 wt % to 0.4 wt %, or from 0.1 wt % to 0.2 wt %, based on weight of the composition.

In some aspects, the present disclosure relates to sustained release drug delivery formulations having low amounts of bupivacaine N-oxide (Formula II):

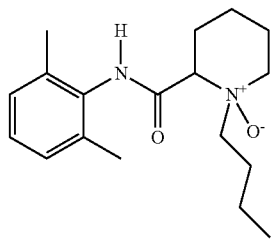

(Formula II)

In some cases, the bupivacaine N-oxide is present in the composition at a level less than 1 wt %, such as less than 0.7 wt %, or less than 0.4 wt %, based on weight of the composition. In some cases, the bupivacaine N-oxide is present in the composition at a level ranging from 0.01 wt % to 1 wt %, such as from 0.05 wt % to 0.4 wt %, or from 0.1 wt % to 0.2 wt %, based on weight of the composition.

In some cases, compositions are made from ingredients having low levels of peroxide. For instance, the compositions may be made by combining: an active pharmaceutical agent; a high viscosity liquid carrier material (HVLCM) comprising sucrose acetate isobutyrate having peroxide that is present at a level less than 200 ppm; and an organic solvent. In some cases, the sucrose acetate isobutyrate has peroxide that is present at a level less than 100 ppm, such as less than 80 ppm or less than 60 ppm. In some cases, the sucrose acetate isobutyrate has peroxide that is present at a level ranging from 1 ppm to 100 ppm, such as from 2 ppm to 80 ppm or from 3 ppm to 60 ppm.

In some cases, the compositions may be made by combining: an active pharmaceutical agent; at least one of a high viscosity liquid carrier material (HVLCM) and a polyorthoester; and an organic solvent having peroxide that is present at a level less than 100 ppm, the organic solvent optionally comprising at least one of benzyl alcohol, dimethyl sulfoxide, and triacetin. In some cases, the organic solvent has peroxide that is present at a level less than 85 ppm, such as less than 10 ppm. In some cases, the organic solvent has peroxide that is present at a level ranging from 1 ppm to 90 ppm, such as from 2 ppm to 85 ppm or from 3 ppm to 10 ppm.

In some cases, the amount of degradation products (e.g., 2,6-dimethylaniline, bupivacaine N-oxide) in the subject compositions may be measured by HPLC with UV detection. In other cases, the amount of 2,6-dimethylaniline is determined by nuclear magnetic resonance (NMR) spectroscopy. In some cases, the amount of 2,6-dimethylaniline is determined by gas chromatography (e.g., gas chromatography-mass spectrometry, GCMS). In some cases, the amount of 2,6-dimethylaniline is determined by liquid chromatography (e.g., liquid chromatography-mass spectrometry, LCMS). Unless specified otherwise, the amount of 2,6-dimethylaniline recited in the claims is determined by LCMS. In some cases, the amount of 2,6-dimethylaniline may be measured by electrochemical detection as described in FIJALEK et al., Journal of Pharmaceutical and Biomedical Analysis, 37:913-918 (2005), which is incorporated herein by reference in its entirety.

In some cases, the amount of peroxide is measured by potentiometric titration, e.g., iodometric titration. Other techniques for measuring the amount of peroxide include voltamperometric method, spectrophotometry (e.g., using cobalt bicarbonate with light absorbance measured at 400 nm, titanium oxalate with light absorbance measured at 260 nm, or peroxidase enzyme with light absorbance measured at 596 nm), fluorometry, fluorescence correlation spectroscopy (FCS), chemiluminescence, electrochemistry, ion chromatography (IC), and resonance light scattering (RLS). Unless specified otherwise, the amount of peroxide recited in the claims is determined by spectrophotometry using cobalt bicarbonate with light absorbance measured at 400 nm.

In one aspect, the present disclosure relates to sterilization of sustained release drug delivery formulations without the formation of unacceptable levels of degradation products including genotoxic impurities.

It was discovered that, in some cases, gamma irradiation is not an acceptable sterilization method because gamma irradiation significantly increased levels of degradation products, including a known genotoxic degradant, 2,6-dimethylaniline.

An evaluation of alternate sterilization techniques was conducted using an exemplary formulation consisting of 12 wt % bupivacaine, 66 wt % sucrose acetate isobutyrate (SAIB), and 22 wt % benzyl alcohol ("Formulation A"). The sterilization techniques included: dry heat sterilization, steam sterilization, and filtration sterilization followed by aseptic processing. The evaluation concluded that:

In some cases, the use of dry heat to sterilize was not acceptable because dry heat sterilization temperatures were above the flash point of the product and required that the product be exposed to elevated temperatures for extended periods of time. The flash point of Formulation A is 116° C. (closed cup); a typical sterilization cycle is 170° C. for not less than 2 hours. Although precautions may be taken to heat product to this temperature, the safety of the personnel and plant did not justify the risk. In addition, in some cases, fluorocarbon-coated stoppers cannot withstand typical dry heat sterilization (e.g., 250° C. for ≥30 minutes).

The use of steam to sterilize Formulation A was not acceptable because the formulation is non-aqueous. Steam sterilization uses saturated steam at high pressure to denature cells. Aqueous products in vials use the water in the formulation to create this steam and pressure within the headspace of the container, sterilizing the contents. Additionally, steam sterilization temperatures are above the flash point of the product, creating the same safety issue as described for dry heat sterilization.

The use of filtration sterilization followed by aseptic processing for Formulation A is acceptable because it provides the product with a sterility assurance level of greater than $10^{-3}$ without compromising the product. In addition, the inherent anti-microbial activity of the Formulation A ensures that pre-filtration bioburden will be consistently low, thereby, ensuring a safe filter sterilization outcome.

Therefore, the optimal sterilization method for manufacturing the exemplary formulation is filtration sterilization followed by aseptic processing. As used herein, "aseptic processing" means processing under sterile conditions. Aseptic processing eliminates the risk of product degradation and toxicity that would arise if the product was subjected to ionizing radiation at doses sufficient to comply with current ISO requirements (e.g., 20 kGy to 25 kGy of gamma irradiation).

In addition to finalizing aseptic processing as the choice of sterilization techniques, a processing study was conducted that identified the optimal compounding and filling temperatures to minimize the formation of 2,6-dimethylaniline during manufacture.

In some cases, methods of the present disclosure include processing the subject compositions. Methods of processing the subject compositions according to certain cases, include filtering a composition having one or more active agents (e.g., anesthetic, NSAID, etc. as described below) and aseptically processing the composition. In some cases, the composition (as described in greater detail below) may be filtered using a filter having pore sizes which vary, ranging from 0.1 nm to 1000 nm, such as from 0.5 nm to 950 nm, such as from 1 nm to 900 nm, such as from 10 nm to 800 nm, such as from 25 nm to 750 nm, such as from 50 nm to 500 nm and including filtering with a filter having pore sizes of from 100 nm to 400 nm. The composition may be filtered under positive, negative or atmospheric pressure. The composition may be filtered while heating the composition. In some instances, the composition is heated by 1° C. or more during filtration, such as by 2° C. or more, such as 3° C. or more, such as by 4° C. or more, such as by 5° C. or more, such as by 10° C. or more, such as by 15° C. or more, such as by 20° C. or more and including by 25° C. or more. In some cases, the composition is heated to a temperature of from 10° C. to 75° C. during filtration, such as from 15° C. to 70° C., such as from 20° C. to 65° C., such as from 25° C. to 60° C., such as from 30° C. to 55° C. and including from 40° C. to 50° C.

In some cases, aseptic processing of the composition includes filling the composition into a container under a gaseous atmosphere. In some instances, the gaseous atmosphere includes an inert gas. Inert gases of interest may include, but are not limited to, nitrogen, helium, neon, argon, krypton, xenon, and carbon dioxide or a combination thereof. In some cases, the amount of gas is sufficient to fill the headspace of the container. The term "headspace" is used herein in its conventional sense to refer to the volume in the container between the interface of the composition and the opening of the container or at the interface of the closure (e.g., when the container is sealed with a stopper). The gas pressure of the inert gas atmosphere in the headspace of the container may be 0.001 torr or more, such as 0.005 torr or more, such as 0.01 torr or more, such as 0.05 torr or more, such as 0.1 torr or more, such as 0.5 torr or more, such as 1 torr or more, such as 5 torr or more, such as 10 torr or more, such as 25 torr or more, such as 50 torr or more, such as 100 torr or more, such as 250 torr or more, such as 500 torr or more, such as 760 torr or more and including 1000 torr or more.

In some instances, aseptic processing of the composition includes closing the container with a closure. In some cases, the closure is formed from (or coated with) a compound that is inert to the components of the subject compositions (as described in greater detail below). In some cases, the closure forms a fluidic seal with the container. In some cases, the closure forms a fluidic and gaseous seal with the container.

It was discovered that, in some cases, exposure to light (e.g., simulated sunlight, sunlight, UV light, and visible light) can result in formation of degradation products in sustained release drug delivery formulations.

It was also discovered that, in some cases, storage of sustained release drug delivery formulations in amber colored glassware causes the levels of 2,6-dimethylaniline to be high.

In some cases, the light induced degradation is prevented by storing the product in appropriate light resistant cartons.

In some cases, the drug delivery formulation is stored in a light resistant container. In some cases, the light resistant container comprises a protective light resistant coating, e.g., RAY-SORB® coating. In some cases, the subject light resistant containers are configured to reduce or eliminate light-induced degradation by preventing exposure of the subject compositions to light having a wavelength that ranges from 200 nm to 800 nm, such as from 225 nm to 775 nm, such as from 250 nm to 750 nm, such as from 275 nm to 725 nm, such as from 300 nm to 700 nm, such as from 325 nm to 675 nm, such as from 350 nm to 650 nm, such as from 375 nm to 625 nm and including from 400 nm to 600 nm. In certain cases, the light resistant containers have an optical density at the wavelength where a reduction in light exposure is desired of 0.5 or more, such as 1 or more, such as 1.5 or more, such as 2.0 or more, such as 2.5 or more, such as 3.0 or more, such as 3.5 or more, such as 4.0 or more, such as 4.5 or more, such as 5.0 or more, such as 5.5 or more, such as 6.0 or more, such as 6.5 or more and including an optical density of 7.0 or more. In certain instances, the light resistant container is completely opaque to the wavelength of light where reduction of light exposure is desired (i.e., no light passes through the walls of the container).

It was discovered that, in some cases, siliconized stoppers leach silicone oil into sustained release drug delivery formulations. In some cases, dose units of the subject compositions are stored (e.g., loaded, dispensed from) in a container having a closure (e.g., a stopper, lid or cap) that is substantially inert to components of the composition, such as to the organic solvent present in the composition (e.g., benzyl alcohol). As used herein, "substantially inert" means that the subject composition does not leach from or react with the closure (i.e., contact between the composition and the closure does not result in the formation or presence of degradation or undesired byproducts in the composition). In some cases, the closure exhibits no reactivity with the composition even when in contact for 1 hour or longer, such as for 2 hours or longer, such as for 6 hours or longer, such as for 12 hours or longer, such as for 24 hours or longer, such as for 1 week or longer, such as for 1 month or longer, such as for 6 months or longer, such as for 1 year or longer and including for 10 years or longer. In some instances, closures of interest include fluorinated polymer. In some cases, the closure is formed from the fluorinated polymer. In some cases, the closure is coated with the fluorinated polymer. Fluorinated polymers of interest may include but are not limited to fluoropolymers formed from one or more monomers selected from the group ethylene-tetrafluoroethylene, perfluorocycloalkene (PFCA), vinyl fluoride (fluoroethylene, VF1), vinylidene fluoride (1,1-difluoroethylene, VDF, VF2), tetrafluoroethylene (TFE), chlorotrifluoroethylene (CTFE), hexafluoropropylene (HFP), perfluoropropylvinylether (PPVE), perfluoromethylvinylether (PMVE). For instance, the closure may be formed from polyvinylfluoride (PVF), polyvinylidene fluoride (PVDF), polytetrafluoroethylene (PTFE), polychlorotrifluoroethylene (PCTFE), perfluoroalkoxypolymer (PFA), fluorinated ethylene-propylene (FEP), polyethylenetetrafluoroethylene (ETFE), polyethylenechlorotrifluoroethylene (ECTFE), perfluorinated elastomer (FFPM/FFKM), fluorocarbon chlorotrifluoroethylenevinylidene fluoride (FPM), fluoroelastomer tetrafluoroethylene-propylene (FEPM), perfluoropolyether (PFPE) or perfluorosulfonic acid (PFSA). In certain cases, the closure does not include silicon.

In some cases, the stopper is paired with a glass container (e.g., glass vial), e.g., a 10 mL USP Type I Glass Vial. In some cases, the glass vial is pyrex glass, a boron silica glass or other type of glass. In certain instances, the glass vial is formed from a glass material which does not contain iron.

In some cases, the presence of organic solvent, e.g., 22 wt % benzyl alcohol, necessitated the selection of a stopper that was chemically resistant to organic solvents.

In some cases, the present disclosure provides dosage systems that are free of silicone oil.

In some cases, the present disclosure provides a fluorocarbon-coated stopper that can release fluoride ions when exposed to gamma irradiation. As a result, in some cases, the dosage system is not exposed to gamma irradiation.

In some cases, the present disclosure involves control of metal content in sustained release drug delivery formulations.

The manufacturing of sustained release drug delivery formulations, from the source of raw materials to the compounding, filling, and storage in containers (e.g., glass vials with stoppers), may be conducted in a way to minimize metals in the final product. In some cases, the metal content is minimized by using steel compounding tanks. In some cases, the metal content is minimized by using silicone tubing. In some cases, the metal content is minimized by using fluorocarbon-coated stoppers.

In some cases, a composition comprises metal present at a level less than 5 ppm, such as less than 4 ppm, or less than 3 ppm. In some cases, the composition comprises metal present at a level ranging from 0.1 ppm to 4 ppm, such as from 0.05 ppm to 3 ppm or from 0.1 ppm to 2 ppm. A skilled artisan would understand that the metal content includes metal in any form, including metal in elemental or ionized form.

In some cases, the present disclosure relates to a composition having low water content. For instance, the water may be present at a level less than 0.5 wt %, such as less than 0.4 wt %, based on weight of the composition, or less than 0.3 wt %, based on weight of the composition. The water may be present in the composition at a level ranging from 0.03 wt % to 0.4 wt %, such as from 0.05 wt % to 0.35 wt %, from 0.08 wt % to 0.3 wt %, based on weight of the composition.

While not wishing to be bound by theory, in some cases, the water content is believed to affect the amount of hydrolysis that occurs in the compositions. In some cases, sucrose acetate isobutyrate and benzyl alcohol undergo a hydrolysis reaction to form benzyl acetate and/or benzyl isobutyrate. It is believed that keeping the water content low reduces the amount of benzyl acetate and benzyl isobutyrate formation. The water content may be kept low by several techniques, such as using ingredients with low water content, storing ingredients in closed containers, and using a nitrogen head space while compounding.

In view of the above, in some cases, the present disclosure involves compositions having low benzyl acetate content. For instance, the benzyl acetate may be present at a level less than 100 mg/mL, such as less than 90 mg/mL, less than 80 mg/mL, less than 70 mg/mL, less than 60 mg/mL, less than 50 mg/mL, less than 40 mg/mL, less than 30 mg/mL, less than 20 mg/mL, less than 15 mg/mL, or less than 10 mg/mL. The benzyl acetate may be present in the composition at a level ranging from 0.1 mg/mL to 80 mg/mL, such as from 0.5 mg/mL to 40 mg/mL, from 1 mg/mL to 20 mg/mL, or 1 mg/mL to 15 mg/mL. In some cases, the benzyl acetate is present in the composition in an amount of 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, 30 mg/mL, 31 mg/mL, 32 mg/mL, 33 mg/mL, 34 mg/mL, 35 mg/mL, 36 mg/mL, 37 mg/mL, 38 mg/mL, 39 mg/mL, 40 mg/mL, 41 mg/mL, 42 mg/mL, 43 mg/mL, 44 mg/mL, 45 mg/mL, 46 mg/mL, 47 mg/mL, 48 mg/mL, 49 mg/mL, 50 mg/mL, 51 mg/mL, 52 mg/mL, 53 mg/mL, 54 mg/mL, 55 mg/mL, 56 mg/mL, 57 mg/mL, 58 mg/mL, 59 mg/mL, 60 mg/mL, 61 mg/mL, 62 mg/mL, 63 mg/mL, 64 mg/mL, 65 mg/mL, 66 mg/mL, 67 mg/mL, 68 mg/mL, 69 mg/mL, 70 mg/mL, 71 mg/mL, 72 mg/mL, 73 mg/mL, 74 mg/mL, 75 mg/mL, 76 mg/mL, 77 mg/mL, 78 mg/mL, 79 mg/mL, 80 mg/mL, 81 mg/mL, 82 mg/mL, 83 mg/mL, 84 mg/mL, 85 mg/mL, 86 mg/mL, 87 mg/mL, 88 mg/mL, 89 mg/mL, 90 mg/mL, 91 mg/mL, 92 mg/mL, 93 mg/mL, 94 mg/mL, 95 mg/mL, 96 mg/mL, 97 mg/mL, 98 mg/mL, 99 mg/mL or 100 mg/mL.

In some cases, the present disclosure involves compositions having low benzyl isobutyrate content. For instance, the benzyl isobutyrate may be present at a level less than 50 mg/mL, such as less than 40 mg/mL, less than 30 mg/mL, less than 20 mg/mL, less than 30 mg/mL, less than 10 mg/mL, or less than 8 mg/mL. The benzyl isobutyrate may be present in the composition at a level ranging from 0.1 mg/mL to 40 mg/mL, such as from 0.5 mg/mL to 30 mg/mL, from 1 mg/mL to 10 mg/mL, or 1 mg/mL to 8 mg/mL. In some cases, the benzyl isobutyrate is present in the composition in an amount of 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, 30 mg/mL, 31 mg/mL, 32 mg/mL, 33 mg/mL, 34 mg/mL, 35 mg/mL, 36 mg/mL, 37 mg/mL, 38 mg/mL, 39 mg/mL, 40 mg/mL, 41 mg/mL, 42 mg/mL, 43 mg/mL, 44 mg/mL, 45 mg/mL, 46 mg/mL, 47 mg/mL, 48 mg/mL, 49 mg/mL or 50 mg/mL.

While not wishing to be bound by theory, in some cases, it is believed that the amount of peroxide in the composition may affect the amount of N-oxide formation. Reducing the amount of peroxide is believed to reduce the amount of N-oxide formation. The amount of peroxide in the composition may be kept low by several techniques, such as using ingredients that have low peroxide content, protecting the composition from light, minimizing the headspace in the container containing the composition, and storing the composition at low temperature, such as room temperature.

In some cases, the present the composition is made with HVLCM (e.g., sucrose acetate isobutyrate) having low peroxide content. For instance, the HVLCM may have peroxide present at a level less than 200 ppm, such less than 100 ppm, less than 80 ppm, or less than 60 ppm. In some cases, the HVLCM has peroxide that is present at a level ranging from 1 ppm to 100 ppm, such as from 2 ppm to 80 ppm or from 3 ppm to 60 ppm.

In some cases, the present the composition is made with organic solvent (e.g., benzyl alcohol) having low peroxide content. For instance, the organic solvent may have peroxide that is present at a level less than 100 ppm, such as less than 85 ppm or less than 10 ppm. In some cases, the organic solvent has peroxide that is present at a level ranging from 1 ppm to 90 ppm, such as from 2 ppm to 85 ppm or from 3 ppm to 10 ppm.

In some aspects, the present disclosure relates to active agent compositions (e.g., bupivacaine compositions) having little to no particulate matter. In some cases, particulate matter is present in the compositions at a level less than 100 ppm, less than 95 ppm, less than 90 ppm, less than 85 ppm, less than 80 ppm, less than 75 ppm, less than 70 ppm, less than 65 ppm, less than 60 ppm, less than 55 ppm and including less than 50 ppm. For example, particulate matter may be present in the compositions at a level of 1 ppm, 2 ppm, 3 ppm, 4 ppm, 5 ppm, 6 ppm, 7 ppm, 8 ppm, 9 ppm, 10 ppm, 11 ppm, 12 ppm, 13 ppm, 14 ppm, 15 ppm, 16 ppm, 17 ppm, 18 ppm, 19 ppm, 20 ppm, 21 ppm, 22 ppm, 23 ppm, 24 ppm, 25 ppm, 26 ppm, 27 ppm, 28 ppm, 29 ppm, 30 ppm, 31 ppm, 32 ppm, 33 ppm, 34 ppm, 35 ppm, 36 ppm, 37 ppm, 38 ppm, 39 ppm, 40 ppm, 41 ppm, 42 ppm, 43 ppm, 44 ppm, 45 ppm, 46 ppm, 47 ppm, 48 ppm, 49 ppm, 50 ppm, 51 ppm, 52 ppm, 53 ppm, 54 ppm, 55 ppm, 56 ppm, 57 ppm, 58 ppm, 59 ppm, 60 ppm, 61 ppm, 62 ppm, 63 ppm, 64 ppm, 65 ppm, 66 ppm, 67 ppm, 68 ppm, 69 ppm, 70 ppm, 71 ppm, 72 ppm, 73 ppm, 74 ppm, 75 ppm, 76 ppm, 77 ppm, 78 ppm, 79 ppm, 80 ppm, 81 ppm, 82 ppm, 83 ppm, 84 ppm, 85 ppm, 86 ppm, 87 ppm, 88 ppm, 89 ppm, 90 ppm, 91 ppm, 92 ppm, 93 ppm, 94 ppm, 95 ppm, 96 ppm, 97 ppm, 98 ppm, 99 ppm, 100 ppm. In certain cases, the composition has no particulate matter, i.e., 0 ppm particulate matter.

The stability of the formulations also depends on storage conditions. High temperature storage typically increases degradation. In some cases, low temperature storage can cause precipitation. Thus, the compositions of the present disclosure are typically stored at a temperature ranging from 15° C. to 30° C., such as from 20° C. to 25° C.

In some cases, when a composition is stored in a sealed, upright, clear glass vial at 25° C./60% RH for 20 months or 36 months, 2,6-dimethylaniline is present at levels disclosed herein, e.g., when the composition is stored in a sealed, upright, clear glass vial at 25° C./60% RH for 20 months or 36 months, the 2,6-dimethylaniline may be present at a level less than 500 ppm. In some cases, when a composition is stored in a sealed, upright, clear glass vial at 25° C./60% RH for 20 months or 36 months, the 2,6-dimethylaniline is present at a level less than 100 times, such as less than 50 times, less than 20 times, less than 10 times, less than 8 times, less than 6 times, less than 4 times, or less than 2 times, relative to an initial level before storage, such as ranging from 1 time to 20 times, such as 2 times to 10 times, or 2 times to 4 times, relative to an initial level before storage.

In some cases, when a composition is stored in a sealed, upright, clear glass vial at 40° C./75% RH for 20 months or 36 months, 2,6-dimethylaniline is present at levels disclosed herein. In some cases, when a composition is stored in a sealed, upright, clear glass vial at 40° C./75% RH for 20 months or 36 months, the 2,6-dimethylaniline is present at a level less than 100 times, such as less than 50 times, less than 20 times, less than 10 times, less than 8 times, less than 6 times, less than 4 times, or less than 2 times, relative to an initial level before storage such as ranging from 1 time to 20 times, such as 2 times to 10 times, or 2 times to 4 times, relative to an initial level before storage.

In some cases, when a composition is stored in a sealed, upright, clear glass vial at 25° C./60% RH for 20 months or 36 months, N-oxide of the active pharmaceutical agent is present at levels disclosed herein, e.g., at a level less than 1 wt %, based on weight of the composition. In some cases, when a composition is stored in a sealed, upright, clear glass vial at 25° C./60% RH for 20 months or 36 months, the N-oxide of the active pharmaceutical agent is present at a level less than 10 times, such as less than 5 times, less than 2 times, or less than 1.5 times relative to an initial level before storage, such as ranging from 1 time to 5 times or 1 time to 2 times, relative to an initial level before storage.

In some cases, when a composition is stored in a sealed, upright, clear glass vial at 40° C./75% RH for 20 months or 36 months, N-oxide of the active pharmaceutical agent is present at levels disclosed herein, e.g., at a level less than 1 wt %, based on weight of the composition. In some cases, when a composition is stored in a sealed, upright, clear glass vial at 40° C./75% RH for 20 months or 36 months, the N-oxide of the active pharmaceutical agent is present at a level less than 10 times, such as less than 5 times, less than 2 times, or less than 1.5 times, relative to an initial level before storage, such as ranging from 1 time to 5 times or 1 time to 2 times, relative to an initial level before storage.

In some cases, when a composition is stored in a sealed, upright, clear glass vial at 25° C./60% RH for 20 months or 36 months, metal is present at levels disclosed herein, e.g., at a level less than 5 ppm. In some cases, when a composition is stored in a sealed, upright, clear glass vial at 40° C./75% RH for 20 months or 36 months, the metal is present at levels disclosed herein.

In some cases, when a composition is stored in a sealed, upright, clear glass vial at 25° C./60% RH for 20 months or 36 months, water is present at levels disclosed herein, e.g., at a level less than 0.5 wt %, based on weight of the composition. In some cases, when a composition is stored in a sealed, upright, clear glass vial at 40° C./75% RH for 20 months or 36 months, the water is present at levels disclosed herein.

In some cases, when a composition is stored in a sealed, upright, clear glass vial at 25° C./60% RH for 20 months or 36 months, benzyl acetate is present at levels disclosed herein, e.g., at a level less than 100 mg/mL. In some cases, when a composition is stored in a sealed, upright, clear glass vial at 25° C./60% RH for 20 months or 36 months, the benzyl acetate is present at a level less than 20 times or less than 15 times, relative to an initial level before storage, such as ranging from 1 time to 20 times or 2 times to 15 times, relative to an initial level before storage.

In some cases, when a composition is stored in a sealed, upright, clear glass vial at 40° C./75% RH for 20 months or 36 months, benzyl acetate is present at levels disclosed herein, e.g., at a level less than 100 mg/mL. In some cases, when a composition is stored in a sealed, upright, clear glass vial at 40° C./75% RH for 20 months or 36 months, the benzyl acetate is present at a level less than 20 times or less than 15 times, relative to an initial level before storage, such as ranging from 1 time to 20 times or 2 times to 15 times, relative to an initial level before storage.

In some cases, when a composition is stored in a sealed, upright, clear glass vial at 25° C./60% RH for 20 months or 36 months, benzyl isobutyrate is present at levels disclosed herein, e.g., at a level less than 50 mg/mL. In some cases, when a composition is stored in a sealed, upright, clear glass vial at 25° C./60% RH for 20 months or 36 months, the benzyl isobutyrate is present at a level less than 20 times, such as less than 10 times, or less than 8 times, relative to an initial level before storage, such as ranging from 1 time to 10 times or 2 times to 8 times, relative to an initial level before storage.

In some cases, when a composition is stored in a sealed, upright, clear glass vial at 40° C./75% RH for 20 months, benzyl isobutyrate is present at levels disclosed herein, e.g., at a level less than 50 mg/mL. In some cases, when a composition is stored in a sealed, upright, clear glass vial at 40° C./75% RH for 20 months, the benzyl isobutyrate is present at a level less than 20 times, such as less than 10 times, or less than 8 times, relative to an initial level before storage, such as ranging from 1 time to 10 times or 2 times to 8 times, relative to an initial level before storage.

In some cases, when a composition is stored in a sealed, upright, clear glass vial at 25° C./60% RH for 20 months or 36 months, sucrose acetate isobutyrate is present at levels disclosed herein, e.g., at a level ranging from 30 wt % to 80 wt %, based on weight of the composition. In some cases, when a composition is stored in a sealed, upright, clear glass vial at 40° C./75% RH for 20 months, the sucrose acetate isobutyrate is present at levels disclosed herein, e.g., at a level ranging from 30 wt % to 80 wt %, based on weight of the composition.

Suitable pharmaceutical agents include locally or systemically acting pharmaceutically active agents which may be administered to a subject by topical or intralesional application (including, for example, applying to abraded skin, lacerations, puncture wounds, etc., as well as into surgical wounds or incisions) or by injection, such as subcutaneous, intradermal, intramuscular, intraocular or intra-articular injection. Suitable pharmaceutical agents include polysaccharides, DNA and other polynucleotides, antisense oligonucleotides, antigens, antibodies, vaccines, vitamins, enzymes, proteins, naturally occurring or bioengineered substances, and the like, anti-infectives (including antibiotics, antivirals, fungicides, scabicides or pediculicides), antiseptics (e.g., benzalkonium chloride, benzethonium chloride, chlorhexidine gluconate, mafenide acetate, methylbenzethonium chloride, nitrofurazone, nitromersol and the like), steroids (e.g., estrogens, progestins, androgens, adrenocorticoids and the like), opioids (e.g., buprenorphine, butorphanol, dezocine, meptazinol, nalbuphine, oxymorphone and pentazocine), therapeutic polypeptides (e.g., insulin, erythropoietin, morphogenic proteins such as bone morphogenic protein, and the like), analgesics and anti-inflammatory agents (e.g., aspirin, ibuprofen, naproxen, ketorolac, COX-1 inhibitors, COX-2 inhibitors and the like), antipsychotic agents (for example, phenothiazines including chlorpromazine, triflupromazine, mesoridazine, piperacetazine and thioridazine; thioxanthenes including chlorprothixene and the like), antiangiogenic agents (e.g., combresiatin, contortrostatin, anti-VEGF and the like), anti-anxiety agents (for example, benzodiazepines including diazepam, alprazolam, clonazepam, oxazepam; and barbiturates), antidepressants (including tricyclic antidepressants and monoamine oxidase inhibitors including imipramine, amitriptyline, doxepin, nortriptyline, amoxapine, tranylcypromine, phenelzine and the like), stimulants (for example, methylphenidate, doxapram, nikethamide and the like), narcotics (for example, buprenorphine, morphine, meperidine, codeine and the like), analgesic-antipyretics and anti-inflammatory agents (for example, aspirin, ibuprofen, naproxen and the like), local anesthetics (e.g., the amide- or anilide-type local anesthetics such as bupivacaine, levobupivacaine, dibucaine, mepivacaine, procaine, lidocaine, tetracaine, ropivacaine, and the like), fertility control agents, chemotherapeutic and anti-neoplastic agents (for example, mechlorethamine, cyclophosphamide, 5-fluorouracil, thioguanine, carmustine, lomustine, melphalan, chlorambucil, streptozocin, methotrexate, vincristine, bleomycin, vinblastine, vindesine, dactinomycin, daunorubicin, doxorubicin, tamoxifen and the like), cardiovascular and anti-hypertensive agents (for example, procainamide, amyl nitrite, nitroglycerin, propranolol, metoprolol, prazosin, phentolamine, trimethaphan, captopril, enalapril and the like), drugs for the therapy of pulmonary disorders, anti-epilepsy agents (for example, phenyloin, ethotoin and the like), anti-hidrotics, keratoplastic agents, pigmentation agents or emollients, antiemetic agents (such as ondansetron, granisetron, tropisetron, metoclopramide, domperidone, scopolamine, palonosetron, and the like). The composition of the present application may also be applied to other locally acting active agents, such as astringents, antiperspirants, irritants, rubefacients, vesicants, sclerosing agents, caustics, escharotics, keratolytic agents, sunscreens and a variety of dermatologics including hypopigmenting and antipruritic agents.

In some cases, the active pharmaceutical agent is present in an amount ranging from 0.5 to 20 percent, 1 to 8 percent, 2 to 6 percent, 2 to 5 percent, or 1 to 5 percent by weight of the composition. In some cases, the active pharmaceutical agent is present in the composition in an amount ranging from 1 wt % to 25 wt %, such as from 5 wt % to 20 wt %, from 10 wt % to 15 wt %, or about 12 wt %, based on weight of the composition.

In some cases, the compositions include an amide- or anilide-type local anesthetic of the "caine" classification, and a non-steroidal anti-inflammatory drug (NSAID), along with related methods, e.g., for treatment of post-operative pain or for prophylactic treatment of pain.

As used herein, the term "anesthetic" intends any agent that provides reversible local numbness, pain relief, blocks impulse conduction along nerve axions and other excitable membranes, such as a regional blockage of nociceptive pathways (afferent and/or efferent), analgesia, and/or anesthesia. See, e.g., Strichartz, G. R. (Ed.) Local Anesthetics, Handbook of Experimental Pharmacology, vol. 81, Springer, Berlin/New York, (1987). The term also includes any agent which, when locally administered provides localized (regional) full or partial inhibition of sensory perception and/or motor function. Examples of commonly used agents suitable for use as anesthetics include, but are not limited to ambucaine, amolanone, amylcaine, benoxinate, benzyl alcohol, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dyclonine, ecogonidine, ecogonine, etidocaine, euprocin, fenalcomine, formocaine, hexylcaine, hydroxyteteracaine, isobuanine, isobutyl p-aminobenzoate, leucinocaine, levobupivacaine, levoxadrol, lidocaine, mepivacaine, meprylcaine, metabutoxycaine, methyl chloride, myrtecaine, naepaine, octacaine, orthocaine, oxethazaine, parenthoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, xylocaine, zolamine, anesthetically active derivatives, analogs and any pharmaceutically acceptable salt thereof, and any mixture thereof.

The amide- and ester-type of local anesthetics are preferred for use herein. Amide-type local anesthetics are characterized by having an amide functionality, while ester-type local anesthetics contain an ester functionality. Preferred amide-type local anesthetics include lidocaine, bupivacaine, prilocaine, mepivacaine, etidocaine, ropivacaine and dibucaine. Preferred ester-type local anesthetics include tetracaine, procaine, benzocaine and chloroprocaine. In one case, the amide-type local anesthetic is selected from the group consisting of bupivacaine, ropivacaine, levobupivacaine, dibucaine, mepivacaine, procaine, lidocaine, and tetracaine. The most preferred local anesthetic is bupivacaine.

In some cases, degradation of the active pharmaceutical agent may result in formation of 2,6-dimethylaniline. For instance, the active pharmaceutical agent may be at least one member selected from bupivacaine, lidocaine, ropivicaine, etidocaine, mepivacaine, pyrrocaine, or salts thereof.

The anesthetic agent is provided in the composition in a neutral form, as a free base form, or in the form of a pharmaceutically acceptable salt. The term "pharmaceutically acceptable salt," as used herein, intends those salts that retain the biological effectiveness and properties of neutral anesthetics and are not otherwise unacceptable for pharmaceutical use. Pharmaceutically acceptable salts include salts of acidic or basic groups, which groups may be present in the anesthetic agents. Those anesthetic agents that are basic in nature are capable of forming a wide variety of salts with various inorganic and organic acids. Pharmaceutically acceptable acid addition salts of basic anesthetics suitable for use herein are those that form non-toxic acid addition salts, i.e., salts comprising pharmacologically acceptable anions, such as the hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Anesthetic agents that include an amino moiety may form pharmaceutically acceptable salts with various amino acids, in addition to the acids mentioned above. Suitable base salts can be formed from bases which form non-toxic salts, for example, aluminium, calcium, lithium, magnesium, potassium, sodium, zinc and diethanolamine salts. See, e.g., Berge et al. (1977) J. Pharm. Sci. 66:1-19.

The ability of an anesthetic agent to provide a condition of sustained local anesthesia refers to the ability of the subject agent to establish an assessable state of localized (regional) full or partial inhibition of sensory perception and/or motor function. Numerous methods and tools for making such an assessment will readily occur to the skilled artisan. With regard to non-human animal subjects, these methods include measurement of spontaneous locomotion in test rats (using, for example, commercially available equipment and software from Med Associates Inc., St. Albans, Vt.), where data can be collected on total distance traveled, ambulatory counts, stereotypy, rearing, time spent in the various motions and time spent at rest for test subjects; visualization of pin prick reaction in rats; and the rat hotplate foot withdrawal model, e.g., according to the procedure described in detail in IACUC No 9511-2199.

With regard to selection of a particular anesthetic agent, the skilled artisan will also recognize that the pharmacological properties of each candidate agent will vary, for example, with respect to onset and intensity of anesthetic effect, duration and the like. Certain agents may provide a mild anesthetic effect, having a fairly rapid onset of activity, but a short duration. Such agents can be used with the compositions in order to provide an "initial anesthetic effect," where they are typically paired with a different anesthetic agent that provides a "sustained local anesthesia," characterized by a more gradual onset of activity, but a stronger effect and one of longer duration. An example of an anesthetic that can be used to provide an initial anesthetic effect is benzyl alcohol. An example of an anesthetic that can be used to provide a sustained local anesthesia is bupivacaine. Still further agents that can be used to provide an initial anesthetic effect can include organic materials commonly used as solvents and/or penetration agents, such as ethanol, dimethyl sulfoxide, N-methylpyrrolidone, polyethylene glycol and certain fatty acid esters. These and other similar agents can provide a very mild initial anesthetic effect, for example, when applied they can cool or otherwise desensitize/numb a tissue site, thereby partially inhibiting sensory perception at that site. Whenever an agent is used in order to provide an initial anesthetic effect, the agent is provided in a suitable composition in an amount sufficient to provide the subject effect, and in such a way that the agent is able to be released from the composition quickly in order to provide the intended effect. Assembly of such suitable compositions (containing an agent for providing an initial anesthetic effect) is within the skill of the art when taken in combination with the guidance and teaching provided by the instant specification.

In certain cases, a composition is provided that includes two anesthetic agents, a first anesthetic and a second anesthetic, wherein the second anesthetic agent is a solvent for the first anesthetic agent. In these particular compositions, the second anesthetic agent is typically used to provide an initial anesthetic effect, and the first anesthetic agent is used to provide a subsequent anesthetic effect characterized by sustained local anesthesia, having an onset within 2 hours of administration to a subject without an initial burst, and a duration of at least 24 hours after administration, or even longer. In certain preferred cases, the first anesthetic agent provides the sustained local anesthesia with an onset within 1 to 2 hours of administration, and in other preferred cases, the first anesthetic agent provides the sustained local anesthesia with an onset within 30 minutes to 1 hour of administration. In certain other cases, the second anesthetic is also a solvent for the sustained release carrier system.

The concentration of the anesthetic in the composition will also depend on absorption, inactivation, and excretion rates of that particular agent, as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The composition may be administered in one dosage, or may be divided into a number of smaller doses to be administered at varying intervals of time, either sequentially or concurrently.

The anesthetic agent or agents will typically be present in the composition in the range from 0.1 to 99.5 percent by weight relative to the total weight of the composition (wt %), from 0.5 to 70 wt %, or from 1 percent to 50 wt %. However, ranges having upper endpoints as low as 40%, 30%, 20%, or 10% can be used, as can ranges having lower limits as high as 5%, 3%, or 2%. For very active anesthetic agents, the ranges may be less than 1% by weight, and possibly less than 0.0001%.

An anesthetic agent will serve as a solvent for another anesthetic agent herein when one agent is at least partially dissolved in the other solvent agent in the manufacture of the composition. In addition, the anesthetic solvent is present in the composition in an amount sufficient to provide both an initial anesthetic effect and at least partially dissolve the other anesthetic agent. In certain cases, the second anesthetic is thus present in an amount of from 95 to 1 percent by weight relative to the total weight of the composition (wt %), or in an amount of from 75 to 10 wt %, or in an amount of from 50 to 15 wt %.

A number of suitable anesthetic agents that also serve as solvents for other anesthetic agents can be used. Suitable agents include aromatic alcohols, acids and acid derivatives, and combinations thereof. A particularly preferred anesthetic agent that can be used as a solvent for an additional anesthetic is benzyl alcohol.

In some cases, the sustained release carrier systems employed in the compositions of the present disclosure are classified as non-polymeric carriers. A pharmaceutically acceptable non-polymeric carrier is typically biocompatible, and preferably biodegradable, bioerodible, or bioabsorbable. A substance is biocompatible if it and any of its degradation products present no significant, deleterious or untoward effects, nor cause substantial tissue irritation or necrosis when administered to living tissue. "Biodegradable" or "bioerodible," used interchangeably herein, means the subject non-polymeric material will degrade or erode in vivo to form smaller chemical species, wherein such degradation can result, for example, from enzymatic, chemical, and physical processes. "Bioabsorbable" means that a given nonpolymeric material can be broken down and absorbed within an animal subject's body, for example, by a cell, tissue or the like.

In some cases, the non-polymeric carrier material is used to control release of at least one anesthetic agent from the compositions, in such a way as to provide a sustained local anesthesia having an onset within 2 hours of administration and a duration of at least 24 hours or longer. In some cases, the non-polymeric carrier material comprises HVLCM (e.g., sucrose acetate isobutyrate) present in the composition in an amount sufficient to provide sustained release of the active pharmaceutical agent from the composition, such as sustained release of about 72 hours. In some compositions, the non-polymeric carrier material is sufficient to provide either a first order sustained-release profile of the at least one anesthetic, or a pseudo-zero order release profile. Accordingly, the non-polymeric carrier will be present in the composition in an amount of from 99.5 to 1 percent by weight relative to the total weight of the composition (wt %), or in an amount of from 95 to 10 wt %, or in an amount of from 75 to 25 wt %. In some cases, the non-polymeric carrier comprises a high viscosity liquid carrier material (HVLCM), e.g., sucrose acetate isobutyrate, present at a level ranging from 30 wt % to 80 wt %, such as from 40 wt % to 70 wt %, from 50 wt % to 70 wt %, from 60 wt % to 70 wt %, from 61 wt % to 69 wt %, from 62 wt % to 68 wt %, or from 63 wt % to 67 wt %, based on weight of the composition.

Selection of a suitable non-polymeric carrier is within the general skill in the art, using the teaching and guidance provided by the instant disclosure and specification. For example, numerous pharmaceutically acceptable non-polymeric carrier systems are available to the skilled artisan to produce liquid, spray, cream, lotion, ointment, gel, slurry, oil, emulsion, microemulsion, solid, plaster, film, particle, microparticle, powder or other suitable form pharmaceutical compositions. These and other carrier systems are described, for example, in Remington's Pharmaceutical Sciences, $16^{th}$ Edition, 1980 and $17^{th}$ Edition, 1985, both published by Mack Publishing Company, Easton, Pa.

The compositions may further include one or more additional components, for example pharmaceutically acceptable excipient materials that can act as dispersing agents, bulking agents, binders, carriers, stabilizers, glidants, antioxidants, pH adjusters, anti-irritants, thickening agents, rheology modifiers, emulsifiers, preservatives, and the like. The skilled artisan will appreciate that certain excipient materials can serve several of the above-referenced functions in any particular formulation. Thus, any number of suitable excipient materials can be mixed with or incorporated into the compositions to provide bulking properties, alter active agent release rates, increase or impede water uptake, control pH, provide structural support, facilitate manufacturing processes and other uses known to those skilled in the art. The term "excipient" generally refers to a substantially inert material that is nontoxic and does not interact with other components of the composition in a deleterious manner. The proportions in which a particular excipient may be present in the composition depend upon the purpose for which the excipient is provided and the identity of the excipient.

For example, suitable excipients that can also act as stabilizers for active agents include pharmaceutical grades of dextrose, sucrose, lactose, trehalose, mannitol, sorbitol, inositol, dextran, and the like. Such stabilizers may thus be a saccharide such as a monosaccharide, a disaccharide, a polysaccharide or a sugar alcohol. Other suitable excipients include starch, cellulose, sodium or calcium phosphates, calcium sulfate, citric acid, tartaric acid, glycine, and combinations thereof. Examples of hydrophobic excipients that can be added to slow hydration and dissolution kinetics include fatty acids and pharmaceutically acceptable salts thereof (e.g., magnesium stearate, steric acid, zinc stearate, palimitic acid, and sodium palitate).

It may also be useful to employ a charged lipid and/or detergent excipient in the compositions. Suitable charged lipids include, without limitation, phosphatidylcholines (lecithin), and the like. Detergents will typically be a non-ionic, anionic, cationic or amphoteric surfactant. Examples of suitable surfactants include, for example, Tergitol® and Triton® surfactants (Union Carbide Chemicals and Plastics); polyoxyethylenesorbitans, e.g., TWEEN® surfactants (Atlas Chemical Industries); polysorbates; polyoxyethylene ethers, e.g., Brij; pharmaceutically acceptable fatty acid esters, e.g., lauryl sulfate and salts thereof; amphiphilic surfactants (glycerides, etc.); and like materials.

Other excipient materials can be added to alter porosity, for example, materials like sucrose, dextrose, sodium chloride, sorbitol, lactose, polyethylene glycol, mannitol, fructose, polyvinyl pyrrolidone or appropriate combinations thereof. Additionally, the anesthetic agent or agents may be dispersed with oils (e.g., sesame oil, corn oil, vegetable, soybean oil, castor oil, peanut oil), or a mixture thereof with a phospholipid (e.g., lecithin), or medium chain fatty acid triglycerides (e.g., Miglyol 812) to provide an oily suspension.

Still further excipient materials that can be incorporated into the compositions include diluents of various buffer content (e.g., Tris-HCl, acetate); pH and ionic strength altering agents; additives such as antioxidants (e.g., ascorbic acid, glutathione, sodium metabisulfite); preservatives (e.g., Thimersol, benzyl alcohol, methyl paraben, propyl paraben); and dispersing agents such as water-soluble polysaccharides (e.g., mannitol, lactose, glucose, starches), hyaluronic acid, glycine, fibrin, collagen and inorganic salts (e.g., sodium chloride).

In certain cases, the non-polymeric carrier is substantially insoluble in water or in an aqueous biological system. Exemplary such non-polymeric carrier materials include, but are not limited to: sterols such as cholesterol, stigmasterol, β-sitosterol, and estradiol; cholestery esters such as cholesteryl stearate; $C_{12}$-$C_{24}$ fatty acids such as lauric acid, myristic acid, palmitic acid, stearic acid, arachidic acid, behenic acid, and lignoceric acid; $C_{18}$-$C_{36}$ mono-, di- and triacylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl didecenoate, glyceryl tridocosanoate, glyceryl trimyristate, glyceryl tridecenoate, glycerol tristearate and mixtures thereof; sucrose fatty acid esters such as sucrose distearate and sucrose palmitate; sorbitan fatty acid esters such as sorbitan monostearate, sorbitan monopalmitate and sorbitan tristearate; $C_{16}$-$C_{18}$ fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof, sphingosine and derivatives thereof; spingomyelins such as stearyl, palmitoyl, and tricosanyl spingomyelins; ceramides such as stearyl and palmitoyl ceramides; glycosphingolipids; lanolin and lanolin alcohols; and combinations and mixtures thereof. Certain preferred non-polymeric carriers include cholesterol, glyceryl monostearate, glycerol tristearate, stearic acid, stearic anhydride, glyceryl monocleate, glyceryl monolinoleate, and acetylated monoglycerides.

If one of the above-noted non-polymeric carrier materials is selected for use in a composition, it will typically be combined with a compatible and suitable organic solvent for the carrier material to form a composition having a consistency ranging from watery to viscous to a spreadable putty or paste. The consistency of the composition will vary according to factors such as the solubility of the non-polymeric carrier in the solvent, the concentration of the non-polymeric carrier, the concentration of the anesthetic agent and/or the presence of additional anesthetic agents, additives and excipients. The solubility of a non-polymeric carrier in a particular solvent will vary according to factors such as its crystallinity, hydrophilicity, ionic character and lipophilicity. Accordingly, the ionic character and the concentration of the non-polymeric carrier in the solvent can be adjusted to achieve the desired solubility. Preferred non-polymeric carrier materials are those that have low crystallinity, nonpolar characteristics, and are more hydrophobic.

Suitable organic solvents for use in the compositions are generally those that are biocompatible, pharmaceutically acceptable, and will at least partially dissolve the non-polymeric carrier. The organic solvent will further have a solubility in water ranging from miscible to soluble to dispersible. In certain cases, the solvent is selected such that it is capable of diffusing, dispersing, or leaching away from the composition in situ in an aqueous system and into fluids found at the administration site, thereby forming a solid implant. Preferably, the solvent has a Hildebrand solubility parameter of from 9 to 13 $(cal/cm^3)^{1/2}$. Preferably, the degree of polarity of the solvent is effective to provide at least 5% solubility in water.

Suitable organic solvents thus include, but are not limited to: substituted heterocyclic compounds such as N-methyl-2-pyrrolidone (NMP) and 2-pyrrolidone (2-pyrol); esters of carbonic acid and alkyl alcohols such as propylene carbonate, ethylene carbonate and dimethyl carbonate; fatty acids such as acetic acid, lactic acid and heptanoic acid; alkyl esters of mono-, di-, and tricarboxylic acids such as 2-ethyoxyethyl acetate, ethyl acetate, methyl acetate, ethyl lactate, ethyl butyrate, diethyl malonate, diethyl glutonate, tributyl citrate, diethyl succinate, tributyrin, isopropyl myristate, dimethyl adipate, dimethyl succinate, dimethyl oxalate, dimethyl citrate, triethyl citrate, acetyl tributyl citrate, glyceryl triacetate; alkyl ketones such as acetone and methyl ethyl ketone; ether alcohols such as 2-ethoxyethanol, ethylene glycol dimethyl ether, glycofurol and glycerol formal; alcohols such as ethanol and propanol; polyhydroxy alcohols such as propylene glycol, polyethylene glycol (PEG), glycerin (glycerol), 1,3-butyleneglycol, and isopropylidene glycol (2,2-dimethyl-1,3-dioxolone-4-methanol); Solketal; dialkylamides such as dimethylformamide, dimethylacetamide; dimethylsulfoxide (DMSO) and dimethylsulfone; tetrahydrofuran; lactones such as ε-caprolactone and butyrolactone; cyclic alkyl amides such as caprolactam; aromatic amides such as N,N-dimethyl-m-toluamide, and 1-dodecylazacycloheptan-2-one; and the like; and mixtures and combinations thereof. Preferred solvents include N-methyl-2-pyrrolidone, 2-pyrrolidone, dimethylsulfoxide, ethyl lactate, propylene carbonate, glycofurol, glycerol formal, and isopropylidene glycol.

In some cases, the organic solvent is present in an amount sufficient to dissolve the active pharmaceutical agent in the composition. For instance, the organic solvent may be present in the composition in an amount of at least 5 wt %, such as at least 10 wt %, at least 15 wt %, or at least 20 wt %, based on weight of the composition. The organic solvent may be present in the composition in an amount ranging from 5 wt % to 45 wt %, such as from 10 wt % to 35 wt %, from 15 wt % to 30 wt %, from 20 wt % to 25 wt %, or about 22 wt %, based on weight of the composition. The organic solvent may be provided in the composition in an amount of from 99.5 to 1 percent by weight relative to the total weight of the composition (wt %), in an amount of from 95 to 10 wt %, in an amount of from 75 to 25 wt %, or in an amount of from 60 to 40 wt %, depending upon the selected non-polymeric carrier, organic solvent, anesthetic agent, additive and/or excipient being used in the composition. In certain cases, the organic solvent diffuses or leaches away from the composition into an aqueous medium upon placement within a biological system, whereby the non-polymeric carrier material coagulates to form a solid matrix. In certain cases, the organic solvent diffuses or leaches away from the composition into an aqueous medium upon placement within a biological system, whereby the non-polymeric carrier material coagulates to form a semi-solid or gel. Preferably, the non-polymeric carrier solidifies in situ to form a solid matrix within 1 to 5 days after administration (implantation), preferably within 1 to 3 days, preferably within 2 hours.

In some cases, a triglyceride viscosity reducing agent is present in an amount ranging from 10 wt % to 50 wt %, 10 wt % to 35 wt %, 15 wt % to 30 wt %, or 20 wt % to 25 wt %, or about 15 wt %, 16 wt %, 17 wt %, 18 wt %, 19 wt %, 20 wt %, 21 wt %, 22 wt %, 23 wt %, 24 wt %, 25 wt %, 27 wt %, 28 wt %, 29 wt %, 30 wt %, 31 wt %, 32 wt %, 33 wt %, 34 wt %, or 35 wt % of the composition.

In some cases, an aprotic solvent is present in an amount ranging from 10 wt % to 35 wt %, 10 wt % to 30 wt %, 10 wt % to 20 wt %, 10 wt % to 15 wt %, or about 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt % 18 wt %, 19 wt %, or 20 wt % of the composition.

In some cases, compositions are provided wherein the non-polymeric carrier is a liquid. The liquid non-polymeric carrier is preferably a high viscosity liquid carrier material ("HVLCM") to be non-water soluble, and has a viscosity of at least 5,000 cP, (and optionally at least 10,000, 15,000; 20,000; 25,000 or even 50,000 cP) at 37° C. that does not crystallize neat under ambient or physiological conditions.

The term "non-water soluble" refers to a material that is soluble in water to a degree of less than one percent by weight under ambient conditions. The term "non-polymeric" refers to esters or mixed esters having essentially no repeating units in the acid moiety of the ester, as well as esters or mixed esters having acid moieties wherein functional units in the acid moiety are repeated a small number of times (i.e., oligomers). Generally, materials having more than five identical and adjacent repeating units or mers in the acid moiety of the ester are excluded by the term "nonpolymeric" as used herein, but materials containing dimers, trimers, tetramers, or pentamers are included within the scope of this term. When the ester is formed from hydroxy-containing carboxylic acid moieties that can further esterify, such as lactic acid or glycolic acid, the number of repeat units is calculated based upon the number of lactide or glycolide moieties, rather than upon the number of lactic acid or glycolic acid moieties, where a lactide repeat unit contains two lactic acid moieties esterified by their respective hydroxy and carboxy moieties, and where a glycolide repeat unit contains two glycolic acid moieties esterified by their respective hydroxy and carboxy moieties. Esters having 1 to 20 etherified polyols in the alcohol moiety thereof, or 1 to 10 glycerol moieties in the alcohol moiety thereof, are considered nonpolymeric as that term is used herein.

In a particular case, the HVLCM decreases in viscosity, in some cases significantly, when mixed with a solvent to form a low viscosity liquid carrier material ("LVLCM") that can be administered using standard medical devices. The LVLCM composition is typically easier to place in the body than a HVLCM composition, because it flows more easily into and out of syringes or other implantation means. It also can easily be formulated as an emulsion. The LVLCM can have any desired viscosity, but its viscosity is generally lower than the corresponding HVLCM. As an example, viscosity ranges for the LVLCM of less than approximately 6,000 cP, less than approximately 4,000 cP, less than approximately 1,000 cP, or less than 200 cP, are typically useful for in vivo applications.

The particular HVLCM used in the compositions can be one or more of a variety of materials. Suitable materials include nonpolymeric esters or mixed esters of one or more carboxylic acids. In a particular case, the ester is formed from carboxylic acids that are esterified with a polyol having from 2 to 20 hydroxy moieties, and which may include 1 to 20 etherified polyols. Particularly suitable carboxylic acids for forming the acid moiety of the ester of the HVLCM include carboxylic acids having one or more hydroxy groups, e.g., those obtained by ring opening alcoholysis of lactones, or cyclic carbonates or by the alcoholysis of carboxylic acid anhydrides. Amino acids are also suitable for forming esters with the polyol. In a particular case, the ester or mixed ester contains an alcohol moiety having one or more terminal hydroxy moieties that have been esterified with one or more carboxylic acids obtained by alcoholysis of a carboxylic acid anhydride, such as a cyclic anhydride.

Nonlimiting examples of suitable carboxylic acids that can be esterified to form the HVLCM include glycolic acid, lactic acid, ε-hydroxycaproic acid, serine, and any corresponding lactones or lactams, trimethylene carbonate, and dioxanone. The hydroxy-containing acids may themselves be further esterified through the reaction of their hydroxy moieties with additional carboxylic acid, which may be the same as or different from other carboxylic acid moieties in the material. Suitable lactones include, but are not limited to, glycolide, lactide, ε-caprolactone, butyrolactone, and valerolactone. Suitable carbonates include but are not limited to trimethylene carbonate and propylene carbonate.

The alcohol moiety of the ester or mixed ester may be derived from a polyhydroxy alcohol having from 2 to 20 hydroxy groups, and as indicated above, may be formed by etherifying 1 to 20 polyol molecules. Suitable alcohol moieties include those derived by removing one or more hydrogen atoms from: monofunctional $C_1$-$C_{20}$ alcohols, difunctional $C_1$-$C_{20}$ alcohols, trifunctional alcohols, hydroxy-containing carboxylic acids, hydroxy-containing amino acids, phosphate-containing alcohols, tetrafunctional alcohols, sugar alcohols, monosaccharides, and disaccharides, sugar acids, and polyether polyols. More specifically, the alcohol moieties may include one or more of: dodecanol, hexanediol, more particularly, 1,6-hexanediol, glycerol, glycolic acid, lactic acid, hydroxybutyric acid, hydroxyvaleric acid, hydroxycaproic acid, serine, ATP, pentaerythritol, mannitol, sorbitol, glucose, fructose, sucrose, glucuronic acid, polyglycerol ethers containing from 1 to 10 glycerol units, polyethylene glycols containing 1 to 20 ethylene glycol units.

In particular cases, at least one of the carboxylic acid moieties of the esters or mixed esters of the HVLCM comprise at least one oxy moiety In an even more particular case, each of the carboxylic acid moieties comprise at least one oxy moiety.

In another particular case, at least one of the carboxylic acid moieties of the esters or mixed esters contains 2 to 4 carbon atoms. In an even more particular case, each of the carboxylic acid moieties of the esters or mixed esters contains 2 to 4 carbon atoms.

In another more particular case, at least one of the carboxylic acid moieties of the ester or mixed ester has 2 to 4 carbon atoms and contains at least one oxy moiety. In another more particular case, each of the carboxylic acid moieties of the ester or mixed ester has 2 to 4 carbon atoms and contains at least one oxy moiety.

In a particular case, the HVLCM may be sucrose acetate isobutyrate (SAIB) or some other ester of a sugar alcohol moiety with one or more alkanoic acid moieties.

In a particular case, the HVLCM has a structure selected from the group consisting of:

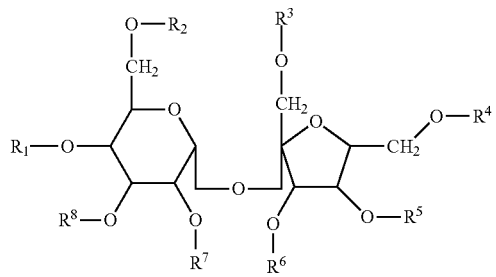

I wherein $R^1$, $R^2$, $R^3$, $R^4$, $R^5$, $R^6$, $R^7$, and $R^8$ are independently selected from the group consisting of hydrogen, alkanoyl, hydroxy-substituted alkanoyl, and acyloxy-substituted alkanoyl;

wherein at least three of $R^1$, $R^2$, $R^3$, $R^4$, $R^5$, $R^6$, $R^7$, and $R^8$ are other than hydrogen; and wherein when $R^1$, $R^2$, $R^3$, $R^4$, $R^5$, $R^6$, $R^7$, and $R^8$ are selected from the group consisting of acetyl and isobutyryl, at least three of $R^1$, $R^2$, $R^3$, $R^4$, $R^5$, $R^6$, $R^7$, and $R^8$ are acetyl;

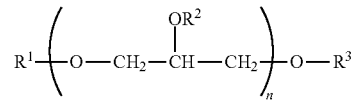

II wherein $R^1$, $R^2$, and $R^3$ are independently selected from the group consisting of hydrogen, alkanoyl, hydroxy-substituted alkanoyl, and acyloxy-substituted alkanoyl and wherein n is between 1 and 20;

$$R^1—O—(CH_2)_n—O—R^2 \quad \text{III:}$$

wherein n is an integer between 4 and 8, and $R^1$ and $R^2$ are independently selected from the group consisting of hydrogen, alkanoyl, hydroxy-substituted alkanoyl, and acyloxy-substituted alkanoyl;

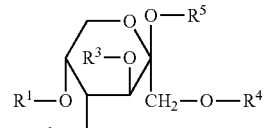

IV

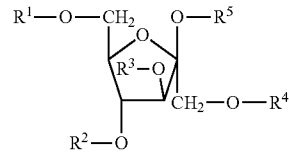

V wherein in formulae IV and V, $R^1$, $R^2$, $R^3$, $R^4$, and $R^5$ are independently selected from the group consisting of hydrogen, alkanoyl, hydroxy-substituted alkanoyl, and acyloxy-substituted alkanoyl;

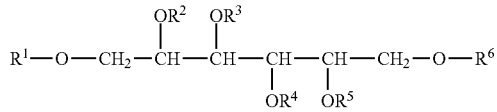

VI wherein in formulae VI and VII, $R^1$, $R^2$, $R^3$, $R^4$, $R^5$, and $R^6$ are independently selected from the group consisting of hydrogen, alkanoyl, hydroxy-substituted alkanoyl, and acyloxy-substituted alkanoyl;

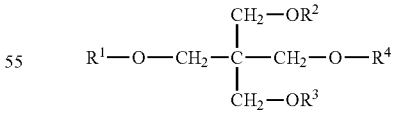

VIII wherein $R^1$, $R^2$, $R^3$, and $R^4$ are independently selected from the group consisting of hydrogen, alkanoyl, hydroxy-substituted alkanoyl, and acyloxy-substituted alkanoyl.

In each of formulae I through VIII, one or more of the alkanoyl, hydroxy-substituted alkanoyl, and acyloxy-substituted alkanoyl groups may comprise alkanoyl moieties having 2 to 6 carbon atoms, including the carbonyl carbon. Moreover, in another more particular case, each of formulae I through VIII comprise at least one hydroxy-substituted or acyloxy-substituted alkanoyl moiety. In an even more particular case, at least one of these hydroxy-substituted or acyloxy-substituted alkanoyl moieties comprise alkanoyl moieties having 2 to 6 carbon atoms, including the carbonyl carbon.

The acyl groups forming the acyloxy substituents of the HVLCM may be any moiety derived from a carboxylic acid in accordance with the commonly accepted definition of the term "acyl." More particularly, the acyl groups of the compositions may be of the form $R^9CO—$, where $R^9$ is optionally oxy-substituted alkyl of 2-6 carbon atoms. This oxy-substitution may take the form of hydroxy substitution, or substitution with additional acyl moieties. For example, $R^9$ may be an oligomer of oxy-substituted carboxylic acids, linked by ester bonding between the hydroxy of one acid and the carboxy of another acid. In a more particular example, $R^9$ may comprise 1 to 5 lactide or glycolide units, where a lactide unit contains two lactic acid moieties esterified together and a glycolide unit contains two glycolic acid moieties esterified together. Alternatively, $R^9$ may contain mixed lactide and glycolide units, or may contain mixed lactic acid and glycolic acid, without the presence of lactide or glycolide units.

Particular HVLCM materials include components according to formulae II or III, wherein $R^1$, $R^2$, and $R^3$ are independently lactoyl, polylactoyl, ε-caproyl, hydroxyacetyl, or polyhydroxyacetyl, in particular, polylactoyl and ε-caproyl, or polylactoyl and polyhydroxyacetyl.

The use of relatively small chain (2 to 6 carbon atoms), oxy-substituted carboxylic acid moieties in the ester or mixed ester is advantageous. When these acid moieties are present in the form of oligomeric esters (i.e., a subsequent acid moiety joined to the previous acid moiety through esterification of the subsequent carboxy with the previous oxy), hydrolysis of the material is considerably easier than for oligomers made with more than 6 carbon atoms because the material is more hydrophilic. In general, for drug delivery it is desired that the HVLCM be water insoluble, but it may be somewhat hydrophilic. In general, HVLCMs synthesized with more hydrophilic units (as determined by a higher O:C ratio) will be expected to absorb water more rapidly and degrade more quickly. For example, a HVLCM made by covalently linking 4 moles of glycolide to one mole of glycerol will be expected to absorb water more rapidly and degrade more quickly than a HVLCM made by covalently linking 2 moles of glycolide and 2 moles of lactide to one mole of glycerol. Similar increases can be expected for more flexible molecules and for more branched, spherical molecules based on free volume arguments. Use of flexible and branched molecules may also have the benefit of lowering the viscosity of the LVLCM. Using carboxylic acids and/or polyols of different chain length and using carboxylic acids having oxy-substitution allows a precise control of the degree of hydrophilicity and of the solubility of the resulting ester. These materials are sufficiently resistant to dissolution in vivo that they are able to provide a sustained release of a carried anesthetic agent into the body accompanied or followed by oxy bonds hydrolyzing in vivo.

In an even more particular case, the HVLCM excludes the acetate and isobutyrate ester of sucrose having a ratio of acetate to isobutyrate acid moieties of 2:6. However, sucrose acetate isobutyrate ester having a ratio of acetate to isobutyrate moieties of 2:6 is included within the scope for use in aerosol formulations. This material can be made according to the procedures described in U.S. Pat. No. 2,931,802.

In general, suitable HVLCM esters can be made by reacting one or more alcohols, in particular one or more polyols, which will form the alcohol moiety of the resulting esters with one or more carboxylic acids, lactones, lactams, carbonates, or anhydrides of the carboxylic acids which will form the acid moieties of the resulting esters. The esterification reaction can be conducted simply by heating, although in some instances addition of a strong acid or strong base esterification catalyst may be used. Alternatively, an esterification catalyst such as stannous 2-ethylhexanoate can be used. The heated reaction mixture, with or without catalyst, is heated with stirring then dried, e.g., under vacuum, to remove any un-reacted starting materials and produce a liquid product. Sucrose acetate isobutyrates can be made by following the procedures described in U.S. Pat. No. 2,931,802.

In this regard, the polyol can be viewed as an oligomerization initiator, in the sense that it provides a substrate for esterification of carboxylic acids, in particular, of oligomers of lactide, glycolide, or other esterified hydroxy-substituted carboxylic acids.

In certain cases, the HVLCM can be mixed with a viscosity-lowering solvent to form a lower viscosity liquid carrier material (LVLCM), which can then be mixed with the one or more anesthetic agent to be delivered, prior to administration. These solvents can be water soluble, non-water soluble, or water miscible, and can include, acetone, benzyl alcohol, benzyl benzoate, N-(betahydroxyethyl) lactamidebutylene glycol, caprolactam, caprolactone, corn oil, decylmethylsulfoxide, dimethyl ether, dimethyl sulfoxide, 1-dodecylazacycloheptan-2-one, ethanol, ethyl acetate, ethyl lactate, ethyl oleate, glycerol, glycofurol (tetraglycol), isopropyl myristate, methyl acetate, methyl ethyl ketone, N-methyl-2-pyrrolidone, MIGLYOLs® (esters of caprylic and/or capric acids with glycerol or alkylene glycols, e.g., MIGLYOL® 810 or 812 (caprylic/capric triglycerides), MIGLYOL® 818 (caprylic/capric/linoleic triglyceride), MIGLYOL® 829 (caprylic/capric/succinic triglyceride), MIGLYOL® 840 (propylene glycol dicaprylate/caprate)), oleic acid, peanut oil, polyethylene glycol, propylene carbonate, 2-pyrrolidone, sesame oil, SOLKETAL ([±]-2,2-dimethyl-1,3-dioxolane-4-methanol), tetrahydrofuran, TRANSCUTOL® (diethylene glycol monoethyl ether, carbitol), triacetin, triethyl citrate, diphenyl phthalate, and combinations thereof. Additionally, if the composition is to be applied as an aerosol, e.g., for topical application, the solvent may be or may include one or more propellants, such as CFC propellants like trichlorofluoromethane and dichlorofluoromethane, non-CFC propellants like tetrafluoroethane (R-134a), 1,1,1,2,3,3,3-heptafluoropropane (R-227), dimethyl ether, propane, and butane.

Particularly suitable solvents and/or propellants include benzyl benzoate, benzyl alcohol, triacetin, triethyl citrate, dimethyl sulfoxide, ethanol, ethyl lactate, glycerol, glycofurol (tetraglycol), N-methyl-2-pyrrolidone, MIGLYOL® 810, polyethylene glycol, propylene carbonate, 2-pyrrolidone, and tetrafluoroethane.

Other possible solvents include perfluorodecalin, perfluorotributylamine, methoxyflurane, glycerolformal, tetrahydrofurfuryl alcohol, diglyme, and dimethyl isosorbide.

When the composition is used as a LVLCM to administer the anesthetic agent, it should contain a solvent that the HVLCM is soluble in. In certain instances, the anesthetic agent is also soluble in the solvent. In still further instances, the solvent is a second anesthetic agent in which the first anesthetic agent is soluble. The solvent is preferably non-toxic and otherwise biocompatible.

In certain cases, the solvent is at least water soluble, so that it will diffuse quickly into bodily fluids or other aqueous environment upon administration, causing the composition to coagulate and/or become more viscous. In some cases, the solvent is not completely miscible with water or bodily fluids so that diffusion of the solvent from the composition, and the corresponding increase in viscosity of the composition, are slowed. Suitable solvents that have this property, at least to some extent, include benzyl benzoate, MIGLYOL® 810, benzyl alcohol, and triethylcitrate. Benzyl alcohol can be particularly suitable, as it also an anesthetic agent.

When esters of 1,6-hexanediol or glycerol are used as the HVLCM, some possible solvents are ethanol, N-methylpyrrolidone, propylene carbonate, and PEG 400.

The solvent is typically added to the compositions in an amount in the range from 99.7 percent to 0.5 percent by weight relative to the total weight of the composition (wt %), from 95 percent to 1 wt %, from 75 to 10 wt %, or from 50 to 15 wt %. The solvent is typically present in the composition in an amount in the range from 55 percent to 10 wt %.

In still further cases, the composition includes a material that is not miscible with the HVLCM, such that when combined with the HVLCM singularly or in combination with a solvent for the HVLCM, the resulting composition forms an emulsion. Such emulsions may contain the HVLCM in the dispersed phase, such as in the case of SAIB/MIGLYOL® mixtures that are emulsified in water or glycerol, or they may contain the HVLCM as a component of the continuous phase, such as in the case of an aqueous solution that is emulsified in the HVLCM or a solution of the HVLCM in a water immiscible solvent.

In some cases, the delivery vehicle or system contains a polyorthoester polymer and a polar aprotic solvent. Also disclosed are low viscosity delivery systems for administration of active agents. In some cases, the low viscosity delivery systems comprise a polyorthoester polymer, a polar aprotic solvent and a solvent containing a triglyceride viscosity reducing agent.

Polyorthoesters useful for the compositions provided herein are generally composed of alternating residues resulting from reaction of a diketene acetal and a diol, where each adjacent pair of diketene acetal derived residues is separated by the residue of a reacted diol. The polyorthoester may comprise .alpha.-hydroxy acid-containing subunits, i.e., subunits derived from an alpha.-hydroxy acid or a cyclic diester thereof, such as subunits comprising glycolide, lactide, or combinations thereof, i.e., poly(lactide-co-glycolide), including all ratios of lactide to glycolide, e.g., 75:25, 65:35, 50:50, etc. Such subunits are also referred to as latent acid subunits; these latent acid subunits also fall within the more general "diol" classification as used herein, due to their terminal hydroxyl groups. Polyorthoesters can be prepared as described, for example, in U.S. Pat. Nos. 4,549,010 and 5,968,543. Exemplary polyorthoesters suitable for use in the compositions provided herein are described in U.S. Pat. No. 8,252,304. The polyorthoester may be of the type and/or made as described in U.S. Pat. Nos. 8,252,305 and 10,213,510, which are herein incorporated by reference in their entireties.

The mole percentage of .alpha.-hydroxy acid containing subunits, $R^1$, generally ranges from 0 to 20 mol % of the total diol components ($R^1$ and $R^3$ as provided below). In one or more cases, the mole percentage of .alpha.-hydroxy acid containing subunits in the polyorthoester formulation is at least 0.01 mole percent. Exemplary percentages of .alpha.-hydroxy acid containing subunits in the polymer are from 0 to 50 mole percent, or from 0 to 25 mole percent, or from 0.05 to 30 mole percent, or from 0.1 to 25 mole percent. For example, in one case, the percentage of .alpha.-hydroxy acid containing subunits in the polymer is from 0 to 50 mole percent. In another case, the percentage of .alpha.-hydroxy acid containing subunits in the polymer is from 0 to 25 mole percent. In yet another particular case, the percentage of .alpha.-hydroxy acid containing subunits in the polymer is from 0.05 to 30 mole percent. In yet another case, the percentage of .alpha.-hydroxy acid containing subunits in the polymer is from 0.1 to 25 mole percent. As an illustration, the percentage of .alpha.-hydroxy acid containing subunits may be 0, 1, 2, 3, 4, 5, 6, 7, 8, 9, 10, 11, 12, 13, 14, 15, 16, 17, 18, 19, 20, 21, 22, 23, 24, 24, 26, 27, 28, 29 or 30 mole percent, including any and all ranges lying therein, formed by combination of any one lower mole percentage number with any higher mole percentage number.

Exemplary polyorthoesters possess a weight average molecular weight of 1000 Da to 200,000 Da, for example from 2,500 Da to 100,000 Da or from 3,500 Da to 20,000 Da or from 4,000 Da to 10,000 Da or from 5,000 Da to 8,000 Da. Illustrative molecular weights, in Da, are 2500, 5000, 5500, 6000, 6500, 7000, 7500, 8000, 8500, 9000, 9500, 10,000, 20,000, 30,000, 40,000, 50,000, 60,000, 70,000, 80,000, 90,000, 100,000, 120,000, 150,000, 175,000 and 200,000, and ranges therein, wherein exemplary ranges include those formed by combining any one lower molecular weight as described above with any one higher molecular weight as provided above, relative to the selected lower molecular weight.

In one particular case related to the polyorthoester in the delivery system, the polyorthoester has a molecular weight ranging from 2,500 daltons to 10,000 daltons.

In some cases, the polyorthoester comprises 40% to 75%, 40% to 60%, 45% to 55%, 65 to 75%, or about 40%, 45%, 50%, 55%, 60%, 65%, 70%, or 75% by weight of the composition.

In some cases, a sustained-release delivery vehicle is a polymeric formulation in the form of a semi-solid polymer formulation comprising a polyorthoester, the amide-type local anesthetic and a non-steroidal anti-inflammatory drug (NSAID). In some cases, the non-steroidal anti-inflammatory drug (NSAID) is an enolic-acid NSAID. Exemplary enolic-acid NSAID include meloxicam, piroxicam, tenoxicam, droxicam, lornoxicam, and isoxicam. In a specific case, the enolic-acid NSAID is meloxicam.

In some cases, a composition comprises:
1-5 wt % bupivacaine;
0.005-0.125 wt % meloxicam;
Optionally, maleic acid;
5-12 wt % dimethylsulfoxide or N-methylpyrrolidone;
10-40 wt % triacetin; and
55-67 wt % polyorthoester (e.g., having a Mw 2.5-10 kDa).

A number of suitable additives may be included with the composition in order to impart selected characteristics upon the composition. For example, they may include a minor amount of a biodegradable thermoplastic polymer such as a polylactide, polycaprolactone, polyglycolide, or copolymer thereof, in order to provide a more coherent solid implant or a composition with greater viscosity so as to hold it in place while it solidifies. Such thermoplastic polymers are disclosed in U.S. Pat. No. 4,938,763 to Dunn et al.

Optionally, a pore-forming agent can be included in the composition. The pore-forming agent can be any organic or inorganic, pharmaceutically-acceptable substance that is substantially soluble in water or body fluid, and will dissipate from the non-polymeric carrier material and/or the solid matrix of an implant into surrounding body fluid at the implant site. The pore-forming agent may preferably be insoluble in the organic solvent to form a uniform mixture with the non-polymeric carrier material. The pore-forming agent may also be a water-immiscible substance that rapidly degrades to a water-soluble substance. In certain compositions, the pore-forming agent is combined with the non-polymeric carrier and organic solvent in admixture. Suitable pore-forming agents that can be used in the composition include, for example, sugars such as sucrose and dextrose, salts such as sodium chloride and sodium carbonate, polymers such as hydroxylpropylcellulose, carboxymethylcellulose, polyethylene glycol and polyvinylpyrrolidone, and the like. Solid crystals that will provide a defined pore size, such as salt or sugar, are preferred.

As discussed above, a variety of additives can optionally be added to the compositions to modify the properties thereof, and in particular to modify the release properties of the composition with respect to the anesthetic agents contained therein. The additives can be present in any amount sufficient to impart the desired properties to the composition. The amount of additive used will in general be a function of the nature of the additive and the effect to be achieved, and can be easily determined by the routineer. Suitable additives are described in U.S. Pat. No. 5,747,058, the entire contents of which are hereby incorporated by reference. More particularly, suitable additives include water, biodegradable polymers, non-biodegradable polymers, natural oils, synthetic oils, carbohydrates or carbohydrate derivatives, inorganic salts, BSA (bovine serum albumin), surfactants, organic compounds, such as sugars, and organic salts, such as sodium citrate. In general, the less water soluble, i.e., the more lipophilic, the additive, the more it will decrease the rate of release of the anesthetic agent, compared to the same composition without the additive. In addition, it may be desirable to include additives that increase properties such as the strength or the porosity of the composition.

The addition of additives can also be used to lengthen the delivery time for the anesthetic agent, making the composition suitable for medical applications requiring or responsive to longer-term administration. Suitable additives in this regard include those disclosed in U.S. Pat. Nos. 5,747,058 and 5,736,152. In particular, suitable additives for this purpose include polymeric additives, such as cellulosic polymers and biodegradable polymers. Suitable cellulosic polymers include cellulose acetates, cellulose ethers, and cellulose acetate butyrates. Suitable biodegradable polymers include polylactones, polyanhydrides, and polyorthoesters, in particular, polylactic acid, polyglycolic acid, polycaprolactone, and copolymers thereof.

When present, the additive is typically present in the compositions in an amount in the range from 0.01 percent to 20 percent by weight, more particularly from 0.1 percent to 20 percent by weight, relative to the total weight of the composition, and more typically, is present in the composition in an amount in the range from 1, 2, or 5 percent to 10 percent by weight. Certain additives, such as buffers, are only present in small amounts in the composition.

The following categories are nonlimiting examples of classes of additives that can be employed in the compositions.

One category of additives are biodegradable polymers and oligomers. The polymers can be used to alter the release profile of the anesthetic agent to be delivered, to add integrity to the composition, or to otherwise modify the properties of the composition. Non-limiting examples of suitable biodegradable polymers and oligomers include: poly(lactide), poly(lactide-co-glycolide), poly(glycolide), poly(caprolactone), polyamides, polyanhydrides, polyamino acids, polyorthoesters, polycyanoacrylates, poly(phosphazines), poly(phosphoesters), polyesteramides, polydioxanones, polyacetals, polyketals, polycarbonates, polyorthocarbonates, degradable polyurethanes, polyhydroxybutyrates, polyhydroxyvalerates, polyalkylene oxalates, polyalkylene succinates, poly(malic acid), chitin, chitosan, and copolymers, terpolymers, oxidized cellulose, or combinations or mixtures of the above materials.

Examples of poly($\alpha$-hydroxy acid)s include poly(glycolic acid), poly(DL-lactic acid) and poly(L-lactic acid), and their copolymers. Examples of polylactones include poly($\varepsilon$-caprolactone), poly($\delta$-valerolactone) and poly($\gamma$-butyrolactone).

While not wishing to be bound by any theory, it is believed that when the composition contains a biodegradable polymer, a portion of the polymer may precipitate or coagulate at the surface of the composition as any included solvent diffuses away from the material after administration to the subject. The polymer may thus be added as a release modifying agent to affect the release of the anesthetic agent or agents, or may be added as part of a composition containing pre-formed microspheres, implants, or ground polymer particles. The precipitation or coagulation of the polymer forms a skin at least partially surrounding the liquid core of such composition. This skin is porous, and allows the solvent to continue to diffuse through it into surrounding tissue. The rate of solvent release and the extent of formation of the skin, as well as its porosity, can be controlled by the amount and type of solvent and polymer used in the composition.

Other additives for use with the present compositions are non-biodegradable polymers. Non-limiting examples of nonerodible polymers which can be used as additives include: polyacrylates, ethylene-vinyl acetate polymers, cellulose and cellulose derivatives, acyl substituted cellulose acetates and derivatives thereof, non-erodible polyurethanes, polystyrenes, polyvinyl chloride, polyvinyl fluoride, polyvinyl (imidazole), chlorosulphonated polyolefins, polyethylene oxide, and polyethylene.

Preferred non-biodegradable polymers include polyvinyl pyrrolidone, ethylene vinylacetate, polyethylene glycol, cellulose acetate butyrate ("CAB") and cellulose acetate propionate ("CAP").

A further class of additives which can be used in the present compositions are natural and synthetic oils and fats. Oils derived from animals or from plant seeds of nuts typically include glycerides of the fatty acids, chiefly oleic, palmitic, stearic, and linoleic. As a rule the more hydrogen the molecule contains the thicker the oil becomes.

Non-limiting examples of suitable natural and synthetic oils include vegetable oil, peanut oil, medium chain triglycerides, soybean oil, almond oil, olive oil, sesame oil, fennel oil, camellia oil, corn oil, castor oil, cotton seed oil, and soybean oil, either crude or refined, and medium chain fatty acid triglycerides.

Fats are typically glyceryl esters of higher fatty acids such as stearic and palmitic. Such esters and their mixtures are solids at room temperatures and exhibit crystalline structure. Lard and tallow are examples. In general oils and fats increase the hydrophobicity of a non-polymeric carrier system, slowing degradation and water uptake.

Any of the above-described sustained release delivery systems can be formulated as liquid, spray, cream, lotion, ointment, gel, slurry, oil, emulsion, microemulsion, solid, plaster, film, particle, microparticle, powder or other suitable form pharmaceutical compositions, suitable for use in the methods. In such compositions, the anesthetic agent (e.g., the first anesthetic agent) is included in an amount sufficient to deliver to the subject to be treated an effective amount to achieve a desired effect. The amount of anesthetic agent incorporated into the composition depends upon the final desired release duration and profile, and the concentration of anesthetic required for the intended effect.

Both soluble and insoluble anesthetic agents can be distributed using the non-polymeric carrier materials for sustained delivery. Moreover, the compositions may be further formulated with polymeric excipients to provide a delivery matrix with modified properties, for example a faster or slower degradation rate. The resulting composition may be formed into microspheres, or into a macroscopic implant, or other geometries and sizes according to techniques known in the art. Alternatively, a pre-formed microsphere, implant, or polymer particle with the anesthetic agent or agents incorporated therein can be combined with the non-polymeric carrier.

Microspheres may be prepared by a number of methods known in the art, as well as methods described in U.S. Pat. Nos. 6,291,013 and 6,440,493. The polymer particle may be formed using melt extrusion, granulation, solvent mixing, absorption, or like techniques, or the anesthetic agent may be adsorbed onto a polymer matrix, such as an ion exchange resin. The resulting material, when combined suitable non-polymeric carrier material may be administered parenterally. In other cases, the anesthetic agent may be combined with a non-polymeric material, such as calcium phosphate or sucrose, to provide layering/barrier properties that lengthen degradation. The non-polymeric carrier will then form a secondary barrier to provide enhanced delivery characteristics. The non-polymeric carrier phase may or may not contain other biologically active substances, according to the specific requirement of the selected application. These other biologically active agents may be any suitable therapeutic and/or prophylactic pharmaceutical, provided that the added substance is suitable for incorporation into microspheres or implants according to techniques known in the art.

All of the above-described compositions may be used in the methods of the present disclosure in order to provide sustained local anesthesia at a target site. In particular, the compositions may be formulated as liquid, spray, cream, lotion, ointment, gel, slurry, oil, emulsion, microemulsion, solid, plaster, film, particle, microparticle, powder or any other suitable pharmaceutical composition form and then administered to a subject via topical, ophthalmic, transdermal, parenteral (e.g, injection, implant, etc.) or like delivery techniques. The compositions, containing an anesthetic and a pharmaceutically acceptable non-polymeric carrier, are used to provide an anesthetic effect characterized by sustained local anesthesia after administration to the subject without an initial burst and a duration of at least 24 hours after administration, preferably 36 to 48 hours after administration, and more preferably 48 to 72 hours after administration. In certain cases, the onset of the local anesthesia occurs within 2 hours of administration to the subject, preferably within 1 hour of administration, and in some cases within 30 minutes of administration to the subject.

The term "subject," as used herein, refers to any vertebrate in which it is desired to provide a state of local anesthesia. The term thus broadly refers to any animal that is to be treated with the compositions of the present disclosure, such as birds, fish and mammals including humans. In certain cases, the methods of the present disclosure are suitable to provide sustained anesthesia in veterinary practice and animal husbandry, e.g., birds and mammals, whenever a long-term state of local anesthesia is convenient or desirable. In certain cases, the compositions are particularly suited for used with companion animals such as dogs or cats, and additionally may be used with horses. In preferred cases, the term "subject" intends a human subject. Furthermore, the term "subject" does not denote a particular age, and the compositions are thus suited for use with subjects of any age, such as infant, adolescent, adult and senior aged subjects.

In preferred cases, the compositions of the present disclosure are particularly suited for use in the treatment of wounds. The non-polymeric carrier systems allow the anesthetic agent or agents to be easily applied to the wound, either directly within the wound and/or adjacent to the wound, using very simple application techniques such dropping on, spraying, painting, spreading, molding or otherwise manually manipulating a liquid, spray, cream, lotion, ointment, gel, slurry, oil, emulsion, microemulsion, pliable solid or plaster, film, particle, microparticle, or powder composition into the wound. The compositions can thus be used with any sized or shaped wound, and will provide an even distribution of the anesthetic agent or agents over the entire area of the wound for better retention and efficacy. Wounds that can be treated using such methods my range for the most superficial to deep, from surface to incisional and from surgical (or otherwise deliberate) to accidental. If the composition is to be injected, it may be applied to the subcutaneous space using a trailing injection alongside the wound on all sides or outside boundaries. Combination approaches may also be employed, such as where the composition is both laid directly into the wound, e.g., prior to surgical closure of the sound, and additionally along the wound. In a particularly preferred case, the methods of the present disclosure involve the use of the instant compositions as a local anesthetic for treatment of post-operative incisional pain. Use of the present compositions in this manner may obviate or at least mitigate the necessity to provide adjunct therapies, such as the administration of systemic narcotic analgesics in order to treat such post-operative pain. Accordingly, the compositions may be used to treat post-operative pain that accompanies all types of medical procedures, such as major surgeries (e.g., thoracotomy, aortic repair, bowel resection), intermediate surgeries (e.g., cesarean section, hysterectomy and appendectomy), and minor surgeries (laparoscopy, arthroscopy, and biopsy procedures), that can otherwise be debilitating and may require pain treatment for 3 to 5 days after surgery. In some cases, methods produce analgesia in a subject undergoing at least one of arthroscopic subacromial decompression surgery, laparoscopic surgery, arthroscopic surgery, biopsy surgery, bony surgery, orthopedic surgery, thoracic surgery, soft tissue surgery, cholecystectomy surgery, colorectal surgery, colectomy surgery, hysterectomy surgery, appendectomy surgery, bunionectomy surgery, hemorrhoidectomy surgery, Caesarean section surgery, total knee arthroplasty surgery, abdominoplasty surgery, nerve block, herniorrhaphy surgery, hernia surgery, inguinal hernia repair surgery, resection liver surgery, resection of small bowel surgery, resection of stomach surgery, resection of spleen surgery, resection of gall bladder surgery, and resection of colon surgery.

The compositions described herein can thus be administered in the practice of the instant methods using a wide variety of methods. For example, the compositions may be administered topically, ophthalmically, systematically (for example, mucosally (orally, rectally, vaginally, or nasally), parenterally (intravenously, subcutaneously, intramuscularly, or intraperitoneally), or the like. The compositions may be applied via injection, pouring, spray dip, aerosol, or coating applicator. Aerosols or mists of the composition can be administered using an aerosol propellant, e.g., for topical administration, or using a suitable nebulizer, e.g., for nasal, or oral mucosal administration.

Preferably, the compositions are administered as liquids via injection, or in an aerosol, paste or emulsion. When used in an aerosol, any solvent present in the aerosol solution will typically evaporate upon application, allowing the composition to set-up as a film. Alternatively, the aerosol or emulsion may be prepared without a solvent. In this situation, the aerosol propellant can also function as a solvent. Formation of aerosols and emulsions can be accomplished using techniques known to those skilled in the art. See, for example, Ansel, H. C. et al., *Pharmaceutical Dosage Forms and Drug Delivery Systems*, Sixth Edition (1995).

In addition to the uses described above, the present compositions can be administered through osmotic pumps. In one case, a device is designed to be implanted in the tissue of the subject, and designed to effect sustained release over time.

It is also possible to administer the compositions using a porous or nonporous tube, desirably made of extruded biodegradable polymer. The tube may be prepared with varying degrees of porosity depending on the characteristics of the composition and the release characteristics desired. The composition is inserted into the tube, and the ends of the tube may be left open, allowing biologically active compound to diffuse out of the ends of the tube, or may be closed off with additional porous or nonporous polymer. Porous endcaps and porous tubes allow active compound to diffuse through the pores over time. Nonporous endcaps, as well as nonporous tubes, allow anesthetic agents that are soluble in the polymer to diffuse through it and into surrounding tissues. Nonporous materials that are not solvents for the anesthetic, but that are biodegradable, will release the anesthetic when they degrade sufficiently. The compositions may be prepared and stored as multi-component systems until ready for administration. The number of different components will depend, in part, on the characteristics of the composition. Prior to administration, the components are combined and mixed, e.g., to achieve a homogeneous composition, which can then be administered to the subject. Solvents or additives may be added to one or all of the components, or may form a separate component, which is also mixed with the others prior to administration. Separation of the composition into a multicomponent mixture allows the storage conditions for each component to be optimized, and minimizes any detrimental interactions between components over time. The result is increased storage stability.

EXAMPLES

The below examples are offered for illustrative purposes only, and are not intended to limit the scope of the present invention in any way.

Example 1

A gamma irradiation dose escalation study was conducted in which the level of the genotoxic degradant, 2,6-dimethylaniline, increased as a function of irradiation dose. A formulation was exposed to 0, 10, 20, or 35 kGy. The formulation consisted of 12 wt % bupivacaine, 66 wt % SAIB, and 22 wt % benzyl alcohol ("Formulation A").

As discussed below, even low level irradiation (10 kGy) of the product generated significant amounts of 2,6-dimethylaniline.

Abstract

Formulation A after terminal sterilization by gamma irradiation at nominal exposures of 10, 20, and 35 kGy showed color changes (light yellow to yellow), an increase of the major degradant bupivacaine N-oxide from 0.27% to 0.43-0.53%, an increase of the degradant 2,6-dimethylaniline (2,6-DMA) from a non-detected level to 0.02-0.08% (or 75-302 parts per million, or ppm), and an increase of unknown drug related degradant peaks from 2 peaks to 4-12 peaks, while the potency decreased from 98.9% to 96.1-97.1%, as determined by reverse phase HPLC.

Stability of Formulation A at 0, 10, 20, and 35 kGy was monitored at 25° C./60% RH and 40° C./75% RH for up to 20 months. The formulation color continued to darken from yellow to brown at 25° C./60% RH and became a darker brown at 40° C./75% RH. After 20 months at 25° C./60% RH, data from HPLC for the different irradiated groups showed an insignificant decrease in potency from the corresponding initial T=0 timepoint, a slight increase (0.09-0.19%) in bupivacaine N-oxide, no significant increase in 2,6-DMA, and a small increase (0.09-0.17%) in the total amount of degradants. The control and 10 kGy exposed formulations showed a slight increase in the numbers of unknown detected peaks compared to that of the 20 and 35 kGy exposed formulations.

Objective

The objective of this study was to evaluate the effect of different exposure levels of gamma irradiation on the stability of Formulation A. The target nominal dose levels of gamma irradiation were 10, 20, and 35 kGy, with a control that was not irradiated (0 kGy).

Background and Introduction

The composition of Formulation A was bupivacaine base/ sucrose acetate isobutyrate (SAIB)/benzyl alcohol (BA) at a % w/w ratio of 12/66/22, respectively. An unfiltered lot was filled into 200 vials, capped with non-siliconized Teflon stoppers, and sealed with aluminum crimp seals. The 200 vials were further divided into four groups of 50 vials each. One group was not irradiated, and the remaining three groups were terminally sterilized by gamma irradiation at 10, 20, and 35 kGy, respectively. All four groups were placed on stability at 25° C./60% RH and 40° C./75% RH in an upright position. A placebo lot exposed to similar gamma irradiation conditions as the active lot was used to identify those impurities related to the excipients, which were therefore excluded from the drug related degradant calculations.

The effect of gamma irradiation dose escalation was evaluated by a visual method and EP (European Pharmacopoeia) 2.2.2 (degree of coloration), and by HPLC. Tests were conducted on stability samples at 6 and 20 months at 25° C./60% RH, and at 3 and 20 months at 40° C./75% RH. Compositions of bupivacaine/sucrose acetate isobutyrate/ benzyl alcohol exhibited a light yellow coloration prior to gamma irradiation. Visual inspection and characterization by EP 2.2.2 was conducted to assess the extent to which the compositions formed darker yellow to brown coloration.

2,6-DMA is a potential genotoxic degradant resulting from degradation of the drug substance or drug product by hydrolysis of the amide bond in bupivacaine. Since 2,6-DMA exhibits a different response factor (RF) from that of bupivacaine, its relative response factor (RRF) from system suitability (SYS) solution injections was applied to convert the % 2,6-DMA value by peak area normalization to 2,6-DMA as expressed as ppm relative to bupivacaine base.

Scope

Physical and chemical stability data were generated for Formulation A after exposure to gamma irradiation at levels of 0 kGy (control), 10 kGy ($9.1_{min}$-$10.1_{max}$), 20 kGy ($19.2_{min}$-$22.0_{max}$), and 35 kGy ($31.7_{min}$-$36.0_{max}$). The stability of non-irradiated and gamma irradiated Formulation A samples was determined for up to 20 months at 25° C./60% RH and 40° C./75% RH. The product was characterized for visual appearance, visual color, potency and degradation products. Placebo vials were stored under the same conditions as that for the actives, and were tested to identify potential excipient related degradants that may form in the active Formulation A. These placebo excipient degradants were excluded from the degradation product calculations for Formulation A.

Equipment, Materials and Analytical Methods

The equipment and material used in this study are listed in the below Table 1.1.

TABLE 1.1

| Items | Vendor / Model |
| --- | --- |
| Bupivacaine Base | Orgamol |
| Benzyl Alcohol | JT Baker |
| Sucrose Acetate Isobutyrate (SAIB) | DURECT Corporation |
| Container | West Pharmaceutical, 10 mL Type 1 borosilicate glass vial |
| Bupivacaine Base Reference Standard | Orgamol |
| Bupivacaine N-Oxide Standard | Chemic Lab Inc |
| Benzaldehyde | Aldrich |
| 2,6-Dimethylaniline (DMA) | Spectrum |
| Benzyl Acetate | Aldrich |
| Benzyl Isobutyrate | Aldrich |
| EP color standards | Fluka |
| Stopper | West Pharmaceutical, 20 mm, 4432/50 gray, non-silconized Teflon faced rubber stopper |
| Seal | West Pharmaceutical, 20 mm flip off aluminum crimp seal |
| HPLC System | Agilent 1100 series |

Results and Discussion

Appearance (Clarity)

There was no noticeable change in solution clarity for non-irradiated and irradiated Formulation A at T=0 and on storage at both 25° C./60% RH and 40° C./75% RH for up to 20 months.

Degree of Coloration

Formulation A was exposed to different target irradiation levels (0, 10, 20, and 35 kGy). Table 1.2 summarizes the results for the formulation color changes due to the gamma-irradiation process, and after storage at 25° C./60% RH and 40° C./75% RH for up to 20 months.

TABLE 1.2

Degree of Coloration Visual Test for Formulation A Exposed to Nominal Gamma Irradiation Levels of 0, 10, 20 and 35 kGy Stored at 25° C./60% RH and 40° C./75% RH up to 20 Months Using EP 2.2.2

| Lot 1.1 | | Dose Level of Gamma Irradiation / EP reference Standard BY[1,2] | | | |
| --- | --- | --- | --- | --- | --- |
| Condition | Month[3] | 0 kGy | 10 kGy | 20 kGy | 35 kGy |
| 25° C./60% RH[4] | 1 | BY3 | BY1 | >BY1 | >BY1 |
| | | Lightly yellow | Yellow++ | Darker yellow | Darker Yellow |
| 25° C./60% RH[4] | 3 | >BY3 | >BY1 | >BY1 | >BY1 |
| | | Light yellow+ | Darker yellow | Darker yellow | Darker yellow |
| 25° C./60% RH[4] | 6 | >BY2 | >BY1 | >BY1 | >BY1 |
| | | Yellow+ | Darker yellow | Darker yellow | Darker yellow |
| 25° C./60% RH | 20[5] | >BY1 | <BO | <BO | BO |
| | | Darker yellow | Lightly brown yellow | Lightly brown yellow | Lightly brown yellow |
| 40° C./75% RH | 1 | BY2 | >BY1 | <BO | BO |
| | | Yellow | Darker yellow | Lightly brown yellow | Brown yellow |
| 40° C./75% RH | 3 | >BY1 | BO | BO | BO |
| | | Darker yellow | Brown yellow | Brown yellow | Brown yellow |
| 40° C./75%RH | 20[5] | <BX | BX | BX | BX |
| | | Lightly dark brown | Dark brown | Dark brown | Dark brown |

[1]EP standard BY series color ranking: BY1 (yellow) > BY2 (yellow) > BY3 (light yellow)

[2]Non-compendias standards from Fluka: BO = brown yellow, BX = dark brown. BX is a darker color than BO.

[3]1-month data results served as initial data.

[4]Color ranking (BY1) for irradiated Formulation A: $BY1_{35\ kGy} > BY1_{20\ kGy} > BY1_{10\ kGy}$

[5]Performed after vials were pulled and stored at ambient temperature for approximately 2 months.

Effect of Gamma-Irradiation

The results indicate that gamma irradiation increased the color in the formulations from light yellow (non-irradiated formulation) to yellow (exposed to irradiation), with each higher level of irradiation causing a darker yellow color.

Effect of Storage at 25° C./60% RH and 40° C./75% RH

For all 4 groups of formulation, the degree of coloration increased with time at both storage conditions, and the accelerated condition (40° C./75% RH) darkened the formulation color faster than that at 25° C./60% RH.

After 20 Months Storage:

Non-irradiated formulation changed color from light yellow (BY3) to darker yellow (>BY1) at 25° C./60% RH, and to dark brown (<BX) at 40° C./75% RH.

10 kGy exposed formulation changed color from yellow (BY1) to brown (<BO) at 25° C./60% RH, and to dark brown (BX) at 40° C./75% RH.

20 kGy exposed formulation changed color from darker yellow (>BY1) to brown (<BO) at 25° C./60% RH, and to dark brown (BX) at 40° C./75% RH.

35 kGy exposed formulation changed color from darker yellow (>BY1) to brown (BO) at 25° C./60% RH, and to dark brown (BX) at 40° C./75% RH.

Potency

Effect of Gamma Irradiation on Formulation A Stability

As shown in Table 1.3, the potency (% LS) of Formulation A at T=0 was affected by gamma irradiation. The % LS of Formulation A was 98.9%, 97.1%, 96.1% and 96.2% after target irradiations of 0, 10, 20 and 35 kGy, respectively.

compared to their corresponding T=0% LS values. After 20 months at 40° C./75% RH (the commercial product would not be stored under these conditions), the non-irradiated formulation potency decreased from 98.9% to 97.3%, while the gamma irradiated groups had no significant potency changes.

Degradation Products

Irradiation Effect on Formulation A at T=0

The major degradant, bupivacaine N-oxide, is formed by the oxidation of the amine group in bupivacaine. Table 1.3 lists the amounts of 2,6-DMA and bupivacaine N-oxide, and the total number of unknown detected peaks resulting from the gamma irradiation process for all four formulation groups.

2,6-DMA

The results show that for the non-irradiated Formulation A samples, 2,6-DMA was not detected by HPLC. However, as irradiation levels increased, the mean % 2,6-DMA increased to 0.02% (75 ppm) at 10 kGy exposure, 0.05% (189 ppm) at 20 kGy exposure, and 0.08% (302 ppm) at 35 kGy exposure.

Bupivacaine N-Oxide

The irradiation process at T=0 also increased the % bupivacaine N-oxide from 0.27% to 0.43%, 0.51% and 0.53% for samples exposed to 10, 20, and 35 kGy, respectively. The presence of bupivacaine N-oxide was confirmed by matching the retention time with the authentic material.

TABLE 1.3

Potency and Degradation Products Stability Testing for Formulation A Exposed to Nominal Gamma Irradiation Levels of 0, 10, 20 and 35 kGy and Analyzed by HPLC

| | | | | % Mean Degradation Products (all detected peaks) | | | |
|---|---|---|---|---|---|---|---|
| | | | | 2,6-Dimethylaniline (2,6-DMA) | | Total Number | % Mean |
| Storage Condition | Time | Irradiation Dose (kGy)[1] | Bupivacaine N-oxide | % (by Peak Area Normalization) | ppm (to Bupivacaine)[2] | of Unknown Detected Peaks (each <0.1%) | Label Strength Bupivacaine |
| Initial | 0 | 0 | 0.27 | Not Detected | Not Detected | 2 peaks | 98.9 |
| | | 10 | 0.43 | 0.02 | 75 | 4 peaks | 97.1 |
| | | 20 | 0.51 | 0.05 | 189 | 9 peaks | 96.1 |
| | | 35 | 0.53 | 0.08 | 302 | 12 peaks | 96.2 |
| 25° C./60% RH | 6 months | 0 | 0.31 | Not Detected | Not Detected | 3 peaks | 96.2 |
| | | 10 | 0.54 | 0.05 | 189 | 6 peaks | 96.7 |
| | | 20 | 0.61 | 0.06 | 226 | 8 peaks | 95.8 |
| | | 35 | 0.60 | 0.08 | 302 | 8 peaks | 94.6 |
| | 20 months | 0 | 0.36 | Not Detected | Not Detected | 5 peaks | 98.5 |
| | | 10 | 0.61 | 0.03 | 113 | 10 peaks | 97.5 |
| | | 20 | 0.70 | 0.06 | 226 | 9 peaks | 97.0 |
| | | 35 | 0.63 | 0.08 | 302 | 10 peaks | 96.6 |
| 40° C./75% RH | 3 months | 0 | 0.23 | Not Detected | Not Detected | 4 peaks | 97.1 |
| | | 10 | 0.47 | 0.04 | 151 | 5 peaks | 95.9 |
| | | 20 | 0.52 | 0.07 | 264 | 7 peaks | 95.5 |
| | | 35 | 0.45 | 0.09 | 340 | 7 peaks | 95.3 |
| | 20 months | 0 | 0.79 | 0.01[4] | 38 | 10 peaks | 97.3 |
| | | 10 | 0.72 | 0.04 | 151 | 13 peaks | 96.8 |
| | | 20 | 0.57 | 0.07 | 264 | 12 peaks | 96.1 |
| | | 35 | 0.47 | 0.09 | 340 | 12 peaks | 96.0 |

[1]The actual dose range for the nominal 10 kGy exposure was 9.1 to 11.1 kGy, for the nominal 20 kGy exposure it was 19.2 to 22.0 kGy, and for the nominal 35 kGy exposure it was 31.7 to 36.0 kGy.
[2]Calculation for ppm 2,6-DMA = % 2,6-DMA (by area normalization) × 10000/relative response factor (2.65). This relative response factor was determined for HPLC. Note that the results in this Table are reported as "ppm (to bupivacaine)." To convert from "ppm (to bupivacaine)" to ppm relative to total formulation, the above numbers should be multiplied by 0.12 considering that Formulation A comprises 12 wt % bupivacaine.

Stability at 25° C./60% RH and 40° C./75% RH

No significant changes in % LS were observed for non-irradiated Formulation A and the three groups of irradiated formulations after 20 months storage at 25° C./60% RH Total Number of Unknown Detected Peaks The irradiation process increased the total of unknown degradation peaks (each ≤0.1%) from 2 peaks at 0 kGy to 4, 9, and 12 peaks at 10, 20, and 35 kGy, respectively.

Total Degradation Products

The irradiation process increased the % total degradation products from 0.33% (non-irradiated) to 0.61% (10 kGy exposure), 0.87% (20 kGy exposure), and 0.94% (35 kGy exposure).

Irradiation Effect on Formulation A Stability at 25° C./60% RH 2,6-DMA

The 2,6-DMA was not detected in the non-irradiated Formulation A samples for up to 20 months at 25° C./60% RH (Table 1.3). The levels of 2,6-DMA in the irradiated samples did not significantly change during stability at 25° C./60% RH for up to 20 months.

Bupivacaine N-Oxide

There was a slight increase in the bupivacaine N-oxide by approximately 0.1 to 0.2% for each group after 20 months storage at 25° C./60% RH (Table 1.3).

Total Degradation Products

There was an insignificant increase of approximately 0.1 to 0.2% in the total amount of degradation products in each of the four groups after 20 months at 25° C./60% RH, as compared to the corresponding values at T=0.

Irradiation Effect on Formulation A Stability at 40° C./75% RH 2,6-DMA

The non-irradiated Formulation A samples after 3 months at 40° C./75% RH had no detectable amount of 2,6-DMA (Table 1.3). After 20 months at 40° C./75% RH, the non-irradiated samples had 0.01% (38 ppm) of 2,6-DMA. For the three irradiated groups of samples, the 2,6-DMA increased slightly (0.01 to 0.02%) from their respective T=0 values during storage at 40° C./75% RH. The final levels of 2,6-DMA after 20 months at 40° C./75% RH were 0.04% (151 ppm) in the 10 kGy-exposed samples, 0.07% (264 ppm) in the 20 kGy exposed samples, and 0.09% (340 pm) in the 35 kGy exposed samples.

Bupivacaine N-Oxide

The major degradant, bupivacaine N-oxide, increased from 0.27% to 0.79% in the non-irradiated samples, and increased from 0.43% to 0.72% in the 10 kGy exposed samples after 20-months storage at 40° C./75% RH (Table 1.3). There was no significant change in the bupivacaine N-oxide levels for the 20 and 35 kGy irradiated samples after 20-months at 40° C./75% RH.

Total Degradation Products

The data indicated that the % total degradants increased from 0.33% to 0.99% for the non-irradiated samples, and increased from 0.61% to 1.01% for the 10 kGy irradiated samples, after 20 months at 40° C./75% RH. The total degradants remained the same for the 20 kGy irradiated samples, and appeared to decrease slightly for the 35 kGy irradiated samples after 20 months at 40° C./75% RH.

Potency and Degradation Products at 20 Months

All four groups of Formulation A samples stored at both 25° C./60% RH and 40° C./75% RH for 20 months were also analyzed by HPLC for potency and degradation products. Similar trends in the % LS bupivacaine, % 2,6-DMA, % bupivacaine N-oxide, and % total degradants in the four groups of Formulation A were observed as that by HPLC.

Conclusion

The gamma irradiation exposure levels and storage conditions (temperature and time) affected both the degree of solution coloration and chemical stability of Formulation A. The formulation color changed from light yellow (before irradiation) to yellow (irradiation range 10 to 35 kGy), and to brown/dark brown (under typical stability storage conditions). Acceptable bupivacaine potency stability (% LS) was observed at 25° C./60% RH and 40° C./75% RH for up to 20 months for both the non-irradiated and irradiated samples. The gamma irradiation process induced the potential genotoxic degradant 2,6-DMA.

Example 2

Formulation A was made aseptically by the following process:
1. Add benzyl alcohol to mixing tank and heat to 40° C. (not to exceed 55° C.).
2. While mixing benzyl alcohol under slight vortex, add in pre-weighed bupivacaine base.
3. Mix for not less than 15 minutes.
4. Heat SAIB to approximately 60° C. (not to exceed 93° C.).
5. Weigh in SAIB.
6. Mix for not less than 45 minutes.
7. Perform in-process potency and bioburden testing.
8. Pressurize the tank with nitrogen gas to force the mixture through twin-series, 30", 0.22 fLm, sterilizing grade filters.
9. Fill the product into 10 mL glass vials.
10. Stopper the vials with 20 mm stoppers under a nitrogen environment.
11. Cap the vials with 20 mm aluminum crimp caps.
12. Inspect each vial.
13. Label and package as appropriate.

Two lots of the resulting formulation had good stability as shown in Table 2.1 and Table 2.2.

TABLE 2.1

Stability Data
Formulation A, Stored at 25° C./60% RH and 40° C./75% RH (Lot # 2.1, 7.5 mL)

| Tests (Acceptance Criteria) | Initial[1] 0 | 40° C./75% RH 1 month | 40° C./75% RH 2 months | 40° C./75% RH 3 months | 25° C./60% RH 3 months |
|---|---|---|---|---|---|
| Appearance | Clear solution | Clear solution | Clear solution | Clear solution | Clear solution |
| Assay (Release)[2] (95.0-105.0% Label Strength) | 98.6 (99.3, 99.4, 98.5, 98.1) | 99.1 (99.8,98.9, 98.5) | 98.3 (97.1, 98.9, 98.8) | 97.5 (97.4, 97.4, 97.6) | 97.6 (97.8, 97.5, 97.6) |
| Assay (Shelf-life)[2] (90.0-105.0% Label Strength) | 98.5, 98.1) | | | | |
| Individual Degradants[3] (Bupivacaine N-oxide ≤2.0%, all other individuals ≤0.2% by Area Normalization) | | | | | |
| 1) Bupivacaine N-oxide | 0.2 | 0.3 | 0.3 | 0.3 | 0.2 |
| 2) 2,6-Dimethylaniline | n.d. | n.d. | n.d. | n.d. | n.d. |
| Total Degradation Products[4] (≤3.0% by Area normalization) | 0.2 | 0.3 | 0.3 | 0.3 | 0.2 |

TABLE 2.1-continued

Stability Data
Formulation A, Stored at 25° C./60% RH and 40° C./75% RH (Lot # 2.1, 7.5 mL)

| | | Initial[1] | 40° C./75% RH | | | 25° C./60% RH |
|---|---|---|---|---|---|---|
| Tests (Acceptance Criteria) | | 0 | 1 month | 2 months | 3 months | 3 months |
| Drug Release (Criteria) % Cumulative Release Average (Range) | | | | | | |
| 1 hr | (0-10% of target) | 6 (5-6) | 5 (5-6) | 6 (5-6) | 6 (5-7) | 6 (5-6) |
| 4 hr | Report value | 17 (15-18) | 17 (17-18) | 17 (17-17) | 17 (17-18) | 17 (16-18) |
| 8 hr | Report value | 26 (23-28) | 27 (26-27) | 26 (26-27) | 27 (26-27) | 27 (26-27) |
| 12 hr | Report value | 37 (32-40) | 37 (35-39) | 37 (36-39) | 35 (34-37) | 36 (35-36) |
| 18 hr | (40-70% of target) | 54 (49-58) | 55 (53-58) | 55 (54-57) | 51 (48-54) | 53 (52-54) |
| 24 hr | Report value | 68 (64-71) | 68 (66-71) | 67 (65-70) | 63 (60-66) | 66 (64-68) |
| 36 hr | Report value | 85 (83-87) | 85 (83-86) | 85 (83-86) | 81 (79-84} | 84 (82-86) |
| 48 hr | Report value | 89 (88-91) | 89 (87-90) | 89 (87-89) | 88 (86-89) | 89 (88-90) |
| 72 hr | (75-105% of target) | 93 (91-96) | 92 (90-94) | 92 (89-93) | 90 (88-92) | 90 (88-92) |
| Degree of Coloration (Record results) | | BY4 | BY2 | BY1 | Darker than BY1 | RY2 |
| Volume in Container [5] (NLT 7.5 mL) | | 9.3-9.6 | Test not performed | Test not performed | Test not performed | Test not performed |
| Bacteria toxins (≤25 EV/mL); | | <24 | Test not performed | Test not performed | Test not performed | Test not performed |
| Particular Matter, Microscopy | | | | | | |
| (≥10 μm: ≤3000 particles/vial) | | 103, 110 | 22 | 4 | 16 | 183 |
| (≥25μm: ≤3000 particles/vial) | | 25, 31 | 5 | 1 | 3 | 29 |
| Sterility (meets USP/EP) | | Pass | Test not performed | Test not performed | Test not performed | Test not performed |

[1] Data at T = 0 are average of duplicate sets of samples. All other time points are average of one set of samples.
[2] Average and individual assay values are reported.
[3] Average values for degradants are reported. The excipient related degradation products (benzyl acetate and benzyl isobutyrate) are not reported in this table. Not detected (n.d.).
[4] The total degradation products are based on the sum of all individual degradants at or greater than 0.1%. Average values are reported.
[5] The range of values is reported.

TABLE 2.2

Stability Data
Formulation A Stored at 25° C./60% RH and 40° C./75% RH (Lot #2.2, 5 mL fill)

| Tests (Acceptance Criteria) | Initial[1] 0 | 40° C. 75% RH 1 month |
|---|---|---|
| Appearance | Clear solution | Clear solution |
| Assay (Release) [2] (95.0-105.0% Label Strength) | 98.6 (98.9, 98.3, 98.7) | 100.0 (101.2, 99.5, 99.4) |
| Assay (Shelf-life) [2] (90.0-105.0% Label Strength) | | |
| Individual Degradants (Bupivacaine N-oxide ≤ 2.0%, all other individuals ≤ 0.2% by Area Normalization) | | |
| 1) Bupivacaine N-oxide | 0.1 | 0.2 |
| 2) 2,6-Dimethylaniline | n.d. | n.d. |
| Total Degradation Products[3] (≤3.0% by Area normalization) | 0.1 | 0.2 |
| Drug Release (Criteria) | % Cumulative Release Average (Range) | |
| 1 hr (0-10% of target) | 6 (6-7) | 5 (5-7) |
| 4 hr Report value | 18 (17-18) | 16 (16-17) |
| 8 hr Report value | 27 (26-28) | 25 (25-26) |
| 12 hr Report value | 36 (34-37) | 34 (33-34) |
| 18 hr (40-70% of target) | 54 (49-58). | 55 (53-58) |
| 24 hr Report value | 66 (64-69) | 63 (62-65) |
| 36 hr Report value | 84 (81-87) | 82 (80-83) |
| 48 hr Report value | 90 (87-93) | 87 (85-88) |
| 72 hr (75-105% of target) | 92 (88-97) | 90 (88-91) |
| Degree of Coloration (Record results) | BY4 | BY2 |
| Volume in Container [4] (NLT 7.5 mL) | 6.1-6.2 | Test not performed |
| Bacteria toxins (≤25 EV/mL); | Test not performed | Test not performed |

TABLE 2.2-continued

Stability Data
Formulation A Stored at 25° C./60% RH and 40° C./75% RH (Lot #2.2, 5 mL fill)

| Tests (Acceptance Criteria) | Initial[1] 0 | 40° C. 75% RH 1 month |
|---|---|---|
| Particular Matter, Microscopy | | |
| (≥10 μm: ≤3000 particles/vial) | 3, 5 | 46 |
| (≥25 μm: ≤3000 particles/vial) | 1, 2 | 17 |
| Sterility (meets USP/EP) | Test not performed | Test not performed |

[1] Duplicate testing in particular matter were performed and individual values are reported
[2] Average and individual assay values are reported.
[3] The total degradation products are based on the sum of all individual degradants at or greater than 0.1%. Average values are reported.
[4] Range of values is reported from 10 vials.

Example 3

Formulation A was filled into glass vials under a nitrogen atmosphere. The oxygen content of the headspace in the vials was tested.

The data was collected on a Lighthouse Instruments Headspace Oxygen Analyzer Model FMS-760. A summary of the data is presented in the below Table 3.1, which shows the average, standard deviation, and % RSD for each lot (in wt % oxygen). BOR is Beginning of Run, MOR is Middle of Run, and EOR is End of Run indicating when vials were pulled for analysis during the filling run.

TABLE 3.1

| Lot | Oxygen Headspace Results (%) | | | Lot | Oxygen Headspace Results (%) | | |
|---|---|---|---|---|---|---|---|
| | BOR | MOR | EOR | | BOR | MOR | EOR |
| 1 | 7.2 | 6.8 | 6.9 | 2 | 5.8 | 7.7 | 8.6 |
|   | 5.1 | 6.7 | 6.2 |   | 7.5 | 8.0 | 7.7 |
|   | 5.5 | 6.9 | 6.6 |   | 7.6 | 7.8 | 7.0 |
|   | 6.5 | 6.4 | 6.3 |   | 6.4 | 7.1 | 6.5 |
|   | 6.4 | 6.6 | 7.3 |   | 7.6 | 9.4 | 7.2 |
|   | 5.8 | 7.1 | 7.5 |   | 7.8 | 7.4 | 7.3 |
|   | 6.3 | 6.3 | 6.0 |   | 7.7 | 7.4 | 7.9 |
|   | 5.9 | 7.1 | 6.3 |   | 6.8 | 8.3 | 9.5 |
|   | 6.0 | 7.0 | 8.5 |   | 6.2 | 8.2 | 8.9 |
|   | 6.2 | 6.6 | 6.9 |   | 7.7 | 7.4 | 8.3 |
|   | 6.4 | 7.0 | 6.7 |   | 6.3 | 7.1 | 8.7 |
|   | 5.8 | 6.4 | 6.5 |   | 6.6 | 7.5 | 8.2 |
|   | 5.6 | 6.4 | 7.4 |   | 7.6 | 7.3 | 8.3 |
|   | 6.6 | 6.6 | 6.6 |   | 7.4 | 8.5 | 8.6 |
|   | 6.0 | 7.1 | 7.1 |   | 7.6 | 7.0 | 7.4 |
| Average | 6.1 | 6.7 | 6.9 | Average | 7.1 | 7.7 | 8.0 |
| SD | 0.5 | 0.3 | 0.6 | SD | 0.7 | 0.6 | 0.8 |
| % RSD | 8.4 | 4.3 | 9.3 | % RSD | 9.5 | 8.4 | 10.2 |
| Grand Ave |   | 6.6 |   | Grand Ave |   | 7.6 |   |
| Grand SD |   | 0.6 |   | Grand SD |   | 0.8 |   |
| Grand % RSD |   | 9.1 |   | Grand % RSD |   | 10.5 |   |

Example 4

A study was conducted to determine the Appearance, Degree of Coloration of Liquids, Assay, and Degradation Products, including 2,6-Dimethylaniline, formed in Formulation A after exposure to accelerated light per ICH Q1B Guidance for Industry: "Photostability Testing of New Drug Substances and Products".

Experimental

Option 2 of the ICH Q1B guidance was followed for the accelerated light conditions. Option 2 states that the same sample should be exposed to both the cool white fluorescent and near ultraviolet lamp. The sources of controlled light were: a cool white fluorescent lamp designed to produce an output similar to that specified in ISO 10977 (1993); and a near UV fluorescent lamp having a spectral distribution from 320 nm to 400 nm with a maximum energy emission between 350 nm and 370 nm; a significant proportion of UV should be in both bands of 320 to 360 nm and 360 to 400 nm. Samples were exposed to light providing an overall illumination of not less than 1.2 million lux hours and an integrated near ultraviolet energy of not less than 200 watt hours/square meter. Three sets of samples, each placed alongside each other, from each lot were exposed to the accelerated light conditions of:

1) Unprotected vials, were directly illuminated.
2) Protected vials, were wrapped in aluminum foil. These were used as dark controls to evaluate the contribution of thermally induced change to the total observed change.
3) Protected vials, were in secondary containers or cartons. These cartons hold 10 vials (in a 2×5 configuration, with a plastic divider separating the two rows) and are composed of white clay coated chipboard of approximate dimensions 2.25×2.25×5.625 inches with a thickness of 0.020 inches. These cartons are from Royal Paper Box Company, Montebello, Calif., who sourced the chipboard material from Clearwater Paper Corporation, Spokane, Wash. using their Candesce CIS stock.

The samples were placed horizontally with respect to the light source.

Stability Results

Tables 4.1 and 4.2 show the photostability results for two different lots of Formulation A. The data in Tables 4.1 and 4.2 show that the amount of 2,6-dimethylaniline ranged from 36.1 to 54.1 ppm in the unprotected vials, far exceeding the specification limit of 10 ppm. The aluminum foil wrapped vials had 2,6-dimethylaniline ranging from 0.4 to 0.6 ppm. The protected vials in cartons had 2,6-dimethylaniline ranging from 1.4 to 1.7 ppm.

The bupivacaine N-oxide degradation product increased to 0.2% in the unprotected vials, but remained below quantitation limit in the aluminum foil wrapped and carton stored vials.

The average bupivacaine assay values were 1.0 to 1.20 higher in the vials stored in the cartons compared to the unprotected vials.

The results in Tables 4.1 and 4.2 show that a carton can sufficiently protect Formulation A from light induced degradation so the drug product remains within specifications.

TABLE 4.1

Photostability Data for Formulation A, Lot #4.1 Appearance, Degree of
Coloration of Liquids, Assay, Degradation Products, and 2,6-Dimethylaniline Test Results

|  |  |  | | Exposed to Accelerated Light (1,218,060 Lux hrs; 232 W hrs/m$^2$) | |
| --- | --- | --- | --- | --- | --- |
| Attributes | Test Method | Acceptance Criteria[1] | Un-protected | Protected-Wrapped in Aluminum Foil | Protected-Stored in Secondary Packaging- Unit Dose Carton |
| Appearance | Visual | Clear light yellow to brown liquid; essentially free of particulate matter | Clear light yellow liquid; essentially free of particulate matter | Clear yellow brown liquid; essentially free of particulate matter | Clear yellow brown liquid; essentially free of particulate matter |
| Degree of Coloration of Liquids | EP-2.2.2 | ≤6x BY1 | BY4 (with yellow tint) BY4 (with yellow tint) | BY3 BY3 | BY3 BY3 |
| Assay | HPLC with UV detector | 90.0-105.0% | 97.2 (97.1. 97.2) | 97.8 (97.7, 97.9) | 98.4 (98.6, 98.2) |
| Degradation Products |  |  |  |  |  |
| Bupivacaine N-oxide | HPLC with UV detector | ≤1.0% | 0.1 (0.1. 0.1) | BQL (BQL, BQL) | BQL (BQL, BQL) |
| Individual Unspecified Degradants |  | ≤0.2% | RRT = 0.79; BQL (BQL, BQL) | ND | ND |
| Total Degradation Products |  | ≤2.0% | 0.1 (0.1, 0.1) | <0.1 (<0.1, <0.1) | <0.1 (<0.1, <0.1) |
| Benzyl Acetate |  | ≤20 mg/mL | 3.4 (3.4, 3.4) | 3.4 (3.4, 3.4) | 3.4 (3.4. 3.4) |
| Benzyl Isobutyrate |  | ≤10 mg/mL | 1.4 (1.4, 1.4) | 1.4 (1.4, 1.4) | 1.5 (1.5, 1.4) |
| 2,6-Dimethylaniline | HPLC with Electrochemical detector | ≤10 ppm | 37.1 (36.1, 38.1) | 0.6 (0.5, 0.6) | 1.7 (1.7, 1.7) |

[1]Acceptance criteria were changed during the development.

TABLE 4.2

Photostability Data for Formulation A, Lot #4.2 Appearance, Degree of Coloration
of Liquids, Assay, Degradation Products, and 2,6-Dimethylaniline Test Results

|  |  |  | | Exposed to Accelerated Light (1,218,060 Lux hrs; 232 W hrs/m$^2$) | |
| --- | --- | --- | --- | --- | --- |
| Attributes | Test Method | Acceptance Criteria | Un-protected | Protected-Wrapped in Aluminum Foil | Protected-Stored in Secondary Packaging- Unit Dose Carton |
| Appearance | Visual | Clear light yellow to brown liquid; essentially free of particulate matter | Clear light yellow liquid; essentially free of particulate matter | Clear yellow brown liquid; essentially free of particulate matter | Clear yellow brown liquid; essentially free of particulate matter |
| Degree of Coloration of Liquids | EP-2.2.2 | ≤6x BY1 | BY4 (with yellow tint) BY4 (with yellow tint) | BY3 BY3 | BY3 BY3 |
| Assay | HPLC with UV detector | 90.0-105.0% | 98.7 (98.7, 98.7) | 99.9 (100.0, 99.7) | 99.7 (99.5, 99.8) |
| Degradation Products |  |  |  |  |  |
| Bupivacaine N-oxide | HPLC with UV detector | ≤1.0% | 0.2 (0.2, 0.2) | BQL (BQL, BQL) | BQL (BQL, BQL) |
| Individual Unspecified Degradants |  | ≤02% . | RRT = 0.57; BQL (BQL, BQL) RRT = 0.79; BQL (BQL, BQL) | RRT = 0.57; BQL (BQL. BQL) | RRT = 0.57; BQL (BQL, BQL) |
| Total Degradation Products |  | ≤2.0% | 0.2 (0.2, 0.2) | <0.1 (<0.1, <0.1) | <0.1 (<0.1, <0.1) |
| Benzyl Acetate |  | ≤20 mg/mL | 4.1 (4.1, 4.1) | 4.1 (4.1, 4.0) | 4.1 (4.1, 4.1) |
| Benzyl Isobutyrate |  | ≤10 mg/mL | 1.6 (1.6, 1.6) | 1.7 (1.7, 1.7) | 1.7 (1.6, 1.7) |
| 2,6-Dimethylaniline | HPLC with Electrochemical Detector | ≤10 ppm | 53.6 (54.1. 53.1) | 0.4 (0.4, 0.4) | 1.5 (1.4, 1.5) |

Formulation A should be protected from light, since photostability testing according to ICH Q1B has shown an increase of 2,6-dimethylaniline. The product is packaged in cartons to provide protection from light.

Example 5

Formulation A was tested for 2,6-dimethylaniline by electrochemical detection. For analysis, an aliquot of formulation was diluted 250 times with an aqueous buffer/methanol/acetonitrile diluent. After solubilization of the sample, a small aliquot is transferred into an HPLC vial for analysis using an electrochemical detector.

A series of experiments was conducted examining the effects of amber and red colored glassware on the stability of the 2,6-dimethylaniline reference standard, using electrochemical detection, at a concentration of 3 ng/mL in an aqueous buffer/methanol solution.

In Experiment 1, the 2,6-dimethylaniline was prepared at a concentration of 3 ng/mL in a clear, colorless glass 100 mL volumetric flask. Aliquots were transferred into clear HPLC glass vials, and assayed against external standards. The 3 injections of the 2,6-dimethylaniline were consistently near 3 ng/mL.

In Experiment 2, the 2,6-dimethylaniline solution at 3 ng/mL prepared in a clear, colorless glass 100 mL volumetric flask was transferred to amber HPLC vials. The 4 samples injected from the amber glass HPLC vials had a 2,6-dimethylaniline content approximately 8 to 12 times higher than the results in Experiment 1.

In Experiment 3, the 2,6-dimethylaniline was prepared at a concentration of 3 ng/mL in a red colored glass 100 mL volumetric flask that had a RAY-SORB® coating to protect from light. An aliquot was transferred into a clear HPLC glass vial, and assayed against external standards. The sample injection had the same 2,6-dimethylaniline concentration value as that in Experiment 1.

In Experiment 4, the 2,6-dimethylaniline solution at 3 ng/mL prepared in the red colored glass 100 mL volumetric flask coated with RAY-SORB® was transferred to an amber HPLC vial. The injected sample from the amber glass HPLC vial had a 2,6-dimethylaniline content approximately 5 times higher than the results in Experiment 1 and Experiment 3.

The conclusion from these experiments is that there is some component from the amber glass HPLC vials that reacts with 2,6-dimethylaniline, creating higher concentrations of 2,6-dimethylaniline, than when the 2,6-dimethylaniline solution is stored in clear glass HPLC vials.

TABLE 5.1

Concentration of 2,6-Dimethlylaniline Standard Stored in Different Color Glassware

| Experiment Number | Color of Volumetric Flask | Color of HPLC Vial | Observed Concentration of Standard (ng/mL) |
|---|---|---|---|
| 1 | Clear[1] | Clear[2] | 3.0, 3.0, 3.1 |
| 2 | Clear[1] | Amber[3] | 24.5, 28.4, 34.6, 38.1 |
| 3 | Red[4] | Clear[2] | 3.0 |
| 4 | Red[4] | Amber[3] | 14.9 |

[1]Clear, colorless, Kimble Glass volumetric flasks catalog 28014, are manufactured from "33 expansion", low extractables borosilicate glass, conforming to USP Type 1 and ASTM E438, Type 1, Class A requirements.
[2]Clear, colorless HPLC vials are from Thermo Fisher Scientific, catalog C40115W.
[3]Amber HPLC vials are from Agilent Technologies, Part Number: 5182-0545. Amber HPLC vials are manufactured by the addition of metal oxides to clear colorless glass. See Table 5.2 for typical composition of amber and clear glass.
[4]Red colored, Kimble Glass volumetric flasks catalog 28016, are manufactured from "33 expansion", low extractables borosilicate glass, conforming to USP Type 1 and ASTM E438, Type 1, Class A requirements, and then RAY-SORB® processed, which is a proprietary technology providing a consistent, durable, and uniform coating for light protection.

Table 5.2 lists the typical composition of clear and amber glass HPLC vials from Waters Corporation. The use of metal oxides, especially iron oxide and titanium oxide, imparts the amber color to the glass. The presence of these metals in amber glass HPLC vials is the probable reason for the analytically measured amounts of 2,6-dimethylaniline being significantly higher in amber HPLC vials compared to clear, colorless vials (Experiments 2 and 4, in Table 5.1). The results of this experiment suggest that the best way to protect the product from light (to reduce the impurities/degradants) is to fill the formulation into clear vials packaged in boxes or cartons rather than to fill the formulation into amber glass vials.

TABLE 5.2

| Type of Glass | Chemical Composition (main components in approx. wt %) | | | | | | | | |
|---|---|---|---|---|---|---|---|---|---|
| | $SiO_2$ | $B_2O_3$ | $Al_2O_3$ | $TiO_2$ | $Fe_2O_3$ | $Na_2O$ | $K_2O$ | BaO | CaO |
| Amber "51 expansion" | 69 | 10 | 6 | 3 | 1 | 6 | 2 | 2 | 0.5 |
| Clear "33 expansion" | 80 | 11 | 7 | | | 7 | 2 | <0.1 | 0.5 |

Example 6

Summary

The purpose of this study was to evaluate the compatibility of Formulation A with three different types of coated serum 20 mm, 4432/50 gray chlorobutyl rubber stoppers from West Pharmaceutical Services (West). The results of this study support the selection of the stopper that has FluroTec® coated on the top and bottom surfaces, West part number 19700038 (Drawing No. WS-792).

Background

Formulation A was filled into vials that were stoppered with 20 mm, Teflon faced, 4432/50 gray chlorobutyl rubber serum stoppers from West (part number 10144806) as part of the primary closure system. The Teflon face was in contact with the formulation. The manufacturing process was on a small scale, and the stoppers were manually inserted into the vials and crimped sealed. This stopper would need to be siliconized to allow for its use in high speed filling lines at a commercial facility because the top and edges of the stopper are not lubricated. The standard siliconization process for stoppers can introduce extractable silicone oil into the finished product, since silicone oil is readily soluble in Formulation A. Therefore, three other kinds of chemically resistant stoppers from West were evaluated that would be more appropriate for use at a commercial facility and would not require siliconization since they have various coatings on both the top and bottom surfaces.

The first serum stopper selected for study was coated with FluroTec on both surfaces, West part number 19700038 (20 mm, 4432/50 gray chlorobutyl rubber; Drawing No. WS-792). The FluroTec film was applied during the molding process of the stopper to the top (flange) and to the bottom (plug) surfaces of the stopper. FluroTec film provides an effective barrier against organic and inorganic stopper extractables to minimize interactions between the drug formulation and closure. The proprietary fluorocarbon film, made from a modified ethylene-tetrafluoroethylenene (ETFE) copolymer, also reduces the sorption of the drug product. In addition, the low surface energy of the FluroTec film provides sufficient lubricity, such that siliconization of the stopper is not needed, thus eliminating a potential source of contamination.

The second and third kinds of serum stoppers used in this study had another type of coating available from West, called B2-coating. The B2-coating is a cross-linkable high molecular weight polydimethylsiloxane coating that is applied to the surface of rubber stoppers. The B2-coating process minimizes the transfer of silicone oil into drug solutions. It also eliminates the need for conventional siliconization to facilitate manufacturing of the product. The B2 coated stoppers evaluated in this study only had the top surfaces coated to the maximum level (level 4), while the bottom surfaces were not coated (level 0). The West nomenclature used to describe the kind of coating applied to the stoppers in this study is B2-40. This B2-40 coating was applied to stoppers that had either a Teflon or a FluroTec coating on the bottom (plug) face. The Teflon and FluroTec coatings are similar, but not identical fluorinated copolymers. The stopper with B2-40 on the top with Teflon on the bottom is West part number 10144942 (20 mm, 4432/50 gray chlorobutyl rubber, Drawing No. WS-577), and the stopper with B2-40 on the top with FluroTec on the bottom is West part number 19700022 (20 mm, 4432/50 gray chlorobutyl rubber, Drawing No. WS-791). Although the amount of extractable silicone oil was significantly reduced with the B2 process, there were still measurable extractables. Because the stoppers were washed and sterilized in bulk, the B2-40 coating on the top of stoppers are randomly in contact with the bottom of other stoppers. Therefore there was the potential for silicone oil transfer onto the FluroTec and Teflon plug faces of these B2-40 coated stoppers, and thus transfer into the product.

Experimental Methods

Formulation Composition and Container/Closure System

Formulation A was prepared with bupivacaine base at 12% w/w, SAIB at 66% w/w, and benzyl alcohol at 22% w/w. The lot was filtered and filled (~8 mL each) into approximately 600 Type 1 10 mL glass vials (manufactured by Schott for West, part number 68000320.

About 200 vials were stoppered with each of the three different kinds of 20 mm stoppers from West. Table 6.1 summarizes the lot information for each set of packaged product. Aluminum crimp seals (West part number 54202059, DURECT code 3094, lots G0050 and G0106) were used to seal the product. To simulate the anticipated aseptic manufacturing process, the filled, stoppered vials were not terminally sterilized by gamma irradiation.

TABLE 6.1

Formulation A Packaged Lot and Packaging Information

| Formulation A Lot Number | Description of the Coated Stoppers for Each Lot Top (Flange)/Bottom (Plug) | West Part No. | West Lot No. | Drawing No. |
|---|---|---|---|---|
| 6.1 | FluroTec/FluroTec | 19700038 | J4204R | WS-792 |
| 6.2 | B2-40/Teflon | 10144942 | J5151B | WS-577 |
| 6.3 | B2-40/FluroTec | 19700022 | J6116 | WS-791 |

Stability Procedure

Ninety three (93) product filled vials of each kind of stopper were labeled and packaged in secondary containers (corrugated cartons), and placed on stability in the inverted position at 25° C./60% RH and 40° C./75% RH.

The analytical tests for the stability studies included appearance, identity, potency and related substances/degradation products. The identity test was performed at the initial time point only.

At the initial time point, two vials were used for assay and degradants testing instead of three vials. This did not impact the quality of the data in this study.

Although the study was set up with the intention to conduct testing up to 12 months at 25° C./60% RH, the study was stopped after analysis of the 6 months stability samples. The stability data for up to 6 months at both 25° C./60% RH and 40° C./75% RH were deemed sufficient to draw conclusions about the compatibility of Formulation A with the three different stoppers.

Visual appearance testing was only performed at initial and 1 month, and particulate matter testing (USP <788>) was only performed at 1 and 3 months. The practice during preparation of assay samples was to visually confirm a clear solution, free of particulates. These observations were not documented since they were as expected.

A visual color assessment test using EP 2.2.2 color standards of the brown yellow (BY series, 2 mL ampoules from Fluka, part number 83952) was added at initial and at 1 month (25° C./60% RH and at 40° C./75% RH). This test was discontinued after 1 month since the sample color was darker than BY1, which is the darkest in the set. The test was conducted by one analyst with confirmation of the visual color assessment by a second analyst. To conduct the test, 1 mL of formulation was transferred into a clear 1.8 mL HPLC glass vial and it was measured under ambient laboratory light against commercial color standards in 2 mL glass ampoules. The inner diameter, or light pathlength, of the 2 mL ampoules (9.53 mm) for the standards was essentially the same as that of the 1.8 mL glass vials (10.03 mm) used for the samples.

Results and Discussion

Tables 6.2 and 6.3 list the results for the three different types of stopper. Testing included visual appearance, solution color by EP 2.2.2 (brown yellow, BY series), assay and degradants by HPLC, and particulate matter by microscopy (USP <788>). For ease of comparison of the stopper data, Table 6.4 summarizes the average % LS bupivacaine, the % remaining bupivacaine relative to the initial values, the % bupivacaine N-oxide and the total % degradants.

TABLE 6.2

Stability Data at 25° C./60% RH for Stoppers with Formulation A

| Attribute | Method | Stopper Top/Bottom Coatings | Initial | 1 Month | 3 Months | 6 Months |
|---|---|---|---|---|---|---|
| | | | | 25° C./60% RH | | |
| Appearance[1] | Visual (EP 2.2.2) | FluroTec / FluroTec | Clear light yellow liquid. (Darker than BY5) | Clear brown yellow liquid (BY3) | not determined not determined | not determined not determined |
| | | B2-40/ Teflon | Clear light yellow liquid. (Darker than BY5) | Clear brown yellow liquid (BY3) | not determined not determined | not determined not determined |
| | | B2-40/ FluroTec | Clear light yellow liquid, (Darker than BY5) | Clear brown yellow liquid (BY3) | not determined not determined | not determined not determined |
| Identity | HPLC | All Stoppers | Bupivacaine is present | not determined | not determined | not determined |
| Assay | HPLC | FluroTec/ FluroTec | 100.9% LS (101.5, 100.2) | 100.5% LS (100.4, 100.7, 100.4) | 99.5% LS (99.9, 98.9, 99.7) | 102.2% LS (101.6, 102.4, 102.7) |
| | | B2-40/ Teflon | 99.8% LS (99.7, 99.8) | 99.8% LS (100.3, 99.5, 99.5) | 98.3% LS (99.2, 98.1, 97.5) | 100.2% LS (100.2, 100.2, 100.2) |
| | | B2-40/ FluroTec | 101.5% LS (101.5, 101.4) | 99.3% LS (99.4, 99.4, 99.1) | 99.4% LS (99.7, 98.5, 99.9) | 100.3% LS (100.5, 100.3, 100.1) |
| Degradation Products | HPLC | FluroTec/ FluroTec | % Bupivacaine N-oxide 0.2% (0.2%, 0.2%) Unknown RRT = 0.24 0.05-0.06% | % Bupivacaine N-oxide 0.1% (0.1%, 0.1%, 0.1%) Unknown RRT = 0.24 0.04-0.04% | % Bupivacaine N-oxide 0.2% (0.2%, 0.2%, 0.2%) Unknown RRT = 0.28 0.04-0.05% | % Bupivacaine N-oxide 0.2%(0.2%, 0.2%, 0.2%) Unknown RRT = 0.28 0.05-0.05% |
| | | B2-40/ Teflon | % Bupivacaine N-oxide 0.1% (0.1%, 0.2%) Unknown RRT = 0.24 0.04-0.06% | % Bupivacaine N-oxide 0.1% (0.1%, 0.1%, 0.1%) Unknown RRT = 0.24 0.04-0.04% | % Bupivacaine N-oxide 0.2% (0.2%, 0.2%, 0.2%) Unknown RRT = 0.28 0.04-0.04% | % Bupivacaine N-oxide 0.2% (0.2%, 0.2%, 0.2%) Unknown RRT = 0.28 0.05-0.05% |
| | | B2-40/ FluroTec | % Bupivacaine N-oxide 0.1% (0.1%, 0.1%) Unknown RRT = 0.24 0.04-0.04% | % Bupivacaine N-oxide 0.1% (0.1%, 0.1%, 0.1%) Unknown RRT = 0.24 0.04-0.05% | % Bupivacaine N-oxide 0.2% (0.2%, 0.2%, 0.2%) Unknown RRT = 0.28 0.05-0.05% | % Bupivacaine N-oxide 0.2% (0.2%, 0.2%, 0.2%) Unknown RRT 0.28 0.05-0.05% |
| Particulate Matter | USP <788> | FluroTec/ FluroTec | Not Determined | Not Determined | ≥10 μm particles/vial: 30 ≥25 μm particles/vial: 3 | ≥10 μm particles/vial: 18 ≥25 μm particles/vial: <10[2] |
| | | B2-40/ Teflon | Not Determined | Not Determined | ≥10 μm particles/vial: 57 ≥25 μm particles/vial: 3 | ≥10 μm particles/vial: 42 ≥25 μm particles/vial: 3 |
| | | B2-40/ FluroTec | Not Determined | Not Determined | ≥10 μm particles/vial: 45 ≥25 μm particles/vial: <10[2] | ≥10 μm particles/vial: 42 ≥25 μm particles/vial: 9 |

[1] Clear liquid, free of particulate matter, yellow to brown. In addition to the visual appearance test, a visual color assessment using EP color standards of the BY series was also performed and verified by a second analyst. The color result is for information only.
[2] A value of <10 indicates that no particles were detected.

TABLE 6.3

Stability Data at 40° C./75% RH for Stoppers with Formulation A

| Attributes | Method | Stopper Coatings Top/Bottom | Initial | 1 Month | 3 Months | 6 Months |
|---|---|---|---|---|---|---|
| | | | | 40° C./75% RH % | | |
| Appearance[1] | Visual (EP 2.2.2) | FluroTec/ FluroTec | Clear light yellow liquid. (Darker than BY5) | Clear brown yellow liquid (BY2) | not determined not determined | not determined not determined |
| | | B2-40/ Teflon | Clear light yellow liquid. (Darker than BY5) | Clear brown yellow liquid (BY2) | not determined not determined | not determined not determined |
| | | B2-40/ FluroTec | Clear light yellow liquid. (Darker than BY5) | Clear brown yellow liquid (BY2) | not determined not determined | not determined not determined |
| Assay | HPLC | FluroTec/ FluroTec | 100.9% LS (101.5, 100.2) | 98.0% LS (100.3, 99.6, 92.6[2], 98.1[2], 98.0, 99.2)[2] | 99.2% LS (99.6, 98.8, 99.2) | 100.9% LS (100.6, 100.4, 101.6) |
| | | B2-40/ Teflon | 99.8% LS (99.7, 99.8) | 99.1% LS (99.9, 98.5, 98.9) | 99.0% LS (98.9, 97.9, 100.2) | 100.6% LS (99.7, 100.9, 101.1) |
| | | B2-40/ FluroTec | 101.5% LS (101.5, 101.4) | 99.1% LS (99.0, 99.1, 99.3) | 98.2% LS (98.1, 98.1, 98.4) | 100.7% LS (100.3, 101.3, 100.6) |
| Degradation Products | HPLC | FluroTec/ FluroTec | % Bupivacaine N-oxide 0.2% (0.2%, 0.2%) Unknown RRT = 0.24 0.05-0.06% | % Bupivacaine N-oxide 0.1% (0.1%, 0.1%, 0.1%) Unknown RRT = 0.24 0.04-0.04% | % Bupivacaine N-oxide 0.3% (0.3%, 0.3%, 0.2%) Unknown RRT = 0.28 0.04-0.05% | % Bupivacaine N-oxide 0.3%(0.3%, 0.3%, 0.3%) Unknown RRT = 0.28, RRT = 0.30 0.05-0.05%; 0.01-0.02% |

TABLE 6.3-continued

Stability Data at 40° C./75% RH for Stoppers with Formulation A

| Attributes | Method | Stopper Coatings Top/Bottom | Initial | 40° C./75% RH % | | |
|---|---|---|---|---|---|---|
| | | | | 1 Month | 3 Months | 6 Months |
| | | B2-40/Teflon | % Bupivacaine N-oxide 0.1% (0.1%, 0.2%) Unknown RRT = 0.24 0.04-0.06% | % Bupivacaine N-oxide 0.1% (0.1%, 0.1%, 0.1%) Unknown RRT = 0.24 0.04-0.04% | % Bupivacaine N-oxide 0.3% (0.3%, 0.3%, 0.3%) Unknown RRT = 0.28 0.04-0.05% | % Bupivacaine N-oxide 0.3% (0.3%, 0.3%, 0.3%) Unknown RRT = 0.28, RRT = 0.30 0.05-0.05%; 0.02-0.02% |
| | | B2-40/FluroTec | % Bupivacaine N-oxide 0.1% (0.1%, 0.1%) Unknown RRT = 0.24 0.04-0.04% | % Bupivacaine N-oxide 0.1% (0.1%, 0.1%, 0.1%) Unknown RRT = 0.24 0.04-0.05% | % Bupivacaine N-oxide 0.3% (0.3%, 0.3%, 0.3%) Unknown RRT = 0.28 0.05-0.05% | % Bupivacaine N-oxide 0.3% (0.3%, 0.3%, 0.3%) Unknown RRT = 0.28, RRT = 0.30 0.04-0.05%; 0.01-0.02% |
| Particulate Matter | USP <788> | FluroTec/FluroTec | Not Determined | ≥10 μm particles/vial: 10 ≥25 μm particles/vial: <50 | >10 μm particles/vial: 48 ≥25 μm particles/vial: <10[3] | ≥10 μm particles/vial: 18 ≥25 μm particles/vial: <10 |
| | | B2-40/Teflon | Not Determined | ≥10 μm particles/vial: 10 ≥25 μm particles/vial: <50 | ≥10 μm particles/vial: 45 ≥25 μm particles/vial: 3 | ≥10 μm particles/vial: 36 ≥25 μm particles/vial: <10 |
| | | B2-40/FluroTec | Not Determined | ≥10 μm particles/vial: 25 ≥25 μm particles/vial: <50 | ≥10 μm particles/vial: 39 ≥25 μm particles/vial: <10 | ≥10 μm particles/vial: 93 ≥25 μm particles/vial: 3 |

[1]Clear liquid, free of particulate matter, yellow to brown. In addition to the visual appearance test, a visual color assessment using EP color standards of the BY series was also performed and verified by a second analyst. The color result is for information only.
[2]The initial value from vial #3 was 92.6%. Because of this out of trend result, another sample was prepared from the same vial, giving a value of 98.1%. During the retest of vial #3, two new vials were sampled and tested. Thus a total of five vials were tested, of which two samples came from vial five vials are reported, and the resulting average was 98.0%.
[3]A value of <10 indicates that no particles were detected.

TABLE 6.4

Chemical Compatibility of Formulation A Packaged with Three Different Types of Stoppers at 25° C./60% RH and 40° C./75% RH for up to 6 Months

| Storage Conditions | Month | Stopper Coatings Top/Bottom | | | | | | | | | | |
|---|---|---|---|---|---|---|---|---|---|---|---|---|
| | | FluroTec/FluroTec | | | | B2-40/Teflon | | | | B2-40/FluroTec | | | |
| | | % LS | % Remaining | % N-oxide | % Total Degradants | % LS | % Remaining | % N-oxide | % Total Degradants | % LS | % Remaining | % N-oxide | % Total Degradants |
| Initial | 0 | 100.9 | 100.0 | 0.2 | 0.2 | 99.8 | 100.0 | 0.1 | 0.1 | 101.5 | 100.0 | 0.1 | 0.1 |
| 25° C./60% RH | 1 | 100.5 | 99.6 | 0.1 | 0.1 | 99.8 | 100.0 | 0.1 | 0.1 | 99.3 | 97.8 | 0.1 | 0.1 |
| | 3 | 99.5 | 98.6 | 0.2 | 0.2 | 98.3 | 98.5 | 0.2 | 0.2 | 99.4 | 97.9 | 0.2 | 0.2 |
| | 6 | 102.2 | 101.3 | 0.2 | 0.2 | 100.2 | 100.4 | 0.2 | 0.2 | 100.3 | 98.8 | 0.2 | 0.2 |
| 40° C./75% RH | 1 | 98.0 | 97.1 | 0.1 | 0.1 | 99.1 | 99.3 | 0.1 | 0.1 | 99.1 | 97.6 | 0.1 | 0.1 |
| | 3 | 99.2 | 98.3 | 0.3 | 0.3 | 99.0 | 99.2 | 0.3 | 0.3 | 98.2 | 96.7 | 0.3 | 0.3 |
| | 6 | 100.9 | 100.0 | 0.3 | 0.3 | 100.6 | 100.8 | 0.3 | 0.3 | 100.7 | 99.2 | 0.3 | 0.3 |

Appearance and Solution Color

The visual appearance of all the samples with different types of stoppers were "clear light yellow liquid" at initial, "clear brown yellow liquid" at 1 month for 25° C./60% RH, and "clear brown yellow liquid" at 1 month for 40° C./75% RH. Using EP 2.2.2 BY color standards (color increases from BY7 to BY1), all the samples at initial were darker than BY5, at 1 month at 25° C./60% RH they were BY3, and at 1 month at 40° C./75% RH they were BY2. The product's color increased as a function of storage temperature and time. The different types of stoppers did not affect the visual appearance of product.

Particulate Matter

Particulate matter was tested by the microscopic method (USP<788>), and the data were similar among the three types of stoppers at 25° C./60% RH for 3 and 6 months (Table 6.2), and at 40° C./75% RH for 1, 3 and 6 months (Table 6.3). The data were significantly below the small volume parenteral specifications of: ≥10 μm: ≤3000 particles/vial and ≥25 μm: ≤300 particles/vial.

Assay and Degradants

The % LS bupivacaine data was similar for each of the type of stoppers after 6 months at both 25° C./60% RH and 40° C./75% RH. Bupivacaine N-oxide (the major product degradant) exhibited similar minor increases over time at 25° C./60% RH and 40° C./75% RH for each of the stoppers. The unknown degradant profiles at RRT 0.24, 0.28, and 0.30 was the same for all three types of stoppers through 6 months at 25° C./60% RH and 40° C./75% RH.

A review of the data summarized in Table 6.4 indicates that there are no formulation stability differences between the stoppers.

Conclusions

In conclusion, the three stoppers had similar physical and chemical performances with Formulation A. Although the B2-40 process is a way of applying a more controlled, less amount of silicone than conventional siliconization, the potential still exists for some extractable silicone to be solubilized in the formulation due to the presence of benzyl alcohol. Therefore, the recommendation is to pursue the FluroTec/FluroTec stopper, since this will avoid the use of any type of silicone, including B2.

Example 7

Sucrose acetate isobutyrate was tested for metal content as follows. The sample was prepared with a 0.1 g weighed portion mixed with 2 mL nitric acid and 0.5 mL hydrochloric acid for 1 hour on a block digester set at 110° C. After cooling, 0.5 mL of 30% hydrogen peroxide was added, and the digestion resumed for 30 minutes (the material appeared dissolved). After cooling, internal standard solution was added and dilution with purified water to 20 g produced a solution for ICP-MS analysis.

The results are shown below:

| Element | ppm | Detection Limit |
|---|---|---|
| Aluminum | ND | 0.8 |
| Antimony | ND | 0.02 |
| Arsenic | ND | 0.02 |
| Barium | ND | 0.02 |
| Beryllium | ND | 0.02 |
| Bismuth | ND | 0.02 |
| Boron | ND | 0.5 |
| Bromine | ND | 2 |
| Cadmium | ND | 0.02 |
| Calcium | ND | 40 |
| Cerium | ND | 0.02 |
| Cesium | ND | 0.02 |
| Chromium | ND | 0.2 |
| Cobalt | ND | 0.8 |
| Copper | ND | 0.3 |
| Dysprosium | ND | 0.02 |
| Erbium | ND | 0.02 |
| Europium | ND | 0.02 |
| Gadolinium | ND | 0.02 |
| Gallium | ND | 0.02 |
| Germanium | ND | 0.02 |
| Gold | 0.4 | 0.02 |
| Hafnium | ND | 0.02 |
| Holmium | ND | 0.02 |
| Iodine | ND | 0.05 |
| Iridium | ND | 0.05 |
| Iron | 2 | 1 |
| Lanthanum | ND | 0.02 |
| Lead | ND | 0.02 |
| Lithium | ND | 0.02 |
| Lutetium | ND | 0.1 |
| Magnesium | ND | 1 |
| Manganese | ND | 0.04 |
| Mercury | ND | 0.1 |
| Molybdenum | ND | 0.02 |
| Neodymium | ND | 0.02 |
| Nickel | ND | 0.02 |
| Niobium | ND | 0.02 |
| Osmium | ND | 0.08 |
| Palladium | ND | 0.06 |
| Phosphorus | ND | 2 |
| Platinum | ND | 0.02 |
| Potassium | ND | 5 |
| Praseodymium | ND | 0.02 |
| Rhenium | ND | 0.02 |
| Rhodium | ND | 0.02 |
| Rubidium | ND | 0.02 |
| Ruthenium | ND | 0.03 |
| Samarium | ND | 0.02 |
| Selenium | ND | 0.1 |
| Silver | ND | 0.02 |
| Sodium | ND | 8 |
| Strontium | ND | 0.08 |
| Tantalum | ND | 0.02 |
| Tellurium | ND | 0.02 |
| Thallium | ND | 0.2 |
| Thorium | ND | 0.03 |
| Thulium | ND | 0.02 |
| Tin | 0.06 | 0.04 |
| Titanium | ND | 0.2 |
| Tungsten | ND | 0.02 |
| Uranium | ND | 0.02 |
| Vanadium | ND | 0.06 |
| Ytterbium | ND | 0.02 |
| Yttrium | ND | 0.04 |
| Zinc | ND | 0.09 |
| Zirconium | ND | 0.02 |

Formulation A was compounded using steel compounding tanks. Silicone tubing was used to transfer Formulation A. Formulation A was filled into glass vials, which were then sealed with fluorocarbon-coated stoppers.

Formulation A was tested for metal content as follows. The sample was prepared with a 0.2 g weighed portion mixed with 2 mL nitric acid, 1 mL hydrochloric acid, and 1 mL hydrofluoric acid, then digested in a closed-vessel microwave system (the material appeared dissolved). After cooling, internal standard solution was added and dilution with purified water to 50 g produced a solution for ICP-MS analysis.

The results are shown below:

| Element | ppm | Detection Limit |
|---|---|---|
| Aluminum | ND | 0.6 |
| Antimony | ND | 0.03 |
| Arsenic | ND | 0.07 |
| Barium | ND | 0.02 |
| Beryllium | ND | 0.02 |
| Bismuth | ND | 0.02 |
| Boron | ND | 0.2 |
| Bromine | ND | 1000 |
| Cadmium | ND | 0.02 |
| Calcium | ND | 2 |
| Cerium | ND | 0.02 |
| Cesium | ND | 0.02 |
| Chromium | ND | 0.07 |
| Cobalt | ND | 0.02 |
| Copper | ND | 0.04 |
| Dysprosium | ND | 0.02 |
| Erbium | ND | 0.02 |
| Europium | ND | 0.02 |
| Gadolinium | ND | 0.02 |
| Gallium | ND | 0.02 |
| Germanium | ND | 0.02 |
| Gold | ND | 0.07 |
| Hafnium | ND | 0.05 |
| Holmium | ND | 0.02 |
| Iodine | ND | 0.1 |
| Iridium | ND | 0.02 |
| Iron | ND | 1 |
| Lanthanum | ND | 0.02 |
| Lead | ND | 0.02 |
| Lithium | ND | 0.04 |
| Lutetium | ND | 0.5 |
| Magnesium | ND | 1 |
| Manganese | ND | 0.02 |
| Mercury | ND | 0.04 |
| Molybdenum | ND | 0.02 |
| Neodymium | ND | 0.02 |
| Nickel | ND | 0.02 |
| Niobium | ND | 0.6 |
| Osmium | ND | 0.2 |
| Palladium | ND | 0.02 |
| Phosphorus | ND | 5 |
| Platinum | ND | 0.02 |
| Potassium | ND | 10 |
| Praseodymium | ND | 0.02 |

-continued

| Element | ppm | Detection Limit |
| --- | --- | --- |
| Rhenium | ND | 0.02 |
| Rhodium | ND | 0.02 |
| Rubidium | ND | 0.02 |
| Ruthenium | ND | 0.02 |
| Samarium | ND | 0.02 |
| Selenium | ND | 0.1 |
| Silver | ND | 0.02 |
| Sodium | ND | 6 |
| Strontium | ND | 0.02 |
| Tantalum | ND | 20 |
| Tellurium | ND | 0.02 |
| Thallium | ND | 0.02 |
| Thorium | ND | 0.03 |
| Thulium | ND | 0.02 |
| Tin | ND | 0.02 |
| Titanium | ND | 0.05 |
| Tungsten | ND | 0.5 |
| Uranium | ND | 0.02 |
| Vanadium | ND | 0.02 |
| Ytterbium | ND | 0.02 |
| Yttrium | ND | 0.02 |
| Zinc | ND | 2 |
| Zirconium | ND | 0.1 |

Example 8

Formulation A and placebo compositions were evaluated for water content. Formulation A in this study included 12% w/w bupivacaine, 66% w/w sucrose acetate isobutyrate (SAIB), and 22% w/w benzyl alcohol, as described above. Placebo compositions were composed of 75% w/w sucrose acetate isobutyrate (SAIB), and 25% w/w benzyl alcohol.

Filters used during aseptic preparation of Formulation A and placebo compositions can include residual water content resulting in compositions having a detectable amount of water. To ensure that water content is minimized or altogether absent from prepared bupivacaine compositions, filters used during aseptic preparation are: 1) tested for integrity by measuring the bubble point of the filter with pressurized sterile water for injection; 2) purged with nitrogen for not less than 5 minutes at 50 psi to remove any residual water in the filter; and 3) bupivacaine composition (e.g., Formulation A containing 12% w/w bupivacaine or placebo composition) is flushed through the filter with the filtrate being discarded. In this example, not less than 6 liters of Formulation A was flushed through the filters before collecting sample composition into vials.

The water content in sample vials collected at the beginning, middle and end of the collection process was evaluated. The water content of the collected sample vials was compared to the water content of bupivacaine composition in the filtrate flushed through the filters. Historical water content from sample vials collected during previous sample preparation runs was also compared.

Methods
Materials
 1) Placebo Composition
  Preparation Filter flushes (1 L, 2 L, 3 L, 4 L, 5 L, and 6 L), and vials from the Beginning, Middle, and End of Run
 2) Formulation A—Sample 1
 Preparation Filter flushes (1 L, 2 L, 3 L, 4 L, 5 L, and 6 L), and vials from the Beginning, Middle, and End of Run
 3) Formulation A—Sample 2
 Preparation Filter flushes (1 L, 2 L, 3 L, 4 L, 5 L, 6 L, 7 L, 8 L, 9 L, and 10 L); and vials from the Beginning, Middle, and End of Run.
 4) Vials from Formulation A: A1, B1, C1, D1, E1, F1, G1, and H1, and I1.
 5) Vials from placebo composition A Water Content Testing Samples were tested according to USP <921>, Method 1c, using an EM Science Aquastar C3000 Coulometric Titrator. Due to the high viscosity of the formulation, the samples required dilution with methanol prior to introduction into the Coulometric Titrator. Approximately 0.5 g of Formulation A or placebo composition was accurately weighed into a 10 mL vial. An approximately equal amount of methanol was added and the weight accurately recorded. If a sample, such as the manufacturing line flushes, was known to have a high amount of water, then proportionally more methanol was mixed with the sample. Each vial was then sealed and shaken vigorously for at least 30 seconds.

Approximately 0.5 g of the sample/methanol mixture was delivered into the Coulometric Titrator by liquid injection. The syringe used to deliver the sample was weighed before and after injection to determine the amount assayed.

Results

Placebo Composition

Table 8.1 summarizes the water content results for the 6 one-liter preparation filter flushes for placebo composition. Each one liter of flush was typically tested in duplicate; with the results being very consistent. The first one liter of product flush was essentially all water. Subsequent flushes steadily reduced the water content to approximately 0.58% by the 6$^{th}$ liter. Table 8.2 shows the water content of the finished placebo composition in vials collected from the beginning, the middle, and the end of the filling process. Each vial was assayed in duplicate, with the results being very consistent. The average vial water content results in Table 8.2 were approximately 0.35% for the beginning, 0.19% for the middle, and 0.30% for the end of filling.

TABLE 8.1

Water Content in Preparation Filter Flushes of placebo composition determined by Karl Fischer Titration

| Flush Fraction | Sample ID | % Water Content (Typically Two Injections per Flush Fraction) | % Water Content (Average for Flush Fraction) |
| --- | --- | --- | --- |
| 1$^{st}$ Liter | Placebo-1L-1 | 96.4341 | 96.4341 |
| 2$^{nd}$ Liter | Placebo-2L-1 | 2.3669 | 2.3641 |
|  | Placebo-2L-2 | 2.3613 |  |
| 3$^{rd}$ Liter | Placebo-3L-1 | 1.0225 | 1.0290 |
|  | Placebo-3L-2 | 1.0354 |  |
| 4$^{th}$ Liter | Placebo-4L-1 | 0.8726 | 0.8825 |
|  | Placebo-4L-2 | 0.8924 |  |
| 5$^{th}$ Liter | Placebo-5L-1 | 0.7625 | 0.7607 |
|  | Placebo-5L-2 | 0.7588 |  |
| 6$^{th}$ Liter | Placebo-6L-1 | 0.5669 | 0.5821 |
|  | Placebo-6L-2 | 0.5972 |  |

TABLE 8.2

Water Content in placebo composition samples by Karl Fischer Titration

| Location of Vial from Lot | Sample ID | % Water Content (Two Injections per Vial) | % Water Content (Vial Average) | % Water Content (Location Average) |
|---|---|---|---|---|
| Beginning of Run (BOR) | Placebo-BOR-1-1 | 0.2970 | 0.2918 | 0.3496 |
| | Placebo-BOR-1-2 | 0.2866 | | |
| | Placebo-BOR-2-1 | 0.4125 | 0.4075 | |
| | Placebo-BOR-2-2 | 0.4024 | | |
| Middle of Run (MOR) | Placebo-MOR-1-1 | 0.1997 | 0.1926 | 0.1906 |
| | Placebo-MOR-1-2 | 0.1854 | | |
| | Placebo-MOR-2-1 | 0.1940 | 0.1887 | |
| | Placebo-MOR-2-2 | 0.1833 | | |
| End of Run (EOR) | Placebo-EOR-1-1 | 0.4165 | 0.4103 | 0.3022 |
| | Placebo-EOR-1-2 | 0.4040 | | |
| | Placebo-EOR-2-1 | 0.2037 | 0.1942 | |
| | Placebo-EOR-2-2 | 0.1847 | | |

Formulation A—Sample 1

Table 8.3 summarizes the water content results for the 6 one-liter preparation filter flushes for Formulation A. Testing was done in the same manner as for the placebo compositions. The first one liter of product flush was essentially all water. Subsequent flushes steadily reduced the water content to approximately 1.06% by the 6$^{th}$ liter. Table 8.4 shows the water content of the finished product in vials collected from the beginning, the middle, and the end of the filling process. The average vial water content results in Table 8.4 were approximately 0.35% for the beginning, 0.11% for the middle, and 0.11% for the end of filling.

TABLE 8.3

Water Content in Preparation Filter Flushes of bupivacaine composition-Sample 1 determined by Karl Fischer Titration

| Flush Fraction | Sample ID | % Water Content (Typically Two Injections per Flush Fraction) | % Water Content (Average for Flush Fraction) |
|---|---|---|---|
| 1$^{st}$ Liter | Bupivacaine S1-1L-1 | 96.9996 | 96.9996 |
| 2$^{nd}$ Liter | Bupivacaine S1-2L-1 | 2.4935 | 2.5835 |
| | Bupivacaine S1-2L-2 | 2.6734 | |
| 3$^{rd}$ Liter | Bupivacaine S1-3L-1 | 2.0673 | 2.0556 |
| | Bupivacaine S1-3L-2 | 2.0438 | |
| 4$^{th}$ Liter | Bupivacaine S1-4L-1 | 1.6314 | 1.6156 |
| | Bupivacaine S1-4L-2 | 1.5997 | |
| 5$^{th}$ Liter | Bupivacaine S1-5L-1 | 1.1264 | 1.1270 |
| | Bupivacaine S1-5L-2 | 1.1275 | |
| 6$^{th}$ Liter | Bupivacaine S1-6L-1 | 1.0605 | 1.0559 |
| | Bupivacaine S1-6L-2 | 1.0512 | |

TABLE 8.4

Water Content in sustained release bupivacaine composition samples-Sample 1 by Karl Fischer Titration

| Vial ID | Sample ID | % Water Content (Two Injections per Vial) | % Water Content (Vial Average) | % Water Content (Location Average) |
|---|---|---|---|---|
| Beginning of Run | Bupivacaine S1-BOR-1-1 | 0.3123 | 0.3102 | 0.3467 |
| | Bupivacaine S1-BOR-1-2 | 0.3080 | | |
| | Bupivacaine S1-BOR-2-1 | 0.3808 | 0.3833 | |
| | Bupivacaine S1-BOR-2-2 | 0.3858 | | |
| Middle of Run | Bupivacaine S1-MOR-1-1 | 0.1083 | 0.1096 | 0.1119 |
| | Bupivacaine S1-MOR-1-2 | 0.1108 | | |
| | Bupivacaine S1-MOR-2-1 | 0.1114 | 0.1143 | |
| | Bupivacaine S1-MOR-2-2 | 0.1171 | | |
| End of Run | Bupivacaine S1-EOR-1-1 | 0.1105 | 0.1099 | 0.1058 |
| | Bupivacaine S1-EOR-1-2 | 0.1092 | | |
| | Bupivacaine S1-EOR-2-1 | 0.1020 | 0.1018 | |
| | Bupivacaine S1-EOR-2-2 | 0.1016 | | |

Formulation A—Sample 2

The objective of the evaluation was to examine if the water content between the last liter of flush could be more consistent with the values obtained in the vials from the beginning of the filling process. For Formulation A, Sample 2, the nitrogen pressure was increased from 50 to 55 psi, and was blown through the filters for not less than 5 minutes. In addition, 10 liters of formulation was flushed through the filters instead of 6 liters as in the previous lots.

The water content for these 10 liters of flushes for Formulation A, Sample 2 is shown in Table 8.5. The 1$^{st}$ one liter of flush started at approximately 2.41% water. This is in contrast to the placebo compositions and Formulation A, Sample 1 (Tables 8.1 and 8.3, respectively) which were greater than 99% water. The increased pressure of the nitrogen purging step of the filters for Sample 2 resulted in less water in the filters prior to flushing the product through it. The water content steadily decreased with the number of flushes, with 0.39% water detected in the 10$^{th}$ one-liter flush. Table 8.6 shows that the average water content of the finished product in vials collected from the beginning, the middle, and the end of the filling process were 0.20%, 0.08%, and 0.06%, respectively.

TABLE 8.5

Water Content in Preparation Filter Flushes of placebo composition-Sample 2 determined by Karl Fischer Titration

| Flush Fraction | Sample ID | % Water Content (Two Injections per Flush Fraction) | % Water Content (Average for Flush Fraction) |
|---|---|---|---|
| 1$^{st}$ Liter | Bupivacaine S2 1L Flush-1 | 2.3215 | 2.4076 |
| | Bupivacaine S2 1L Flush-2 | 2.4936 | |
| 2$^{nd}$ Liter | Bupivacaine S2 2L Flush-1 | 2.0838 | 2.0499 |
| | Bupivacaine S2 2L Flush-2 | 2.0159 | |
| 3$^{rd}$ Liter | Bupivacaine S2 3L Flush-1 | 1.1442 | 1.1378 |
| | Bupivacaine S2 3L Flush-2 | 1.1313 | |
| 4$^{th}$ Liter | Bupivacaine S2 4L Flush-1 | 0.7282 | 0.7327 |
| | Bupivacaine S2 4L Flush-2 | 0.7371 | |
| 5$^{th}$ Liter | Bupivacaine S2 5L Flush-1 | 0.6185 | 0.6153 |
| | Bupivacaine S2 5L Flush-2 | 0.6120 | |
| 6$^{th}$ Liter | Bupivacaine S2 6L Flush-1 | 0.5543 | 0.5528 |
| | Bupivacaine S2 6L Flush-2 | 0.5513 | |
| 7$^{th}$ Liter | Bupivacaine S2 7L Flush-1 | 0.4848 | 0.4892 |
| | Bupivacaine S2 7L Flush-2 | 0.4936 | |
| 8$^{th}$ Liter | Bupivacaine S2 8L Flush-1 | 0.4748 | 0.4730 |
| | Bupivacaine S2 8L Flush-2 | 0.4712 | |

TABLE 8.5-continued

Water Content in Preparation Filter Flushes of placebo composition-
Sample 2 determined by Karl Fischer Titration

| Flush Fraction | Sample ID | % Water Content (Two Injections per Flush Fraction) | % Water Content (Average for Flush Fraction) |
|---|---|---|---|
| 9th Liter | Bupivacaine S2 9L Flush-1 | 0.3413 | 0.3477 |
| | Bupivacaine S2 9L Flush-2 | 0.3541 | |
| 10th Liter | Bupivacaine S2 10L Flush-1 | 0.3960 | 0.3949 |
| | Bupivacaine S2 10L Flush-2 | 0.3937 | |

TABLE 8.6

Water Content in Formulation A-Sample 2 determined by Karl Fischer Titration

| Location of Vial from the Lot | Sample ID | % Water Content (Two Injections per Vial) | % Water Content (Vial Average) | % Water Content (Location Average) |
|---|---|---|---|---|
| Beginning of Run | Bupivacaine S2 BOR-1-1 | 0.1840 | 0.1840 | 0.2024 |
| | Bupivacaine S2 BOR-1-2 | 0.1840 | | |
| | Bupivacaine S2 BOR-2-1 | 0.2202 | 0.2208 | |
| | Bupivacaine S2 BOR-2-2 | 0.2214 | | |
| Middle of Run | Bupivacaine S2 MOR-1-1 | 0.0841 | 0.0849 | 0.0839 |
| | Bupivacaine S2 MOR-1-2 | 0.0857 | | |
| | Bupivacaine S2 MOR-2-1 | 0.0840 | 0.0830 | |
| | Bupivacaine S2 MOR-2-2 | 0.0819 | | |
| End of Run | Bupivacaine S2 EOR-1-1 | 0.0652 | 0.0648 | 0.0640 |
| | Bupivacaine S2 EOR-1-2 | 0.0643 | | |
| | Bupivacaine S2 EOR-2-1 | 0.0638 | 0.0633 | |
| | Bupivacaine S2 EOR-2-2 | 0.0627 | | |

Although the data shows the changes in the preparation process (increased nitrogen pressure and larger volume of product flush) were effective in reducing the water content in Formulation A, the results for the filled vials did not appear to be practically different from the prior drying process.

ICH and Prior Clinical Lots of Formulation A

Table 8.7 summarizes the water content results for the 4 ICH lots (each with fill sizes of 5 mL and 7.5 mL) and the 2 clinical lots (Formulation A and a placebo) manufactured previously. These lots were manufactured with a nitrogen purge of the filters at 50 psi for not less than 5 minutes with not less than 6 L flush of product. Two or four vials from each lot were tested. The % water content ranged from approximately 0.13% to 0.34% for these historical lots that were about 3-4 years old at the time of testing.

TABLE 8.7

Water Content in Formulation A and placebo compositions by Karl Fischer Titration

| Formulation A ID | Sample ID | % Water Content (Single Injection per Vial) | % Water Content (Lot Average) |
|---|---|---|---|
| A | A-1 | 0.2503 | 0.2366 |
| | A-2 | 0.2229 | |
| B | B-1 | 0.1516 | 0.1478 |
| | B-2 | 0.1439 | |
| C | C-1 | 0.1561 | 0.1632 |
| | C-2 | 0.1702 | |
| D | D-1 | 0.1311 | 0.1291 |
| | D-2 | 0.1271 | |
| E | E-1 | 0.2192 | 0.2246 |
| | E-2 | 0.2299 | |
| F | F-1 | 0.1504 | 0.1473 |
| | F-2 | 0.1442 | |
| G | G-1 | 0.1451 | 0.1527 |
| | G-2 | 0.1602 | |
| H | H-1 | 0.3296 | 0.3404 |
| | H-2 | 0.3512 | |
| I | I-1 | 0.1344 | 0.1286 |
| | I-2 | 0.1246 | |
| | I-3 | 0.1264 | |
| | I-4 | 0.1290 | |
| Placebo Composition A | Placebo A-1 | 0.1600 | 0.1618 |
| | Placebo A-2 | 0.1635 | |

Conclusions

To reduce or altogether eliminate the water content in Formulation A, the nitrogen purging pressure may be increased from 50 to 55 psi for not less than 5 minutes or until no more water is observed. The total amount of composition flushed through the filters prior to the vial filling step is recommended to remain as not less than 6 liters.

Example 9

The degree of coloration at 36 months, 25°/60% RH, for Formulation A, primary and supportive stability lots were compared to the water content that were determined at approximately 52 months after the date of manufacture, to see if a correlation exists between those two parameters. In addition, the degree of coloration at 36 months, 25°/60% RH, for a clinical lot of Formulation A was compared to its water content determined 34 months after manufacture.

Methods

Materials

1) Formulation A—Primary Stability Samples: PS-A, PS-B, PS-C and PS-D (5 mL fill)
2) Formulation A—Supportive Stability Samples: SS-A, SS-B, SS-C and SS-D (7.5 mL fill)
3) Formulation A—Clinical Samples: CS-A Water Content Testing Samples were tested according to USP <921>, Method 1c, using an EM Science Aquastar C3000 Coulometric Titrator. Due to the high viscosity of the formulation, the samples required dilution with methanol prior to introduction into the Coulometric Titrator. Approximately 0.5 g of Formulation A was accurately weighed into a 10 mL vial. An approximately equal amount of methanol was added and the weight accurately recorded. Each vial was then sealed and shaken vigorously for at least 30 seconds. Approximately 0.5 g of the sample/methanol mixture was delivered into the Coulometric Titrator by liquid injection. The syringe used to deliver the sample was weighed before and after injection to determine the amount assayed. Two vials per ICH stability lot were tested for water content, while four vials from Formulation A clinical samples CS-A were tested.

Degree of Coloration of Liquids

Samples were tested at the 36 months time point for Formulation A primary stability sample compositions, Formulation A supportive stability sample compositions and Formulation A clinical sample compositions. Color was determined on samples stored both upright and inverted. Formulation A clinical samples CS-A only had vials stored inverted.

0.15% water, the color ranged from 4x-5xBY1 to 6xBY1; at approximately 0.23% water the color ranged from 5xBY1 to 6xBY1; and at approximately 0.34% water the color ranged from 5xBY to 5x-6xBY1.

Figure 1:
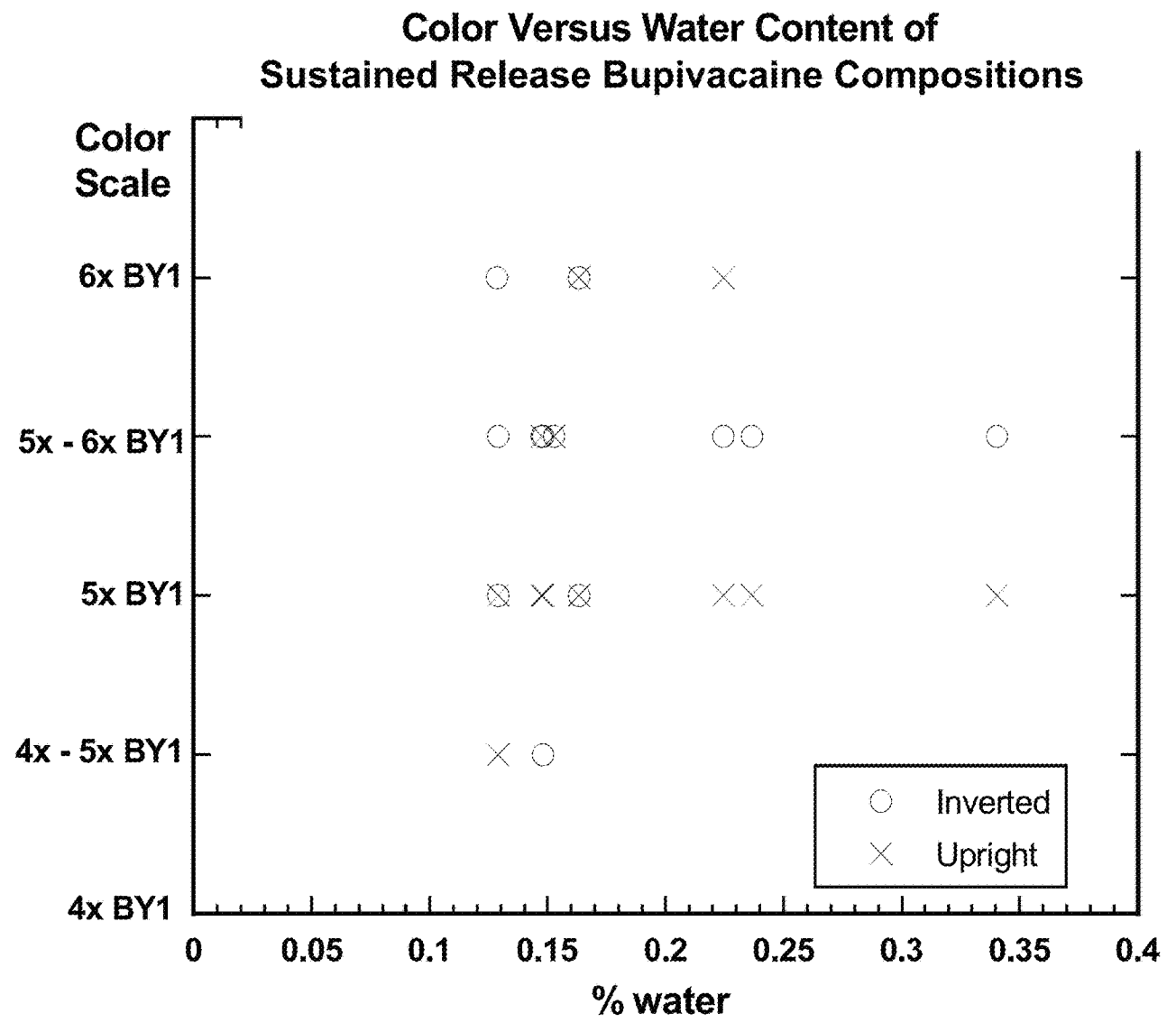

Based on the results depicted in FIG. 1 and summarized in Table 9.1, the color of the Formulation A does not darken with an increase of water content in the approximate range of 0.13% to 0.34%.

TABLE 9.1

Water Content in Formulation A by Karl Fischer Titration and the Degree of Coloration of Liquids Data at 36 Months, at 25° C./60% RH, Stored Inverted and Upright

| Composition ID | Fill Size (mL) | Sample ID | % Water Content (Single Injection per Vial) | % Water Content (Lot Average) | Degree of Coloration at 36 Months at 25° C./60% RH, Stored Inverted, by PR-1562 on Other Vials Not Tested for Water Content | Degree of Coloration at 36 Months at 25° C./60% RH, Stored Upright, by PR-1562 on Other Vials Not Tested for Water Content |
|---|---|---|---|---|---|---|
| PS-A | 5 | PS-A-1 | 0.2503 | 0.2366 | Between 5x-6x BY1, Between 5x-6x BY1 | 5x BY1, 5x BY1 |
|  |  | PS-A-2 | 0.2229 |  |  |  |
| SS-A | 7.5 | SS-A-1 | 0.1516 | 0.1478 | Between 4x-5x BY1, Between 5x-6x BY1 | 5x BY1, 5x BY1 |
|  |  | SS-A-2 | 0.1439 |  |  |  |
| PS-B | 5 | PS-B-1 | 0.1561 | 0.1632 | 5x BY1, 6x BY1 | 5x BY1, 6x BY1 |
|  |  | PS-B-2 | 0.1702 |  |  |  |
| SS-B | 7.5 | SS-B-1 | 0.1311 | 0.1291 | 5x BY1, Between 5x-6x BY1 | 5x BY1, Between 4x-5x BY1 |
|  |  | SS-B-2 | 0.1271 |  |  |  |
| PS-C | 5 | PS-C-1 | 0.2192 | 0.2246 | Between 5x-6x BY1, Between 5x-6x BY1 | 5x BY1, 6x BY1 |
|  |  | PS-C-2 | 0.2299 |  |  |  |
| SS-C | 7.5 | SS-C-1 | 0.1504 | 0.1473 | Between 5x-6x BY1, Between 5x-6x BY1 | 5x BY1, Between 5x-6x BY1 |
|  |  | SS-C-2 | 0.1442 |  |  |  |
| PS-D | 5 | PS-D-1 | 0.1451 | 0.1527 | Between 5x-6x BY1, Between 5x-6x BY1 | Between 5x-6x BY1, Between 5x-6x BY1 |
|  |  | PS-D-2 | 0.1602 |  |  |  |
| SS-D | 7.5 | SS-D-1 | 0.3296 | 0.3404 | Between 5x-6x BY1, Between 5x-6x BY1 | 5x BY1, 5x BY1 |
|  |  | SS-D-2 | 0.3512 |  |  |  |
| CS-A | 7.5 | CS-A-1 | 0.1344 | 0.1286 | 6x BY1, 6x BY1 | Not stored upright |
|  |  | CS-A-2 | 0.1246 |  |  |  |
|  |  | CS-A-3 | 0.1264 |  |  |  |
|  |  | CS-A-4 | 0.1290 |  |  |  |

Results

Table 9.1 summarizes the Degree of Coloration of Liquid results for the sustained release bupivacaine compositions at the 36 month time point, for samples stored at 25° C./60% RH in the inverted and upright orientations. The color data for samples CS-A at 36 months, stored only in the inverted orientation, is also included. The color results among the compositions were similar, with most of the results between 5xBY1 and 6xBY1. The color results for Formulation A indicate that the orientation of the vial during storage had no effect on color. Formulation A clinical samples CS-A was described as 6xBY1.

Included in Table 9.1 is the water content of the compositions of Formulation A, measured approximately 16 months after the color assessments were done at the 36 months stability time point. The water content ranged from approximately 0.13% to 0.34% for the compositions of Formulation A. In addition, the water content for Formulation A clinical samples CS-A was measured approximately 2 months before color was determined at the 36 months time point. Formulation A clinical samples CS-A had approximately 0.13% water.

FIG. 1 depicts the water content and coloration for each sample in Table 9.1. As seen in FIG. 1, at approximately Example 10

The effect of peroxide from sucrose acetate isobutyrate or benzyl alcohol on Formulation A and placebo compositions was evaluated. Formulation A in this study includes 12% w/w bupivacaine, 66% w/w sucrose acetate isobutyrate (SAIB), and 22% w/w benzyl alcohol, as described above. Placebo compositions were composed of 75% w/w sucrose acetate isobutyrate (SAIB), and 25% w/w benzyl alcohol. Bupivacaine N-oxide in the sustained release bupivacaine compositions can be formed by an oxidative reaction between bupivacaine and peroxides.

Methods

The peroxide content for several lots of sucrose acetate isobutyrate were determined by potentiometric titration involving iodometric titration. The bupivacaine N-oxide levels in samples of Formulation A were determined using HPLC with UV detection. Primary stability sample compositions, clinical samples, and the two optimization sample compositions of Formulation A were prepared at a scale of 150 L. Samples used for the heating study were prepared at a scale of 2.5 L. The heating study evaluated the effect of temperature during preparation.

Results

The levels of bupivacaine N-oxide in Formulation A on stability at 25° C./60% RH and the peroxide content in SAIB compositions used to prepare samples of Formulation A are listed in Table 10.1. The bupivacaine N-oxide data in Table 10.1 are for the longest available stability time points for each set of samples. These range from 3 months for the two optimization lots, up to 36 months for the four primary stability samples (each filled to 5 mL and 7.5 mL) of Formulation A and the clinical sample of Formulation A.

TABLE 10.1

Correlation of Peroxide Content of SAIB for preparing Samples of Formulation A and Bupivacaine N-Oxide

| Composition ID | Bupivacaine Sample ID | Peroxide Content (ppm) | Observed Amount % Bupivacaine N-Oxide on Stability | Time (Months) on Stability at 25° C./60% RH for Data in Column to the Left | Orientation on Stability |
|---|---|---|---|---|---|
| Bupivacaine Composition | PS-A | 66 | 0.3 | 36 | inverted |
| Bupivacaine Composition | SS-A | 66 | 0.3 | 36 | inverted |
| Bupivacaine Composition | PS-B | 86 | 0.3 | 36 | inverted |
| Bupivacaine Composition | SS-B | 86 | 0.3 | 36 | inverted |
| Bupivacaine Composition | PS-C | 60 | 0.3 | 36 | inverted |
| Bupivacaine Composition | SS-C | 60 | 0.3 | 36 | inverted |
| Bupivacaine Composition | PS-D | 66 | 0.3 | 36 | inverted |
| Bupivacaine Composition | SS-D | 66 | 0.3 | 36 | inverted |
| Clinical Bupivacaine Composition | CS-A | 236 | 1.6% of total SAIB in product lot | | |
| | | 222 | 15.1% of total SAIB in product lot | | |
| | | 198 | 29.6% of total SAIB in product lot | | |
| | | 211 | 53.7% of total SAIB in product lot | | |

Table 10.2 summarizes the result of peroxide content from a heating study that evaluated the effect of temperature during preparation.

TABLE 10.2

Peroxide Content of SAIB for preparing Samples of Formulation A and Bupivacaine N-Oxide in Optimization Lots and Heating Study

| Composition ID | Peroxide Content (ppm) | Observed Amount % Bupivacaine N-Oxide on Stability | Time (Months) on Stability at 25° C./60% RH for Data in Column to the Left | Orientation On Stability |
|---|---|---|---|---|
| Heating Study | HS-A | 184 | 0.6 | 6 | inverted |
| Heating Study | HS-B | 184 | 0.6 | 6 | inverted |
| Optimization Lot - 1 | OL-A | 19 | BQL | 3 | inverted |
| Optimization Lot - 2 | OL-B | 19 | BQL | 3 | inverted |

FIG. 2 illustrates a linear regression line fitted to the SAIB peroxide content data versus the bupivacaine N-oxide levels data. Based on the linear regression equation, it is estimated that the 1.0% specification limit for bupivacaine N-oxide corresponds to 296.4 ppm peroxide in SAIB. To ensure not exceeding the 1.0% limit for bupivacaine N-oxide, the target peroxide content can be adjusted to a value that corresponds to 0.8% bupivacaine N-oxide. This peroxide content value is calculated to be 232.5 ppm using the equation in FIG. 2.

To determine the fraction of bupivacaine N-oxide that may result from the peroxide impurities in benzyl alcohol, benzyl alcohol lots used in the preparation of the samples of Formulation A listed in Table 10.3 were examined. Table 10.3 lists the benzyl alcohol compositions with their determined peroxide values (PV). All of the benzyl alcohol compositions had peroxide values of less than 0.5. The peroxide value can be converted to peroxide content, expressed as hydrogen peroxide, by multiplying PV by 17. This results in peroxide content data for all the benzyl alcohol lots as <8.5 ppm. Since the samples of Formulation A contain benzyl alcohol and SA in a 1:3 w/w ratio, the effective peroxide content of benzyl alcohol that would contribute to oxidizing bupivacaine to bupivacaine N-oxide is one third that of the peroxide content of SAIB. With this calculation, each lot of benzyl alcohol that was used in the samples of Formulation A listed in Table 10.3 effectively had <2.8 ppm (8.5 ppm divided by 3 equals 2.8 ppm) contribution to the formation of bupivacaine N-oxide. The maximum contribution to peroxide content from benzyl alcohol is 85 ppm divided by 3, or 28 ppm.

TABLE 10.3

Peroxide Content of Benzyl Alcohol used for preparing samples of Formulation A

| Composition ID | Bupivacaine Composition No. | Benzyl Alcohol ID | Benzyl Alcohol Peroxide Value (PV) from CofA | Benzyl Alcohol Peroxide Content (ppm) | Effective Benzyl Alcohol Peroxide Content (ppm) |
|---|---|---|---|---|---|
| Bupivacaine Composition | PS-A | BA Composition 1 | <0.5 | <8.5 | <2.8 |
| Bupivacaine Composition | SS-A | BA Composition 1 | <0.5 | <8.5 | <2.8 |
| Bupivacaine Composition | PS-B | BA Composition 2 | <0.5 | <8.5 | <2.8 |
| Bupivacaine Composition | SS-B | BA Composition 2 | <0.5 | <8.5 | <2.8 |
| Bupivacaine Composition | PS-C | BA Composition 3 | <0.5 | <8.5 | <2.8 |
| Bupivacaine Composition | SS-C | BA Composition 3 | <0.5 | <8.5 | <2.8 |
| Bupivacaine Composition | PS-D | BA Composition 2 | <0.5 | <8.5 | <2.8 |
| Bupivacaine Composition | SS-D | BA Composition 2 | <0.5 | <8.5 | <2.8 |
| Clinical Bupivacaine Composition | CS-A | BA Composition 4 | <0.5 | <8.5 | <2.8 |
| Heating Study | HS-A | BA Composition 5 | <0.5 | <8.5 | <2.8 |
| Heating Study | HS-B | BA Composition 5 | <0.5 | <8.5 | <2.8 |
| Optimization Lot - 1 | OL-A | BA Composition 6 | <0.5 | <8.5 | <2.8 |
| Optimization Lot - 2 | OL-B | BA Composition 6 and BA Composition 7 | <0.5 | <8.5 | <2.8, <2.8 |

Example 11

The stability of various batches of Formulation A was studied. The results of these exemplary batches are summarized in Tables 11.1 and 11.2 and FIGS. 3-11. The stability of the samples of Formulation A in this study was assayed using HPLC with UV detection.

Samples of Formulation A (5 mL) were examined for photostability. Four different sample lots of Formulation A (11A-11C) were characterized and summarized in Tables 11.1 and 11.2. The photostability of each sample of Formulation A was studied under three different conditions: 1) light unprotected; 2) light protected using foil; and 3) light protected and packaged. The colors exhibited by each of the tested samples as well as the degree of coloration of the samples are summarized in Tables 11.1 and 11.2. In addition, Tables 11.1 and 11.2 summarize the label strength as well as presence of benzyl acetate and benzyl isobutyrate in the tested samples.

Figure 3:
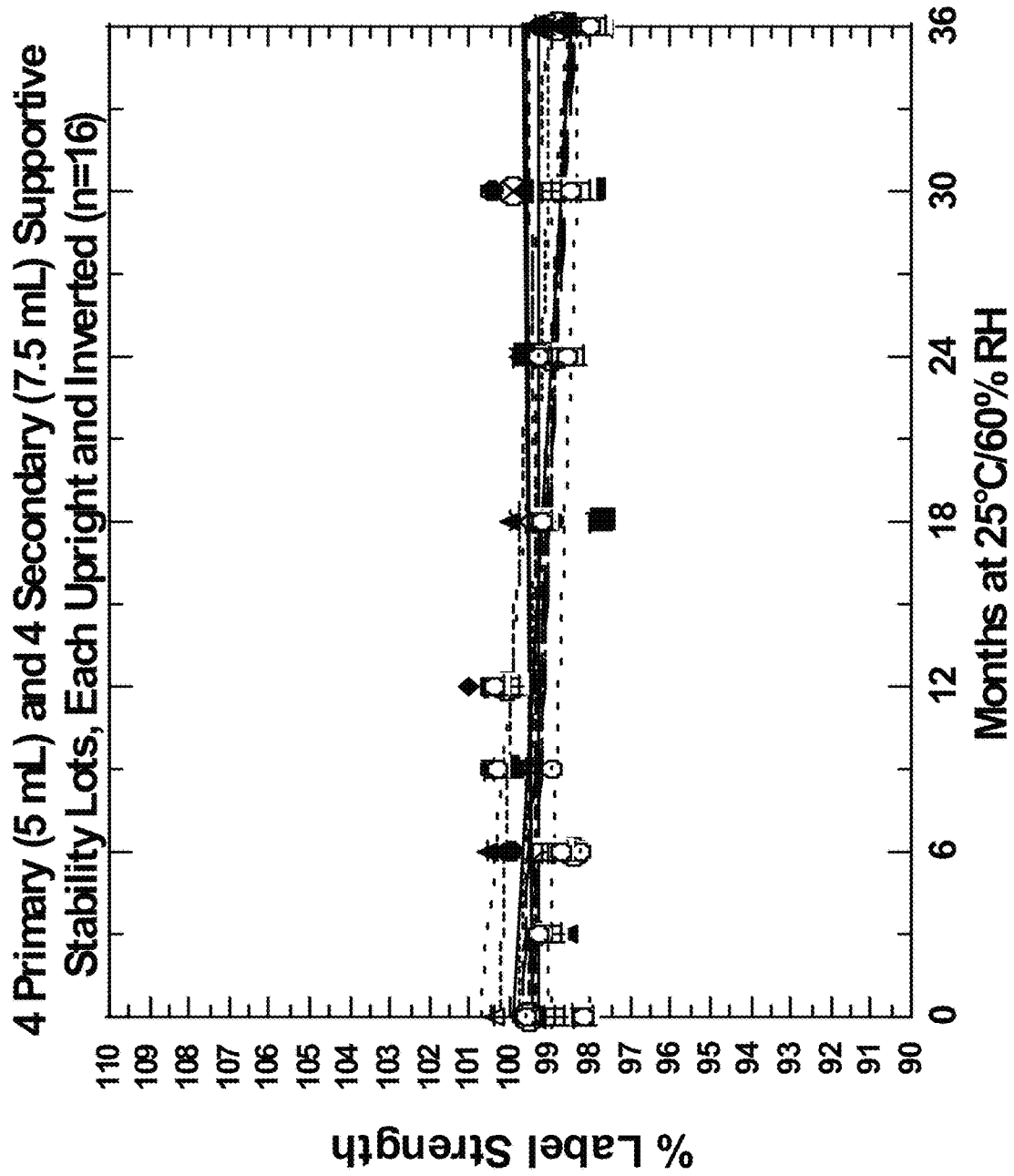
FIG. 3 shows label strength of 4 primary (5 mL) and 4 secondary (7.5 mL) lots of samples of Formulation A over a 36-month period.

FIG. 3 depicts the label strength of 4 primary (5 mL) and 4 secondary (7.5 mL) lots of samples of Formulation A over a 36-month period. The label strength was measured for each sample at a temperature of 25° C. and 60% relative humidity.

Figure 4:
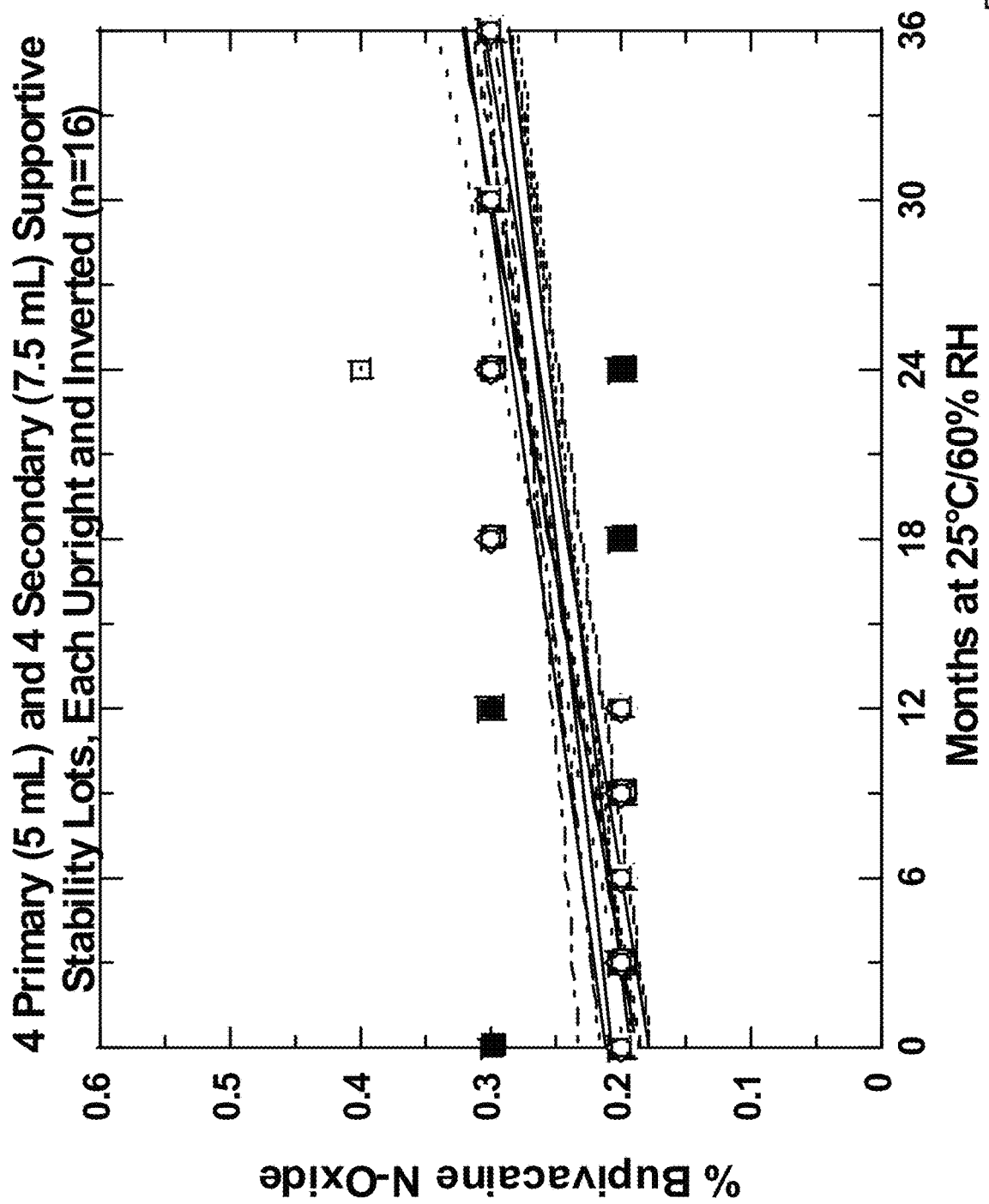
FIG. 4 shows change in bupivacaine N-oxide (measure in % bupivacaine N-oxide) in 4 primary (5 mL) and 4 secondary (7.5 mL) lots of samples of Formulation A over a 36-month period.

FIG. 4 depicts the change in the presence of the N-oxide of bupivacaine (measure in % bupivacaine N-oxide) in 4 primary (5 mL) and 4 secondary (7.5 mL) lots of samples of Formulation A over a 36-month period. The amount of bupivacaine N-oxide in the samples was measured for each sample at a temperature of 25° C. and 60% relative humidity.

Figure 5:
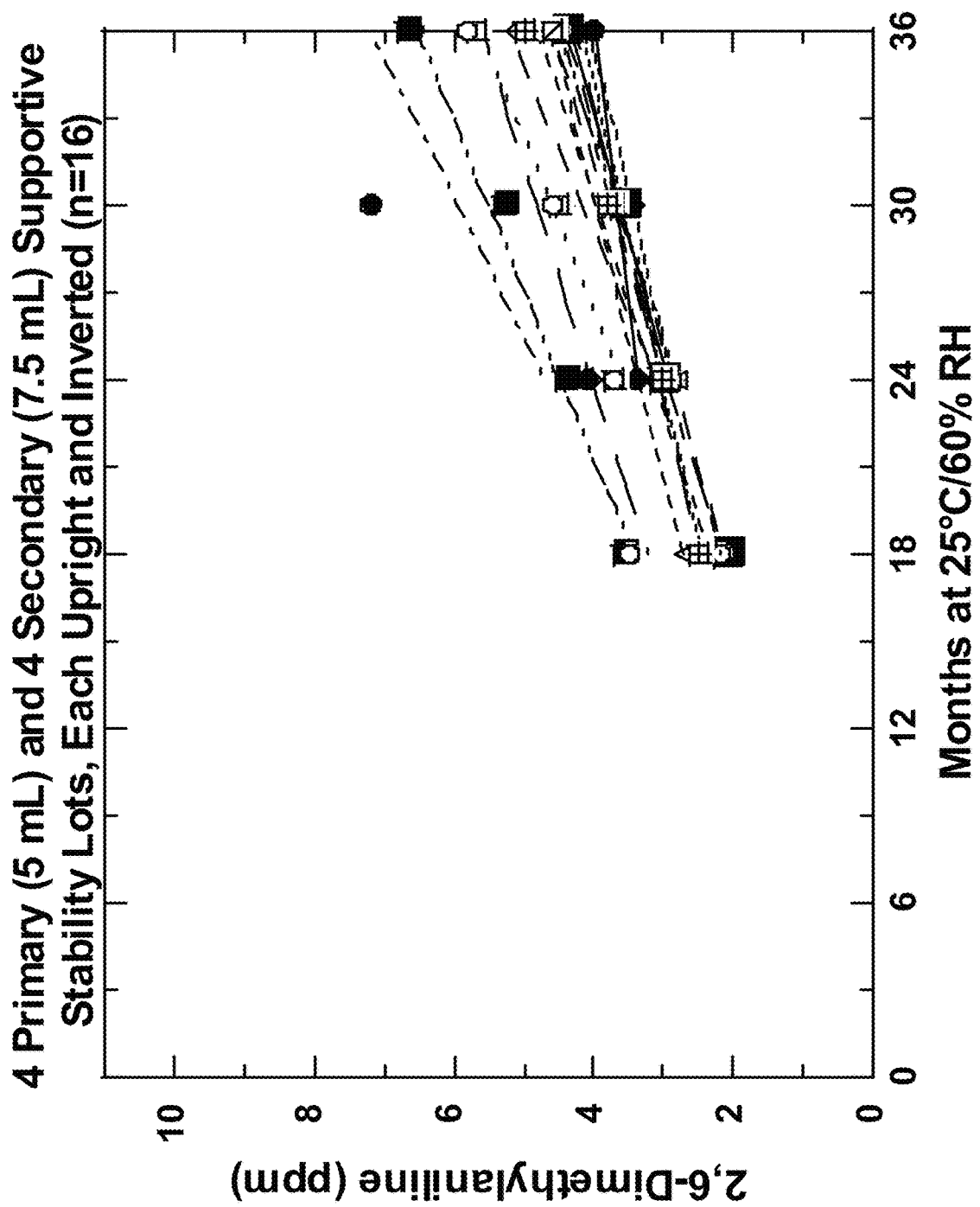
FIG. 5 shows presence of 2,6-dimethylaniline (measure in ppm) in 4 primary (5 mL) and 4 secondary (7.5 mL) lots of samples of Formulation A over an 18-month period (months 18-36).
Figure 6:
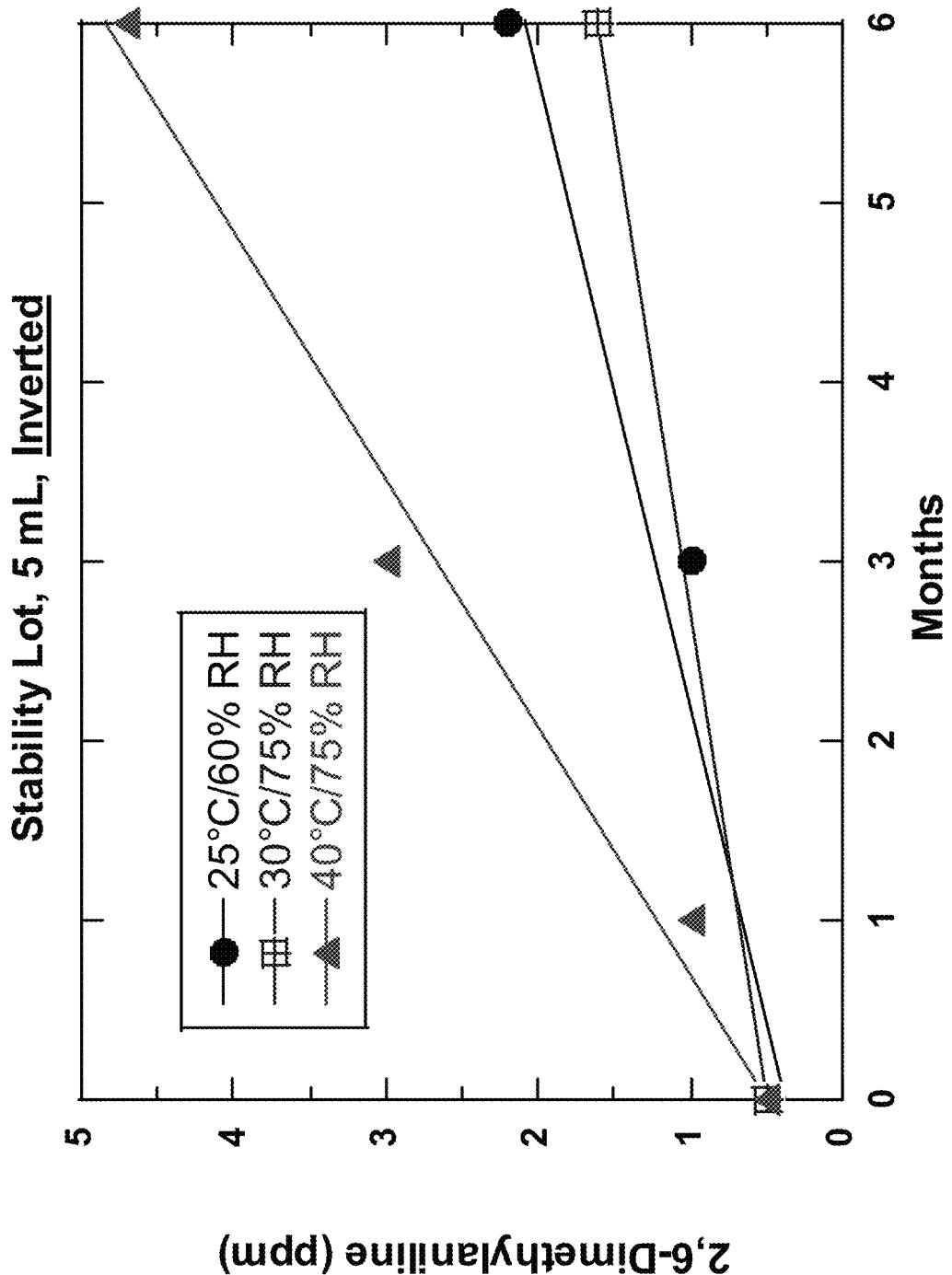
FIG. 6 shows presence of 2,6-dimethylaniline in samples of Formulation A stored for a 6-month period at 3 different temperatures (25° C., 30° C. and 40° C.) and 2 different relative humidities (60% RH, 75% RH).

FIG. 5 depicts the presence of 2,6-dimethylaniline (measure in ppm) in 4 primary (5 mL) and 4 secondary (7.5 mL) lots of samples of Formulation A over an 18-month period (months 18-36). The amount of 2,6-dimethylaniline in the samples was measured for each sample stored at a temperature of 25° C. and 60% relative humidity. FIG. 6 depicts the presence of 2,6-dimethylaniline in samples of Formulation A stored for a 6-month period at 3 different temperatures (25° C., 30° C. and 40° C.) and 2 different relative humidities (60% RH, 75% RH).

Figure 7:
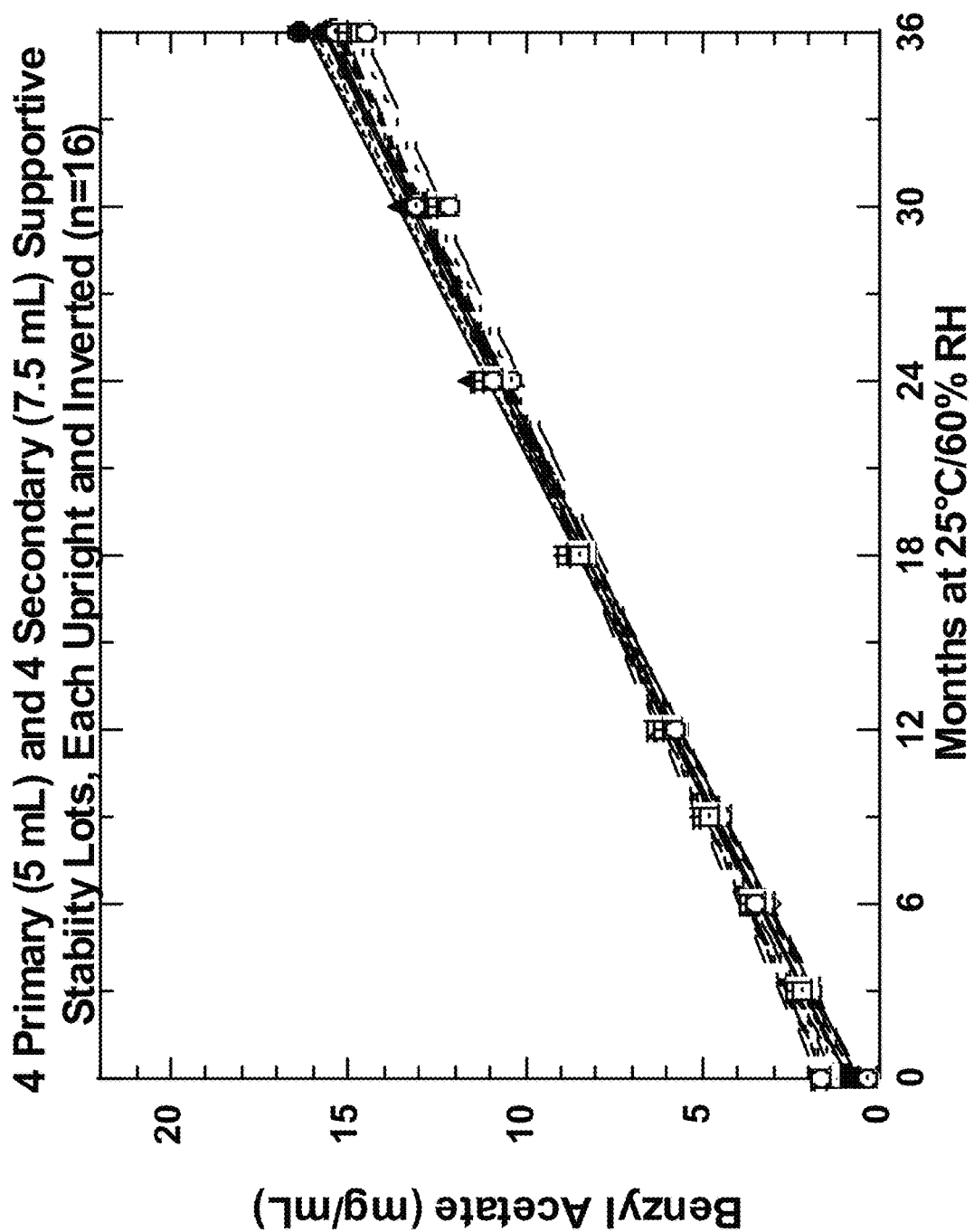
FIG. 7 shows presence of benzyl acetate (measure in mg/mL) in 4 primary (5 mL) and 4 secondary (7.5 mL) lots of samples of Formulation A over a 36-month period.
Figure 8:
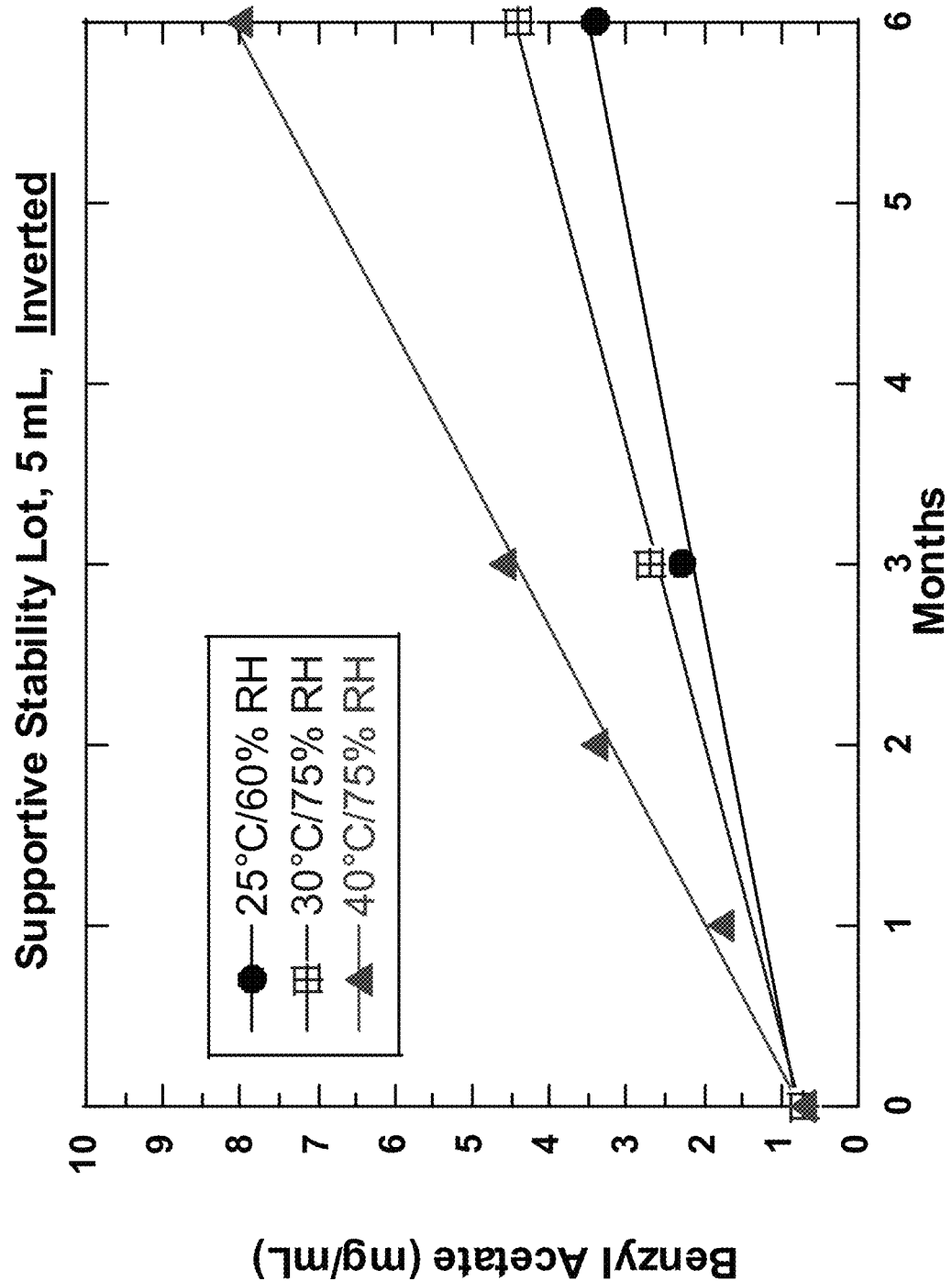
FIG. 8 shows presence of benzyl acetate in samples of Formulation A stored for a 6-month period at 3 different temperatures (25° C., 30° C. and 40° C.) and 2 different relative humidities (60% RH, 75% RH).

FIG. 7 depicts the presence of benzyl acetate (measure in mg/mL) in 4 primary (5 mL) and 4 secondary (7.5 mL) lots of samples of Formulation A over a 36-month period. The amount of benzyl acetate in the samples was measured for each sample stored at a temperature of 25° C. and 60% relative humidity. FIG. 8 depicts the presence of benzyl acetate in samples of Formulation A stored for a 6-month period at 3 different temperatures (25° C., 30° C. and 40° C.) and 2 different relative humidities (60% RH, 750RH).

Figure 9:
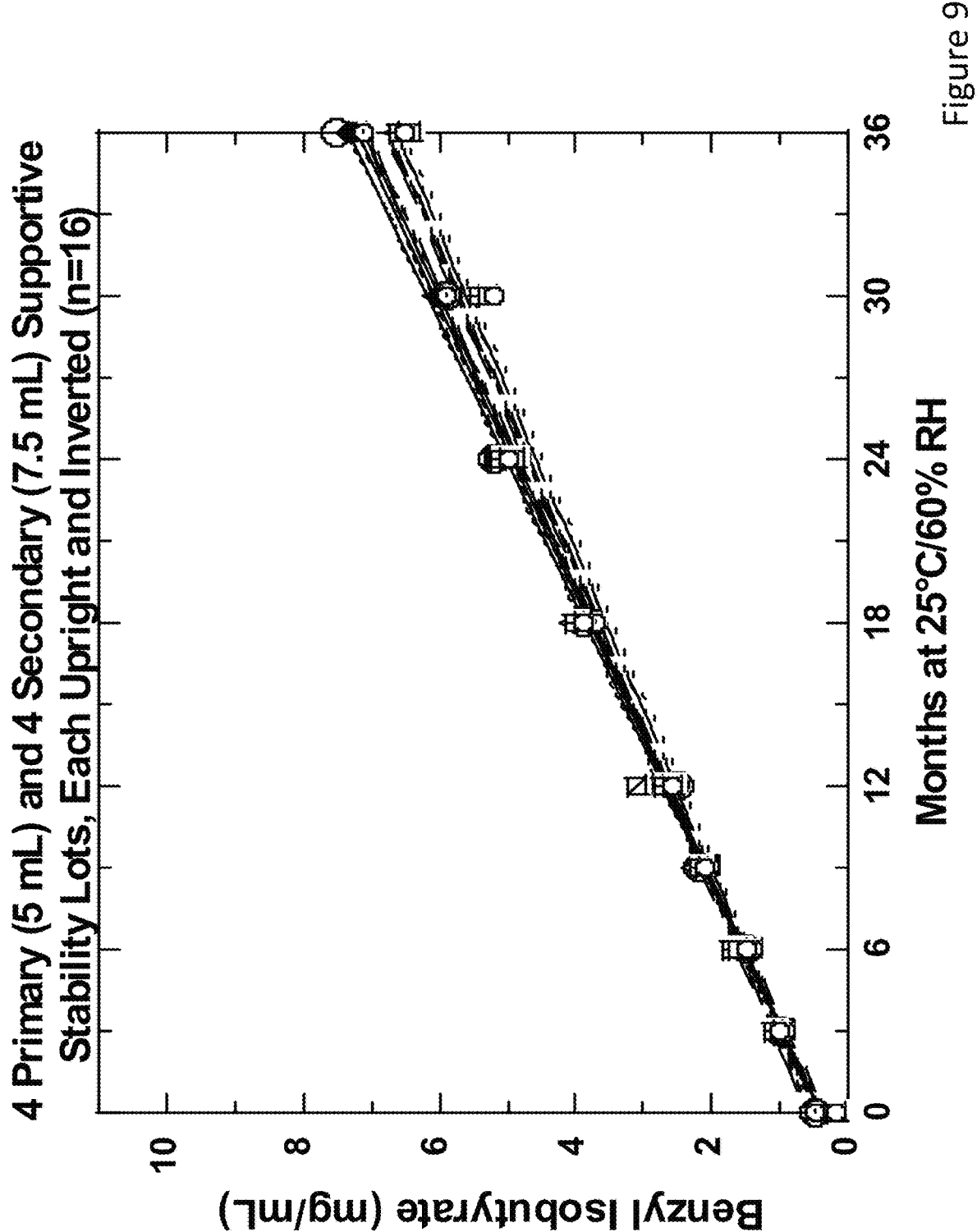
FIG. 9 shows presence of benzyl isobutyrate (measure in mg/mL) in 4 primary (5 mL) and 4 secondary (7.5 mL) lots of samples of Formulation A over a 36-month period.
Figure 10:
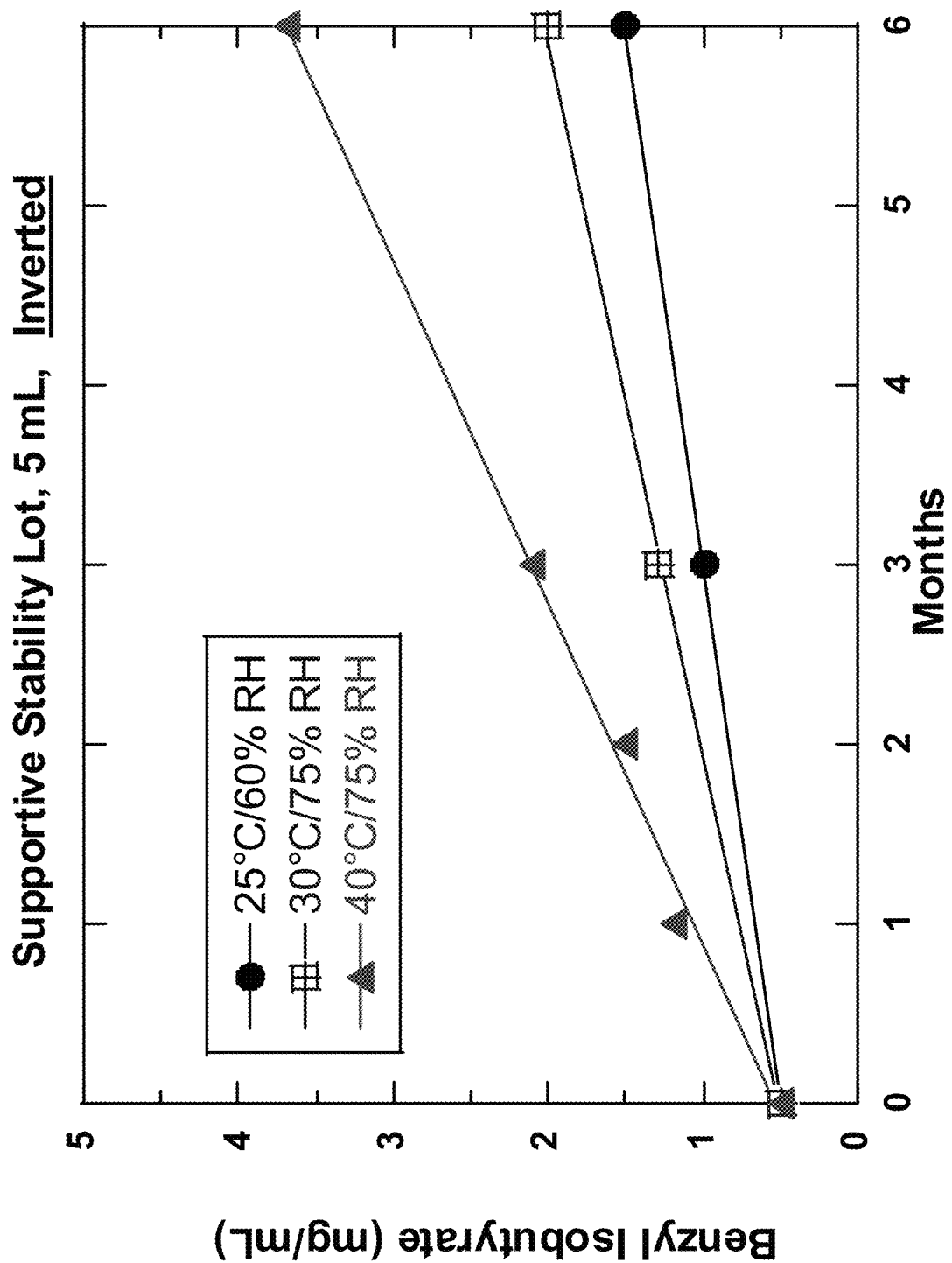
FIG. 10 shows presence of benzyl isobutyrate in samples of Formulation A stored for a 6-month period at 3 different temperatures (25° C., 30° C. and 40° C.) and 2 different relative humidities (60% RH, 75% RH).

FIG. 9 depicts the presence of benzyl isobutyrate (measure in mg/mL) in 4 primary (5 mL) and 4 secondary (7.5 mL) lots of samples of Formulation A over a 36-month period. The amount of benzyl isobutyrate in the samples was measured for each sample stored at a temperature of 25° C. and 60% relative humidity. FIG. 10 depicts the presence of benzyl isobutyrate in samples of Formulation A stored for a 6-month period at 3 different temperatures (25° C., 30° C. and 40° C.) and 2 different relative humidities (60% RH, 75% RH).

Figure 11:
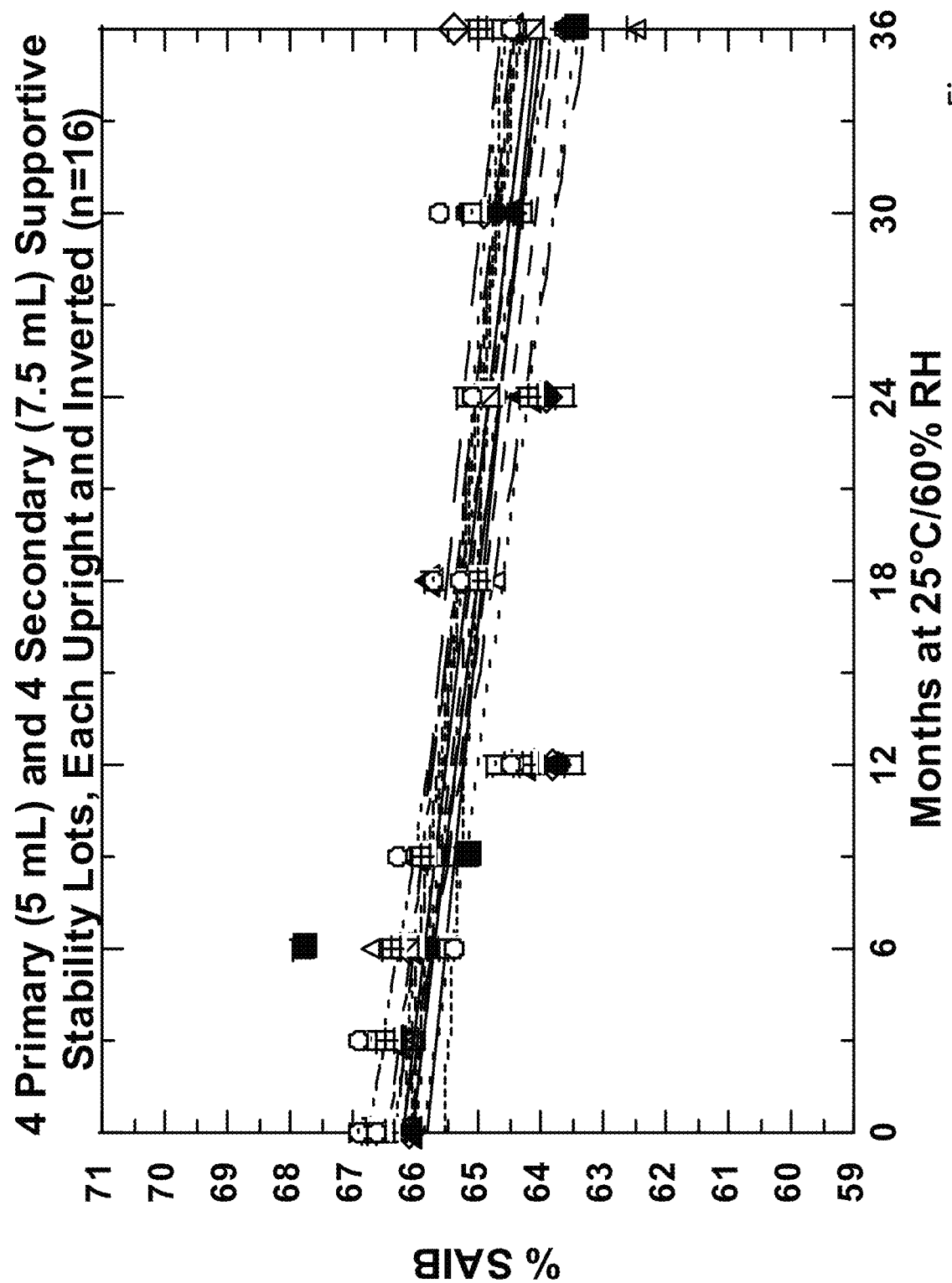
FIG. 11 shows change in percent SAIB in 4 primary (5 mL) and 4 secondary (7.5 mL) lots of samples of Formulation A over a 36-month period.

FIG. 11 depicts the change in the percent SAB in 4 primary (5 mL) and 4 secondary (7.5 mL) lots of samples of Formulation A over a 36-month period. The change in the percent SAIB of samples of Formulation A was measured for each sample stored at a temperature of 25° C. and 60% relative humidity.

TABLE 11.1

Stability Results for Formulation A-Sample 1-Photostability Study, 5 mL

| | | | Acceptance Criteria | | | | |
|---|---|---|---|---|---|---|---|
| Lot Number | Size (mL) | Condition | Appearance Clear light yellow to amber solution; essentially free of particulate matter | Degree of Coloration of Liquids NMT 6x BY1 | Assay[1] 93.0-105.0% label strength | Benzyl Acetate [a] NMT 20.0 mg/mL | Benzyl Isobutyrate [a] NMT 10.0 mg/mL |
| 11A | 5 | Light Storage-Unprotected[2] | Pass[3]/Light Yellow | BY4 (with yellow tint), BY4 (with yellow tint) | 97.2 (97.1, 97.2) | 3.4 (3.4, 3.4) | 1.4 (1.4, 1.4) |
|  |  | Light Storage-Protected, Foil | Pass/Yellow Brown | BY3, BY3 | 97.8 (97.7, 97.9) | 3.4 (3.4, 3.4) | 1.4 (1.4, 1.4) |
|  |  | Light Storage-Protected, Package | Pass/Yellow Brown | BY3, BY3 | 98.4 (98.6, 98.2) | 3.4 (3.4, 3.4) | 1.5 (1.5, 1.4) |
| 11B | 5 | Light Storage-Unprotected | Pass/Light Yellow | BY4 (with yellow tint), BY4 (with yellow tint) | 98.7 (98.7, 98.7) | 4.1 (4.1, 4.1) | 1.6 (1.6, 1.6) |
|  |  | Light Storage-Protected, Foil | Pass/Yellow Brown | BY3, BY3 | 99.9 (100.0, 99.7) | 4.1 (4.1, 4.0) | 1.7 (1.7, 1.7) |

TABLE 11.1-continued

Stability Results for Formulation A-Sample 1-Photostability Study, 5 mL

| | | | Acceptance Criteria | | | | |
|---|---|---|---|---|---|---|---|
| Lot Number | Size (mL) | Condition | Appearance Clear light yellow to amber solution; essentially free of particulate matter | Degree of Coloration of Liquids NMT 6x BY1 | Assay[1] 93.0-105.0% label strength | Benzyl Acetate [a] NMT 20.0 mg/mL | Benzyl Isobutyrate [a] NMT 10.0 mg/mL |
| | | Light Storage-Protected, Package | Pass/Yellow Brown | BY3, BY3 | 99.7 (99.5, 99.8) | 4.1 (4.1, 4.1) | 1.7 (1.6, 1.7) |

[1]Average (Individual) results reported
[2]Light Storage = Accelerated light storage condition
[3]Pass = clear, essentially free of particulate matter

TABLE 11.2

Stability Results for Formulation A-Sample 2-Photostability Study, 5 mL

| | | | Acceptance Criteria | | | | |
|---|---|---|---|---|---|---|---|
| Lot Number | Size (mL) | Condition | Appearance Clear light yellow to amber solution; essentially free of particulate matter | Degree of Coloration of Liquids NMT 6x BY1 | Assay[1] 93.0-105.0% label strength | Benzyl Acetate [a] NMT 20.0 mg/mL | Benzyl Isobutyrate [a] NMT 10.0 mg/mL |
| 11C | 5 | Light Storage-Unprotected[2] | Pass[3]/Light Yellow | BY4 (with yellow tint), BY4 (with yellow tint) | 97.2 (97.1, 97.2) | 3.4 (3.4, 3.4) | 1.4 (1.4, 1.4) |
| | | Light Storage-Protected, Foil | Pass/Yellow Brown | BY3, BY3 | 97.8 (97.7, 97.9) | 3.4 (3.4, 3.4) | 1.4 (1.4, 1.4) |
| | | Light Storage-Protected, Package | Pass/Yellow Brown | BY3, BY3 | 98.4 (98.6, 98.2) | 3.4 (3.4, 3.4) | 1.5 (1.5, 1.4) |
| 11D | 5 | Light Storage-Unprotected | Pass/Light Yellow | BY4 (with yellow tint), BY4 (with yellow tint) | 98.7 (98.7, 98.7) | 4.1 (4.1, 4.1) | 1.6 (1.6, 1.6) |
| | | Light Storage-Protected, Foil | Pass/Yellow Brown | BY3, BY3 | 99.9 (100.0, 99.7) | 4.1 (4.1, 4.0) | 1.7 (1.7, 1.7) |
| | | Light Storage-Protected, Package | Pass/Yellow Brown | BY3, BY3 | 99.7 (99.5, 99.8) | 4.1 (4.1, 4.1) | 1.7 (1.6, 1.7) |

[1]Average (Individual) results reported
[2]Light Storage = Accelerated light storage condition
[3]Pass = clear, essentially free of particulate matter

Example 12

Comparison of In Vitro Dissolution Profiles for Bupivacaine Formulations with Varying Amounts of SAIB and Solvent (N=3 or 4)

To compare dissolution profiles, formulations having 12% w/w bupivacaine but differing ratios of sucrose acetate isobutyrate (SAIB)/solvent were made and tested as described in the below Methods and Materials. Table 12.1 is a summary of the compositions of the formulations tested.

TABLE 12.1

Bupivacaine/SAIB/BA (target % w/w) composition of each formulation tested

| | Compositions (target % w/w) | | | |
|---|---|---|---|---|
| Formulation Variant | Bupivacaine | Benzyl Alcohol | SAIB | Visual Appearance |
| Control | 12.0 | 22.0 | 66.0 | solution |
| −30% SAIB | 12.0 | 41.8 | 46.2 | solution |

TABLE 12.1-continued

Bupivacaine/SAIB/BA (target % w/w) composition of each formulation tested

| Formulation Variant | Compositions (target % w/w) | | | Visual Appearance |
|---|---|---|---|---|
| | Bupivacaine | Benzyl Alcohol | SAIB | |
| −40% SAIB | 12.0 | 48.4 | 39.6 | solution |
| −50% SAIB | 12.0 | 55.0 | 33.0 | solution |
| −70% SAIB | 12.0 | 68.2 | 19.8 | solution |
| −90% SAIB | 12.0 | 81.4 | 6.6 | solution |

Figure 12:
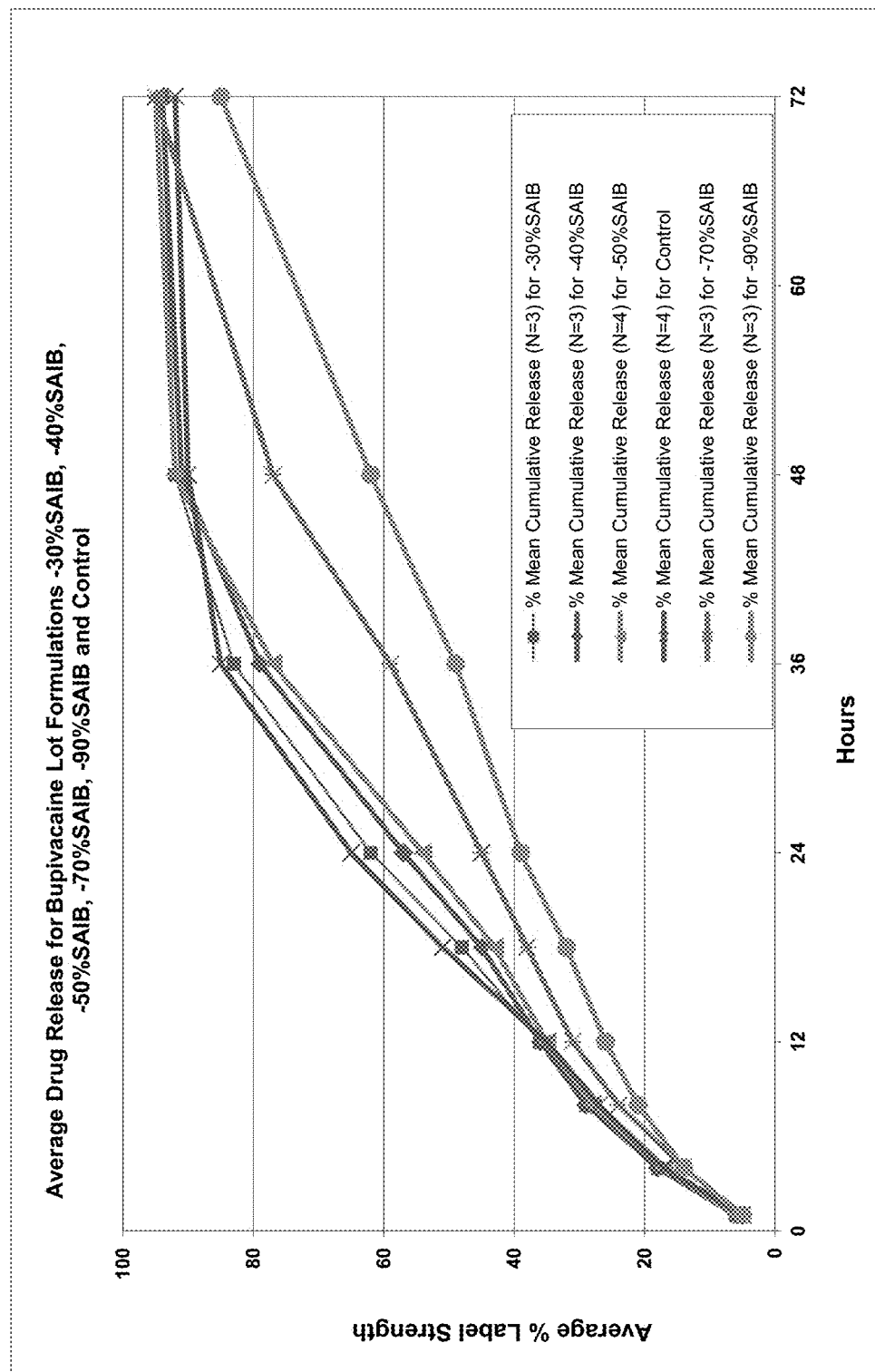
FIG. 12 shows mean cumulative release of a control formulation (N=4), −30% SAIB formulation (N=3), −40% SAB formulation (N=3), −50% SAIB formulation (N=4), −70% SAIB formulation (N=3), and −90% SAIB formulation (N=3).

In vitro release of bupivacaine for the formulations shown in Table 12.1 was assessed according to the methods described in the below Methods and Materials. FIG. 12 shows the mean cumulative release of the control formulation (N=4), −30% SAIB formulation (N=3), −40% SAIB formulation (N=3), −50% SAIB formulation (N=4), −70% SAIB formulation (N=3), and −90% SAIB formulation (N=3).

FIG. 12 shows that the cumulative release profile of the control is similar to those of the −30%, −40%, and −50% SAIB formulations. The cumulative release profile of the control is faster than those of the −70% and −90% SAIB formulations. Using the average dissolution data from the control as a reference, the similarity factor $f_2$ and difference factor $f_1$ were calculated for the −30%, −40%, −50%, −70%, and −90% SAIB formulations. See below for an explanation of the $f_1$ and $f_2$ factors. As shown in Table 12.2, the −30%, −40%, and −50% SAIB formulations had $f_1$ and $f_2$ factors that would indicate that they are not different relative to the control.

TABLE 12.2

Difference ($f_1$) and Similarity ($f_2$) Factors of Formulations Relative to Control

| Formulation Variant | Compositions (target % w/w) | | | Difference Factor $f_1$ | Similarity Factor $f_2$ |
|---|---|---|---|---|---|
| | Bupivacaine | Benzyl Alcohol | SAIB | | |
| Control | 12.0 | 22.0 | 66.0 | NA | NA |
| −30% SAIB | 12.0 | 41.8 | 46.2 | 4 | 82 |
| −40% SAIB | 12.0 | 48.4 | 39.6 | 7 | 68 |
| −50% SAIB | 12.0 | 55.0 | 33.0 | 8 | 62 |
| −70% SAIB | 12.0 | 68.2 | 19.8 | 18 | 45 |
| −90% SAIB | 12.0 | 81.4 | 6.6 | 29 | 36 |

Comparison of In Vitro Dissolution Profiles for Bupivacaine Formulations with Varying Amounts of SAIB and Solvent (N=12)

To compare dissolution profiles, formulations having 12% w/w bupivacaine but differing ratios of sucrose acetate isobutyrate (SAIB)/solvent were made and tested as described below. Table 12.3 is a summary of the compositions of the formulations tested.

TABLE 12.3

Bupivacaine/SAIB/BA (target % w/w) composition of each formulation tested

| Formulation Variant | Compositions (target % w/w) | | | Visual Appearance |
|---|---|---|---|---|
| | Bupivacaine | Benzyl Alcohol | SAIB | |
| Control | 12.0 | 22.0 | 66.0 | solution |
| +20% SAIB | 12.0 | 8.8 | 79.2 | suspension |
| −20% SAIB | 12.0 | 35.2 | 52.8 | solution |
| −70% SAIB | 12.0 | 68.2 | 19.8 | solution |

Figure 13:
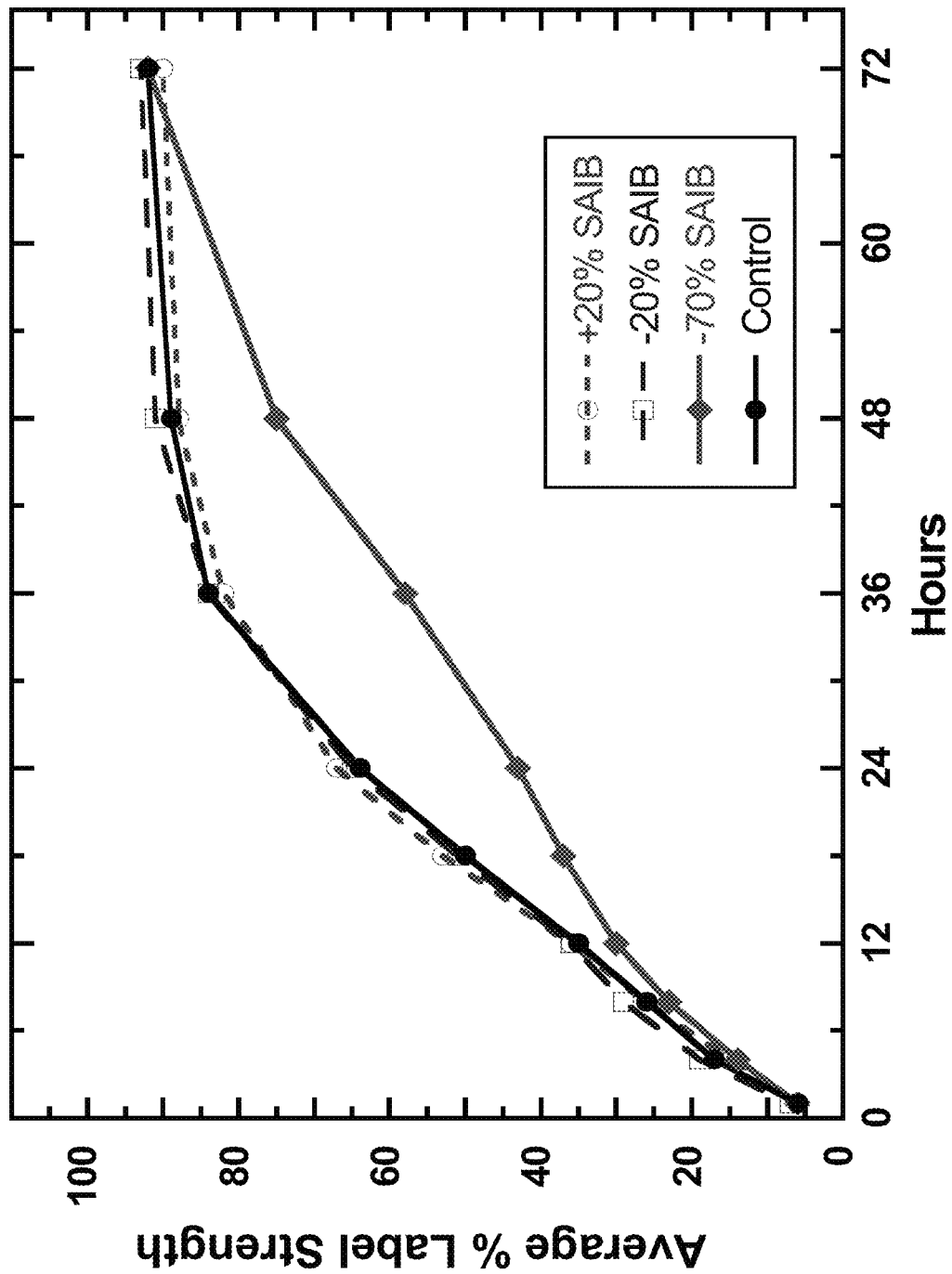
FIG. 13 shows mean cumulative release of a control formulation (N=12), +20% SAB formulation (N=12), −20% SAB formulation (N=12), and −70% SAB formulation (N=12).

In vitro release of bupivacaine for the formulations shown in Table 12.3 was assessed according to the methods described in the below Methods and Materials. FIG. 13 shows the mean cumulative release of the control formulation (N=12), +20% SAIB formulation (N=12), −20% SAIB formulation (N=12), and −70% SAIB formulation (N=12).

FIG. 13 shows that the release profile of the control is similar to those of the +20% and −20% SAIB formulations. The cumulative release profile of the control is faster than that of the −70% SAIB formulation. Using the average dissolution data from the control as a reference, the similarity factor $f_2$ and difference factor $f_1$ were calculated for the +20%, −20%, and −70% SAIB formulations. See below for an explanation of the $f_1$ and $f_2$ factors. As shown in Table 12.4, the +20% and −20% SAIB formulations had $f_1$ and $f_2$ factors that would indicate that they are not different relative to the control.

TABLE 12.4

Difference ($f_1$) and Similarity ($f_2$) Factors of Formulations Relative to Control

| Formulation Variant | Compositions (target % w/w) | | | Difference Factor $f_1$ | Similarity Factor $f_2$ |
|---|---|---|---|---|---|
| | Bupivacaine | Benzyl Alcohol | SAIB | | |
| Control | 12.0 | 22.0 | 66.0 | NA | NA |
| +20% SAIB | 12.0 | 8.8 | 79.2 | 3 | 84 |
| −20% SAIB | 12.0 | 35.2 | 52.8 | 3 | 86 |
| −70% SAIB | 12.0 | 68.2 | 19.8 | 18 | 44 |

Comparison of In Vitro Dissolution Profiles for Bupivacaine Formulations Made with Variable Heating To compare dissolution profiles, a control formulation and a heat-stressed SAIB formulation were made and tested as described the below Methods and Materials. Both the control and heat-stressed SAIB formulations nominally consisted of 12% w/w bupivacaine, 22% w/w benzyl alcohol, and 66% w/w SAIB.

Figure 14:
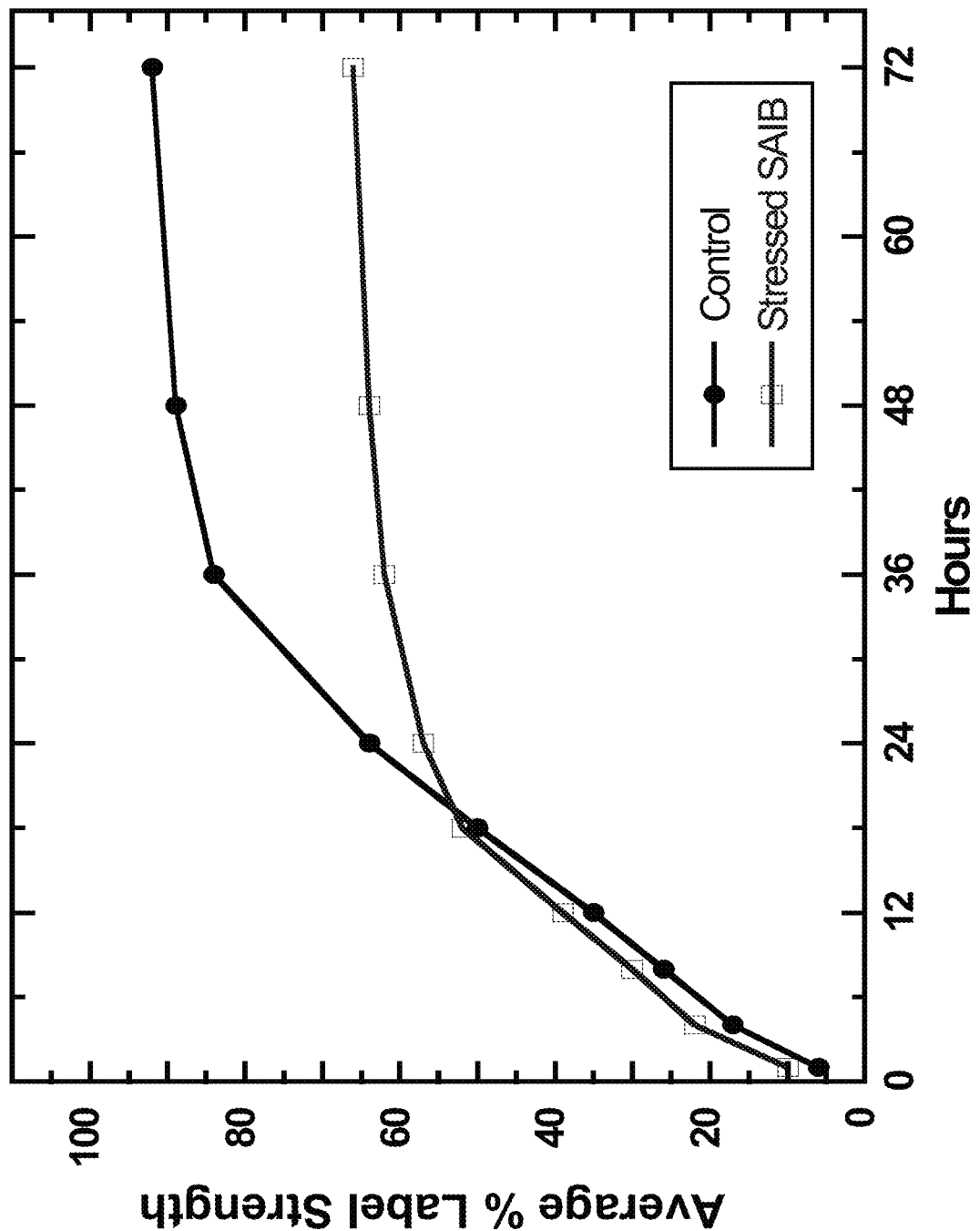
FIG. 14 shows mean cumulative release of a control formulation (N=12) and heat-stressed SAB formulation (N=12).

In vitro release of bupivacaine for the formulations described above was assessed according to the methods described below. FIG. 14 shows the mean cumulative release of the control formulation (N=12) and heat-stressed SAIB formulation (N=12).

Comparison of the heat-stressed SAIB formulation with the control in FIG. 14 shows that both formulations were similar from 1 to 18 hours. Starting at 24 hours, the release profile of the heat-stressed SAIB formulation levels off reaching about 66% drug released at 72 hours.

Methods and Materials

Cumulative Release of Bupivacaine In Vitro

The in vitro cumulative release of bupivacaine from formulations was determined as follows.

Materials

The bupivacaine formulations, other than the heat-stressed formulation, were prepared by dissolving appropriate amounts of bupivacaine in appropriate amounts of benzyl alcohol (BA), adding an appropriate amount of sucrose acetate isobutyrate (SAIB), and stirring not less than 45 minutes at about 35° C. For the heat-stressed SAIB formulation, the same process was followed except the SAIB was pre-heated in an oven at 225° C. for 4 hours before use. A portion of the pre-heated SAIB was tested and found to have 98% SAIB remaining.

Dissolution Testing

Dissolution was measured using a USP Apparatus II. Approximately 0.5 mL of each formulation was loaded via cannula and syringed into 900 mL±5 mL of 37±0.5° C. dissolution media (phosphate buffer at pH 7.4±0.05 with 0.03% sodium lauryl sulfate). The USP Apparatus II was set at 50 RPM, and samples were collected at 1, 4, 8, 12, 18, 24, 36, 48, and 72 hours. The number of replicates (N) per sample per time point varied as described above. The collected samples were assayed for bupivacaine content by HPLC.

Statistical Analysis

The dissolution profile comparisons were conducted using a difference factor ($f_1$) and a similarity factor ($f_2$) approach (FDA Guidance for Industry "Dissolution Testing of Immediate Release Solid Oral Dosage Forms" August 1997). The difference factor calculates the percent difference between two curves at each time point and is a measurement of the relative error between the two curves, as shown in Equation 1:

$$f_1 = \{[\Sigma_{t=1}^{n}|R_t - T_t|]/[\Sigma_{t=1}^{n} R_t]\} \times 100 \qquad (1)$$

In Equation 1, $R_t$ and $T_t$ represent the mean dissolution results obtained from the reference and test lots respectively, at each dissolution time point t, while n represents the number of dissolution time points.

The similarity factor ($f_2$) is a logarithmic reciprocal square root transformation of the sum of squared error and is a measurement of the similarity in the percent dissolution between the two curves, as shown in Equation 2.

$$f_2 = 50 \times \log\{[1 + (1/n)\Sigma_{t=1}^{n}(R_t - T_t)^2]^{-0.5} \times 100\} \qquad (2)$$

The terms in Equation 2 are as defined in Equation 1. The value of $f_2$ can range from 0 to 100, with a larger $f_2$ indicating greater similarity between the reference and test article. A $f_2$ value of 50 corresponds to an average difference of 10% at each time point.

For two curves to be considered similar, the f1 value should be close to 0, and the f2 value should be close to 100. Generally, $f_1$ values of 0-15 and $f_2$ values of 50-100 ensure sameness or equivalence of two curves, and thus of the performance of the test and reference products.

Example 13

A randomized, double-blinded, active- and placebo-controlled study was conducted to evaluate the efficacy and safety of Formulation A for post-operative pain control in patients following arthroscopic shoulder surgery.

Objectives

The objective was to identify the optimal dose of Formulation A for post-operative pain control administered into the subacromial space in patients undergoing elective arthroscopic shoulder surgery on the basis of efficacy, pharmacokinetics (PK), and safety evaluations.

Methods

The study was a parallel group, randomized, double-blinded, active- and placebo-controlled, dose response trial of Formulation A with post-operative assessments of pain intensity (PI), PK, safety, and health economics in patients undergoing elective arthroscopic shoulder surgery, comprising up to a 14-day screening period, a 7-day post-surgical period, an EOT visit at Day 14, and a follow-up visit after six months.

| | |
|---|---|
| Composition: | Formulation A |
| Active ingredient: | Bupivacaine base |
| Inactive ingredients: | Sucrose acetate isobutyrate, benzyl alcohol |
| Administration: | Varied, based on surgical procedure, interstitial (FDA Code 088) either by tissue infiltration, injection or needle-free deposition for general surgical applications. |
| Strength: | 132 mg/mL, 660 mg bupivacaine |

| | |
|---|---|
| Composition | Placebo |
| Active ingredient: | Not applicable |
| Inactive ingredients: | Sucrose acetate isobytyrate, benzyl alcohol |
| Administration: | Varied, based on surgical procedure, interstitial (FDA Code 088) either by tissue infiltration, injection or needle-free deposition for general surgical applications. |

| | |
|---|---|
| Composition: | Active Control |
| Active ingredient: | Bupivacaine HCl |
| Inactive ingredients: | Sterile isotonic solution containing sodium chloride |
| Administration: | Varied, based on surgical procedure, interstitial (FDA Code 088) either by tissue infiltration, injection or needle-free deposition for general surgical applications. |
| Strength: | 20 mL of 2.5 mg/mL, 50 mg |

Patients were screened 1 to 14 days before surgery at which time informed consent was obtained. Surgery was performed and the trial drug administered on Day 0. The trial was planned to be divided into two sequential cohorts, each with three treatment groups (a, b and c). After screening, the first patients were randomized 2:1:1 to the treatment groups in cohort 1: 1a) 5 mL Formulation A (660 mg bupivacaine)

subacromial administration; 1b) 5 mL placebo subacromial administration; and 1c) 20 mL standard bupivacaine hydrochloride (HCl) 0.25% w/v (50 mg bupivacaine) administered subacromially. After finalization of cohort 1, data was analyzed and, based on the efficacy, safety and PK results presented in this clinical trial report (CTR), a decision was made regarding whether the second cohort (cohort 2) would be initiated, and whether new patients would be recruited and treated at the higher dosage of Formulation A: 2a) 7.5 mL Formulation A (990 mg bupivacaine) administered subacromially; 2b) 7.5 mL placebo administered subacromially; and 2c) 20 mL standard bupivacaine HCl (50 mg bupivacaine) administered subacromially. The Data Review Committee recommended that an increase in dose to 7.5 mL of Formulation A was not expected to provide a clinically significant improvement in efficacy. Therefore, the trial did not include the 7.5 mL Cohort 2.

All patients received paracetamol (4 grams/day; 2 grams/day for body weight <66 kg for the first 72 hours) as background treatment. In case sufficient pain relief was not obtained, patients were allowed rescue medication in the form of morphine administered intravenously or orally, which consisted of oral morphine 10 mg at 1-hour intervals or, if unable to tolerate orally intake, intravenous (IV) morphine 2 g at 5-minute intervals. After 72 hours, subjects were allowed paracetamol and oral morphine on an as-needed basis. Patients recorded pain intensity as well as rescue medication in an electronic diary (eDiary).

Diagnosis and Main Criteria for Inclusion/Exclusion:

Subjects with subacromial impingement syndrome and an intact rotator cuff established by magnetic resonance imaging (MRI) and who were suitable for general anesthesia were eligible for inclusion. Patients with other shoulder pathology or who had serious medical conditions or who were unable to tolerate the study drug were excluded.

Formulation A, Dose and Mode of Administration:

9.0 mL Formulation A (132 mg bupivacaine/mL) per vial. Following surgery, 5 mL Formulation A (660 mg bupivacaine) (cohort 1) was administered into the subacromial space through one of the arthroscopic portals or by injection through intact skin under direct arthroscopic vision to confirm placement of the needle tip within the suvacromial space. Formulation A was administered once only following completion of surgery.

Reference Composition, Dose and Mode of Administration:

This trial was placebo-controlled and had an active comparator arm. Placebo (5 mL) was administered using the same method as for Formulation A. The active comparator was standard bupivacaine HCl (20 mL of 2.5 mg/mL) was administered subacromially as a single dose.

Criteria for Evaluation

Efficacy

Primary: The study had two primary endpoints. The primary efficacy endpoints were: PI on movement area under the curve AUC over the time period 1 to 72 hours post-surgery measured by an 11-point Numerical Rating Scale (NRS); and total use of opioid rescue analgesia 0 to 72 hours after surgery. For the primary endpoints to be met, non-inferiority of PI on movement compared to placebo as well as superiority in total use of opioid analgesia needed to be shown. PI "on movement" reported on the NRS scale was summarized by treatment group and time, using descriptive statistics for continuous variables.

Secondary: Time to first opioid rescue medication usage; Opioid-Related Symptom Distress Scale (OR-SDS) score Days 0 to 7 post-surgery; PI at rest AUC over the period 1 to 72 hours post-surgery; patient's pain treatment satisfaction score on Day 4 post-surgery; proportion of patients who were dischargeable (according to the Post-Anaesthetic Discharge Scoring System [PADS]) on Days 1, 2, 3, 4 and 7 post-surgery; and proportion of patients who had returned to work by Day 14 post-surgery. Time to first opioid rescue medication usage was defined as the duration between time of trial drug administration and the time of first opioid use Pharmacokinetics Total and free bupivacaine plasma concentrations were measured for the Formulation A and standard bupivacaine HCl groups for evaluation of bupivacaine PK, including maximum concentrations of bupivacaine. Additionally, alpha 1 acid glycoprotein (AAG) plasma concentrations were measured in these two groups for correlation with free bupivacaine concentrations.

Pharmacokinetic/pharmacodynamic (PK/PD) relationships were to be assessed as part of central nervous system (CNS) toxicity monitoring and cardiac monitoring. For patients not selected for PK-profiling, if a cardiac or CNS event occurred that met the criteria for a serious adverse event (SAE) or a severe non-SAE, a blood sample for PK analysis was to be taken as close to the event as possible.

Safety

The incidence of adverse events (AEs); the incidence of bupivacaine-related CNS side effects; clinical laboratory tests; vital signs; 12-lead ECGs; and physical examinations.

Other Assessments

Evaluation by the investigator of wound healing and tissue conditions at the surgical wound on Days 7 and 14, and at the 6-month follow-up visit. An MRI of the shoulder as well as a functionality assessment of the shoulder using the Constant-Murley score were to be performed at the 6-month follow-up visit.

Results

Primary Efficacy Endpoints

Figure 15:
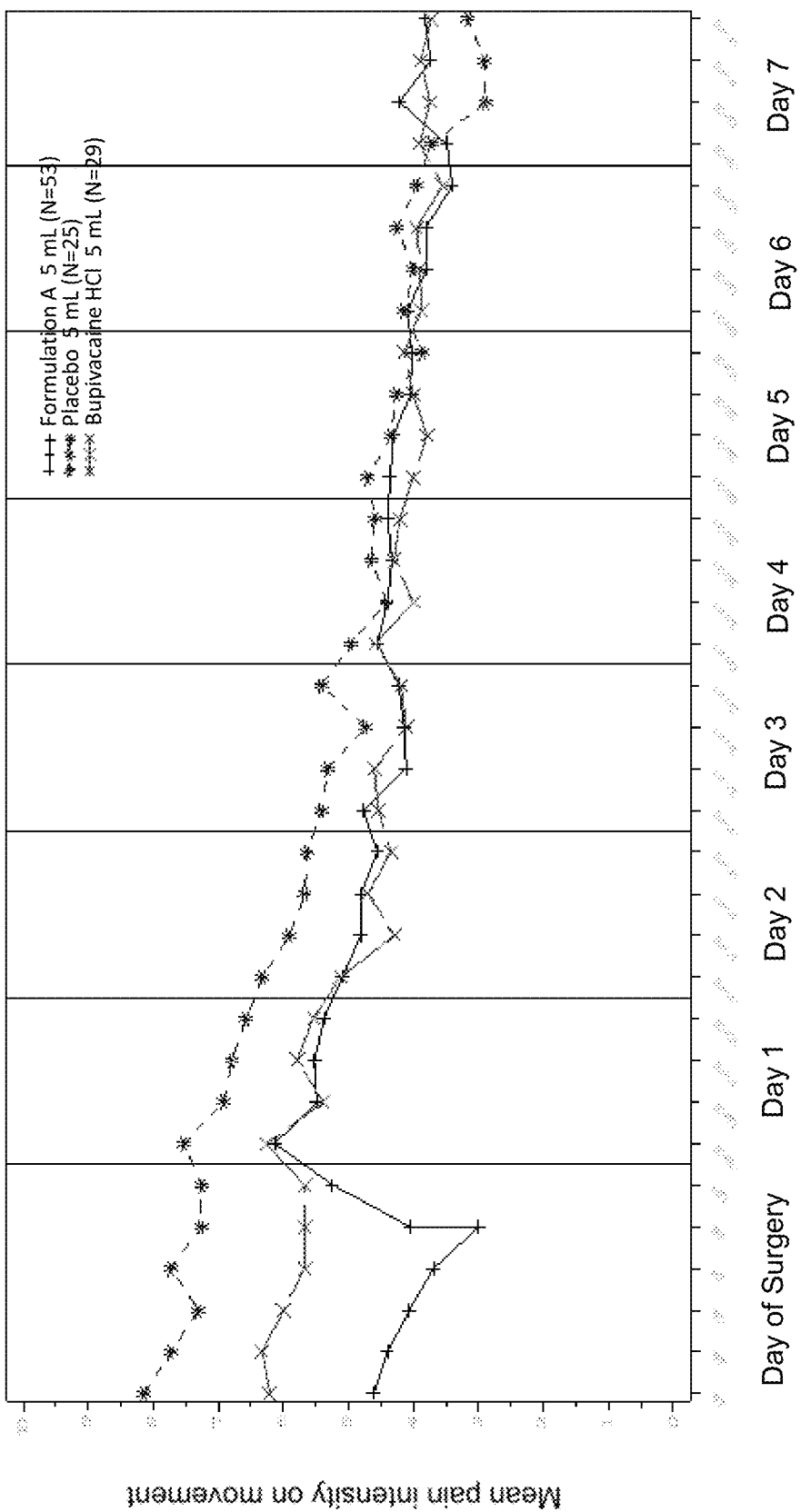
FIG. 15 shows pain intensity (PI) on movement over time for the intent-to-treat (ITT) population.

The mean PI on movement AUC over the time period 1 to 72 hours post-surgery (ITT population) is summarized in Table 13.1. The Formulation A group was shown to be statistically superior over placebo for the time period 1 to 72 hours post-surgery (p-value: 0.012). The PI on movement over time for the ITT population is shown in FIG. 15.

TABLE 13.1

Pain intensity on movement, mean AUC (LOCF) (ITT population)

| Treatment | Variable | n | Mean | SD | 95% CI | p-value |
|---|---|---|---|---|---|---|
| Formulation A 5 mL | AUC (1-24 | 53 | 5.16 | 2.04 | | |
| | AUC (24-48 | 51 | 5.38 | 2.23 | | |
| | AUC (48-72 | 53 | 4.87 | 2.33 | | |
| | AUC (1-48 | 53 | 5.31 | 1.94 | | |
| | AUC (1-72 | 53 | 5.16 | 1.94 | | |
| Placebo 5 mL | AUC (1-24 | 24 | 7.31 | 1.89 | | |
| | AUC (24-48 | 24 | 6.62 | 1.93 | | |
| | AUC (48-72 | 25 | 5.57 | 2.06 | | |
| | AUC (1-48 | 25 | 6.88 | 1.82 | | |
| | AUC (1-72 | 25 | 6.43 | 1.77 | | |
| Standard Bupivacaine HCl | AUC (1-24 | 29 | 5.82 | 2.30 | | |
| | AUC (24-48 | 29 | 5.31 | 2.70 | | |
| | AUC (48-72 | 29 | 4.38 | 2.48 | | |
| | AUC (1-48 | 29 | 5.56 | 2.43 | | |
| | AUC (1-72 | 29 | 5.16 | 2.38 | | |
| Difference: Formulation A 5 mL minus Placebo 5 mL | AUC (1-24 | 106 | −2.14 | 0.52 | | |
| | AUC (24-48 | 104 | −1.22 | 0.58 | | |
| | AUC (48-72 | 107 | −0.68 | 0.56 | | |
| | AUC (1-48 | 107 | −1.56 | 0.50 | [−2.56; −0.56] | 0.002 |
| | AUC (1-72 | 107 | −1.27 | 0.50 | [−2.25; −0.28] | 0.012 |

TABLE 13.1-continued

Pain intensity on movement, mean AUC (LOCF) (ITT population)

| Treatment | Variable | n | Mean | SD | 95% CI | p-value |
|---|---|---|---|---|---|---|
| Difference: | AUC (1-24 | 106 | −0.66 | 0.49 | | |
| Formulation A | AUC (24-48 | 104 | 0.03 | 0.54 | | |
| 5 mL minus | AUC (48-72 | 107 | 0.48 | 0.54 | | |
| Standard | AUC (1-48 | 107 | −0.27 | 0.48 | [−1.22; 0.69] | |
| Bupivacaine HCl | AUC (1-72 | 107 | −0.02 | 0.47 | [−0.96; 0.92] | | n = number of patients with available data; SD = standard deviation; CI = confidence interval; AUC = area under the curve; LOCF = last observation carried forward; ITT = intention to treat.
LS Mean difference and standard error is presented for treatment differences.
P-value from ANOVA with treatment group and trial site in the model.

Significantly less opioid rescue medication was taken by subjects treated with Formulation A than placebo (Table 13.2). The median cumulative IV morphine-equivalent dose of opioids from 0 to 72 hours after treatment was 4.0 mg for the Formulation A group and 12.0 mg for the placebo group (p=0.0130). The median cumulative dose was 8.0 mg for the bupivacaine HCl group. Postoperative opioid rescue medication use was analyzed nonparametrically because it did not meet prespecified normality assumptions. The percentage of subjects that remained opioid free during the 72 hours after surgery was also significantly greater in the Formulation A group than the placebo group: 39.6% v. 16.0% (P=0.027). The percentage abstaining from opioids in the bupivacaine HCl group was 27.6%.

TABLE 13.2

Total IV morphine equivalent dose of opioid rescue medication taken from 0-72 hours after surgery, ITT population

| | Placebo (N = 25) | Formulation A (N = 53) | Bupivacaine HCl (N = 29) |
|---|---|---|---|
| Min, max, mg | 0, 92 | 0, 176 | 0, 66 |
| Median, mg | 12.0 | 4.0 | 8.0 |
| Median difference vs placebo, mg [1] | | −8.0 | |
| 95% CI | | −12.0, 0.0 | |
| P-value [2] | | 0.0100 | |
| Median difference vs bupivacaine HCl, mg [1] | | | 0.0 |
| 95% CI | | | −4.6, 0.0 |
| P-value [2] | | | — |

CI, confidence interval; ITT, intent-to-treat; IV, intravenous
[1] Hodges-Lehmann estimates for median difference
[2] Wilcoxon rank-sum test Secondary Efficacy Variables Treatment with Formulation A significantly prolonged the time to first postsurgical use of opioid rescue medication compared with placebo (Table 13.3). The median time to first use was 12.4 hours for the Formulation A group and 1.2 hours for the placebo group (p=0.0137). The median time to first use was 1.4 hours for the bupivacaine HCl group.

TABLE 13.3

Time to first use of opioid rescue medication, ITT population

| | Placebo (N = 25) | Formulation A (N = 53) | Bupivacaine HCl (N = 29) |
|---|---|---|---|
| Min, Max | 0.0, 14.2 | 0.0, 36.6 | 0.0, 10.9 |
| Median (95% CI), hours [1] | 1.2 (0.7, 1.5) | 12.4 (1.2, −) | 1.4 (1.0, 4.1) |
| P-value for median difference vs placebo [2] | | 0.0137 | |

TABLE 13.3-continued

Time to first use of opioid rescue medication, ITT population

| | Placebo (N = 25) | Formulation A (N = 53) | Bupivacaine HCl (N = 29) |
|---|---|---|---|
| P-value for median difference vs bupivacaine HCl [2] | | | — |

CI, confidence interval; ITT, intention-to-treat; min, minimum; max, maximum
Note:
Subjects who did not use opioid rescue medication on-study were censored at their last study visit.
[1] Median time from study treatment to administration of an opioid medication reported as a concomitant medication, based on Kaplan-Meier survival estimates.
[2] Log-rank test.

Comparison of the OR-SDS scores on Day 0 to 7 did not reveal any statistically significant differences between treatment groups (Formulation A versus placebo and Formulation A versus standard bupivacaine HCl).

Overall, 81 patients (75.7% of patients in the ITT population) experienced at least one opioid-related side effect in the period Day 0 to 3, the frequency and number of patients experiencing all opioid-related side effects was similar across all treatment groups. Drowsiness, fatigue and dizziness were the most frequent opioid-related symptoms recorded for the total (ITT) population in the period Day 0 to 3.

Table 13.4 summarizes PI at rest normalized AUC 1-72 hours post surgery for the ITT population. As with P; on movement, Formulation A significantly reduced PI over 72 hours compared to Placebo. The difference between Formulation A and Bupivacaine HCl was not significant.

TABLE 13.4

Pain intensity at rest normalized AUC 1-72 hours, ITT population

| | Placebo (N = 25) | Formulation A (N = 53) | Bupivacaine HCl (N = 29) |
|---|---|---|---|
| Mean (SD) [1] | 3.43 (2.05) | 2.50 (1.34) | 2.33 (1.76) |
| LS mean difference (SE) vs placebo [1] | | −0.91 (0.39) | |
| 95% CI | | −1.68, −0.14 | |
| P-value [2] | | 0.021 | |
| LS mean difference (SE) vs bupivacaine HCl [1] | | | 0.12 (0.37) |
| 95% CI | | | −0.62, 0.85 |
| P-value [2] | | | — |

AUC, area under the curve;
CI, confidence interval;
SD, standard deviation;
SE, standard error of the mean
[1] ANOVA model with treatment group and country as factors;
missing pain scores imputed by last observation carried forward for subjects discontinuing before 72 hours, first observation carried backward for missing initial pain scores, and linear interpolation for missing pain scores between two non-missing scores.
[2] t-test in an ANOVA model.

On Day 4, the majority of patients were either satisfied (59.8% of patients) or very satisfied (27.1% of patients) with the pain treatment they had received for their surgery. Only one patient was very dissatisfied with her pain treatment (in the Formulation A group) and four patients were dissatisfied (three in the Formulation A group and one in the standard bupivacaine HCl group).

There were no statistically significant differences in the patients' pain satisfaction score (on Day 4 after surgery had been performed) between the treatment groups; Formulation A against placebo (p-value: 0.995) and Formulation A against standard bupivacaine HCl (p-value 0.699).

There were no statistically significant differences between the treatment groups in the patients' home-readiness on either day. The odds ratio for the pair-wise comparisons of Formulation A against placebo and Formulation A against standard bupivacaine HCl were 1.894 (CI: 0.693; 5.177, p-value: 0.213) and 1.240 (CI: 0.457; 3.366, p-value 0.673) on Day 1 (afternoon) and 2.654 (CI: 0.948; 7.428, p-value: 0.063) and 1.137 (CI: 0.419; 3.089, p-value 0.801) on Day 2 (afternoon).

There were also no statistically significant differences between the treatment groups in the number of patients who had returned to work after 14 days. The odds ratio for the pair-wise comparisons of Formulation A against placebo and Formulation A against standard bupivacaine HCl were 1.210 (CI: 0.325; 4.498, p-value: 0.776) and 1.505 (CI: 0.358; 6.329, p-value 0.577) on Day 14.

Pharmacokinetics

Total and free (unbound) bupivacaine plasma concentrations in patients undergoing arthroscopic subacromial decompression were measured following either administration of 5.0 mL Formulation A (660 mg bupivacaine) or administration of 20 mL standard bupivacaine HCl (50 mg bupivacaine). Using non-compartmental methods the following PK parameters were calculated from the plasma concentrations of each compound: area under the plasma concentration vs. time curve until the last measured concentration ($AUC_t$), area under the plasma concentration vs. time curve extrapolated until infinity ($AUC_{inf}$), the maximum concentration ($C_{max}$), the time of its occurrence ($t_{max}$) and the apparent terminal elimination half-life ($t_{1/2}$). Due to the extended release characteristics of the Formulation A, bupivacaine plasma concentrations increased relatively slowly and extended profiles of both total and free bupivacaine were observed. At 96 h post dose there are still measureable plasma concentrations in most patients of the Formulation A group. Bupivacaine HCl plasma concentrations were considerably lower than in the Formulation A group at all timepoints. The average plasma protein binding of bupivacaine was approximately 5.2%; free bupivacaine plasma concentrations generally paralleled those of total bupivacaine. There was a large interindividual variability of $C_{max}$ of both total and free bupivacaine. The highest individual $C_{max}$-values of total and free bupivacaine were 1.320 mg/L and 0.074 mg/L, respectively. Note: Table 13.5 presents Geometric mean, ±68$^{th}$ percentile for $C_{max}$ rather than absolute min, max.

Mean $C_{max}$ and AUC of bupivacaine in the current study were considerably lower than expected from historic studies. A variable amount of the administered dose may have escaped from the wound between administration and closure of the wound, possibly leading to a significantly reduced exposure to bupivacaine.

Figure 16:
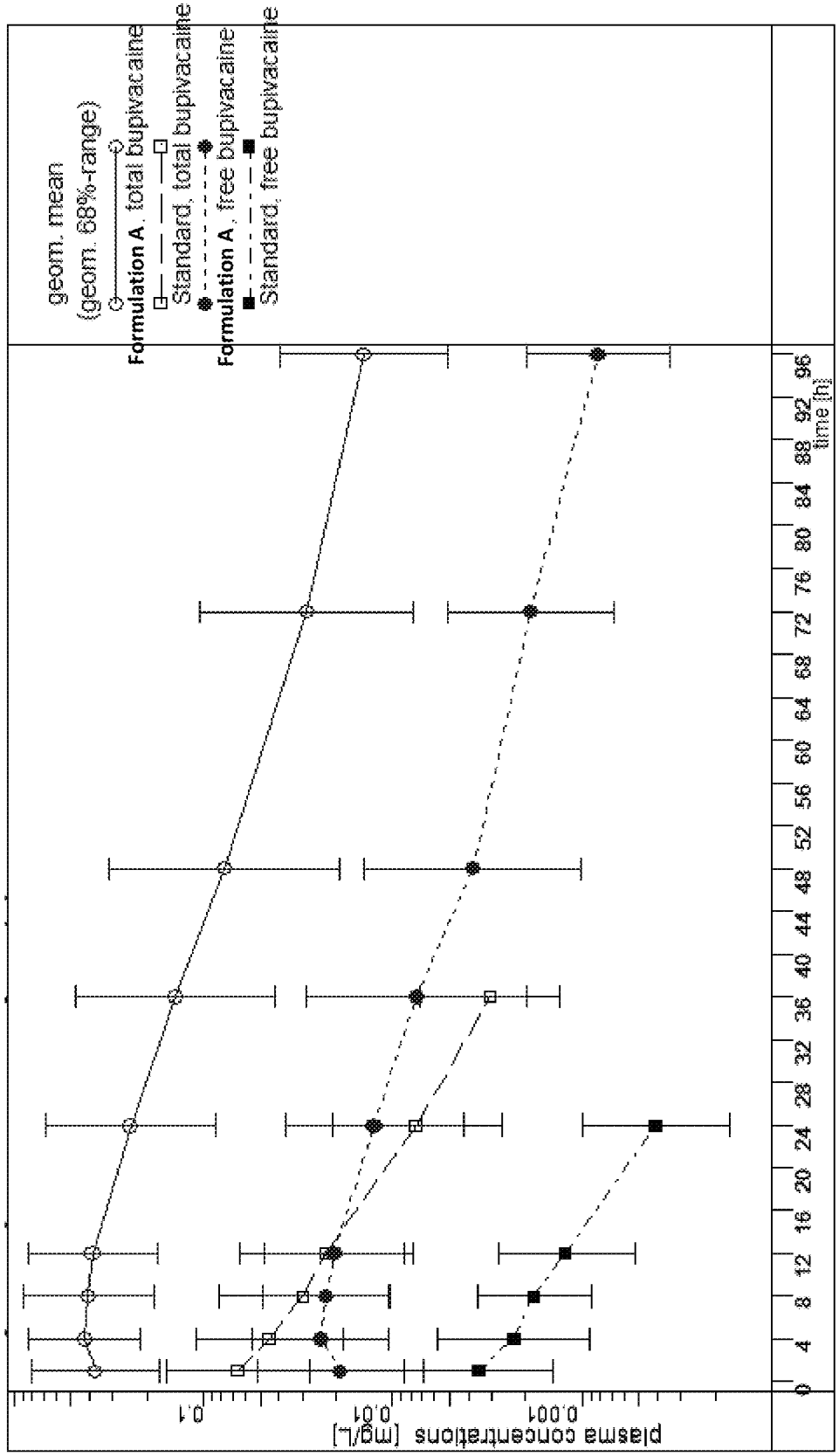
FIG. 16 shows geometric mean total and free bupivacaine plasma concentration following bupivacaine concentration following administration of Formulation A or standard bupivacaine.

There was no apparent influence of either total or free bupivacaine on any cardiovascular parameters (QTcF, QTcB and QRS) even at the highest observed bupivacaine plasma concentrations. The few reported CNS side effects did not correlate with either $C_{max}$ or $t_{max}$ of free bupivacaine. Geometric mean total and free bupivacaine plasma concentration following bupivacaine concentration following Formulation A or standard bupivacaine are presented in FIG. 16.

Figure 17:
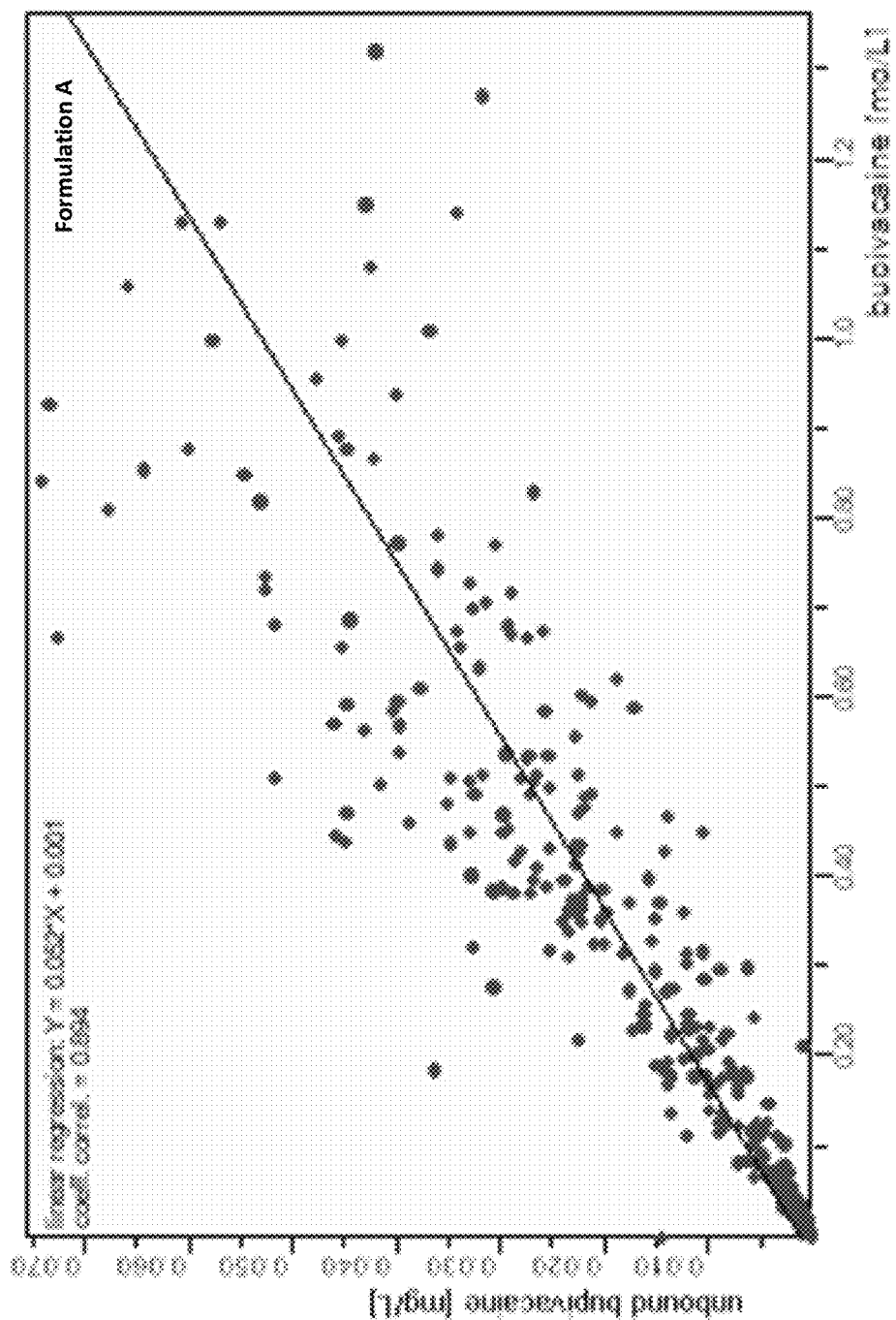
FIG. 17 shows a correlation of all individual plasma concentrations of free versus total bupivacaine for Formulation A.

FIG. 17 shows a correlation of all individual plasma concentrations of free versus total bupivacaine for Formulation A. Free bupivacaine plasma concentrations increase in proportion with total bupivacaine concentrations. The slope of the regression line indicates the average free fraction (5.2%) over all timepoints and all patients. The plot also shows a high interindividual variability of the free fraction of bupivacaine, which means that high total bupivacaine concentrations do not necessarily imply high free bupivacaine concentrations and vice versa. A summary of the plasma PK-parameters of total and free bupivacaine following Formulation A or standard bupivacaine is presented in Table 13.5.

TABLE 13.5

Plasma PK-parameters of total and free bupivacaine following administration of Formulation A or standard bupivacaine HCl:

| PK-parameter Mean (min, max) | Formulation A (total) | Formulation A (free) | Standard bupivacaine HCl (total) | Standard bupivacaine HCl (free) |
|---|---|---|---|---|
| $t_{1/2}$ [h] | 16.4 (8.4, 29) | 15.8 (5.9, 35) | 5.93 (2.6, 9.6) | 6.65 (2.9, 15.2) |
| $t_{max}$ median [h] | 5.94 (0, 24) | 4.00 (1.0, 24.0) | 1.03 (0.92, 12.0) | 1.03 (0.92, 12.0) |
| $C_{max}$ [ng/mL] | 593 (70, 1320) | 36.3 (2.5, 74) | 90 (8, 195) | 5.0 (0.3, 10.1) |
| $AUC_t$ [mg·h·L$^{-1}$] | 14.98 (6.47, 34.69) | 0.795 (0.323, 1.96) | 0.686 (0.249, 1.90) | 0.033 (0.010, 0.102) |
| $AUC_{inf}$ [h.ng/mL] | 19395 (1030, 55370) | 1045 (44, 2306) | 940 (30, 2210) | 48 (0.7, 134) |

Safety

There were no deaths in the trial and six patients experienced one SAE (one pregnancy case was reported as SAE). One SAE (pulmonary arterial hypertension, reported 113 days after treatment with Formulation A) was considered related to trial drug. Overall, 37 patients (34.6%) experienced at least one TEAE (65 TEAEs were reported in total), of which the majority were of mild or moderate intensity. Nine patients (8.4%) reported TEAEs that were considered to be related to treatment with no notable differences between treatment groups. The most commonly reported TEAEs (see Table 13.6) were within the following System Organ Classes (SOCs): Nervous system disorders; Investigations; and Gastrointestinal disorders. The most commonly reported events (by preferred term) were nausea, headache and musculoskeletal pain (4.7% of patients for each). No patients withdrew due to a TEAE. Between Day 0 and Day 3, three patients in the safety population reported six CNS TEAEs.

The majority of patients in each treatment group had haematology and clinical chemistry parameter values that were either normal or were abnormal but not clinically significant throughout the trial. Clinically significant clinical chemistry abnormalities were reported for four patients (two in the placebo group and one each in the Formulation A and standard bupivacaine HCl groups); the vast majority of increases or decreases were in line with what could be expected after the surgical insult performed. They were assessed to be of no major safety concern.

There were no important differences in the mean and median blood pressure and heart rate on any day from screening to Day 7. There was no significant effect of Formulation A on ECG parameters.

Surgical site healing and/or local tissue conditions were as expected in all patients examined at Day 7, at EOT and at the 6-month follow-up visit. No patients were recorded as experiencing unexpected surgical site healing throughout the trial.

For the vast majority of patients analysed, MRI results from the MRI scan performed at the 6-month follow-up reflected changes from baseline that were consistent with either the surgical procedure insult injection; there were no notable differences between the Formulation A and standard bupivacaine groups.

Secondary efficacy endpoints, with the exception of PI at rest 1 to 72 hours postsurgery, did not reach statistical significance. Secondary efficacy analyses supported the results of the primary endpoint analyses.

Pharmacokinetics

PK-profiles supported the extended release characteristics of the Formulation A providing long-lasting plasma concentrations with a median Tmax of approximately 6 hours post dose. In contrast, plasma concentrations following standard bupivacaine were considerably lower than in the Formulation A at all timepoints. The average percentage of unbound bupivacaine was similar to the values known from literature for comparable studies.

The highest individual plasma concentrations of total and free bupivacaine were considerably lower than reported concentrations for the onset of potential CNS and/or cardiovascular side-effects. AAG plasma concentrations increased as expected post surgery, causing a slight decrease in the percentage of unbound bupivacaine.

TABLE 13.6

Summary of TEAEs by primary SOC (>2% total), preferred term and treatment group (safety population)

| Primary SOC<br>Preferred term | Formulation A<br>5 mL<br>N = 53 | | Placebo<br>5 mL<br>N = 25 | | Standard<br>Bupivacaine HCl<br>N = 29 | |
|---|---|---|---|---|---|---|
| | n | % | n | % | n | % |
| All TEAEs | 16 | 30.2 | 10 | 40.0 | 11 | 37.9 |
| Nervous system disorders | 5 | 9.4 | 2 | 8.0 | 4 | 13.8 |
| Headache | 3 | 5.7 | 1 | 4.0 | 1 | 3.4 |
| Investigations | 5 | 9.4 | 2 | 8.0 | 2 | 6.9 |
| Alanine aminotransferase increased | 1 | 1.9 | 2 | 8.0 | 0 | 0.0 |
| Gastrointestinal disorders | 2 | 3.8 | 3 | 12.0 | 1 | 3.4 |
| Nausea | 1 | 1.9 | 3 | 12.0 | 1 | 3.4 |
| Cardiac disorders | 1 | 1.9 | 2 | 8.0 | 3 | 10.3 |
| Musculoskeletal and connective tissue disorders | 3 | 5.7 | 1 | 4.0 | 2 | 6.9 |
| Musculoskeletal pain | 2 | 3.8 | 1 | 4.0 | 2 | 6.9 |
| Skin and subcutaneous tissue disorders | 2 | 3.8 | 2 | 8.0 | 2 | 6.9 |
| Injury, poisoning and procedural complications | 3 | 5.7 | 1 | 4.0 | 0 | 0.0 |
| General disorders and administration site conditions | 1 | 1.9 | 2 | 8.0 | 0 | 0.0 |
| Respiratory, thoracic and mediastinal disorders | 1 | 1.9 | 0 | 0.0 | 2 | 6.9 |

Primary SOCs are presented in descending frequency.
Preferred terms are sorted within primary SOC in descending total frequency, based on MedDRA. A patient with multiple occurrences of a TEAE under one treatment was counted only once in the preferred term for that treatment. A patient with multiple TEAEs within a primary SOC was counted only once in the total row.
MedDRA = Medical dictionary for regulatory activities; N = number of patients in a treatment group; n = number of patients with at least one event in the category; % = percentage of patients with at least one event in the category based on N; SOC = system organ class; TEAE = treatment-emergent adverse event.

Conclusions

Efficacy

Superiority of Formulation A to placebo was shown for mean PI on movement 1 to 72 hours post-surgery. Superiority over standard bupivacaine HCl was not met.

The total use of rescue analgesia at 0 to 72 hours for the Formulation A treatment group was statistically superior to placebo but not for standard bupivacaine HCl. The lack of statistical significance over bupivacaine HCl may have been a result of the small size of the study and the effects of background and rescue analgesia. Subjects in the bupivacaine HCl group used twice as much (based on median amount) opioid rescue medication as those in the Formulation A group.

Overall Formulation A demonstrated analgesic and opioid-sparing effects against placebo.

There was no apparent influence of either total or free bupivacaine on any cardiovascular parameters (QTcF, QTcB and QRS) even at the highest observed bupivacaine plasma concentrations.

Safety

The incidence and severity of treatment-emergent adverse events were similar for all treatment groups, and no functional or radiographic differences were noted at 6-month follow-up.

Formulation A was safe and well-tolerated, with no long-term safety signals observed at 6-month follow-up.

There were no deaths and the incidence of SAEs in this trial was low; one SAE was considered related to trial drug (in the Formulation A group).

In terms of systemic safety, Formulation A, standard bupivacaine HCl and placebo were generally safe and well tolerated. There were no notable differences between treatment groups regarding bupivacaine-related side effects. This suggests that concentrations of free bupivacaine remained below or at the low end of reported CNS toxicity threshold levels. Additionally, the reported CNS side effects did not correlate with either $C_{max}$ or $t_{max}$ of free bupivacaine.

There was no effect of Formulation A on ECG parameters.

There were no clinically meaningful differences between treatment groups regarding changes in the shoulder functionality test (Constant-Murley score) from baseline to 6 months follow-up.

There were no differences between treatment groups regarding wound healing and local tissue conditions.

Example 14

A clinical trial was conducted to explore therapeutic benefits of 5.0 mL Formulation A administered into the subacromial space in patients undergoing arthroscopic subacromial decompression. This trial further investigated systemic and local safety of Formulation A as compared to placebo in patients who will receive analgesic supplementation as needed with oral opioids per common clinical practice.

Objectives

Primary objective—Explore analgesic effectiveness and characterize the safety profile of Formulation A in an orthopedic surgical model compared to placebo.

Secondary objective—Explore the reduction in frequency of opioid-related adverse events (AEs) by Formulation A in an orthopedic surgical model compared to placebo.

Methods

The study was a randomized, double-blind, multi-center, placebo-controlled, parallel-group trial of a single dose of 5.0 mL Formulation A in subjects undergoing arthroscopic shoulder surgery. Subjects were assessed for pain and supplemental analgesia recorded (efficacy endpoints) and AEs, surgical site healing, local tissue condition, laboratory tests, physical examination and vital signs (safety endpoints).

| Composition: | Formulation A |
|---|---|
| Active ingredient: | Bupivacaine base |
| Inactive ingredients: | Sucrose acetate isobutyrate, benzyl alcohol |
| Administration: | Varied, based on surgical procedure, interstitial (FDA Code 088) either by tissue infiltration, injection or needle-free deposition for general surgical applications. |
| Strength: | 132 mg/mL, 660 mg bupivacaine |

| Composition | Placebo |
|---|---|
| Active ingredient: | Not applicable |
| Inactive ingredients: | Sucrose acetate isobutyrate, benzyl alcohol |
| Administration: | Varied, based on surgical procedure, interstitial (FDA Code 088) either by tissue infiltration, injection or needle-free deposition for general surgical applications. |

Number of subjects: 60 subjects were enrolled in the study. All 60 subjects enrolled in the study received at least part of a dose of Formulation A or placebo and have been included in the Modified Intent To Treat (MITT) population and the Safety Population. Fifty eight subjects were included in the Per-Protocol Population (subjects that received a complete administration of Formulation A or placebo, met surgical and anesthesia requirements, successfully underwent the surgical procedure and had at least one post-dose pain intensity recorded).

Diagnosis and criteria for inclusion: Male and female subjects, aged 18 to 65 years with clinical syndrome of subacromial impingement and scheduled for arthroscopic shoulder surgery; with American Society of Anesthesiologists (ASA) Physical Status Classification of P1 or P2 based on medical history, physical exam, 12 lead electrocardiogram (ECG) and laboratory tests; systolic blood pressure ≤139 mmHg and diastolic blood pressure ≤89 mmHg; willing to use medically acceptable method of contraception, and to refrain from strenuous activities and provide written consent were eligible to participate in the study.

Exclusion Criteria: Subjects with glenohumeral arthritis; major or full thickness rotator cuff tears diagnosed by Magnetic Resonance Imaging (MRI); prior arthroscopic surgery or open surgery on the study shoulder; chronic pain conditions requiring continuous use of corticosteroids for >three months; fibromyalgia; rheumatoid arthritis; seronegative inflammatory athropathies; calculated creatinine clearance <30 mL/min; pregnant or lactating; receiving more than 20 mg of hydrocodone daily (or equivalent) for three or more days within seven days of surgery; opioid tolerance; required use of non-steroidal anti-inflammatory drugs (NSAIDs) within 24 hours of surgery; regular use of anticonvulsants, antiepileptics, antidepressants, or monoamine oxidase inhibitors; regular use of drugs known to prolong QTc interval within seven days of surgery or five times the drugs half life whichever was longer; known hypersensitivity to local anesthetic agents of the amide type or morphine or other opioids; conditions contraindicated for use of opioids; known or suspected abuse of opioids, illicit drugs or alcohol abuse; participation in another trial within 30 days of surgery; not suitable according to the Investigator Surgical Requirements: The subject was not to receive Investigational Product if the following requirements were not met: index procedure was subacromonial decompression performed arthroscopically; other procedures included inspection of glenohumeral joint, synovectomy, removal or loose body, minor debridement of articular cartilage, minor debridement or minor repair of rotator cuff, distal clavicle excision, bursectomy, resection of coracoacromial ligament and subacromial spurs; any conduit between the subacromial space and glenohumeral joint that would allow seepage and entrapment of the Investigational Product in the joint capsule were to be avoided; procedures for shoulder instability were not allowed; biceptal tenodesis or tenotomy were not allowed.

Anesthesia Requirements: The arthroscopic shoulder surgery was performed under general anesthesia with propofol induction using intravenous (IV) fentanyl or equivalent; use of local anesthetics for wound perfusion or nerve blocks during the shoulder surgery was not allowed; use of NSAIDS during the shoulder surgery was not allowed; epinephrine could be used in perfusion solution for reduction of bleeding; short-acting opioids used during general anesthesia were not restricted, post-operative opioids given prophylactically for pain were not allowed; antiemetic medications used for general anesthesia were not restricted, post-operative antiemetic medications were not given prophylactically.

Formulation A: Single dose of 5.0 mL Formulation A (132 mg/mL, 660 mg bupivacaine) injected into the subacromial space on completion of arthroscopic shoulder surgery. The formulation includes 3 components (sucrose acetate isobutyrate 66 wt %, benzyl alcohol 22.0 wt %, and bupivacaine base 12.0 wt %) that are administered together as a sterile solution.
Reference therapy, dose and mode of administration: Single dose of 5.0 mL placebo composition was injected into the subacromial space on completion of arthroscopic shoulder surgery
Duration of Treatment: The study was expected to be approximately 4 weeks in duration per subject. This comprised; a 14 day screening period, a single dose administration on the day of surgery, and a follow-up period of 14 days.
Criteria for Evaluation:
    Assessment for efficacy: Shoulder pain intensity 'on movement'; Use of supplemental analgesia for post-operative pain relief.
    Assessment of safety: Frequency and severity of AEs; surgical site healing and local tissue condition evaluation; Laboratory tests (chemistry, hematology and urinalysis); Physical examination, ECGs and vital signs.
Statistical Methods:
Randomization: Patients will be randomized (2-to-1 ratio) to Formulation A or Placebo.
Co-Primary Efficacy Endpoints:
Mean Pain Intensity on Movement Area Under the Curve (AUC) normalized over the time period 0 to 72 hours post-dose and Mean total IV morphine-equivalent dose during the period 0 to 72 hours post-dose.
Results
Efficacy Results:
Pain Intensity Normalized AUC Over 0-72 Hours Post-Dose
    Pain intensity normalized AUC over 0-72 hours was compared between treatment groups using ANCOVA with treatment group and trial site as factors and age as a covariate. Although not statistically significant, there was a trend towards the Formulation A group in pain intensity normalized AUC over 0-72 hours. The LS means were 5.33 for the Formulation A group and 5.97 for the placebo group. The pain scores in the Formulation A group were consistently lower than in the placebo group the mean difference between the groups being most prominent in the first 24 hours (Table 14.1 below).

TABLE 14.1

Pain Intensity Normalized AUC over Scheduled Assessments by Treatment (MITT Subjects Set)

| Least-Squares Means[1] | Formulation A (n = 40) | Placebo (n = 20) | Difference in Means (Active-Placebo) |
|---|---|---|---|
| AUC 0-24 hours | 5.56 | 6.38 | −0.81 |
| AUC 0-36 hours | 5.72 | 6.38 | −0.66 |
| AUC 0-48 hours | 5.62 | 6.30 | −0.67 |
| AUC 0-72 hours | 5.33 | 5.97 | −0.64 |
| AUC 0-96 hours | 5.07 | 5.62 | −0.55 |
| AUC 0-last hours | 4.04 | 4.27 | −0.23 |
| AUC 24-48 hours | 5.59 | 6.27 | −0.68 |
| AUC 36-72 hours | 4.77 | 5.34 | −0.57 |
| AUC 48-72 hours | 4.72 | 5.27 | −0.55 |
| AUC 72-96 hours | 4.31 | 4.62 | −0.31 |

[1]Least-Squares Means estimated using an ANOVA model with treatment group and study site as factors Cumulative IV Morphine-Equivalent Dose Over 0-72 Hours Post-Dose
    Opioid rescue analgesia cumulative IV morphine equivalent dose is presented by treatment in Table 14.2 below. Cumulative morphine equivalent dose over 0-72 hours was compared between treatment groups using ANCOVA with treatment group and trial site as factors and age as a covariate. Although not statistically significant, there was a trend towards the 5.0 mL Formulation A group in cumulative IV morphine equivalent dose over 0-72 hours. The LS mean were 44.27 for the 5.0 mL Formulation A group and 54.51 for the placebo group.

TABLE 14.2

Opioid Rescue Analgesia Cumulative IV Morphine Equivalent Dose (mg) by Treatment (MITT Subjects Set)

| Least-Squares Means[1] | Formulation A (n = 40) | Placebo (n = 20) | Difference in Means (Active-Placebo) |
|---|---|---|---|
| Day 0-Day 2 (0-48 Hours) | 36.47 | 47.21 | −10.74 |
| Day 0-Day 3 (0-72 Hours) | 44.27 | 54.51 | −10.25 |
| Day 0-Day 14 | 69.13 | 77.91 | −8.77 |
| 0-24 Hours | 24.19 | 35.37 | −11.18 |
| 24-48 Hours | 12.35 | 12.51 | −0.16 |
| 48-72 Hours | 7.77 | 7.60 | 0.17 |

Figure 18:
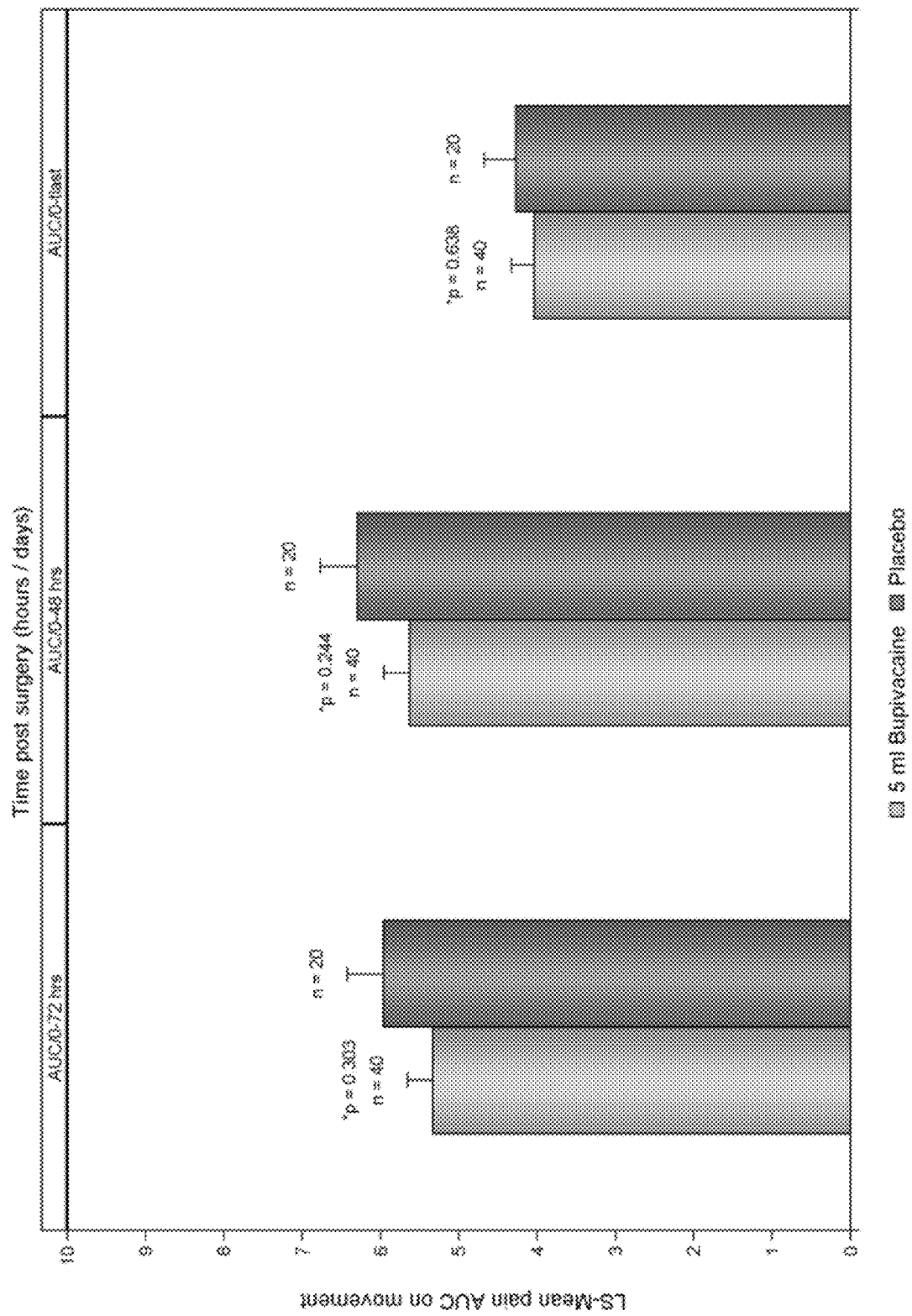
FIG. 18 shows pain intensity normalized AUC was compared between treatment groups using ANCOVA with treatment group and trial site as factors and age as a covariate.
Figure 19A:
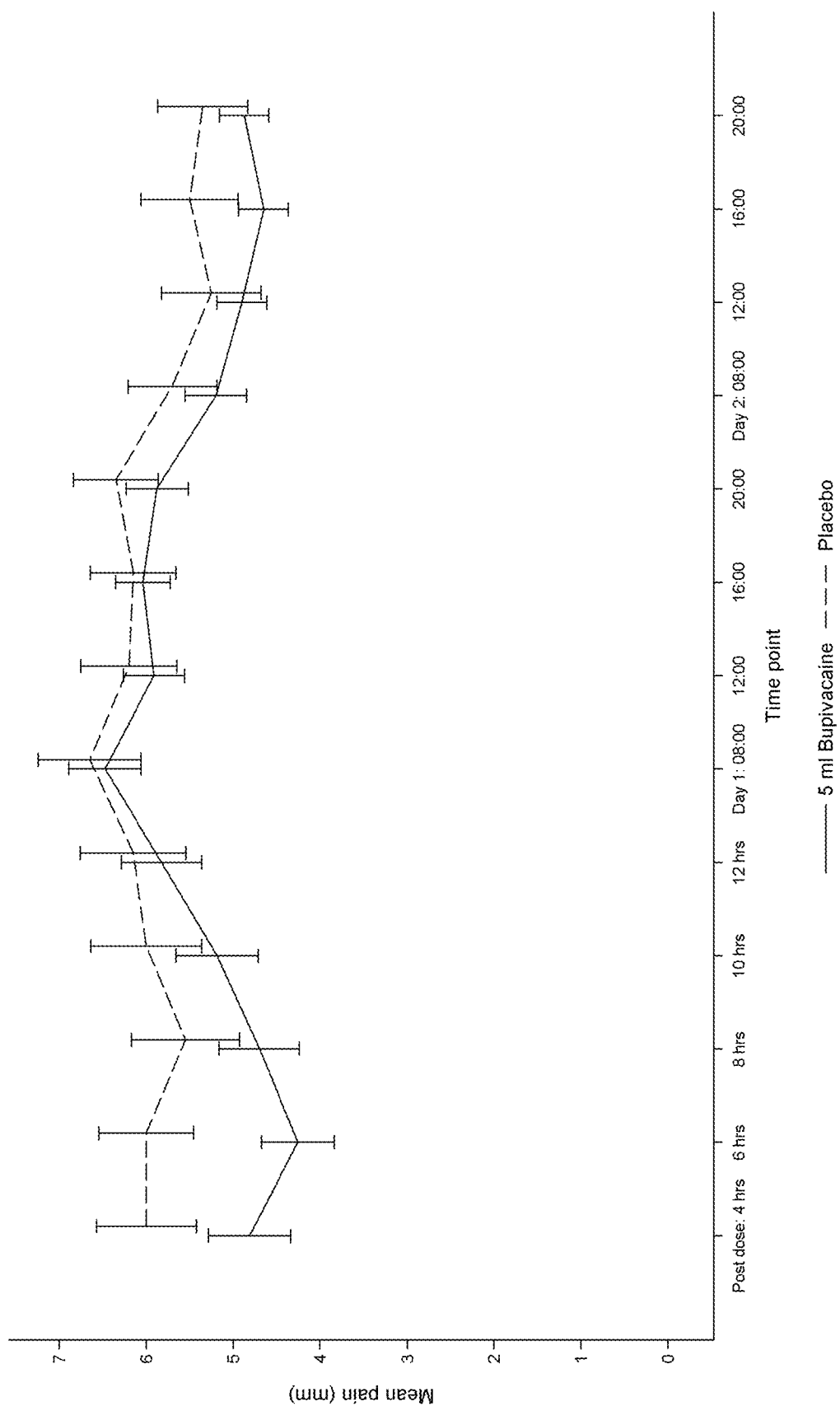
FIG. 19A shows the mean pain intensity on movement by subjects in the modified intent-to-treat (MITT) set administered Formulation A as compared to subjects administered placebo at time points post dose.
Figure 19B:
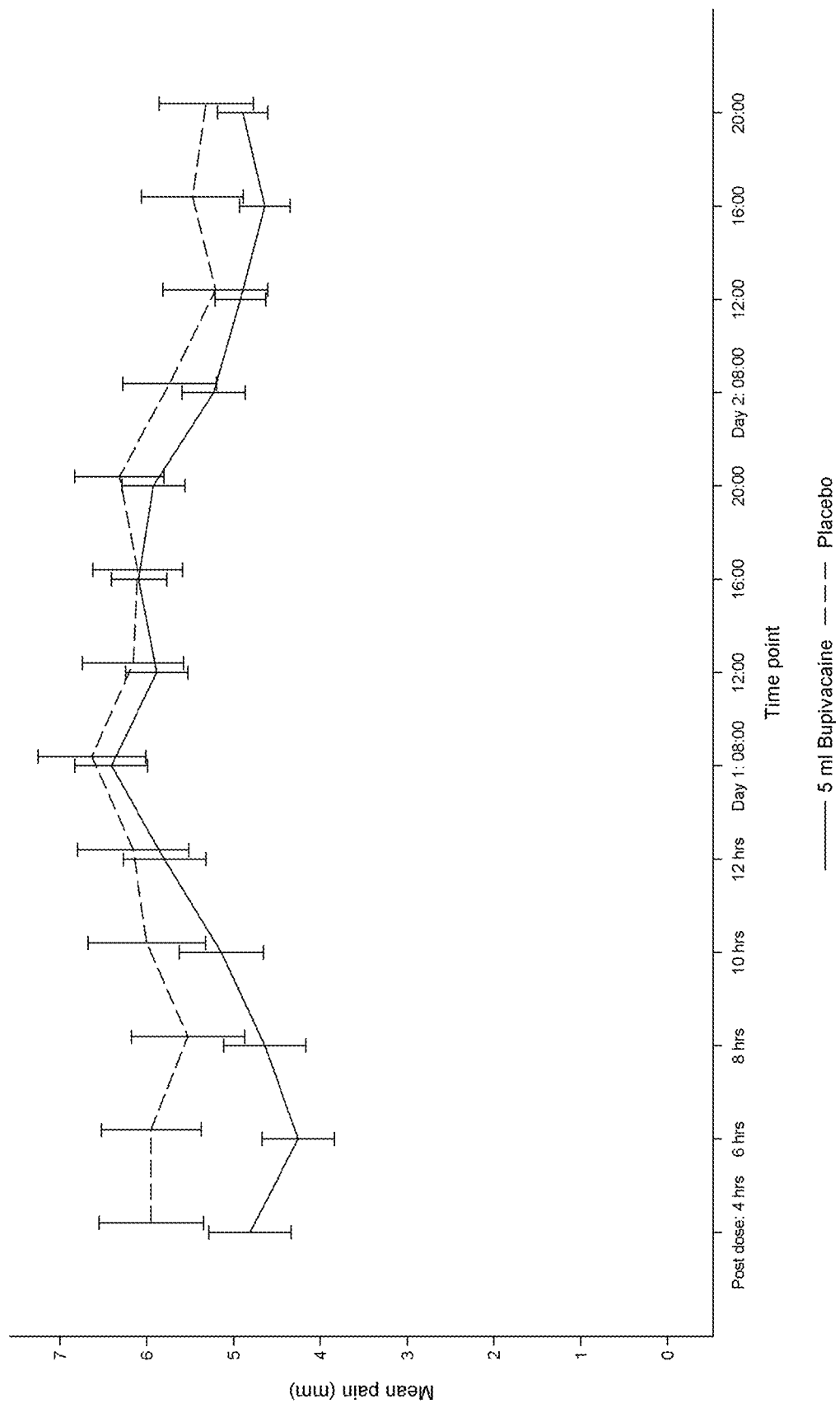
FIG. 19B depicts the mean pain intensity on movement by subjects in the per protocol (PP) set administered Formulation A as compared to subjects administered placebo at time points post dose.
Figure 20:
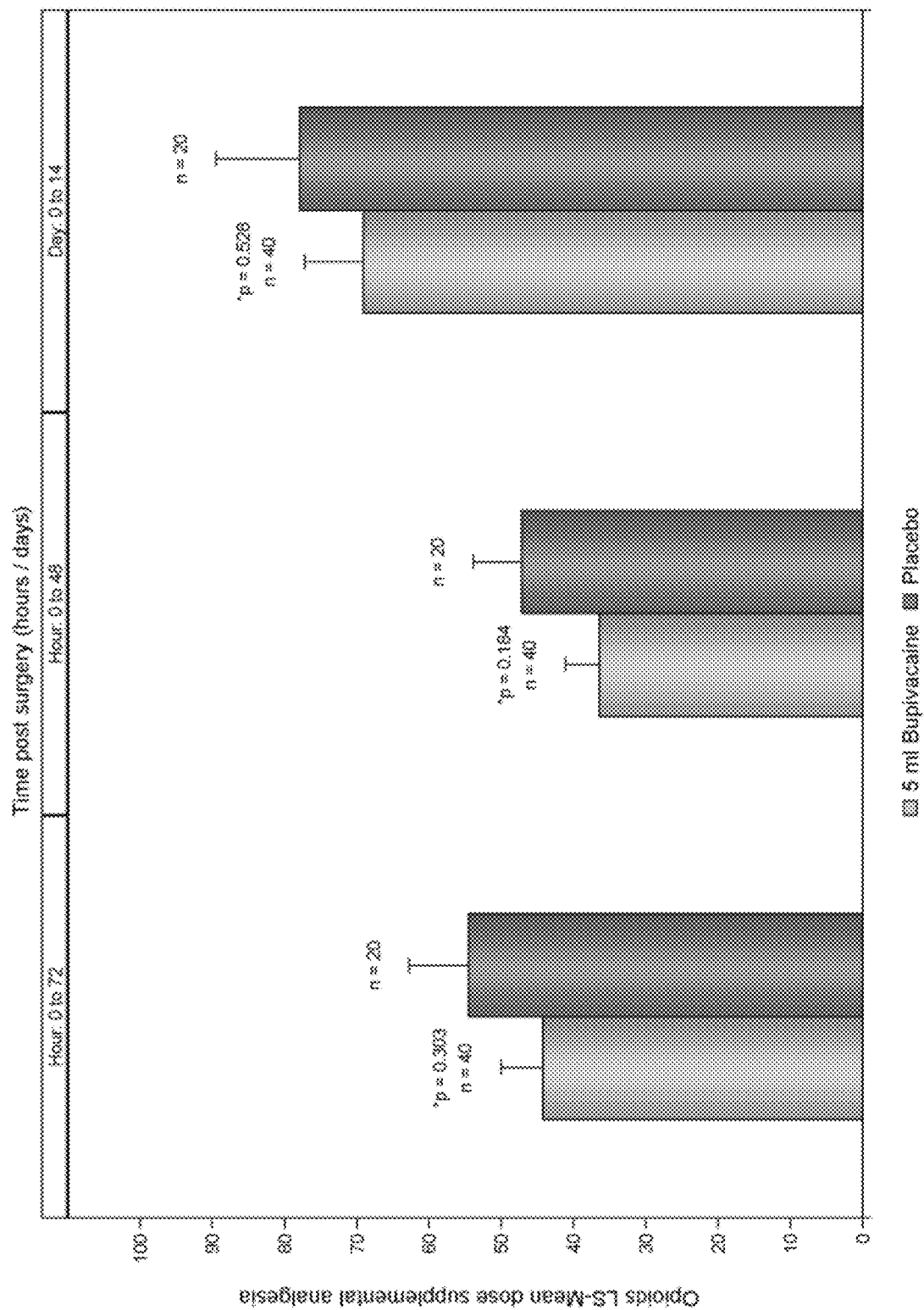
FIG. 20 shows cumulative morphine equivalent dose compared between treatment groups using ANCOVA with treatment group and trial site as factors and age as a covariate.

[1]Least-Squares Means estimated using an ANOVA model with treatment group and study site as factors For the secondary study endpoints, pain intensity on movement normalized AUC (0-48 hours), mean total IV morphine equivalent opioid dose (0-48 hours) and time to first opioid dose, was observed between the two treatment groups. There was a trend towards the 5.0 mL Formulation A group in pain intensity normalized AUC over 0-48 hours. The cumulative morphine equivalent dose over 0-24 hours, 0-48 hours, Days 0-14, and 24-48 hours showed a trend towards the 5.0 mL Formulation A group for all timepoints.
    Pain Intensity on Movement
    Analyses were performed for pain intensity normalized AUC over 0-48 hours, 0-last hours, 0-24 hours, 0-36 hours, 0-96 hours, 24-48 hours, 36-72 hours, 48-72 hours and 72-96 hours. Pain intensity normalized AUC was compared between treatment groups using ANCOVA with treatment group and trial site as factors and age as a covariate (FIG. 18). Although not statistically significant, there is a trend towards the 5.0 mL Formulation A group in pain intensity normalized AUC for all time points. For the MITT Subjects Set, at all time points, the LS means were lower for the 5.0 mL Formulation A group than the placebo group. FIG. 19A depicts the mean pain intensity on movement by subjects in the MITT set administered Formulation A as compared to subjects administered placebo at time points post dose. FIG. 19B depicts the mean pain intensity on movement by subjects in the PP set administered Formulation A as compared to subjects administered placebo at time points post dose.
    Cumulative Morphine Equivalent Dose
    Analyses were performed for cumulative morphine equivalent dose over 0-48 hours, Days 0-14, 0-24 hours, 24-48 hours and 48-72 hours. Cumulative morphine equivalent dose was compared between treatment groups using ANCOVA with treatment group and trial site as factors and age as a covariate (FIG. 20). Although not statistically significant, there was a trend towards the 5.0 mL Formulation A group in cumulative morphine equivalent dose for all time points.
    For the MITT Subjects Set, apart from 48-72 hours, at all other time points, the LS means were lower for the 5.0 mL Formulation A group than the placebo group. For the PP Subjects Set, the LS means were lower for the 5.0 mL Formulation A group than the placebo group for 0-72 hours, 0-48 hours and 0-24 hours.

Time to First Opioid Use

Figure 21:
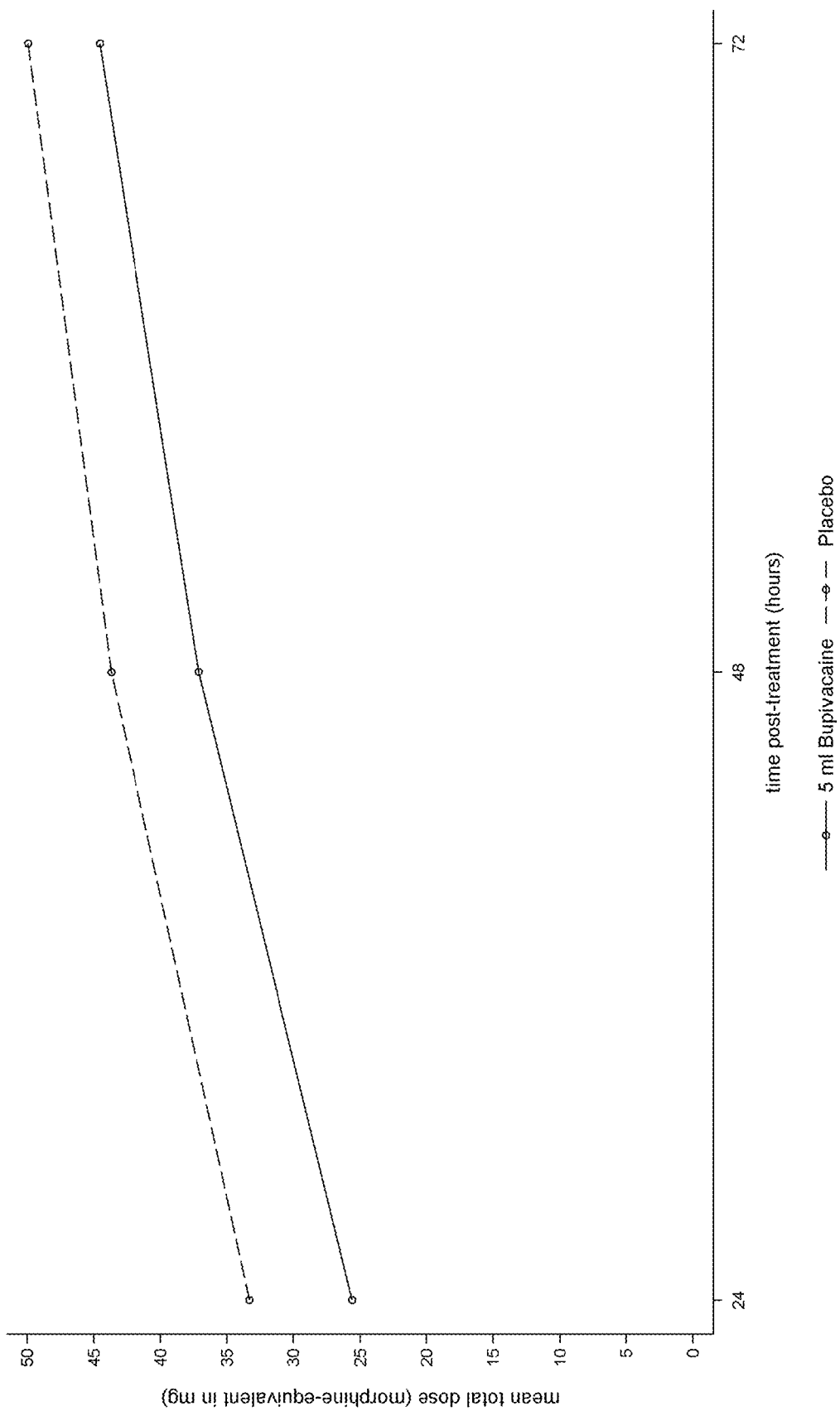
FIG. 21 depicts the cumulative morphine equivalent dose in the MITT set administered Formulation A as compared to subjects administered placebo at time points post dose.

Time to first opioid use was analyzed using a log-rank test to compare the two treatment groups. The median time to first opioid use for the MITT Subjects Set (0.43 hours for Formulation A 5.0 mL compared to 0.48 hours for placebo) and the PP Subjects Set (0.42 hours for Formulation A 5.0 mL compared to 0.50 hours for placebo) was not statistically significant. FIG. 21 depicts the cumulative morphine equivalent dose in the MITT set administered Formulation A as compared to subjects administered placebo at time points post dose.

Efficacy Conclusions

For the primary study endpoints, although statistically significant treatment effects were not seen in this study, there were indications of reduction of pain scores and opioid use in the 5.0 mL Formulation A group compared to placebo. The LS mean pain intensity on movement AUC over 0 to 72 hours post-dose was 5.33 in the 5.0 mL Formulation A group compared to 5.97 for placebo. This difference was lower than the estimated value used in the sample size calculation (an observed mean difference of 0.64 compared to an estimated mean of 1.9). The inferential aspects of the statistical analysis however, were not of primary importance in this study as the study was intended to be of an exploratory nature. The difference in cumulative morphine equivalent dose between the treatment groups was not statistically significant. LS mean cumulative morphine equivalent dose over 0 to 72 hours was 44.27 in the 5.0 mL Formulation A group compared to 54.51 in the placebo group. For both primary endpoints, the differences compared to placebo were most prominent during the first 6-10 hours post-surgery.

For the secondary study endpoints, pain intensity on movement normalized AUC (0-48 hours), mean total morphine equivalent opioid dose (0-48 hours) and time to first opioid dose, no statistically significant differences were observed between the two treatment groups. There was a trend towards the 5.0 mL Formulation A group in pain intensity normalized AUC over 0-48 hours. The cumulative morphine equivalent dose over 0-24 hours, 0-48 hours, Days 0-14, 24-48 hours and 48-72 hours were not statistically significant, although there was a trend towards the 5.0 mL Formulation A group for all timepoints. The median time to first opioid use was not statistically significant.

Safety Results:

All 60 subjects received at least part of their allocated treatment and were included in the safety analysis. Equal proportions of subjects experienced at least one AE—38 (95.0%) subjects in the 5.0 mL Formulation A group and 19 (95.0%) subjects in the placebo group. Seventeen (42.5%) subjects in the 5.0 mL Formulation A group experienced at least one AE with a maximum relationship of related, compared with seven (35.0%) subjects in the placebo group. Most AEs were either mild or moderate in intensity. Eight (20.0%) subjects in the 5.0 mL Formulation A group experienced at least one AE with a maximum severity of severe, compared with 5 (25.0%) subjects in the placebo group. The severity of TEAEs reported was similar between the two treatment groups. The most common AEs in the 5.0 mL Formulation A group were constipation, nausea, vomiting, dizziness, paranesthesia and somnolence. In the placebo group, the most common AEs were constipation, nausea, dizziness and somnolence. In general, the TEAEs expressed with high frequency were similar between the two treatment groups. There were no statistically significant differences or trends in frequency of opioid related TEAEs (constipation, dizziness, drowsiness, nausea, respiratory depression, urinary retention, or vomiting) at any time point in the study. Only one SAE was reported during the study. The event was pyrexia and was reported by subject 03-007 in the 5.0 mL Formulation A group. The event was considered to be mild and unlikely to be related to study drug. Administration of 5.0 mL Formulation A was safe and well tolerated based on review of hematology, biochemistry and urinalysis data, vital sign assessment, and evaluation of physical examination findings and concomitant medication use. All subjects had surgical site healing and local tissue condition at Day 14 as expected. TEAEs by system, organ, class and preferred term are summarized by system organ class in Table 14.3 below.

TABLE 14.3

TEAEs by System, Organ, Class

| System Organ Class | 5 mL Formulation A (N = 40) n % | Placebo (N = 20) n % |
|---|---|---|
| Number of subjects with at least one TEAE | 38 (95.0) | 19 (95.0) |
| Ear And Labyrinth Disorders | 8 (20.0) | 1 (5.0) |
| Eye Disorders | 1 (2.5) | 0 (0.0) |
| Gastrointestinal Disorders | 32 (80.0) | 17 (85.0) |
| General Disorders And Administration Site Conditions | 7 (17.5) | 2 (10.0) |
| Infections And Infestations | 1 (2.5) | 1 (5.0) |
| Injury, Poisoning And Procedural Complications | 6 (15.0) | 2 (10.0) |
| Investigations | 4 (10.0) | 2 (10.0) |
| Metabolism And Nutrition Disorders | 0 (0.0) | 1 (5.0) |
| Musculoskeletal And Connective Tissue Disorders | 6 (15.0) | 1 (5.0) |
| Nervous System Disorders | 33 (82.5) | 18 (90.0) |
| Psychiatric Disorders | 1 (2.5) | 1 (5.0) |
| Renal And Urinary Disorders | 9 (22.5) | 4 (20.0) |
| Reproductive System And Breast Disorders | 1 (2.5) | 0 (0.0) |
| Respiratory, Thoracic And Mediastinal Disorders | 7 (17.5) | 2 (10.0) |
| Skin And Subcutaneous Tissue Disorders | 8 (20.0) | 2 (10.0) |

A summary of TEAEs experienced by >7.5% of subjects, by preferred term and treatment group is presented in Table 14.4 below. 7.5% was selected to review frequency of TEAEs as this included TEAEs experienced by at least two subjects in the smaller treatment group. The most common AEs in the 5.0 mL Formulation A group were constipation, nausea, vomiting, dizziness, paranesthesia and somnolence. In the placebo group, the most common AEs were constipation, nausea, dizziness and somnolence. In general, the TEAEs expressed with high frequency were similar between the two treatment groups.

TABLE 14.4

TEAEs with Frequency > 7.5% by Treatment Group

| Preferred Term | 5 mL Formulation A (N = 40) n % | Placebo (N = 20) n % |
|---|---|---|
| Somnolence | 29 (72.5) | 16 (80.0) |
| Nausea | 26 (65.0) | 15 (75.0) |
| Constipation | 18 (45.0) | 10 (50.0) |
| Vomiting | 14 (35.0) | 4 (20.0) |
| Dizziness | 14 (35.0) | 7 (35.0) |
| Paraesthesia | 9 (22.5) | 2 (10.0) |
| Dysuria | 8 (20.0) | 4 (20.0) |
| Pruritus | 8 (20.0) | 2 (10.0) |
| Hypoaesthesia | 7 (17.5) | 3 (15.0) |

TABLE 14.4-continued

TEAEs with Frequency > 7.5% by Treatment Group

| Preferred Term | 5 mL Formulation A (N = 40) n % | Placebo (N = 20) n % |
|---|---|---|
| Tinnitus | 6 (15.0) | 1 (5.0) |
| Dysgeusia | 5 (12.5) | 1 (5.0) |
| Headache | 5 (12.5) | 4 (20.0) |
| Dry Mouth | 4 (10.0) | 2 (10.0) |
| Pyrexia | 4 (10.0) | 1 (5.0) |
| Muscle Twitching | 3 (7.5) | 0 (0.0) |
| Dyspnoea | 3 (7.5) | 0 (0.0) |
| Pharyngolaryngeal Pain | 3 (7.5) | 1 (5.0) |

Conclusion

The efficacy data in this study showed a consistent reduction of pain scores (as measured by mean pain intensity on movement AUC, time normalized under the curve, during the period 0 to 72 hours post-surgery) in subjects randomized to receive 5.0 mL Formulation A compared to placebo. There was also a reduction of opioid use (as measured by the amount of opioids taken in the three days post-surgery) in subjects randomized to receive 5.0 mL Formulation A compared to placebo. These reductions were not statistically significant. The findings related to pain scores and opioid use were most prominent during the first 6-10 hours post-surgery. The incidence of AEs, vital signs and laboratory abnormalities indicate that administration of 5.0 mL Formulation A is safe, and the lack of withdrawals and mild nature of AEs indicate that administration of 5.0 mL Formulation A is well tolerated in this patient population.

Example 15

A clinical trial was conducted to study the administration of a bupivacaine composition into the subacromial space in patients undergoing arthroscopic subacromial decompression. The study further investigated systemic and local safety of the bupivacaine composition as compared to placebo in patients.

The bupivacaine composition (Formulation A) used in these studies is a clear, light yellow to brown liquid, intended for use as a postsurgical analgesic after a variety of surgical procedures. The bupivacaine composition contains bupivacaine base in a sustained-release matrix comprised of a fully esterified sugar derivative. In this study, the intent of Formulation A is to provide effective postoperative local analgesia by providing sustained local release of bupivacaine over a period of several days. The formulation includes 3 components (sucrose acetate isobutyrate 66 wt %, benzyl alcohol 22.0 wt %, and bupivacaine base 12.0 wt %) that are administered together as a sterile solution.

| | |
|---|---|
| Composition: | Formulation A |
| Active ingredient: | Bupivacaine base |
| Inactive ingredients: | Sucrose acetate isobutyrate, benzyl alcohol |
| Administration: | Varied, based on surgical procedure, interstitial (FDA Code 088) either by tissue infiltration, injection or needle-free deposition for general surgical applications. |
| Strength: | 132 mg/mL, 660 mg bupivacaine |
| Composition | Placebo |
| Active ingredient: | Not applicable |
| Inactive ingredients: | Sucrose acetate isobytyrate, benzyl alcohol |
| Administration: | Varied, based on surgical procedure, interstitial (FDA Code 088) either by tissue infiltration, injection or needle-free deposition for general surgical applications. |

Objectives

Primary objective—To determine the efficacy of Formulation A (bupivacaine, benzyl alcohol, sucrose acetate isobutyrate) administered subcutaneously or into the subacromial space in subjects undergoing elective arthroscopic shoulder surgery involving subacromial decompression.

Secondary objective—To determine the safety and tolerability of Formulation A (bupivacaine, benzyl alcohol, sucrose acetate isobutyrate) administered subcutaneously or into the subacromial space in subjects undergoing arthroscopic shoulder surgery involving subacromial decompression.

Study objectives were defined specifically for each of Cohort 1 and Cohort 2.

Methods

The study was a randomized, double-blind, placebo-controlled study of the efficacy and safety of subcutaneous or subacromial bupivacaine in patients undergoing rotator cuff repair and to assess the safety and tolerability of Formulation A (bupivacaine, benzyl alcohol, sucrose acetate isobutyrate) as a delivery system. Surgery in all subjects was performed under local or general anesthesia according to standard local practice.

The study was conducted in 2 separate and sequential cohorts (Cohort 1 and Cohort 2). Approximately equal numbers of subjects were to be enrolled, in sequence, to each cohort. The study duration was up to 21 days including screening, admission to clinic and surgery (Day 0), postoperative evaluations, discharge from clinic, and follow-up through Day 14.

The subjects were evaluated on Days 1 and 2 in the clinic or at home, on Day 3 in the clinic, and on Days 4 through 7 by telephone following surgery and treatment. Subjects returned on Day 14 for follow-up evaluation and plasma collection. Subjects recorded pain intensity (PI), concomitant medications, adverse events (AEs), and rescue analgesia on diary cards from Day 0 through Day 7. Subjects also recorded AEs and concomitant medications through Day 14.

Cohort 1:

Immediately prior to surgery 45 subjects were randomly assigned in a 1:1:1 ratio (Treatment Group 1, Treatment Group 2, Treatment Group 3) to receive 1 of the following treatments:

Treatment Group 1: Prior to wound closure, 5.0 mL of placebo composition was injected into the subacromial space. After wound closure, a total volume of 5.0 mL of Formulation A was administered as 2 trailing subcutaneous injections along each side of the incision line. The total amount of bupivacaine was 660 mg.

Treatment Group 2: Prior to wound closure, 5.0 mL of Formulation A was injected into the subacromial space. After wound closure, a total volume of 5.0 mL of placebo composition was administered as 2 trailing subcutaneous injections along each side of the incision line. The total amount of bupivacaine was 660 mg.

Treatment Group 3: Prior to wound closure, 5.0 mL of placebo composition was injected into the subacromial space. After wound closure, a total volume of 5.0 mL of placebo composition was administered as 2 trailing subcutaneous injections along each side of the incision line. (The total delivered volume of placebo composition was 10.0 mL.)

For all treatment groups if the procedure was performed arthroscopically, the subcutaneous doses of study drug were administered evenly around all arthroscopic portals.

Cohort 2:

Upon completion of Cohort 1, enrollment of subjects into Cohort 2 was started. Immediately prior to surgery, 45 subjects were randomly assigned in a 1:1 enrollment ratio (Treatment Group 4 and Treatment Group 5) to receive 1 of the following treatments:

Treatment Group 4: During wound closure, 5.0 mL of placebo composition was injected into the subacromial space.

Treatment Group 5: During wound closure, 5.0 mL of Formulation A was injected into the subacromial space During the study, the amount of drug to be administered in Cohort 2 was changed from 7.5 mL (990 mg bupivacaine) to 5.0 mL (660 mg bupivacaine). However, 4 subjects were administered Treatment 4a (7.5 mL placebo composition) and 3 subjects were administered Treatment 5a (7.5 mL Formulation A)

Nine subjects were randomized to receive placebo composition or 5.0 mL Formulation A at 1 participating center in order to obtain PK (pharmacokinetic) measurements in the double-blind portion of the study. Of these 9 subjects, 4 received 5.0 mL Formulation A and 5 received placebo composition. Upon completion of the double-blind portion of the study, a supplemental PK sub-study protocol was implemented to enroll up to 14 additional PK subjects to receive 5.0 mL open-label Formulation A subacromially. The overall PK results for the 18 PK subjects who received 5.0 mL Formulation A is discussed in greater detail below.

Preparation of Study Drug for Administration:

The study drug was administered with 5 mL syringes which were used to withdraw 5.0 mL of study drug from 10.0 mL vials of either Formulation A or Placebo Composition.

Postoperative Rescue Analgesia

Postoperative rescue analgesia was to be prescribed on request. The time, name, and dose of all rescue analgesics were recorded throughout the study period by all subjects on either paper or electronic diaries. Distinction was made between those analgesics taken for surgical wound pain and those taken for other indications. A pain intensity (PI) evaluation was completed immediately prior to each time rescue analgesic medication was requested by a subject.

Subject CRITERIA

Number of subjects: The planned enrollment was 90 subjects in order to ensure at least 72 evaluable subjects (approximately 36 subjects in each cohort, 12 subjects in each treatment group of Cohort 1 and 18 in each treatment group of Cohort 2). A total of 40 subjects were enrolled in Cohort 1; 14 to Treatment 1, 10 to Treatment 2, and 16 to Treatment 3. All 40 subjects completed Cohort 1. A total of 52 subjects were enrolled in Cohort 2; 4 to Treatment 4a, 24 to Treatment 4, 3 to Treatment 5a, and 21 to Treatment 5. Fifty subjects completed Cohort 2; 1 subject in Treatment 4 and 1 subject in Treatment 5a voluntarily withdrew.

Upon completion of the double-blind portion of the study, a supplemental PK sub-study protocol was implemented which enrolled 14 additional PK subjects to receive 5.0 mL open-label Formulation A subacromially.

Diagnosis and main criteria for inclusion: Males and females, 18 years of age and older who underwent elective rotator cuff repair, were in good general health, and met all the inclusion and exclusion criteria, were eligible to participate in the study.

Duration of treatment: Subjects received a single dose of study drug. The study duration was up to 21 days comprising screening, admission to clinic and surgery (Day 0), postoperative evaluations, discharge from clinic, and follow-up through Day 14.

Criteria for Evaluation:

Efficacy:

Efficacy was assessed using the subjects' self-evaluation of PI and pain control collected on subject diaries (Days 0 to 7), the Modified Brief Pain Inventory (Days 1 to 7), and the subjects' use of concomitant rescue analgesic medication (Days 0 to 14).

The primary efficacy endpoints were PI on movement, PI at rest, and pain control poor (1), fair (2), good (3), very good (4), excellent (5) collected on Days 0 through Day 7. The secondary efficacy endpoints were worst and least pain scores, rescue analgesia usage, function, overall treatment satisfaction, and individual PI over time.

Safety:

Safety evaluations included AEs; assessments of laboratory tests such as chemistry, hematology, and urinalysis; a serum pregnancy test (if applicable); periodic monitoring of vital signs; 12 lead electrocardiogram (ECG); concomitant medications; and physical examinations. Evaluations also included surgical site healing and local tissue conditions Statistical Methods:

Unless otherwise stated, all statistical tests were performed using 2-sided tests at the 5% significance level. No multiplicity adjustment was made for any of the analyses. The per-protocol (PP) population includes all subjects who successfully underwent the surgical procedure, received study drug, and had postoperative data on pain evaluations recorded at 1 or more postoperative time points. Summary tables and statistical analysis of all efficacy endpoints are based on the PP population. Safety summaries are based on the safety population, which includes all randomized subjects who received any amount of study drug.

Data was determined for the following treatment groups:
   Treatment 1 (Formulation A subcutaneous)
   Treatment 2 (Formulation A subacromial)
   Treatment 5 (Formulation A subacromial)
   Formulation A (Treatments 2 and 5)
   Treatment 5a (7.5 mL Formulation A)
   Pooled Placebo comprising:
      Treatment 3 (10.0 mL placebo composition)
      Treatment 4 (5.0 mL placebo composition)
      Treatment 4a (7.5 mL placebo composition)

The comparison of primary interest was between Treatment 5 and Pooled Placebo. The significance of comparisons between Formulation A, Treatment 2, and Treatment 1 and Pooled Placebo were also determined.

The incidence (number and percentage) of treatment-emergent AEs was determined for each treatment group in accordance with the Medical Dictionary for Regulatory Activities (MedDRA) Version 8.0 system organ class and preferred term. A separate overall incidence was determined on AEs with onset on Day 0. The worst severity of the AEs and their relationship to study medication was also determined.

Separate overall incidence summaries were determined for anticipated events as checked on subject diaries: nausea/vomiting, drowsiness, itching, constipation, dizziness, tinnitus, dysgeusia, and paresthesia.

Specific safety evaluations of the Modified Brief Pain Inventory were tabulated by study day and treatment. Incidence across all study days was also determined by treatment.

Surgical site healing and local tissue condition evaluations were summarized and tabulated by subject incidence (number and percentage) for each treatment group over time.

Abnormal or change from screening physical examination results were determined. Vital signs were listed descriptively for each treatment group at each collection time point. Changes from baseline (predose) vital signs were summarized for each treatment and scheduled interval. Screening and unscheduled ECGs were used.

Results

Efficacy Results:

The primary endpoint PI scores (AUC/120 hours) during movement and at rest are summarized by treatment group in Table 15.1 and Table 15.2 respectively. Mean $PI_{move}$ values in the Formulation A treatment groups were 5.47, 3.27, and 5.12 (Treatments 1, 2, and 5, respectively), compared to 5.22 in the Pooled placebo group. Treatment 2 had the lowest mean value (least pain). The comparison to the Pooled Placebo group demonstrates that Treatment 2 was significantly better than Pooled Placebo (treatment difference=−1.95, 95% CI=−3.59 to −0.31, P=0.02). The Formulation A group was numerically better than Pooled placebo (treatment difference=−1.03, 95% CI=−2.14 to 0.09); this difference did not reach statistical significance (P=0.072). For average PI during rest, Treatment 2, Treatment 5, and Formulation A were numerically better than Pooled placebo; these differences did not reach statistical significance.

TABLE 15.1

Summary of Pain Intensity During Movement
Time-weighted Average Scores (AUC/120), PP Population

| Treatment | n | Mean (SD) | Comparison to Pooled Placebo | |
|---|---|---|---|---|
| | | | Mean Difference (95% CI) | P-value |
| Treatment 1 | 14 | 5.47 (2.352) | 0.25 (−1.13-1.62) | 0.720 |
| Treatment 2 | 9 | 3.27 (1.648) | −1.95 (−3.59--0.31) | 0.020 |

TABLE 15.1-continued

Summary of Pain Intensity During Movement
Time-weighted Average Scores (AUC/120), PP Population

| Treatment | n | Mean (SD) | Comparison to Pooled Placebo | |
|---|---|---|---|---|
| | | | Mean Difference (95% CI) | P-value |
| Treatment 5 | 21 | 5.12 (2.230) | −0.10 (−1.29-1.09) | 0.866 |
| Formulation A | 30 | 4.56 (2.219) | −1.03 (−2.14-0.09) | 0.072 |
| Pooled Placebo | 44 | 5.22 (2.281) | | |

Treatments (5.0 mL):
1 = Formulation A Subcutaneous
2 = Formulation A Subacromial
3 = Placebo
4 = Placebo
5 = Formulation A
Treatments 4a and 5a are the same as Treatments 4 and 5, but using 7.5 mL
Formulation A = Treatments 2 and 5
Pooled placebo = Treatments 3, 4a, and 4

TABLE 15.2

Summary of Pain Intensity During Rest
Time-weighted Average Scores (AUC/120), PP Population

| Treatment | n | Mean (SD) | Comparison to Pooled Placebo | |
|---|---|---|---|---|
| | | | Mean Difference (95% CI) | P-value |
| Treatment 1 | 14 | 3.53 (2.331) | 0.43 (−0.76-1.63) | 0.473 |
| Treatment 2 | 9 | 2.16 (1.496) | −0.95 (−2.37-0.48) | 0.190 |
| Treatment 5 | 21 | 2.58 (1.674) | −0.52 (−1.56-0.51) | 0.315 |
| Formulation A | 30 | 2.45 (1.609) | −0.73 (−1.71-0.24) | 0.136 |
| Pooled Placebo | 44 | 3.10 (1.995) | | |

Treatments (5.0 mL):
1 = Formulation A Subcutaneous
2 = Formulation A Subacromial
3 = Placebo
4 = Placebo
5 = Formulation A
Treatments 4a and 5a are the same as Treatments 4 and 5, but using 7.5 mL
Formulation A = Treatments 2 and 5
Pooled placebo = Treatments 3, 4a, and 4

The other primary efficacy variable was pain control by study day and treatment, assessed using the numerical score for the PP Population (1=Poor, 5=Excellent). The average pain control scores for Day 1 through Day 7 are summarized by treatment group in Table 15.3 Statistical comparisons were limited to the Formulation A versus Pooled placebo. The only statistically significant difference observed was on Day 1 (P=0.008) where the Formulation A and Pooled placebo treatment groups had average pain control scores of 3.3 and 2.5, respectively; no statistically significant differences were observed during the rest of the study (Days 2 through 7) for pain control.

TABLE 15.3

Pain Control on Study Days 1 through 7 by Treatment, PP Population

| Treatment Group | Mean Pain Control by Day | | | | | | |
|---|---|---|---|---|---|---|---|
| | Day 1 | Day 2 | Day 3 | Day 4 | Day 5 | Day 6 | Day 7 |
| Treatment 1 | 3.0 | 2.7 | 3.1 | 3.0 | 3.2 | 3.1 | 3.1 |
| Treatment 2 | 3.3 | 3.4 | 3.2 | 3.4 | 3.4 | 3.7 | 3.8 |
| Treatment 5 | 3.3 | 3.4 | 3.4 | 3.7 | 3.6 | 3.6 | 3.7 |
| Formulation A | 3.3 | 3.4 | 3.3 | 3.6 | 3.5 | 3.6 | 3.7 |
| Pooled Placebo | 2.5 | 3.0 | 3.4 | 3.4 | 3.4 | 3.4 | 3.6 |

TABLE 15.3-continued

Pain Control on Study Days 1 through 7 by Treatment, PP Population

| | Mean Pain Control by Day | | | | | | |
|---|---|---|---|---|---|---|---|
| Treatment Group | Day 1 | Day 2 | Day 3 | Day 4 | Day 5 | Day 6 | Day 7 |
| P-value (Formulation A vs. Pooled Placebo) | 0.008 | 0.111 | 0.767 | 0.532 | 0.608 | 0.380 | 0.689 |

Treatments (5.0 mL):
1 = Formulation A Subcutaneous
2 = Formulation A Subacromial
3 = Placebo
4 = Placebo
5 = Formulation A
Treatments 4a and 5a are the same as Treatments 4 and 5, but using 7.5 mL
Formulation A = Treatments 2 and 5
Pooled placebo = Treatments 3, 4a, and 4

The opioid rescue medication, expressed as cumulative IV morphine equivalent doses are summarized in Table 15.4 for Days 0 to 5. Mean values in Formulation A treatment groups for opioid rescue analgesia cumulative morphine equivalent doses were 70.30, 24.96, and 42.74 (Treatments 1, 2, and 5, respectively), compared to 55.27 in the Pooled placebo group. Treatment 2 had the lowest mean value (least cumulative morphine equivalent dose). Compared to the Pooled placebo group, Treatment 2 was numerically better than Pooled placebo; the difference did not reach statistical significance (P=0.147).

TABLE 15.4

Opioid Rescue Analgesia Cumulative (Day 0 through 5) IV Morphine Equivalent Dose (unit/unit) by Treatment, PP Population

| Treatment | n | Mean (SD) | Comparison to Pooled Placebo P-Value |
|---|---|---|---|
| Treatment 1 | 14 | 70.30 (62.984) | 0.389 |
| Treatment 2 | 9 | 24.96 (20.175) | 0.147 |
| Treatment 5 | 21 | 50.36 (66.102) | 0.744 |
| Formulation A | 30 | 42.74 (57.148) | 0.216 |
| Pooled Placebo | 44 | 55.27 (55.509) | |

Treatments (5.0 mL):
1 = Formulation A Subcutaneous
2 = Formulation A Subacromial
3 = Placebo
4 = Placebo
5 = Formulation A
Treatments 4a and 5a are the same as Treatments 4 and 5, but using 7.5 mL
Formulation A = Treatments 2 and 5
Pooled placebo = Treatments 3, 4a, and 4

In Formulation A treatment groups (Treatments 1, 2, and 5), as well as in the Pooled placebo group, all subjects required rescue analgesia.

All of the other secondary endpoints (worst and least pain scores, function, overall treatment satisfaction, and individual PI over time did not show any significant results.

A post hoc analysis of PI over time was conducted for the 2 cohorts separately. In Cohort 1, the Formulation A subacromial treatment group (Treatment 2) had a lower PI on movement compared with the placebo group (Treatment 3) and no difference was observed between the Formulation A subcutaneous treatment group (Treatment 1) and the placebo group (Treatment 3). In Cohort 2, no reduction in PI on movement was observed in the Formulation A subacromial treatment group (Treatment 5) versus placebo (Treatment 4). No differences in opioid rescue analgesia use were observed between the treatment groups in Cohort 1 and Cohort 2.

Figure 22:
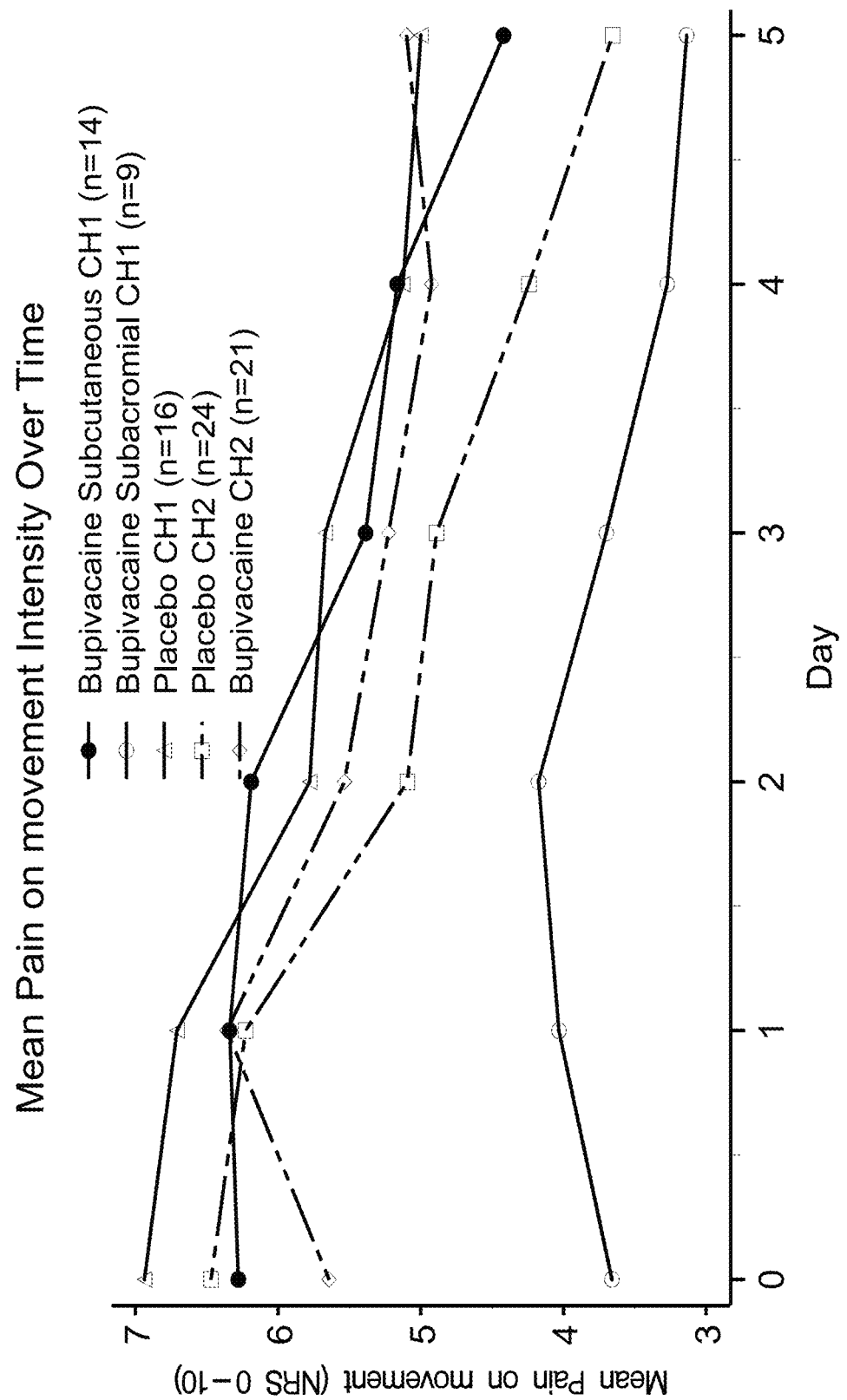
FIG. 22 shows mean $PI_{move}$ over time, analyzed separately for Cohort 1 and Cohort 2.

FIG. 22 shows mean $PI_{move}$ over time, analyzed separately for Cohort 1 and Cohort 2. This Figure demonstrates that for Cohort 1, the average PI on movement score for Treatment 2 (5.0 mL Formulation A subacromial) was lower than the average PI on movement score for placebo (Treatment 3). No difference in PI on movement scores between Treatment 1 (5.0 mL Formulation A subcutaneous) and placebo (Treatment 3) was observed. In Cohort 2, no reduction in PI on movement in Treatment 4 (Formulation A subacromial) versus placebo (Treatment 5) was observed.

A subgroup analysis was performed on subjects from both cohorts who had minimal or no glenohumeral pathology. The difference between the pooled subacromial active treatment groups and the pooled placebo was tested using the pre-specified ANOVA model including study center and treatment group as factors. The mean pain intensity on movement AUC (over the 72-hour period) for active and placebo were 3.6 and 6.1, respectively. The corresponding difference in mean pain intensity on movement AUC (over the 72-hour period, active-placebo) was −2.6 (95% CI: (−4.1,−1.1)). This result is statistically significant (p=0.0012), and supports analgesic benefit in favor of active subacromial treatment representing a 41.8% reduction in pain (while the ITT analysis showed 16.5% reduction).

Figure 23:
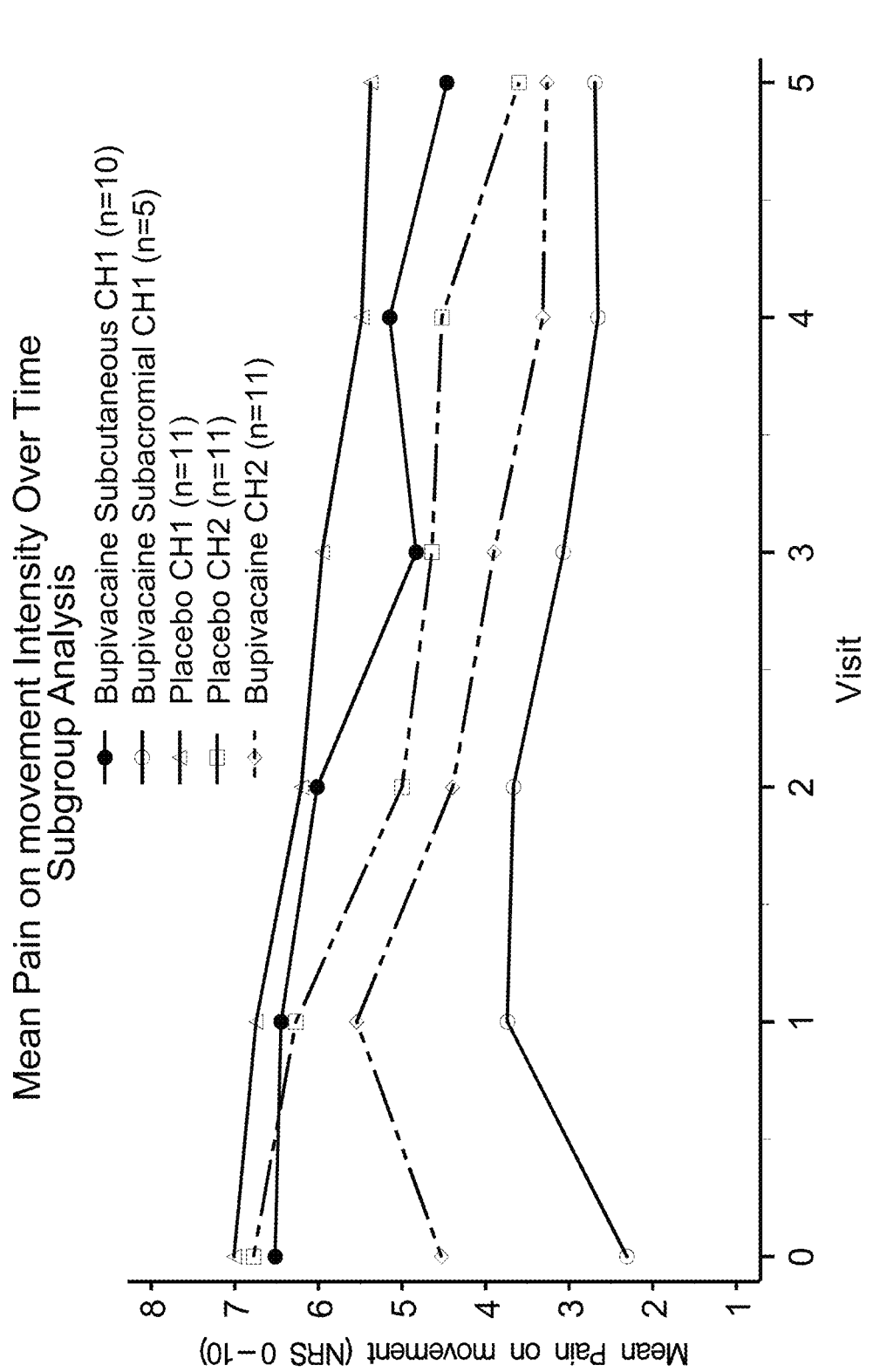
FIG. 23 shows $PI_{move}$ over time in a subgroup of subjects who had minimal or no glenohumeral pathology.

FIG. 23 shows $PI_{move}$ over time in the subgroup of subjects who had minimal or no glenohumeral pathology. It demonstrates increased analgesia in those treatment groups using subacromial administration of Formulation A (Treatments 2 and 5) compared to placebo (Treatments 3 and 4). Treatment 1, which used subcutaneous administration of Formulation A, did not show a reduction in $PI_{move}$ compared to placebo (Treatments 3 and 4).

The mean total morphine-equivalent dose for active and placebo were 33.5 and 56.9, respectively. The corresponding difference in means between (placebo-active) was 23.4 (95% CI: (−1.1, 47.9)). This result represents a 41.1% reduction in opioid use (while the ITT analysis showed a 16.1%) in favor of active subacromial treatment, but was not statistically significant.

Safety Results:

The overall frequency of AEs was similar between treatment groups. The most commonly reported treatment-emergent AEs were nausea, somnolence, pruritus, and constipation. The majority of treatment-emergent AEs were of mild or moderate severity. There were no deaths or discontinuations due to AEs. One serious AE occurred in treatment group 4 (postprocedural pain), which was severe in intensity and considered unrelated to study drug by the investigator.

An analysis of specific safety evaluations of interest did not indicate any opioid-related safety issues.

A summary of treatment-emergent adverse events (TEAE) by treatment is shown in Table 15.5.

TABLE 15.5

Specific Safety Evaluations Observed Over Days 0 to 7 (Safety Population)

|  | Treatment 1 (n = 14) | Treatment 2 (n = 10) | Treatment 5 (n = 21) | Treatment 5a (n = 3) | Formulation A (n = 31) | Pooled Placebo (n = 44) |
|---|---|---|---|---|---|---|
| Nausea | 11 (78.6%) | 7 (70.0%) | 14 (66.7%) | 3 (100.0%) | 20 (64.5%) | 34 (77.3%) |
| Vomiting | 5 (35.7%) | 3 (30.0%) | 5 (23.8%) | 2 (66.7%) | 7 (22.6%) | 15 (34.1%) |
| Somnolence | 8 (57.1%) | 9 (90.0%) | 12 (57.1%) | 3 (100.0%) | 20 (64.5%) | 33 (75.0%) |
| Dizziness | 10 (71.4%) | 5 (50.0%) | 11 (52.4%) | 3 (100.0%) | 15 (48.4%) | 22 (50.0%) |
| Tinnitus | 4 (28.6%) | 2 (20.0%) | 2 (9.5%) | 1 (33.3%) | 3 (9.7%) | 7 (15.9%) |
| Pruritus | 10 (71.4%) | 8 (80.0%) | 12 (57.1%) | 3 (100.0%) | 19 (61.3%) | 29 (65.9%) |
| Dysgeusia | 6 (42.9%) | 3 (30.0%) | 6 (28.6%) | 1 (33.3%) | 8 (25.8%) | 13 (29.5%) |
| Paresthesia | 5 (35.7%) | 2 (20.0%) | 4 (19.0%) | 2 (66.7%) | 5 (16.1%) | 12 (27.3%) |
| Constipation | 10 (71.4%) | 5 (50.0%) | 12 (57.1%) | 3 (100.0%) | 16 (51.6%) | 24 (54.5%) |

Treatments (5.0 mL):
1 = Formulation A Subcutaneous
2 = Formulation A Subacromial
3 = placebo
4 = placebo
5 = Formulation A
Treatments 4a and 5a are the same as Treatments 4 and 5, but using 7.5 mL
Formulation A = Treatments 2 and 5
Pooled Placebo = Treatments 3, 4a, and 4

Conclusions

Formulation A is an injectable solution specifically formulated to prolong regional postoperative analgesia and is intended for use as a postoperative analgesic after a variety of surgical procedures. Each milliliter of Formulation A contains 12% wt bupivacaine representing 132 mg/mL of bupivacaine. The primary efficacy endpoint of PI move was shown to be significantly better in Treatment 2 (Formulation A Subacromial) compared to the Pooled placebo group (Treatments 3, 4a, and 4), and was not significantly better in Treatment 1 (Formulation A Subcutaneous), Treatment 5 (Formulation A), and Formulation A (Treatments 2 and 5, Formulation A Subacromial and Formulation A, respectively) compared to the Pooled placebo group (Treatments 3, 4a and 4). The results of the post hoc analyses in Cohort 1 showed that the Formulation A subacromial treatment group (Treatment 2) had a lower PI on movement compared with the placebo group (Treatment 3) and no difference was observed between Formulation A subcutaneous treatment group (Treatment 1) and the placebo group (Treatment 3). In the subanalysis performed on subjects from both cohorts who had minimal or no glenohumeral pathology, those treatment groups using subacromial administration of Formulation A (Treatments 2 and 5) had a lower PI on movement compared to placebo (Treatments 3 and 4). Treatment 1, which used subcutaneous administration of Formulation A, did not show a reduction in PI on movement compared to placebo. The overall frequency of AEs was similar between treatment groups.

Example 16

A randomized, parallel-group, double-blind, saline placebo-controlled and bupivacaine HCl active-controlled clinical trial evaluating the safety and efficacy of 5 mL of Formulation A in subjects undergoing elective outpatient laparoscopic cholecystectomy was conducted. In this study, Formulation A was prepared as described above and includes 3 components (sucrose acetate isobutyrate 66 wt %, benzyl alcohol 22.0 wt %, and bupivacaine base 12.0 wt %) that are administered together as a sterile solution.

Methods

The trial included: 1) a randomized, parallel-group, double-blind, placebo-controlled study (Part 1) and a randomized, parallel-group, double-blind, bupivacaine HCl active-controlled study (Part 2). The trial evaluated the efficacy and safety of Formulation A (bupivacaine, benzyl alcohol, sucrose acetate isobutyrate) as a delivery system in subjects undergoing elective outpatient laparoscopic cholecystectomy.

In Part 1, subjects were randomized in a nominal 1:1 ratio to receive 1 of 2 treatments, Formulation A or saline placebo. In Part 2, subjects were randomized in a 1:1 ratio to receive 1 of 2 treatments, Formulation A or bupivacaine HCl.

The study was conducted as 2 separate parts (Part 1 and Part 2). For part 1, 92 subjects were randomized and treated by instilling either 5 mL of Formulation A or saline placebo with a blunt-tipped applicator directly into the laparoscopic port incisions at the close of surgery. For part 2, subjects were randomized in a 1:1 ratio to receive 5 mL of Formulation A instilled with a blunt-tipped applicator directly into the laparoscopic port incisions or 15 mL (75 mg) bupivacaine HCl 0.5% infiltrated with a 22 gauge needle into the margins of the port incisions.

Subjects underwent surgery on Day 1, during which they were administered a single dose of Formulation A, placebo or bupivacaine HCl at the close of surgery while still anesthetized.

All subjects had access to adequate pain relief through the use of rescue medication. While in the post-anesthesia care unit (PACU), subjects were administered IV fentanyl 12.5-25 µg upon request for breakthrough pain. Upon discharge, subjects were provided with acetaminophen 500 mg tablets for mild-to-moderate pain and a prescription for oxycodone 5 mg immediate-release tablets for moderate-to-severe pain. Subjects self-administered these medications on an as-needed basis according to written dosing instructions provided by the site investigator or study staff.

Subjects were issued an electronic diary (LogPad) to record the specified data after surgery.

In part 1 of the study 92 patients in total were administered Formulation A or saline placebo. 45 patients were administered 5 mL of Formulation A and 47 patients received the placebo. For part 2 of the study, 296 patients were treated with Formulation A or active control, bupivacaine HCl. 148 patients were administered 5 mL of Formulation A and 148 patients received active control bupivacaine HCl.

Formulation A, Dose and Mode of Administration:

In Part 1 and Part 2, subjects randomized to the test product were administered 5 mL Formulation A (132 mg/mL bupivacaine base, 660 mg total) by direct instillation into the surgical incisions. The 5 mL of Formulation A was divided between the 4 ports according to a protocol-specified dosing schedule, to provide coverage of all surgical incisions. The fascia was closed, as required, prior to instillation of Formulation A. Formulation A was instilled into the incisions via a blunt-tipped syringe-tip applicator just prior to skin closure. After administration, the skin was closed in standard fashion with subcuticular sutures and cyanoacrylate skin adhesive or Steri-Strips™.

Reference Comparator, Dose and Mode of Administration:

Part 1:

In Part 1, subjects randomized to saline-placebo were administered sterile normal saline 5 mL (0.9% sodium chloride injection, USP) by direct instillation into the surgical incisions. The 5 mL of placebo was divided between the 4 ports according to a protocol-specified dosing schedule, to provide coverage of all surgical incisions. The fascia was closed, as required, prior to instillation of the placebo composition. The placebo composition was instilled into the incisions via a blunt-tipped syringe-tip applicator just prior to skin closure. After administration, the skin was closed in standard fashion with subcuticular sutures and cyanoacrylate skin adhesive or Steri-Strips™.

Part 2:

In Part 2, subjects randomized to active control were administered bupivacaine HCl 0.5% 15 mL (75 mg; without epinephrine) by infiltration into the margins of the surgical incisions with a 22 gauge needle. The 15 mL of bupivacaine HCl composition was divided between the 4 ports according to a protocol-specified dosing schedule, to provide coverage of all surgical incisions. The fascia was closed, as required, prior to administration of the bupivacaine HCl active control composition. After infiltration, the skin was closed in standard fashion with subcuticular sutures and cyanoacrylate skin adhesive or Steri-Strips™.

Efficacy Analyses

Primary

The primary efficacy endpoints for Part 1 and Part 2 were as follows:

Part 1: Pain intensity on movement measured at scheduled time points from 0 to 72 hours following test drug administration, adjusted for prior rescue medication use and analyzed by a mixed effect ANOVA model of repeated measures (MMRM).

Part 2: Pain intensity on movement measured at scheduled time points from 0 to 48 hours following test drug administration, adjusted for prior rescue medication use and analyzed by a mixed effect ANOVA model of repeated measures (MMRM).

Results

Efficacy Results:

Primary Endpoint

The primary efficacy endpoint was pain intensity on movement measured at scheduled time points from 0-72 hours (Part 1) and 0-48 hours (Part 2) following administration of test composition, adjusted for prior rescue medication use. For Part 1, the comparison was between Formulation A (Part 1 subjects only) and saline placebo, and for Part 2, the comparison was between Formulation A (Part 2 subjects only) and bupivacaine HCl. Results of the primary endpoint analysis are summarized in Table 16.1 below.

TABLE 16.1

Primary Outcomes by Study Part: Pain Intensity on Movement from 0 to 72 Hours Post-treatment (Part 1) and from 0 to 48 Hours Post-treatment (Part 2)

| | Part 1 | | Part 2 | |
|---|---|---|---|---|
| | Formulation A (N = 46) | Saline Placebo (N = 46) | Formulation A (N = 148) | Bupivacaine HCl (N = 148) |
| | Pain intensity on movement 0 to 72 hours | | | |
| Mean (SE) | 4.38 (0.091) | 5.17 (0.107) | | |
| 95% CI | (4.21, 4.56) | (4.96, 5.38) | | |
| | Pain intensity on movement 0 to 48 hours | | | |
| Mean (SE) | | | 5.55 (0.065) | 5.87 (0.059) |
| 95% CI | | | (5.42, 5.67) | (5.76, 5.99) |
| | Formulation A versus comparator [1] | | | |
| LS Mean Difference (SE) | −0.785 (0.432) | | −0.371 (0.2412) | |
| 95% CI | (−1.631, 0.062) | | (−0.844, 0.101) | |
| p-value | 0.0692 | | 0.1235 | |

CI = confidence interval;
SE = standard error;
LS = least squares;
WOCF = worst observation carried forward Safety Results:

There were no fatalities in this trial. Nine treated subjects (6 Formulation A and 3 bupivacaine HCl) experienced treatment-emergent serious adverse events (SAE), all of which were considered unrelated to study drug administration. Table 16.2 summarizes the safety data.

TABLE 16.2

Overall Summary of Treatment Emergent Adverse Events (Safety Population)

|  | Part 1 | | Part 2 | |
| --- | --- | --- | --- | --- |
|  | Formulation A (N = 45) | Saline Placebo (N = 47) | Formulation A (N = 148) | Bupivacaine HCl (N = 148) |
| At Least One TEAE | 43 (95.6%) | 47 (100%) | 148 (100%) | 146 (98.6%) |
| At Least One Spontaneously-reported TEAE | 43 (95.6%) | 45 (95.7%) | 148 (100%) | 138 (93.2%) |
| At Least One LogPad-Solicited TEAE | 36 (80.0%) | 39 (83.0%) | 134 (90.5%) | 132 (89.2%) |
| At Least One Serious TEAE | 1 (2.2%) | 0 (0.0%) | 5 (3.4%) | 3 (2.0%) |
| At Least One TEAE Leading to Study Discontinuation | 0 (0.0%) | 0 (0.0%) | 0 (0.0%) | 1 (0.7%) |
| Maximum Relationship to Study Drug | | | | |
| Related | 32 (71.1%) | 26 (55.3%) | 125 (84.5%) | 104 (70.3%) |
| Not Related | 11 (24.4%) | 21 (44.7%) | 23 (15.5%) | 42 (28.4%) |
| Maximum Severity | | | | |
| Mild | 13 (28.9%) | 22 (46.8%) | 83 (56.1%) | 92 (62.2%) |
| Moderate | 23 (51.1%) | 25 (53.2%) | 55 (37.2%) | 49 (33.1%) |
| Severe | 7 (15.6%) | 0 (0.0%) | 10 (6.8%) | 5 (3.4%) |
| At Least One Severe and Related TEAE | 5 (11.1%) | 0 (0.0%) | 0 (0.0%) | 0 (0.0%) |
| At Least One Serious and Related TEAE | 0 (0.0%) | 0 (0.0%) | 0 (0.0%) | 0 (0.0%) |
| Fatal TEAE | 0 (0.0%) | 0 (0.0%) | 0 (0.0%) | 0 (0.0%) |

Example 17

A phase 3 international, multicenter, randomized, double-blind, parallel-group trial of 5 mL Formulation A (132 mg/mL, 660 mg bupivacaine) in patients undergoing a variety of general surgical procedures with various wound sizes was conducted.

Methods

The study was an international, multicenter, randomized, double-blind, parallel-group controlled trial evaluating the safety, efficacy, effectiveness, and pharmacokinetics (PK) of 5 mL of Formulation A in patients undergoing a variety of general surgical procedures with various wound sizes. All surgical procedures were elective, non-urgent, and indicated for the conditions identified below.

Randomization was stratified by surgical procedure (cohort) and by clinical site. The cohorts were as follows:

Cohort 1: Laparotomy. Approximately 50 patients were randomized to receive either 5 mL of Formulation A or Bupivacaine HCl 30 mL 0.5% solution in a 3:2 ratio, respectively. This cohort included patients undergoing open laparotomy for resection of liver, small bowel, stomach, spleen, gall bladder, or colon.

Cohort 2: Laparoscopic cholecystectomy. Approximately 50 patients were randomized to receive either 5 mL of Formulation A or Bupivacaine HCl 30 mL 0.5% solution in a 3:2 ratio, respectively.

Cohort 3: Laparoscopically-assisted colectomy. Approximately 204 patients were randomized to receive either 5 mL of Formulation A or vehicle-Placebo 5 mL in a 3:2 ratio, respectively. This cohort included patients undergoing laparoscopically-assisted colectomy without planned formation or closure of stoma for colon cancer, diverticulitis, or polyps. A pneumoperitoneal and an intracorporeal approach was used to explore the abdomen, mobilize the colon, identify critical structures, and ligate the vascular pedicle for left-sided and sigmoid colectomies.

Active Control, Dose and Mode of Administration:

In the active comparator treatment groups (Cohorts 1 and 2); 30 mL of Bupivacaine HCl 0.5% solution (5 mg/mL, 150 mg bupivacaine) was administered by infiltration with a hypodermic needle into the peri-incisional tissues.

Formulation A, Dose and Mode of Administration:

For the Formulation A (132 mg/mL, 660 mg bupivacaine as described above) and vehicle placebo treatment groups, 5 mL of each composition was drawn up and administered using a NORM-JECT® 5-mL Luer Lock syringe connected to a Tunneltip™ irrigation catheter with a Luer Lock fitting. The supplied Tunneltip irrigation catheter was flexible, 15 cm long, 2 mm in diameter, with smooth rounded tip and graduated centimeter markings for wound length measurement and control of instillation. To account for the dead space in the catheter, sites were instructed to draw 5.5 mL of investigational product in the syringe with the provided 16 gauge needle. Sites were instructed to purge excess air and investigational product from the syringe and catheter once connected to ensure administration of 5 mL of each composition. The syringes, needles, and catheters were supplied sterile and individually packaged.

For laparoscopic portals, each composition was administered directly into the open port incision through an irrigation catheter and/or by the syringe tip. The port incision was then closed with a suture after dosing. For linear incisions, after closure of the peritoneum and securing hemostasis in the subcutaneous space, the irrigation catheter was placed into the wound and the cutaneous layer was closed over the catheter with subcuticular stitches. The syringe containing each composition was then attached to the catheter and test drug was gradually injected while slowly withdrawing the catheter. In this way, each composition (e.g., Formulation A or vehicle control) was evenly distributed along the length of the incision with minimal leakage of the drug. A final stitch was used to close the space where the catheter was withdrawn. The volume delivered per centimeter of wound length was calculated based on incision length measured using the centimeter marking on the irrigation catheter.

In Cohort 1, the entire 5 mL dose of Formulation A was evenly distributed within the laparotomy incision. In Cohort 2, the larger port incisions received a larger volume of Formulation A than did the smaller port incisions. In Cohort 3, there was generally a 5-10 cm linear incision for exteriorizing the colon for resection and anastomosis (the hand port). Approximately 80-90% of Formulation A was instilled into the hand port using the irrigation catheter method. The remaining 10-20% of test drug was directly instilled into the laparoscopic port incisions.

To avoid seepage of the product from the wound, instillation was performed after a tight closure of the skin with subcuticular stitches (no staples) and Steri-Strips. No drains were placed in the area of investigational product placement.

Results

Efficacy

Two co-primary endpoints were chosen to evaluate the efficacy of Formulation A compared to control: 1) time normalized AUC of pain intensity on movement over 0-72 hours and 2) total amount of rescue opioids taken over 0-72 hours expressed as IV morphine equivalents. The primary pain endpoint was defined as the time normalized AUC of pain on movement over 0-72 hours. The AUC was calculated by the trapezoid method using both scheduled pain intensity scores on movement (recorded electronically on a LogPad device) as well as pain scores recorded each time rescue opioids were administered for postoperative pain relief.

Table 17.1 summarizes the primary endpoint AUC of 0-72 hours as well as the secondary endpoint AUC of 0-48 hours. In addition, the AUC by day was presented to assess the duration of treatment effect.

Figure 24:
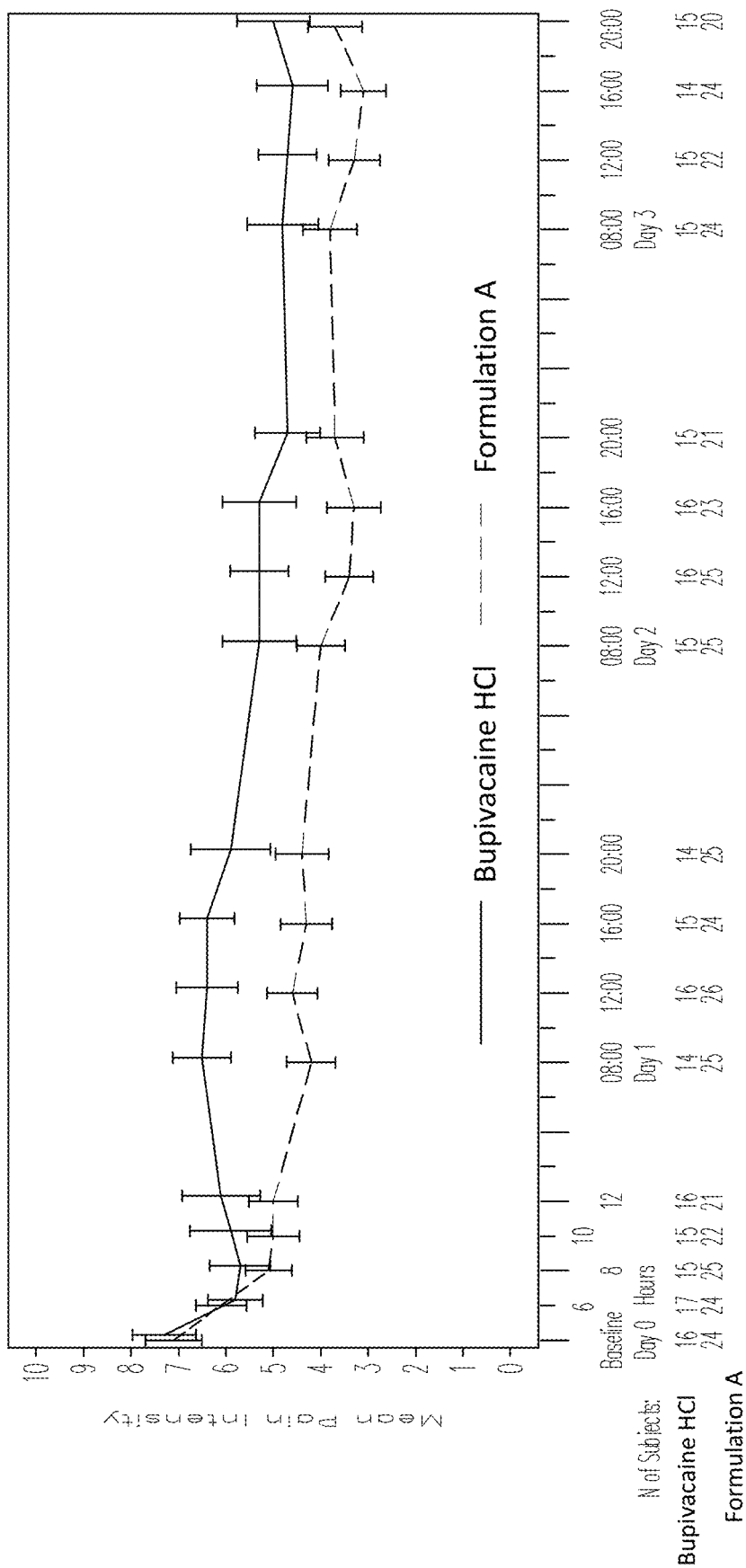
FIGS. 24 to 26 show line graphs of mean pain intensity on movement±standard error of the mean (SEM) versus the scheduled time of pain assessment for each cohort.
Figure 25:
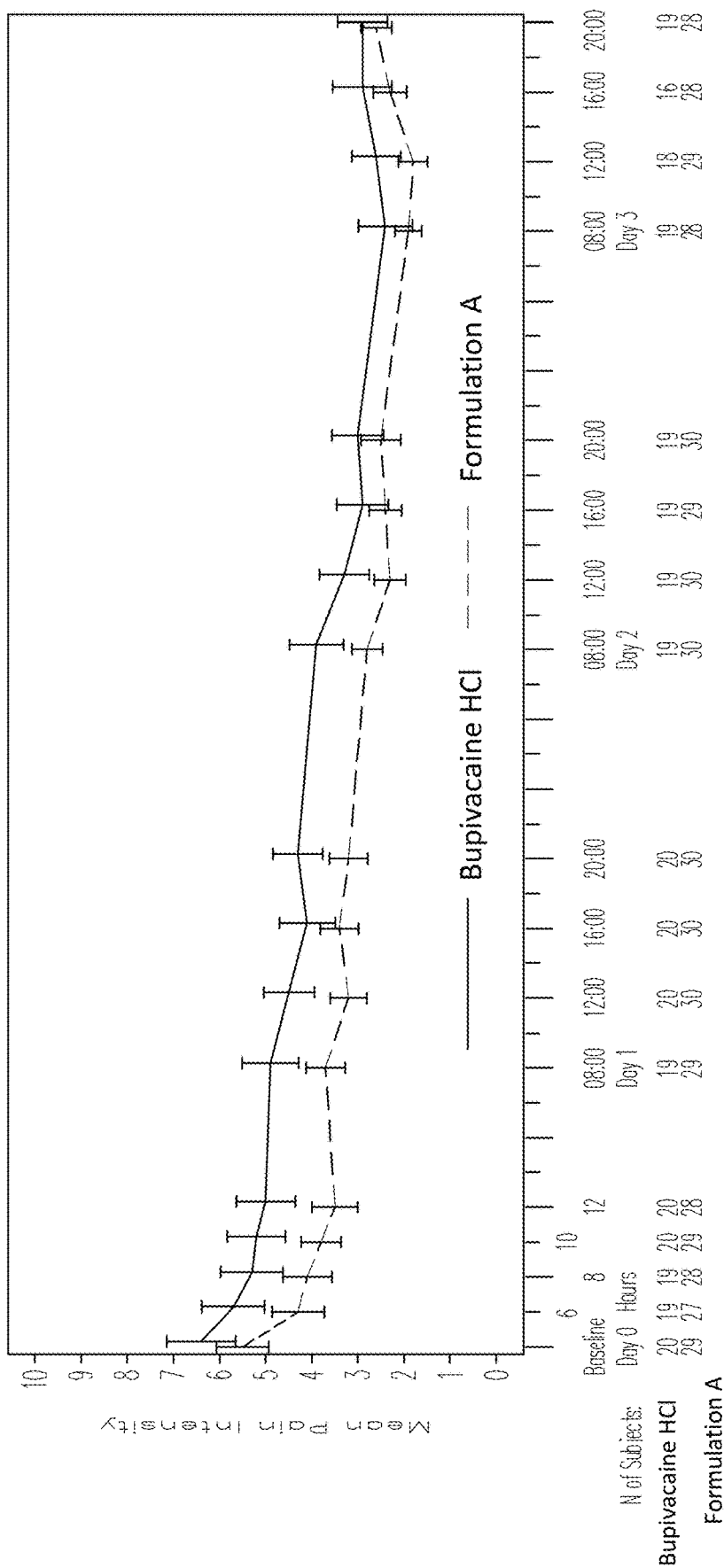
Figure 26:
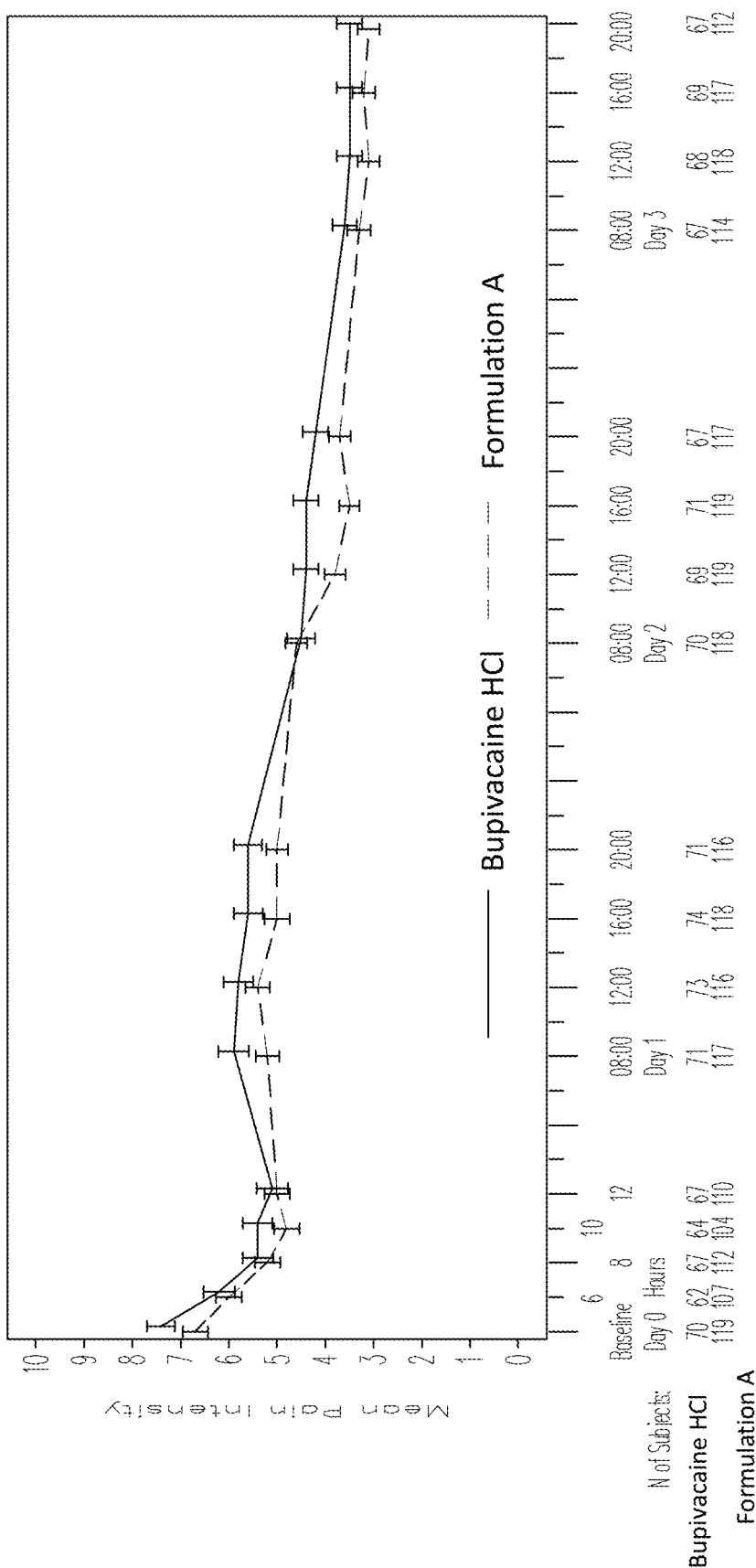

FIGS. 24 to 26 present line graphs of the mean pain intensity on movement±standard error of the mean (SEM) versus the scheduled time of pain assessment for each cohort. It can be seen from these Figures that the initial pain intensity of Cohorts 1 and 3 was similar, as both cohorts involved colectomy or other major abdominal surgery, and ranged from pain scores of 7 to 8, which was considered severe pain. Cohort 2 had a lower initial pain score, ranging from 5 to 6, which was considered moderate to severe pain. In all 3 cohorts, the mean pain intensity on movement decreased by 2 to 3 units over a 3-day postoperative period, with Cohorts 1 and 3 reaching moderate pain levels whereas Cohort 2 declined to mild pain levels. Cohorts 1 and 2 showed an early separation of the treatment groups that was maintained over the entire 72-hour period. Cohort 3 had little separation of the treatment groups, which was consistent with the relatively small therapeutic effect observed with the primary endpoint.

Pre-Specified Sensitivity Analyses of Pain Intensity on Movement

A pre-specified sensitivity analysis was a repeated measures mixed model and is summarized in Table 17.2.

TABLE 17.1

Pain Intensity on Movement AUCs by Period (Includes both Log Pad and Opioid Pain Scores)

| Period | Treatment | N | LS Mean (SE) | 95% CI | LS Mean for the difference | 95% CI for the difference | p-value (ANCOVA) |
|---|---|---|---|---|---|---|---|
| Cohort 1 (Laparotomy) | | | | | | | |
| AUC 0-72 hours | Formulation A (5 mL) | 26 | 4.9 (0.43) | (4.0, 5.7) | −0.89 | (−2.11, 0.33) | 0.1473 |
| | Bupivacaine HCl | 17 | 5.8 (0.51) | (4.7, 6.8) | | | |
| AUC 0-48 hours | Formulation A (5 mL) | 26 | 5.2 (0.42) | (4.4, 6.1) | −0.77 | (−1.96, 0.42) | 0.1953 |
| | Bupivacaine HCl | 17 | 6.0 (0.49) | (5.0, 7.0) | | | |
| AUC 0-24 hours | Formulation A (5 mL) | 26 | 5.7 (0.42) | (4.9, 6.6) | −0.54 | (−1.71, 0.62) | 0.3507 |
| | Bupivacaine HCl | 17 | 6.3 (0.48) | (5.3, 7.2) | | | |
| AUC 24-48 hours | Formulation A (5 mL) | 26 | 4.7 (0.47) | (3.8, 5.7) | −1.01 | (−2.36, 0.33) | 0.1332 |
| | Bupivacaine HCl | 17 | 5.7 (0.56) | (4.6, 6.9) | | | |
| AUC 48-72 hours | Formulation A (5 mL) | 26 | 4.1 (0.50) | (3.1, 5.1) | −1.13 | (−2.56, 0.30) | 0.1168 |
| | Bupivacaine HCl | 17 | 5.3 (0.60) | (4.0, 6.5) | | | |
| Cohort 2 (Laparoscopic Cholecystectomy) | | | | | | | |
| AUC 0-72 hours | Formulation A (5 mL) | 30 | 2.8 (0.38) | (2.0, 3.6) | −1.06 | (−2.16, 0.05) | 0.0601 |
| | Bupivacaine HCl | 20 | 3.9 (0.45) | (3.0, 4.8) | | | |
| AUC 0-48 hours | Formulation A (5 mL) | 30 | 3.2 (0.39) | (2.5, 4.0) | −1.19 | (−2.30, −0.07) | 0.0371 |
| | Bupivacaine HCl | 20 | 4.4 (0.45) | (3.5, 5.3) | | | |
| AUC 0-24 hours | Formulation A (5 mL) | 30 | 3.7 (0.40) | (2.9, 4.5) | −1.17 | (−2.33, −0.01) | 0.0488 |
| | Bupivacaine HCl | 20 | 4.8 (0.47) | (3.9, 5.8) | | | |
| AUC 24-48 hours | Formulation A (5 mL) | 30 | 2.8 (0.16) | (2.5, 3.1) | −1.20 | (−1.84, −0.56) | 0.0002 |
| | Bupivacaine HCl | 20 | 4.0 (0.22) | (3.5, 4.4) | | | |
| AUC 48-72 hours | Formulation A (5 mL) | 30 | 2.0 (0.44) | (1.1, 2.9) | −0.79 | (−2.07, 0.48) | 0.2158 |
| | Bupivacaine HCl | 20 | 2.8 (0.52) | (1.7, 3.8) | | | |
| Cohort 3 (Laparoscopically Assisted Colectomy) | | | | | | | |
| AUC 0-72 hours | Formulation A (5 mL) | 126 | 4.8 (0.19) | (4.4, 5.2) | −0.34 | (−0.80, 0.12) | 0.1483 |
| | Vehicle placebo | 77 | 5.1 (0.23) | (4.7, 5.6) | | | |
| AUC 0-48 hours | Formulation A (5 mL) | 126 | 5.2 (0.19) | (4.8, 5.5) | −0.30 | (−0.74, 0.14) | 0.1829 |
| | Vehicle placebo | 77 | 5.5 (0.22) | (5.0, 5.9) | | | |
| AUC 0-24 hours | Formulation A (5 mL) | 126 | 5.4 (0.19) | (5.0, 5.8) | −0.33 | (−0.79, 0.12) | 0.1489 |
| | Vehicle placebo | 77 | 5.8 (0.23) | (5.3, 6.2) | | | |
| AUC 24-48 hours | Formulation A (5 mL) | 126 | 4.9 (0.22) | (4.4, 5.3) | −0.31 | (−0.83, 0.20) | 0.2275 |
| | Vehicle placebo | 77 | 5.2 (0.25) | (4.7, 5.7) | | | |
| AUC 48-72 hours | Formulation A (5 mL) | 126 | 4.0 (0.24) | (3.6, 4.5) | −0.40 | (−0.97, 0.18) | 0.1784 |
| | Vehicle placebo | 77 | 4.4 (0.29) | (3.9, 5.0) | | | |

TABLE 17.2

Repeated Measures Pain Intensity on Movement 0-72 Hours Based on LogPad Scores Only (ITT Population)

| Period | Treatment | N | LS Mean (SE) | 95% CI | LS Mean for the difference | 95% CI for the difference | p-value (ANCOVA) |
|---|---|---|---|---|---|---|---|
| Cohort 1 (Laparotomy) | | | | | | | |
| All Timepoints 0-72 hr | Formulation A (5 mL) | 26 | 4.9 (0.30) | (4.2, 5.5) | −1.0 | (−1.83, −0.17) | 0.0202 |
| | Bupivacaine HCl | 17 | 5.9 (0.35) | (5.1, 6.6) | | | |
| Cohort 2 (Laparoscopic Cholecystectomy) | | | | | | | |
| All Timepoints 0-72 hr | Formulation A (5 mL) | 30 | 2.7 (0.27) | (2.2, 3.2) | −0.9 | (−1.66, −0.13) | 0.0235 |
| | Bupivacaine HCl | 20 | 3.6 (0.32) | (3.0, 4.2) | | | |
| Cohort 3 (Laparoscopically Assisted Colectomy) | | | | | | | |
| All Timepoints 0-72 hr | Formulation A (5 mL) | 126 | 4.7 (0.15) | (4.4, 5.0) | −0.6 | (−0.93, −0.21) | 0.0020 |
| | Vehicle-Placebo | 77 | 5.3 (0.18) | (4.9, 5.6) | | | |

ANCOVA = analysis of covariance, CI = confidence interval, ITT = intent-to-treat, LS = least squares, SE = standard error Use of Rescue Medication The second co-primary endpoint was the mean total amount of opioids administered over 0-72 hours, expressed as IV morphine equivalents in milligrams using standard conversion factors to convert different opioids to morphine equivalents.

Table 17.3 summarizes the results with respect to the second co-primary endpoint.

TABLE 17.3

Total Morphine-equivalent Opioid Medication Use by Period and Cohort (ITT Population)

| Period | Treatment Group | N | Median (Q1, Q3) | Median Difference | 95% CI for the Difference | P-value (Wilcoxon Rank-Sum) |
|---|---|---|---|---|---|---|
| Cohort 1 (Laparotomy) | | | | | | |
| MEDD 0-72 hours (mg) | Formulation A (5 mL) | 26 | 87.0 (30.0, 157.0) | −1.0 | (−54.5, 52.0) | 0.9901 |
| | Bupivacaine HCl | 17 | 63.0 (34.0, 152.0) | | | |
| Cohort 2 (Laparoscopic Cholecystectomy) | | | | | | |
| MEDD 0-72 hours (mg) | Formulation A (5 mL) | 30 | 17.0 (8.0, 26.0) | −5.0 | (−14.0, 3.4) | 0.2010 |
| | Bupivacaine HCl | 20 | 22.5 (12.5, 34.5) | | | |
| Cohort 3 (Laparoscopically Assisted Colectomy | | | | | | |
| MEDD 0-72 hours (mg) | Formulation A (5 mL) | 126 | 52.0 (24.0, 86.6) | −3.0 | (−15.0, 8.0) | 0.5897 |
| | Vehicle-Placebo | 77 | 62.0 (24.0, 86.0) | | | |

Figure 27:
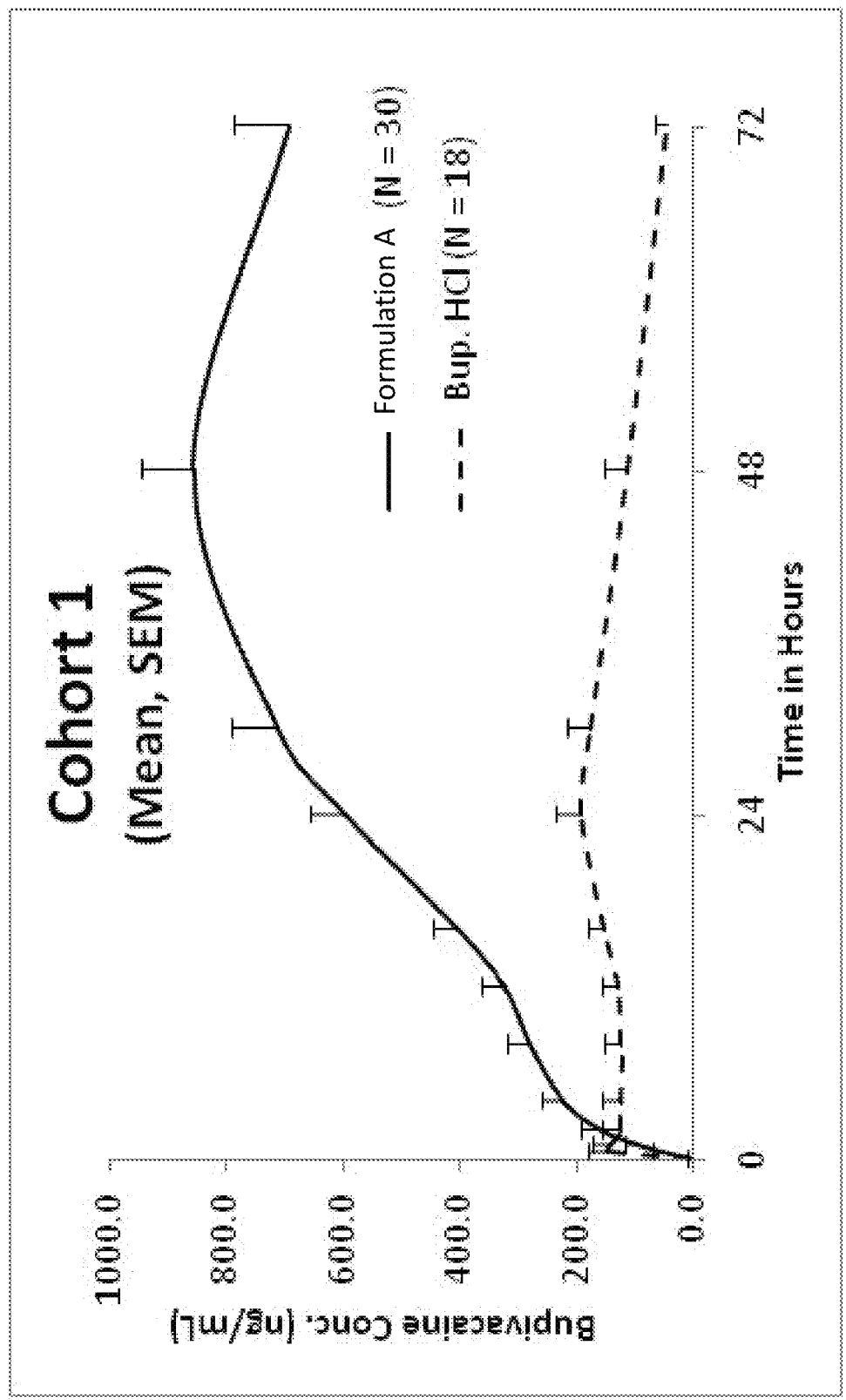
FIGS. 27 to 29 show graphs of plasma bupivacaine concentration vs. time after treatment.
Figure 28:
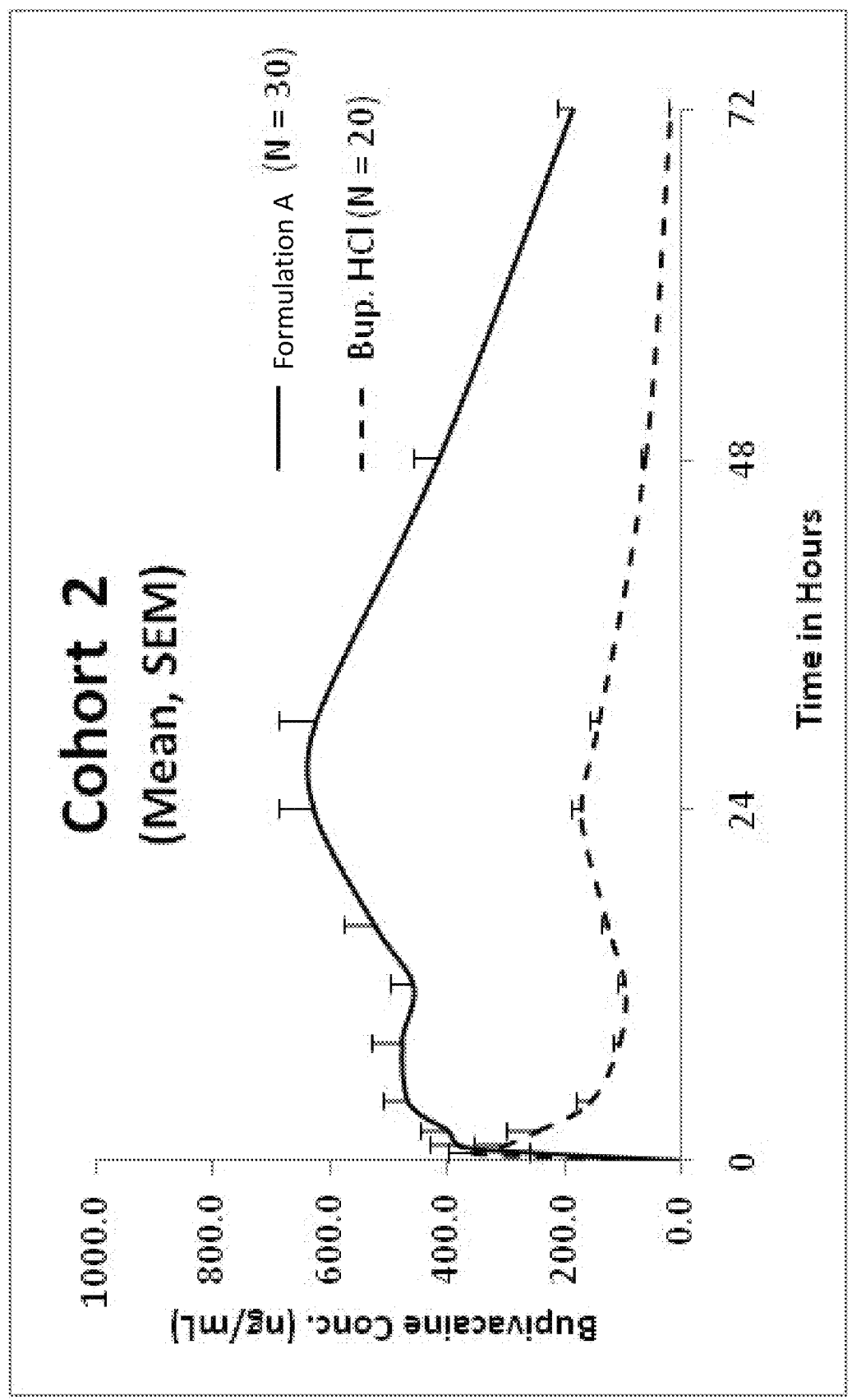
Figure 29:
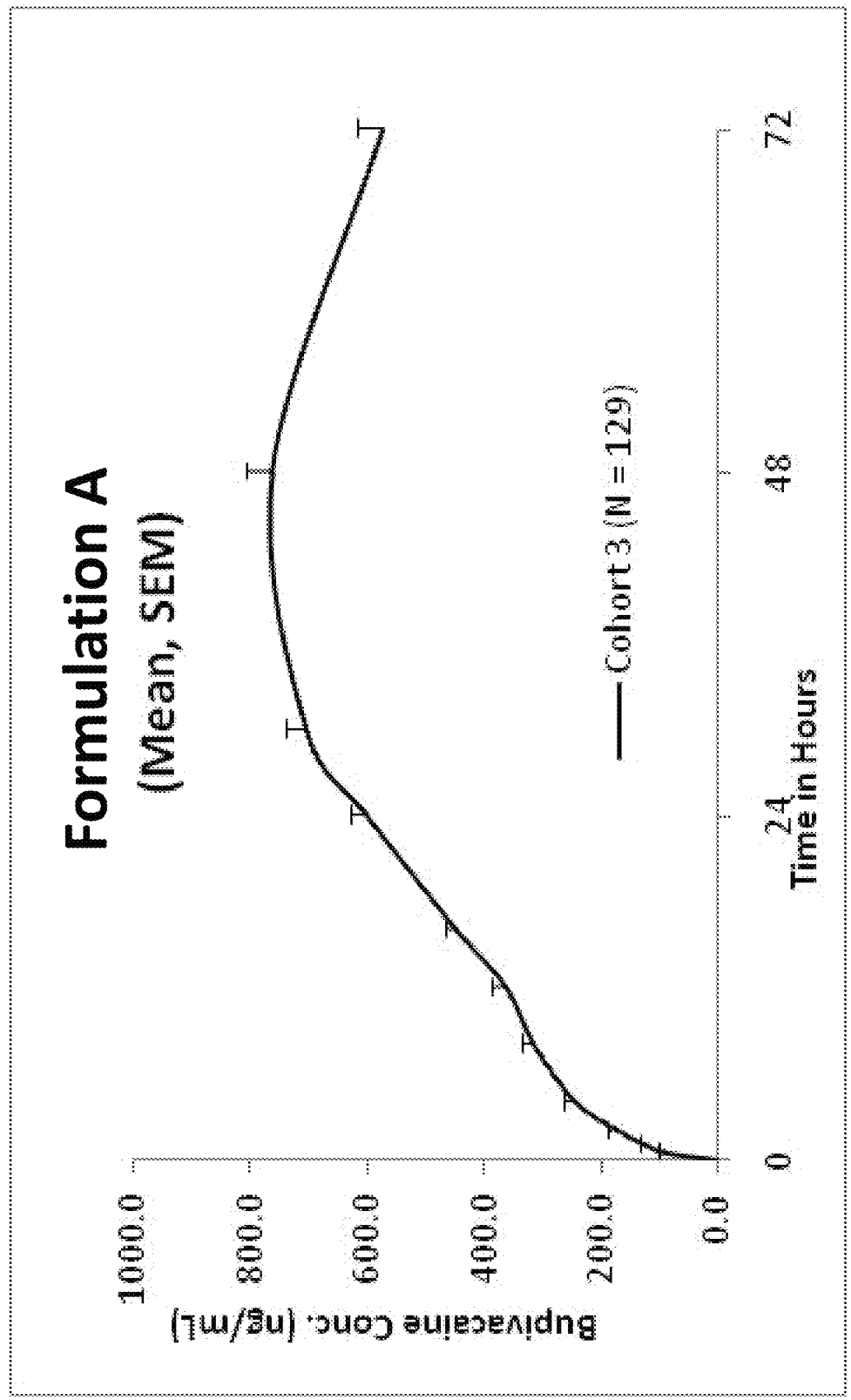

CI = confidence interval, MEDD = mean equivalent daily dose of morphine, ITT = intent-to-treat, Q = quartile Pharmacokinetics Plasma PK samples were analyzed for determination of total bupivacaine concentration only and none of the samples were analyzed for determination of free drug concentration. Table 17.4 summarizes the PK parameters for all three cohorts. The graphs of plasma bupivacaine concentration vs. time after treatment are presented in FIGS. 27 to 29.

TABLE 17.4

Plasma Pharmacokinetic Parameters by Cohort-mean [range]

| PK Parameter | Cohort 1 Formulation A (N = 30) | Cohort 1 Bupivacaine HCl (N = 18) | Cohort 2 Formulation A (N = 30) | Cohort 2 Bupivacaine HCl (N = 20) | Cohort 3 Formulation A (N = 129) |
|---|---|---|---|---|---|
| $C_{max}$ (ng/mL) | 956 [133-1870] | 251 [19-551] | 752 [357-1850] | 371 [101-1170] | 850 [92-2850] |
| $T_{max}$ (hr) median | 48 [2-73] | 16 [1-48] | 24 [1-49] | 1 [1-24] | 47 [1-74] |
| $AUC_{(0-72)}$ (ng*hr/mL) | 40755 [5113-79464] | 8465 [495-26306] | 29466 [11095-68124] | 6772 [1777-11985] | 39437 [3613-110222] |
| $AUC_{(0-last)}$ (ng*hr/mL) | 41942 [635-96625] | 7784 [465-26364] | 30997 [11100-68108] | 6623 [1771-11868] | 39602 [1626-136309] |

Safety Evaluation

Patient safety was carefully monitored throughout the trial with traditional assessments of AEs, vital signs, routine laboratory testing, and Holter monitoring (i.e., continuous recording of electrocardiogram) for 3 days after dosing. Special attention was given to cardiovascular and neurological AE, as bupivacaine toxic effects are manifest in those two body systems. In addition, special assessments were done to monitor surgical wound condition and healing over the 30 days of the trial.

Table 17.5 summarizes the overall adverse experience by cohort.

There were no consistent treatment-related effects on vital signs. Changes in serum chemistry and hematological parameters were those expected after major surgery, with few consistent differences between treatment groups. Cardiac safety was carefully studied using Holter monitoring for 72 hours post-dose, starting about one hour before surgery. In addition, baseline 24-hour ambulatory Holter monitoring was done after the screening visit. Careful analysis of the Holter data and correlation of the QTc interval with bupivacaine plasma concentration did not reveal any evidence for QTc prolongation by Formulation A. The Holter recordings

TABLE 17.5

Overall Summary of Treatment-Emergent Adverse Events, Serious Adverse Events, and Deaths
(Safety Population)

| | Cohort 1 Formulation A (N = 30) | Cohort 1 Bupivacaine HCl (N = 18) | Cohort 2 Formulation A (N = 30) | Cohort 2 Bupivacaine HCl (N = 20) | Cohort 3 Formulation A (N = 129) | Cohort 3 Vehicle Placebo (N = 78) |
|---|---|---|---|---|---|---|
| At Least One TEAE | 30 (100%) | 17 (94%) | 28 (93%) | 20 (100%) | 126 (98%) | 75 (96%) |
| At Least One Cardiovascular TEAE | 4 (13%) | 7 (39%) | 2 (7%) | 2 (10%) | 19 (15%) | 6 (8%) |
| At Least One Neurological TEAE | 6 (20%) | 4 (22%) | 17 (57%) | 10 (50%) | 23 (18%) | 29 (37%) |
| At Least One Wound Infection REAE | 4 (13%) | 2 (11%) | 1 (3%) | 1 (5%) | 12 (9%) | 2 (3%) |
| At Least One Non-Opioid TEAE | 27 (90%) | 17 (94%) | 27 (90%) | 19 (95%) | 124 (96%) | 74 (95%) |
| At Least One Serious TEAE | 9 (30%) | 4 (22%) | 0 | 1 (5%) | 16 (12%) | 9 (12%) |
| At Least One TEAE Leading to Study Discontinuation | 1 (3%) | 0 | 0 | 1 (5%) | 0 | 0 |
| Maximum Relationship to Study Drug | | | | | | |
| Related | 12 (40%) | 4 (22%) | 17 (57%) | 10 (50%) | 79 (61%) | 47 (60%) |
| Not Related | 18 (60%) | 13 (72%) | 11 (37%) | 10 (50%) | 47 (36%) | 28 (36%) |
| Maximum Severity | | | | | | |
| Mild | 5 (17%) | 2 (11%) | 4 (13%) | 2 (10%) | 54 (42%) | 29 (37%) |
| Moderate | 16 (53%) | 11 (61%) | 16 (53%) | 13 (65%) | 51 (40%) | 32 (41%) |
| Severe | 9 (30%) | 4 (22%) | 8 (27%) | 5 (25%) | 21 (16%) | 14 (18%) |
| At Least One Severe and Related TEAE | 1 (3%) | 0 | 2 (7%) | 1 (5%) | 0 | 2 (3%) |
| At Least One Serious and Related TEAE | 1 (3%) | 0 | 0 | 0 | 0 | 1 (1%) |
| Deaths | 0 | 0 | 0 | 0 | 1 (<1%) | 0 | were further analyzed for arrhythmias and no instances of ventricular tachycardia were detected in any of the recordings.

It is concluded that Formulation A was well tolerated when instilled into a variety of abdominal surgical wounds at a dose of 5 mL (660 mg) and that there was no evidence of systemic bupivacaine toxicity as assessed by AEs, laboratory testing, and intensive Holter monitoring. With the exception of an increased incidence of post-operative bruising, tissue tolerability of Formulation A compares well to bupivacaine HCl.

Example 18

A double-blind, placebo-controlled pharmacodynamic and pharmacokinetic dose response study was conducted to Formulation A instilled directly into the wound in patients undergoing open inguinal hernia repair. In this study, Formulation A was prepared as described above and includes 3 components (sucrose acetate isobutyrate 66 wt %, benzyl alcohol 22.0 wt %, and bupivacaine base 12.0 wt %) that are administered together as a sterile solution.
Objectives To examine the dose response efficacy, pharmacokinetics, safety and tolerability of Formulation A instilled into the wound in patients undergoing open inguinal hernia repair.
Methods
 Study Design This was a Phase II, multicenter, randomized, double-blind, placebo-controlled, parallel-group, dose-finding study.
 Participants Patients were male or female, 18 to 65 years of age, and were planned to undergo elective open unilateral tension-free Lichtenstein-type inguinal hernia repair under general anesthesia. Patients were in good health prior to study participation, based on a medical history, physical examination, 12-lead electrocardiogram (ECG), and laboratory tests. All patients had to have a systolic blood pressure (BP) of ≤160 mmHg and a diastolic BP of ≤95 mmHg, use a medically acceptable method of contraception throughout the study period and for 1 week after completion of the study, refrain from strenuous activities throughout the study period and avoid modifications to prescribed exercise levels throughout the study period, and read, understand, communicate, and voluntarily sign the approved informed consent form prior to the performance of any study specific procedures.

Patients were excluded if they were pregnant or lactating; had previous abdominal surgery with scar tissue that would limit the patients' ability to participate; had clinically significant hepatic, gastrointestinal, renal, hematologic, urologic, neurologic, respiratory, endocrine, or cardiovascular system abnormalities, psychiatric disorders, or acute infection unrelated to the disease under study; had connective tissue disorders (systemic lupus erythematosus, scleroderma, mixed connective tissue disease); or had a known sensitivity to bupivacaine, or benzyl alcohol (BA). Patients with known or suspected alcohol abuse within the 6 months prior to study enrollment or illicit drug use, current or regular use of analgesic medication for other indication(s), current or regular use of triptyline or imipramine antidepressants, or monoamine oxidase inhibitors; or use of any prescription drugs or over the counter medication that started within 7 days before treatment and throughout the study (except for birth control medications) that might interfere with the conduct or interpretation of the study results were excluded, as were patients who participated in another clinical study concurrent or within 30 days of enrollment and those who were unwilling or unable to comply with the study procedures.
 Interventions The inguinal hernia operative procedure was performed according to standard local practice under general anesthesia. Patients were randomized to receive 2.5 mL or 5.0 mL of Formulation A (12.0 wt %, 132 mg/mL bupivacaine), or 2.5 mL or 5.0 mL of Placebo. All treatments were administered during wound closure, and were instilled gradually throughout the inguinal canal and the abdominal wall layers to cover all raw surfaces of the wound, filling the sub-aponeurotic and subcutaneous spaces.
 Outcome Measures Pain intensity at rest and on movement was evaluated using a numerical rating scale ([NRS] 0=no pain; 10=worst pain possible) on Day 0 at 1, 2, 3, 4, 6, 8, 10, and 12 hours following medication administration, on Days 1 to 4 at 8:00 am, 12:00 pm, 4:00 pm, and 8:00 pm, on Day 5 at 8:00 am, and prior to dosing with any rescue medication from Day 0 to 14. The modified Brief Pain Inventory was completed once daily at 12:00 pm on Days 1 to 5. Postoperative analgesia was prescribed according to a suggested guideline, and rescue medication use, concomitant medications, and adverse events (AEs) were recorded throughout the study. Time from surgery to patient mobilization, typical bowel movement pattern, last bowel movement prior to surgery, and the number of bowel movements after treatment were measured. Blood samples were collected for pharmacokinetic analysis for a minimum of 32 patients on Day 0 at −5 min, and 1, 2, 3, 4, 8, and 12 hours, and on Days 1 to 4, and 7 at approximately the same time of day that the treatment was administered on Day 0. Surgical site healing and local tissue conditions evaluated at follow up visits on Days 1 to 4, 7, and 14, where appropriate. Specific safety evaluations performed as part of the modified Brief Pain Inventory included nausea/vomiting, drowsiness, itching, constipation, dizziness, tinnitus, dysgeusia, and paresthesia. Vital signs were recorded at screening, on Day 0 prior to and immediately following treatment administration, and hourly thereafter up to the 8-hour evaluation time point or discharge (whichever occurred first), as well as on Days 1 to 3, and 14. Physical examinations and safety laboratory assays were performed at screening and on Day 14. A 12-lead ECG was performed at screening and when clinically indicated to evaluate and record all clinically significant abnormalities (e.g., bradycardia episodes); 2 study centers performed continuous ECG monitoring for 24 hours as soon as practical after the surgical procedure and, if clinically indicated, a 12-lead ECG was performed. Patients returned to clinic for 3- and 6-month follow-up visits for physical examinations, evaluations of surgical site healing and local tissue conditions, and collections of adverse event and concomitant medication data.
 Sample Size Approximately 144 patients were randomized to the study in order to yield 120 total evaluable patients (60 patients per cohort with a 3:1 randomization in favor of active treatment within each cohort). A relative treatment effect of 0.67 (between Formulation A 5.0 mL and Formulation A 5.0 mL groups) was detected based on the mean pain intensity on movement area under the curve (AUC) over the period of 1 to 72 hours with 80% power and a 5% significance level.
 Randomization Prior to surgery, eligible patients were randomly assigned to receive one of the following 4 treatments: Formulation A 5.0 mL (660 mg of bupivacaine), Formulation A 2.5 mL (330 mg of bupivacaine), Placebo 5.0 mL, or Placebo 2.5 mL. Each randomized patient received a randomization number comprising the cohort membership (Cohort 1 or Cohort 2; 60 randomized patients per cohort as defined below) and a treatment group (3:1 randomization in favor of active treatment). Placebo groups (2.5 mL and 5.0 mL) were pooled a priori to potentially increase the statistical analysis power. The 2 cohorts were as follows:

Cohort 1: Patients were randomized to receive either 2.5 mL of Formulation A or 2.5 mL of Placebo;
Cohort 2: Patients were randomized to receive either 5.0 mL of Formulation A or 5.0 mL of Placebo.

This randomization scheme resulted in 3 distinct treatment groups, as follows:

Treatment Group 1: Formulation A 2.5 mL (330 mg of bupivacaine);
Treatment Group 2: Formulation A 5.0 mL (660 mg of bupivacaine);
Treatment Group 3: Placebo 2.5 mL or 5.0 mL, as randomly assigned.

Number of Patients
Number of Patients Planned

Up to 144 patients were to be enrolled to obtain 120 evaluable patients.

Patients Analyzed

There were 135 patients enrolled and 124 were randomized as follows: Formulation A 2.5 mL, N=45; Formulation A 5.0 mL, N=47; placebo, N=32. Four patients discontinued the study (Formulation A 2.5 mL, N=3; placebo, N=1); thus, 120 patients completed the study and comprised the efficacy evaluable population: Formulation A 2.5 mL, N=42; Formulation A 5.0 mL, N=47; placebo, N=31. The safety/per protocol (PP) population included 123 patients (Formulation A 2.5 mL, N=44; Formulation A 5.0 mL, N=47; placebo, N=32), and the intention-to-treat (ITT) population included 122 patients (Formulation A 2.5 mL, N=43; Formulation A 5.0 mL, N=47; placebo, N=32).

Diagnosis and Main Criteria for Inclusion

Male and female patients, in good general health, 18 to 65 years of age, who were planned to undergo elective open unilateral tension-free Lichtenstein-type inguinal hernia repair under general anesthesia.

Duration of Treatment

Treatment was administered at one time on the day of surgery (Day 0).

Criteria for Evaluation

Efficacy

There were 2 coprimary efficacy endpoints: the mean pain intensity on movement normalized AUC over the time period 1 to 72 hours post-surgery, and the proportion of patients who received opioid rescue medication during the study. Primary null hypotheses were no differences between treatment groups in terms of mean pain intensity on movement normalized AUC or opioid rescue medication. Secondary efficacy endpoints included the following: mean pain intensity normalized AUC over the time period of 1 to 48 hours post-surgery, post-surgery time-to-opioid medication use, overall treatment satisfaction, mean total opioid dose converted into morphine equivalence for analgesia rescue during the study, and mean function activities (Days 1 through 5). Exploratory analyses included calculations of normalized mean pain intensity AUCs (on movement and at rest) for 1 to 24 hours, 1 to 96 hours, and 1 to 120 hours (using the last observation carried forward [LOCF] method).

Pharmacokinetics

Plasma samples were collected in a subset of patients at one selected study center for pharmacokinetic assessments.

Safety

Safety outcomes included AEs, surgical site healing and local tissue condition evaluations, ECGs, laboratory tests, vital signs, and physical examinations.

Statistical Methods

Primary Endpoints

The mean pain intensity AUC was compared between treatment groups using an Analysis of Variance (ANOVA) model that included treatment group and study site as factors. A Dunnett test was used to carry out the pairwise comparison of the placebo group (aggregated) and the two Formulation A doses. The proportion of patients who received opioid rescue medication was analyzed using a Cochran-Mantel-Haenszel (CMH) test.

Secondary Endpoints

Time-to-opioid use was analyzed using a log-rank test. The Cox proportional hazards model was also used to estimate the hazard ratio and its 95% confidence interval (CI).

Dose Response

The quantification of the efficacy dose response was examined by testing the monotonic relationship between the 3 treatment groups (placebo [aggregated], and Formulation A 2.5 mL and 5.0 mL) as a function of pain intensity. A step-down approach was used to address multiplicity of comparisons.

Results

Efficacy Results

Efficacy results for the primary pain on movement endpoint are summarized in Table 18.1. The 5 mL dose of Formulation A was highly significant compared to placebo, whereas the 2.5 mL Formulation A did not reach significance, but pain intensity AUC was lower than placebo. A reduction in mean pain intensity at rest normalized AUC from 1 to 72 hours was observed in favor of both active doses of Formulation A against placebo, albeit not statistically significant.

TABLE 18.1

Normalized AUC of Pain Intensity on Movement (1-72 hours), ITT

|  | Formulation A 2.5 mL | Formulation A 5.0 mL | Placebo |
| --- | --- | --- | --- |
| Mean (SEM) | 3.11 (0.25) | 2.47 (0.19) | 3.60 (0.30) |
| p-value vs Placebo | 0.157 | 0.0033 |  |

The mean pain intensity on movement normalized AUC from 1 to 48 hours was improved with Formulation A versus placebo, with a statistically significant difference (p=0.0007) observed between 5.0 mL of Formulation A (mean [SEM], 2.52 [0.19]) and placebo (3.86 [0.31]), and a trend toward significance with 2.5 mL of Formulation A (3.18 [0.24]) versus placebo (p=0.0654). In addition, the mean pain intensity at rest normalized AUC from 1 to 48 hours trended toward a significant improvement with 5.0 mL of Formulation A versus placebo (mean [SEM], 1.54 [0.13] vs. 2.18 [0.23]; p=0.0515), but the difference between 2.5 mL of Formulation A (2.15 [0.22]) and placebo was not statistically significant.

Opioid rescue analgesia after surgery was used in approximately 53.2% (25/47; 95% CI: 38.1%, 67.9%) of patients in the 5.0 mL Formulation A group, 72.1% (31/43; 95% CI: 56.3%, 84.7%) of patients in the 2.5 mL Formulation A group, and 71.9% (23/32; 95% CI: 53.3%, 86.3%)

of patients in the placebo group; the difference between 5.0 mL of Formulation A and placebo approached statistical significance in the ITT population (p=0.0909).

The median time-to-first opioid use was greatest with 5.0 mL of Formulation A (131.8 hours; 95% CI: 31.9, not defined), followed by 2.5 mL of Formulation A (10.8 hours; 95% CI: 1.1, 52.7), and then placebo (2.7 hours; 95% CI: 1.1, 25.3); the difference between 5.0 mL of Formulation A and placebo was statistically significant (p=0.0174).

The IV morphine equivalent dose of rescue medication taken from 0-72 hours after treatment is summarized in Table 18.2. Rescue medication use was significantly lower for Formulation A 5 mL compared to placebo, whereas the 2.5 mL dose of formulation did not reach statistical significance.

TABLE 18.2

IV Morphine Equivalent Use 0-72 Hours (ITT Population)

|  | Formulation A 2.5 ml | Formulation A 5 ml | Placebo |
|---|---|---|---|
| N | 43 | 47 | 32 |
| Mean (SE) | 11.2 (2.01) | 7.9 (1.60) | 23.5 (6.85) |
| Median | 5.0 | 2.5 | 12.5 |
| Formulation A 5 ml vs Placebo | | | |
| Median difference [1] | −7.5 | | |
| 95% CI [1] | (0.0. 15.0) | | |
| P-value [2] | 0.0085 | | |
| Formulation A 2.5 ml vs | | | |
| Median difference [1] | −5.0 | | |
| 95% CI [1] | (0.0. 10.0) | | |
| P-value [2] | 0.1333 | | |

[1] Hodges-Lehmann estimates for median difference
[2] [Wilcoxon rank-sum test

Most patients (>90%) in each treatment group were satisfied or very satisfied, and mean scores for each function activity improved from Day 1 to 5 in all 3 treatment groups.

A statistically significant improvement was observed with 5.0 mL of Formulation A versus placebo in the mean pain intensity on movement normalized AUC from 1 hour to last (mean [SEM], 2.27 [0.18] vs. 3.03 [0.25], respectively; p=0.0211), but not with Formulation A 2.5 mL (2.96 [0.25]) versus placebo. Similarly, normalized mean AUCs of pain intensity on movement from 1 to 24, 1 to 96, and 1 to 120 hours was lowest with 5.0 mL of Formulation A (mean [SEM], 2.21 [0.21], 2.37 [0.18], and 2.30 [0.18], respectively), followed by 2.5 mL of Formulation A (2.85 [0.25], 3.04 [0.26], and 2.93 [0.26], respectively), and last placebo (4.05 [0.31], 3.31 [0.29], and 3.03 [0.28], respectively).

Pharmacokinetic Results

Plasma concentrations of bupivacaine increased proportionally with the dose administered and there was no burst of drug delivery observed upon administration of Formulation A. The observed mean (SEM) pharmacokinetic parameters of bupivacaine are listed in Table 18.3

Safety Results

Safety results reported here refer to the safety population. The most common AEs (incidence of >10% in at least 1 treatment group) in the safety population (N=123) included somnolence, constipation, dizziness, pruritus, bradycardia, headache, postprocedural hemorrhage, postoperative wound complication, nausea, and dysgeusia. Adverse events from the modified Brief Pain Inventory (i.e., nausea/vomiting, drowsiness, itching, constipation, dizziness, ringing ears, metallic taste, and numbness or tingling of the toes or fingers) were reported in each treatment group. The incidence of all AEs probably or possibly related to treatment was 18.2% (8/44) in the 2.5 mL Formulation A group, 27.7% (13/47) in the 5.0 mL Formulation A group, and 28.1% (9/32) in the placebo group, and all were mild or moderate in severity.

Two safety analyses were performed: the original analysis imputed missing severity data as mild, and an ad-hoc analysis imputed missing severity data as severe. In both analyses, most AEs (>95% for original analysis, >70% for ad-hoc analysis) were mild or moderate in severity; 2 patients in each Formulation A group and no patients in the placebo group in the original analysis and 21 patients treated with Formulation A and 10 placebo-treated patients in the ad-hoc analysis experienced or had imputed a severe adverse event. Serious adverse events were reported in 6.8% (3/44), 4.3% (2/47), and 3.1% (1/32) of Formulation A 2.5-mL-, Formulation A 5.0-mL-, and placebo-treated patients, respectively; one event (vasovagal syncope) was considered possibly related to Formulation A treatment. Serious adverse events included acute coronary syndrome, vasovagal syncope, syncope, and postoperative wound complication. There were no deaths or other significant adverse events.

Nervous system adverse events were reported in 29 (66%), 25 (53%), and 23 (72%) Formulation A 2.5-mL-,

TABLE 18.3

| Pharmacokinetic Parameters | 2.5 mL Formulation A | 5.0 mL Formulation A |
|---|---|---|
| $C_{max}$ (ng/mL), mean (SEM) | 466.79 (60.48) | 866.57 (114.02) |
| $T_{max}$ (hr), median (range) | 12.0 (2.9-24.10) | 23.95 (4.0-24.10) |
| $AUC_{last}$ (ng*hr/mL), mean (SEM) | 18327.8 (2597.7) | 40822.9 (5428.5) |
| $AUC_{inf}$ (ng*hr/mL), mean (SEM) | 18542.8 (2636.6) | 41461.4 (5404.3) |

Formulation A 5.0-mL-, and placebo-treated patients, respectively. Cardiac adverse events were experienced by 10 (23%), 15 (32%), and 7 (22%) patients treated with 2.5 mL of Formulation A, 5.0 mL of Formulation A, and placebo, respectively. There were 5 vasovagal syncopal episodes during recovery from general anesthesia among patients from all dose groups, including placebo. Cardiovascular causes of syncopes were ruled out.

Clinically significant laboratory abnormalities were infrequent and consisted of 1 positive glucose urine test at screening in the 2.5 mL Formulation A group and 1 high creatine kinase blood level at Day 14 in the placebo group. Heart rate (HR), BP, respiratory rate, temperature, and physical examination (except gastrointestinal hernia for repair) findings were similar from screening to Day 14 in all treatment groups. The surgical site healed as expected and local tissue conditions were as expected/normal in 95% of patients in each treatment group at all time points evaluated.

On ECG, Formulation A did not result in any clinically relevant changes in HR, PR, QRS, and QT interval corrected for HR durations. The QTcF result in the regular set of 12-lead ECGs showed a mean change from baseline placebo corrected +2 ms in the 2.5 mL Formulation A dose group and −8 ms in the 5.0 mL Formulation A dose group; changes which would not indicate any signal that Formulation A affected cardiac depolarization or repolarization. However, in the telemetry set of ECGs, the mean change in QTcF duration for 2.5 mL and 5.0 mL of Formulation A from baseline to 12 hours was +15 and +9 ms, respectively, and from baseline to 24 hours was +8 and −11 ms, respectively. These data showed a non-dose related increase in QTcF duration, likely due to lack of power, concomitant general anesthesia, and large spontaneous variability in QTc durations rather than a direct effect of Formulation A.

During the 6-month follow-up period, there were fewer AEs in the 5.0-mL Formulation A group (35.7%) compared with the placebo group (42.3%) or the 2.5-mL Formulation A group (58.3%). Most AEs were mild or moderate in severity. Serious AEs were reported at a rate of 11.1% in the 2.5-mL Formulation A group and 7.7% in the placebo group; no serious AEs were reported in the 5.0-mL Formulation A group. Postoperative wound complication was the only AE reported in >10% of patients, occurring in 7 (19.4%) of patients in the 2.5 mL Formulation A group and 3 (11.5%) of patients in the placebo group. Surgical site healing and local tissue conditions were as expected/normal in all patients at 6 months.

Conclusions 5.0 mL of Formulation A (660 mg bupivacaine) instilled directly into the wound was safe and effective in the management of pain in patients who underwent elective, open, unilateral, tension-free, inguinal hernia repair. 2.5 mL of Formulation A (330 mg bupivacaine) was not demonstrated to be sufficiently efficacious for pain management in inguinal hernia repair. 5.0 mL of Formulation A (660 mg) significantly improved mean pain intensity on movement normalized AUC compared with Placebo post-surgery for 48 and 72 hours. Patients treated with 5.0 mL of Formulation A (660 mg) required significantly less opioid rescue medication post-surgery compared with Placebo for 48 and 72 hours. Over the study period, 5.0 mL of Formulation A (660 mg) significantly prolonged the time to first opioid use compared with Placebo.

Efficacy endpoints in the 2.5 mL Formulation A (330 mg) group were not statistically significantly different from Placebo. However, a trend toward a significant difference versus Placebo was observed with mean pain intensity on movement normalized AUC from 1 to 48 hours and MEDD taken on Day 2. Patient satisfaction with overall pain treatment was observed in each treatment group and persisted throughout the duration of the study. Functional activity improved over time in all treatment groups. Pharmacokinetics of bupivacaine is observed to be dose proportional, with no drug release burst observed after administration of Formulation A.

Most AEs were mild or moderate in severity, and no deaths or other significant AEs occurred. During the 6-month follow-up period, serious AEs were reported at a similar incidence in patients treated with 2.5 mL of Formulation A (330 mg) and placebo, while none were reported in patients treated with 5.0 mL of Formulation A (660 mg). The active monitoring of cardiovascular toxicities suggests that no causal association was present between the single episodic exposure to Formulation A and cardiac events. Constipation, nausea, pruritus, tinnitus, somnolence, dizziness, headache, dysgeusia, and paresthesia were reported less frequently with 5.0 mL of Formulation A (660 mg) compared with placebo; however, postprocedural hemorrhage, postoperative wound complication, and bradycardia were reported more frequently with 5.0 mL of Formulation A (660 mg) compared with placebo.

The reduction in opioid rescue dose associated with 5.0 mL of Formulation A (660 mg) reduced the incidence of opioid-related AEs, including dizziness, nausea, and vomiting, and significantly reduced the incidence of constipation compared with placebo. Vital sign or physical examination changes over time were minimal. Abnormal or unexpected surgical site healing or tissue evaluation, or clinically significant laboratory abnormalities was observed infrequently and incidences were similar between treatment groups. On ECG, Formulation A did not demonstrate any clinically relevant changes in HR, PR, QRS, or QTc durations. However, QTcF prolongation was observed, which was not dose-related and was likely due to a small sample size, concomitant general anesthesia, and large spontaneous variability in QTc durations. This study did not demonstrate clear and consistent ECG effects for either the lower (2.5 mL [330 mg]) or higher (5.0 mL [660 mg]) dose of Formulation A, suggesting that the higher dose does not expose patients to a greater risk of untoward cardiovascular effects.

Example 19

A patient-blinded, Phase II study was conducted to examine the pharmacokinetics (PK), safety, tolerability and efficacy of Formulation A instilled directly into the wound in patients undergoing elective open inguinal hernia repair. Operative procedures were performed under general anesthesia. In this study, Formulation A was prepared as described above and includes 3 components (sucrose acetate isobutyrate 66 wt %, benzyl alcohol 22.0 wt %, and bupivacaine base 12.0 wt %) that are administered together as a sterile solution. The aim of using the formulation is to provide prolonged local analgesia by slowly releasing bupivacaine over a period of several days.

Objectives

Primary objective—To examine the pharmacokinetics of a sustained release bupivacaine composition (i.e., Formulation A containing bupivacaine, benzyl alcohol, sucrose acetate isobutyrate as described above) instilled directly into the wound in patients undergoing elective open inguinal hernia repair.

Secondary objective—To examine the safety, efficacy and tolerability of Formulation A instilled directly into the wound in patients undergoing elective open inguinal hernia repair.

Methods

The studies was a pilot, patient-blinded, Phase II study to assess the pharmacokinetics, safety, tolerability and efficacy of Formulation A as a delivery system in open inguinal hernia repair patients. The study investigated instillation of Formulation A directly into the wound, with patients being enrolled into two treatment groups:

Treatment Group 1—During wound closure 2.5 mL of Formulation A was placed topically, in approximately equal volumes, into the superior, medial and inferior subaponeurotic spaces. After closure of the external oblique aponeurosis (and prior to skin closure) a further 2.5 mL of Formulation A was placed topically along the length of the sutured external oblique aponeurosis. The total delivered volume of Formulation A instilled into the wound was 5.0 mL.

Treatment Group 2—After closure of the external oblique aponeurosis (and prior to skin closure) 5.0 mL of Formulation A was placed topically along the length of the sutured external oblique aponeurosis. The total delivered volume of Formulation A instilled into the wound was 5.0 mL.

Number of patients: Patients planned—Up to 12 patients, with six per treatment group to achieve five evaluable patients per group; Patients Entered—12 patients, with six per treatment group; Patients Completed—12 patients, with six per treatment group.

Diagnosis and main criteria for inclusion of patient into study: The study population included male and female patients undergoing open repair of inguinal hernia under general anaesthesia.

Duration of Treatment

The study period lasted up to 21 days.

Criteria for Evaluation:

Efficacy: Daily pain intensity (numerical rating scale), daily opioid rescue analgesia and total daily analgesia. A modified brief pain inventory was used to assess daily pain control, worst pain, least pain, analysis of function, treatment satisfaction and individual pain intensity over time.

Safety: Adverse effects (AEs), wound healing and local tissue conditions, laboratory tests, physical examination and vital signs. The modified brief pain inventory also recorded certain safety evaluations including: nausea, vomiting, drowsiness, itching, constipation, dizziness, tinnitus, dysgeusia, parasthesia and the number of bowel movements following injection of study drug.

Pharmacokinetic: Non-compartmental PK analysis was performed on all patient data from whom PK blood samples were collected.

Statistical Methods:

The aim was for five evaluable patients to complete treatment in each group was used as the sample size calculation for this study.

Plasma bupivacaine concentration was summarized at each timepoint and WinNonLin was used to assess the data. The parameters of maximum plasma concentration (Cmax), time taken to reach Cmax (Tmax) and area under the curve (AUC), using the linear trapezoid rule, were summarized by treatment group and compared using a linear general method.

A plot of mean pain intensity score at pre-determined time points was used to assess both treatment groups simultaneously. Modified brief pain inventory data were summarized by treatment group, with pain control, worst pain and least pain summarized using an AUC. All pain assessment data were summarized by treatment group.

All opioid containing drugs were coded into morphine equivalents and the total morphine equivalent daily dose was calculated for each day. The average number of rescue analgesic tablets taken per day for Days 0-5, 6-14 and overall (Days 0-14) were calculated and summarized by treatment group. The proportion of patients who required no rescue analgesia during Days 0-5 was summarized by treatment group.

The overall incidence (number and percentage) of treatment emergent AEs and serious adverse events (SAEs) were summarized by treatment group. The incidence of AEs was also assessed in terms of maximum severity and relationship to study medication, for each MedDRA system organ class and preferred term. The proportion of patients reporting each common safety event recorded by the modified brief pain inventory was summarized by treatment group. Surgical site healing and local tissue condition data were listed and summarized by treatment group.

Vital signs data, changes from baseline and the number and proportion of patients with abnormal findings in each body system were summarized by treatment group at each visit. Data on typical bowel function were summarized and the number of bowel functions in each 24-hour period was summarized by treatment group. Concomitant medications taken were summarized by treatment group using ATC and WHO drug codes.

Laboratory data were listed, compared with sex-specific normal ranges and any changes from screening to the end of the study were calculated. The observed data and changes from screening were summarized by treatment group. Shift tables of hematology and biochemistry parameters between abnormally low/normal/abnormally high values from baseline to the end of treatment were produced by treatment group. The proportion of patients with abnormal values considered clinically significant was compared between treatment groups.

Results

Efficacy Results

In Treatment Group 1 where Formulation A was instilled into the subaponeurotic space and along the external oblique aponeurosis, the mean pain intensity scores at rest remained at a similar level over Days 0-1 and began to fall on Day 2. In Treatment Group 2 where Formulation A was instilled along the external oblique aponeurosis alone there was a slight increase in mean pain intensity scores from Day 0 to Day 1, with a subsequent reduction in pain levels on Days 2-3. Overall the mean pain intensity scores for Days 2-5 were consistently higher in Treatment Group 2 patients than in Treatment Group 1 patients and the pain intensity AUCs were also higher for patients in Treatment Group 2. (Table 19.1)

TABLE 19.1

Pain Intensity Scores at Rest (ITT Population)

| | Time | Subaponeurotic Spaces + Oblique Aponeurosis (Group 1) (N = 6) | | Oblique Aponeurosis Alone (Group 2) (N = 6) | |
|---|---|---|---|---|---|
| | | Mean ± SEM | Median (95% CI) | Mean ± SEM | Median (95% CI) |
| Day 0 | 4 hours | 1.2 ± 0.65 | 0.5 (0.0, 4.0) | 0.8 ± 0.40 | 0.5 (0.0, 2.0) |
| | 6 hours | 0.8 ± 0.65 | 0.0 (0.0, 4.0) | 0.5 ± 0.22 | 0.5 (0.0, 1.0) |
| | 8 hours | 0.8 ± 0.65 | 0.0 (0.0, 4.0) | 0.7 ± 0.33 | 0.5 (0.0, 2.0) |
| | 10 hours | 0.8 ± 0.65 | 0.0 (0.0, 4.0) | 1.5 ± 0.22 | 1.5 (1.0, 2.0) |
| | 12 hours | 0.7 ± 0.49 | 0.0 (0.0, 3.0) | 1.5 ± 0.22 | 1.5 (1.0, 2.0) |
| Day 1 | 08:00 hours | 0.5 ± 0.34 | 0.0 (0.0, 2.0) | 2.3 ± 0.61 | 2.0 (1.0, 4.0) |
| | 12:00 hours | 0.8 ± 0.40 | 0.5 (0.0, 2.0) | 1.2 ± 0.48 | 1.0 (0.0, 3.0) |
| | 16:00 hours | 1.3 ± 0.49 | 1.5 (0.0, 3.0) | 1.5 ± 0.67 | 1.0 (0.0, 4.0) |
| | 20:00 hours | 1.3 ± 0.49 | 1.5 (0.0, 3.0) | 1.3 ± 0.76 | 1.0 (0.0, 5.0) |
| Day 2 | 08:00 hours | 0.8 ± 0.40 | 0.5 (0.0, 2.0) | 1.2 ± 0.60 | 1.0 (0.0, 4.0) |
| | 12:00 hours | 0.8 ± 0.31 | 1.0 (0.0, 2.0) | 1.3 ± 0.61 | 1.0 (0.0, 4.0) |
| | 16:00 hours | 0.2 ± 0.17 | 0.0 (0.0, 1.0) | 1.2 ± 0.60 | 1.0 (0.0, 4.0) |
| | 20:00 hours | 0.5 ± 0.34 | 0.0 (0.0, 2.0) | 1.0 ± 0.60 | 0.5 (0.0, 4.0) |
| Day 3 | 08:00 hours | 0.2 ± 0.17 | 0.0 (0.0, 1.0) | 0.8 ± 0.65 | 0.0 (0.0, 4.0) |
| | 12:00 hours | 0.2 ± 0.17 | 0.0 (0.0, 1.0) | 1.0 ± 0.63 | 0.5 (0.0, 4.0) |
| | 16:00 hours | 0.3 ± 0.21 | 0.0 (0.0, 1.0) | 0.8 ± 0.65 | 0.0 (0.0, 4.0) |
| | 20:00 hours | 0.2 ± 0.17 | 0.0 (0.0, 1.0) | 0.8 ± 0.65 | 0.0 (0.0, 4.0) |
| Day 4 | 08:00 hours | 0.2 ± 0.17 | 0.0 (0.0, 1.0) | 1.0 ± 0.82 | 0.0 (0.0, 5.0) |
| | 12:00 hours | 0.3 ± 0.33 | 0.0 (0.0, 2.0) | 1.2 ± 0.79 | 0.5 (0.0, 5.0) |
| | 16:00 hours | 0.2 ± 0.17 | 0.0 (0.0, 1.0) | 1.0 ± 0.82 | 0.0 (0.0, 5.0) |
| | 20:00 hours | 0.3 ± 0.21 | 0.0 (0.0, 1.0) | 1.0 ± 0.82 | 0.0 (0.0, 5.0) |
| Day 5 | 08:00 hours | 0.2 ± 0.17 | 0.0 (0.0, 1.0) | 0.8 ± 0.65 | 0.0 (0.0, 4.0) |
| | 12:00 hours | 0.3 ± 0.21 | 0.0 (0.0, 1.0) | 0.8 ± 0.65 | 0.0 (0.0, 4.0) |
| AUC | 0-120 hours | 68.4 ± 36.86 | 31.0 (3.0, 240.2) | 140.3 ± 67.88 | 61.4 (29.3, 462.8) |

SEM = standard error of mean;
CI = confidence interval

A similar pattern was seen for pain intensity scores on movement. Most patients experienced good, very good or excellent pain control from Formulation A instillation into the wound, with only two patients in Treatment Group 2 experiencing fair pain control. No notable differences between treatment groups were seen when comparing pain control AUC values. The worst pain scores were higher on Day 1 in Treatment Group 2 but by Day 2 there were no notable differences between the treatment groups. The impact of post-surgical pain on ability to walk, social interactions, stay asleep and to cough was higher in Treatment Group 2 on Day 1, but by Day 2 was comparable between the two groups for most parameters. Most patients were satisfied or very satisfied with Formulation A treatment, with only two patients in Treatment Group 2 (i.e., where Formulation A was instilled along the external oblique aponeurosis alone) being fairly dissatisfied or only fairly satisfied with treatment. No differences between the two groups were seen for the other efficacy parameters evaluated.

More patients in Treatment Group 2 where Formulation A was instilled along the external oblique aponeurosis alone required rescue analgesia between Days 0-5 compared to patients in Treatment Group 1 where Formulation A was instilled into the subaponeurotic space as well as along the external oblique aponeurosis. However, patients in Treatment Group 2 only required rescue analgesia over Days 0-5, whereas one patient in Treatment Group 1 required rescue analgesia during Days 6-14.

TABLE 19.2

Total Daily Dose of Rescue Analgesia (tablets, ITT Population)

| | Subaponeurotic Spaces + Oblique Aponeurosis (Group 1) (N = 6) | | Oblique Aponeurosis Alone (Group 2) (N = 6) | |
|---|---|---|---|---|
| Time | Mean ± SEM | Median (95% CI) | Mean ± SEM | Median (95% CI) |
| Days 0-5 | 2.0 ± 1.63 | 0.0 (0.00, 10.00) | 3.0 ± 1.24 | 3.0 (0.00, 8.00) |
| Days 6-14 | 0.3 ± 0.33 | 0.0 (0.00, 2.00) | 0.0 ± 0.00 | 0.0 (0.00, 0.00) |
| Overall | 2.3 ± 1.96 | 0.0 (0.00, 12.00) | 3.0 ± 1.24 | 3.0 (0.00, 8.00) |

Opioid analgesia used during the study was converted into intravenous morphine equivalent daily doses (MEDD) unit and the resulting supplemental opioid analgesia usage is summarized the table below. During the first 24 hours post-surgery, patients in Treatment Group 2 required more opioid therapy than patients in Treatment Group 1. However, after this 24-hour period, none of the patients in Treatment Group 2 required additional opioid analgesia, whereas some patients in Treatment Group 1 required opioid analgesia throughout Days 1-5.

TABLE 19.3

Summary of Opioid Analgesia Usage (MEDD, ITT Population)

| Time | Subaponeurotic Spaces + Oblique Aponeurosis (Group 1) (N = 6) | | | Oblique Aponeurosis Alone (Group 2) (N = 6) | | |
|---|---|---|---|---|---|---|
| | Mean ± SEM | Median | Range | Mean ± SEM | Median | Range |
| 1-24 hours | 0.83 ± 0.833 | 0.00 | 0.0-5.0 | 2.50 ± 5.500 | 0.00 | 0.0-15.0 |
| 24-48 hours | 1.67 ± 1.667 | 0.00 | 0.0-10.0 | 0.00 ± 0.000 | 0.00 | 0.0-0.0 |
| 48-72 hours | 1.67 ± 1.054 | 0.00 | 0.0-5.0 | 0.00 ± 0.000 | 0.00 | 0.0-0.0 |
| 72-96 hours | 0.00 ± 0.000 | 0.00 | 0.0-0.0 | 0.00 ± 0.000 | 0.00 | 0.0-0.0 |
| 96-120 hours | 0.83 ± 0.833 | 0.00 | 0.0-5.0 | 0.00 ± 0.000 | 0.00 | 0.0-0.0 |
| Days 1-5 | 1.00 ± 0.816 | 0.00 | 0.0-5.0 | 0.50 ± 0.500 | 0.00 | 0.0-3.0 |

Safety Results

The incidence of AEs was comparable between treatment groups. The only AEs reported in more than one patient per treatment group were post-procedural hemorrhage (three of six patients) and nausea (two of six patients). Nausea was experienced across both treatment groups on the day following surgery, whereas post-procedural hemorrhage was only experienced by patients in Treatment Group 1. Drowsiness and constipation were reported by individual patients within the first two days of the study. All AEs were mild (three of six patients in Treatment Group 2) or moderate (four of six patients in Treatment Group 1) in severity and none were considered related to the study treatment.

There were no deaths or withdrawals during the study. Only one patient experienced a severe adverse effect (SAE), comprising recurrence of inguinal hernia in a patient in Treatment Group 1. The SAE was not considered related to the study treatment and resolved over the course of the study.

The administration of Formulation A directly into the wound at a dose of 5.0 mL did not raise safety concerns over clinical laboratory, vital signs or physical examination parameters. In addition, the use of Formulation A did not appear to compromise wound healing, though abnormal local tissue conditions were recorded for three of the 12 patients. Administration of Formulation A to the subaponeurotic space and along the external oblique aponeurosis appeared to be associated with a slightly faster return to normal bowel function.

Pharmacokinetic Results

Quantifiable plasma bupivacaine concentrations were observed within 1-4 hours of Formulation A administration, which increased gradually to maximum concentrations around 12-24 hours in both the treatment groups. Sustained levels (between 100-400 ng/mL) were generally maintained for a period of 48-72 hours and then the concentrations started to decline in mono-exponential order.

In this study, the two treatment groups were different with respect to the method of drug administration, but the total volume of drug administered was 5.0 mL for both the groups. Overall pharmacokinetic parameters of bupivacaine between the two groups were similar, with somewhat higher variability in Group 2 (entire amount as wound infiltrate).

After correcting for the actual dose administered and normalizing to 1 mL dose, the plasma bupivacaine concentration seemed almost superimposable.

Conclusions

The pharmacokinetics of bupivacaine were similar between the two groups evaluated in this study. This study showed that Formulation A, instilled into either the subaponeurotic space and along the external oblique aponeurosis (Treatment Group 1) or instilled along the external oblique aponeurosis alone (Treatment Group 2), at a dose of 5.0 mL was well tolerated and not result in any clinically significant AEs. Instillation of Formulation A into the subaponeurotic space and along the external oblique aponeurosis (Treatment Group 1) showed better efficacy, particularly on Day 1, in terms of pain intensity scores, as well as the amount of time pain interfered with the ability to walk, social interactions, ability to stay awake and to cough. The patient's assessment of their overall pain control and satisfaction with treatment was higher when Formulation A was instilled into the subaponeurotic space and along the external oblique aponeurosis (Treatment Group 1) compared to along the external oblique aponeurosis alone (Treatment Group 2). Instillation of Formulation A into the subaponeurotic space and along the external oblique aponeurosis (Treatment Group 1) was associated with a reduced requirement for supplemental rescue and opioid analgesia in the first few days post-surgery.

Example 20

A randomized, double-blind, placebo-controlled study was conducted to examine the efficacy, tolerability and safety of Formulation A administered subcutaneously or into the subaponeurotic space in subjects undergoing elective open inguinal hernia repair. In this study, Formulation A and placebo was prepared as described above and is summarized below:

| Composition: | Formulation A-Sustained Release Bupivacaine Composition |
|---|---|
| Active ingredient: | Bupivacaine base |
| Inactive ingredients: | Sucrose acetate isobutyrate, benzyl alcohol |
| Strength: | 132 mg/mL, 660 mg bupivacaine |

| Composition | Placebo |
|---|---|
| Active ingredient: | Not applicable |
| Inactive ingredients: | Sucrose acetate isobytyrate, benzyl alcohol |

Objectives

Primary objective—The primary objective was to determine the efficacy of Formulation A administered subcutaneously or into the subaponeurotic space in subjects undergoing elective open inguinal hernia repair.

Secondary objective—The secondary objectives were to determine the safety and tolerability of Formulation A administered subcutaneously or into the subaponeurotic space in subjects undergoing elective open inguinal hernia repair.

Since the mode of administration was different between Cohort 1 and Cohort 2, the study objectives were defined specifically for each cohort.

Methods

This was a randomized, double-blind, placebo-controlled, Phase 2 study to examine the efficacy of Formulation A instilled throughout the subaponeurotic and subcutaneous spaces, administered by injection into the subaponeurotic space, or administered subcutaneously in subjects undergoing elective open inguinal hernia repair and to assess the safety and tolerability of Formulation A as a delivery system.

The study was conducted in 2 separate and sequential cohorts (Cohort 1 and Cohort 2, summarized below). Approximately equal numbers of subjects were to be enrolled, in sequence, to each cohort. The study duration was up to 21 days that included screening, admission to clinic and surgery (Day 0), postoperative evaluations, discharge from clinic, and follow-up through Day 14.

The subjects were evaluated on Days 1, 2, 4, and 5 by telephone and returned to the clinic on Days 3 and 14 (follow-up). Subjects recorded pain intensity (PI), concomitant medications, adverse events (AEs), and rescue analgesia on diary cards from Days 0 through 5. Subjects also recorded AEs and concomitant medications through Day 14.

Cohort 1

Immediately prior to surgery, the first 45 subjects were randomly assigned in a 1:1:1 ratio to receive 1 of the following treatments:

Treatment Group 1: Prior to wound closure, 5.0 mL of Placebo was injected into the superior, medial, and inferior subaponeurotic spaces. After wound closure, Formulation A was administered as 2 trailing subcutaneous injections along each side of the incision line (suggested incision total length to be 4 to 6 cm). The total delivered volume of Formulation A was 5.0 mL.

Treatment Group 2: Prior to wound closure, 5.0 mL of Formulation A (12.0 wt %, 132 mg/mL bupivacaine was injected into the superior, medial, and inferior subaponeurotic spaces. After wound closure, Placebo was administered as 2 trailing subcutaneous injections along each side of the incision line (suggested incision total length to be 4 to 6 cm). The total delivered volume of Placebo was 5.0 mL.

Treatment Group 3: Prior to wound closure, 5.0 mL of Placebo was injected into the superior, medial, and inferior subaponeurotic spaces. After wound closure, Placebo was administered as 2 trailing subcutaneous injections along each side of the incision line (suggested incision total length to be 4 to 6 cm). The total subcutaneously delivered volume of Placebo was 5.0 mL. The total delivered volume of Placebo was 10.0 mL.

Cohort 2

Immediately prior to surgery, the second group of 45 subjects was randomly assigned in a 1:1 enrollment ratio to receive 1 of the following treatments:

Treatment Group 4: During the wound closure, 5.0 mL of Placebo was instilled gradually throughout the inguinal canal and the abdominal wall layers to cover all raw surfaces of the wound, filling up subaponeurotic and subcutaneous spaces.

Treatment Group 5: During the wound closure, 5.0 mL of Formulation A was instilled gradually throughout the inguinal canal and the abdominal wall layers to cover all raw surfaces of the wound, filling up subaponeurotic and subcutaneous spaces (7.5 mL specified for Cohort 2a comprising Treatment 5a).

Number of Subjects: The planned enrollment was 90 subjects in order to ensure 72 evaluable subjects who planned to undergo ambulatory open repair of inguinal hernia. The 90 subjects were to be divided evenly into 45 subjects in each cohort.

The final goal was for at least 72 evaluable subjects to complete the study (36 subjects in each cohort, 12 subjects in each treatment group of Cohort 1 and 18 in each treatment group of Cohort 2).

A total of 45 subjects were enrolled in Cohort 1; 13 to Treatment 1, 18 to Treatment 2, and 14 to Treatment 3. All 45 subjects completed Cohort 1. A total of 44 subjects were enrolled in Cohort 2; 21 to Treatment 4, 1 to Treatment 5a, and 22 to Treatment 5. Forty-one subjects completed Cohort 2; 1 subject in Treatment 4 and 2 subjects in Treatment 5 were lost to follow-up.

Diagnosis and main criteria for inclusion of patient into study: The study population included male and female subjects who were planning to undergo ambulatory open repair of inguinal hernia requiring an incision of 4 to 6 cm in length, were in good health, and were above 18 years of age.

Test Product, Dose and Mode of Administration

Cohort 1

Treatment 1: 10.0-mL vials of Formulation A (12.0 wt %) were used to fill 5.0-mL syringes for a 5.0-mL subcutaneous injection.

Treatment 2: 10.0-mL vials of Formulation A (12.0 wt %) were used to fill 5.0-mL syringes for injection of 5.0 mL into the superior, medial, and inferior subaponeurotic spaces.

Cohort 2

Treatment 5a: 10.0-mL vials of Formulation A (12.0 wt %) were used to fill 10.0-mL syringes to instill 7.5 mL into subaponeurotic and subcutaneous spaces.

Treatment 5: 10.0-mL vials of Formulation A (12.0 wt %) were used to fill 10.0-mL syringes to instill 5.0 mL into subaponeurotic and subcutaneous spaces.

Reference Therapy, Dose and Mode of Administration

Cohort 1

Treatment 1: 10.0-mL vials of Placebo were used to draw 5.0-mL syringes for injection of 5.0 mL into the superior, medial, and inferior subaponeurotic spaces.

Treatment 2: 10.0-mL vials of Placebo were used to draw 5.0-mL syringes for a 5.0-mL subcutaneous injection.

Treatment 3: 10.0-mL vials of Placebo were used to draw 5.0-mL syringes for a 5.0-mL subcutaneous injection and an injection of 5.0 mL into the superior, medial, and inferior subaponeurotic spaces.

Cohort 2

Treatment 4: 10.0-mL vials of Placebo (12.0 wt %) were used to draw 10.0-mL syringes to instill 5.0 mL into subaponeurotic and subcutaneous spaces.

Duration of Treatment

Subjects received a single dose of Formulation A. The study duration was up to 21 days comprising screening, admission to clinic and surgery (Day 0), postoperative evaluations, discharge from clinic, and follow-up through Day 14.

Criteria for Evaluation:

Efficacy: Efficacy was assessed using the subjects' self-evaluation of PI and pain management collected on subject diaries (Days 0 to 5), the Modified Brief Pain Inventory (Days 1 to 5), and the subjects' use of concomitant rescue analgesic medication (Days 0 to 14). The primary efficacy endpoints were PI and pain control. The secondary efficacy endpoints were worst and least pain scores, rescue analgesia usage, function, overall treatment satisfaction, and individual PI scores over time.

Safety: Safety evaluations included AEs; assessments of laboratory tests such as chemistry, hematology, and urinalysis; a serum pregnancy test (if applicable); periodic monitoring of vital signs; 12 lead electrocardiogram (ECG); concomitant medications; and physical examinations. Evaluations also included surgical site healing and local tissue conditions.

Statistical Methods:

Tables and listings were produced using SAS version 8.2. All efficacy and safety data collected on the case report form (CRF) were presented in listings ordered by treatment group, site, subject number, date, and time. Data summaries by treatment group were presented. For continuous variables, data were summarized with the number of subjects (n), mean, standard deviation (SD), median, minimum, and maximum by treatment group. For categorical variables, data were tabulated with number and proportion of subjects for each category by treatment group.

Statistical tests were performed using 2-sided tests at the 5% significance level. Because of the exploratory nature of this Phase 2 study, no multiplicity adjustment was made for any of the analyses.

The comparison of primary interest was between Treatment 5 and Pooled Placebo. The significance of comparisons between Formulation A, Treatment 2 and Treatment 1 and Pooled Placebo were also reported.

The incidence (number and percentage) of treatment-emergent AEs was reported for each treatment group by Medical Dictionary for Regulatory Activities (MedDRA) Version 8.0 system organ class and preferred term. A separate overall incidence summary was presented for AEs with onset on Day 0.

Specific safety evaluations of the Modified Brief Pain Inventory were tabulated by study day and treatment. Incidence across all study days was also summarized by treatment.

Surgical site healing and local tissue condition evaluation was summarized and tabulated by subject incidence (n and percent) for each treatment group over time.

All laboratory test results were listed by subject, laboratory panel and parameter, and collection time.

Abnormal or change from screening physical examination results were presented in a listing.

Vital signs were listed descriptively for each treatment group at each collection time point. Changes from baseline (predose) vital signs were summarized for each treatment and scheduled interval. Repeat readings were not used in these summaries.

Screening and unscheduled ECGs were presented in a listing.

Results

Efficacy Results:

The results of the per-protocol (PP) population analysis showed that, for the primary endpoint of PI during movement, the Formulation A treatment groups were not significantly better than the pooled Placebo group. Treatments 1 (5.0 mL Formulation A, subcutaneous) and 2 (5.0 mL Formulation A, subaponeurotic) were numerically better than placebo, but these differences did not reach statistical significance. For the primary endpoint of PI at rest, similar results were observed. The only statistically significant difference represented a higher PI value in Treatment 5 (5.0 mL Formulation A) compared to Pooled Placebo (P=0.014). In the analysis of secondary endpoints, the time to first rescue analgesia was significantly longer for Treatment 2 (5.0 mL Formulation A, subaponeurotic) than for Pooled Placebo (P=0.009).

A post hoc analysis of PI over time was conducted for the 2 cohorts separately. In Cohort 1, pain assessments were not significantly different between the 3 treatment groups. The Formulation A subaponeurotic and subcutaneous treatment groups required less opioid use during the evaluation period compared to placebo. In Cohort 2, no trend in reduction of overall cumulative opioid rescue medication use in the Formulation A treatment groups versus placebo was observed.

Safety Results:

The overall frequency of adverse effects (AEs) was similar between treatment groups. The most commonly reported treatment-emergent AEs were nausea (46 events total; 6 in Treatment 1, 10 in Treatment 2, 12 in Treatment 5, 1 in Treatment 5a, and 17 in Pooled Placebo), dizziness (42 events total; 4 in Treatment 1, 5 in Treatment 2, 13 in Treatment 5, 0 in Treatment 5a, and 20 in Pooled Placebo), constipation (40 events total; 5 in Treatment 1, 7 in Treatment 2, 15 in Treatment 5, 0 in Treatment 5a, and 13 in Pooled Placebo), and somnolence (38 events total; 4 in Treatment 1, 2 in Treatment 2, 13 in Treatment 5, 1 in Treatment 5a, and 18 in Pooled Placebo). The majority of treatment-emergent AEs were of mild or moderate severity. There were no deaths or discontinuations due to AEs. Three severe adverse effects (SAEs) occurred (syncope vasovagal, orthostatic hypotension, and oliguria); all of these events were moderate in intensity and none were considered related to study drug by the investigator.

An analysis of specific safety evaluations of interest did not indicate any opioid-related safety issues. Nausea, somnolence, dizziness, and constipation were reported by approximately 50% of subjects in all treatment groups. Vomiting, tinnitus, pruritus, dysgeusia, and paresthesia also occurred with high frequency. There were several differences in the frequency of occurrence of these events between the Formulation A and Pooled Placebo treatment groups: vomiting occurred in 7 subjects (7/40, 17.5%) in the Formulation A treatment group compared to 3 subjects (3/35, 8.6%) in the placebo group; dysgeusia occurred in 3 subjects (3/40, 7.5%) in the Formulation A treatment group compared to 6 subjects (6/35, 17.1%) in the placebo group; and paresthesia occurred in 4 subjects (4/40, 10.0%) in the Formulation A treatment group compared to 7 subjects (7/35, 20.0%) in the placebo group.

Post hoc analyses of specific safety evaluations of interest showed a decreased incidence of opioid-related side effects with Formulation A treatment in Cohort 1. The frequency of the nervous system disorders of dizziness and somnolence was less in the Formulation A treatment groups compared to placebo. Specifically, the frequency of dizziness was 64.3% in the placebo group, 27.8% in the Formulation A subaponeurotic treatment group (Treatment 2), and 30.8% in the Formulation A subcutaneous treatment group (Treatment 1). The frequency of somnolence was 50.0% in the placebo group, 11.1% in the Formulation A subaponeurotic treatment group (Treatment 2), and 30.8% in the Formulation A subcutaneous treatment group (Treatment 1). This decreased incidence of opioid-related side effects correlates with a reduction in opioid use in the Formulation A treatment group compared to placebo.

Conclusions

The primary specified analysis, while numerically better than placebo, did not provide statistical support for the overall hypotheses of efficacy. The results of the post hoc analyses in Cohort 1 showed that the frequency of opioid-related side effects was reduced in the Formulation A treatment groups compared to placebo, which corresponded to a reduction in opioid use in the Formulation A treatment groups compared to the placebo group. Furthermore, these post hoc analyses showed a reduction in pain within the first postoperative day in the Formulation A subaponeurotic treatment group compared to the placebo group, while no difference in pain scores was observed between the Formulation A subcutaneous treatment group and the placebo group.

Example 21

Dissolution profiles were compared from formulations having bupivacaine free base, triacetin, and either poly (lactide-co-glycolide) (PLGA) or a polyorthoester (POE).

In Vitro Dissolution Profile

To compare dissolution profiles, compositions having the same weight percent bupivacaine and having the same polymer/solvent ratio were made and tested as described in Exhibit A. As summarized below in Table 21.1, the tested compositions differed in having either a poly(lactide-co-glycolide) (PLGA) having a weight average molecular weight of 16 kDa or a polyorthoester (POE) having a weight average molecular weight of 5 kDa.

TABLE 21.1

Composition of each formulation tested

| | PLGA Composition | POE Composition |
|---|---|---|
| Drug (10 wt %) | Bupivacaine | Bupivacaine |
| Solvent (45 wt %) | Triacetin | Triacetin |
| Polymer (45 wt %) | Poly(lactide-co-glycolide) (PLGA) | Polyorthoester (POE) |
| | $M_w$ = 16 kDa | $M_w$ = 5 kDa |
| | $M_n$ = 8 kDa | $M_n$ = 3 kDa |

Figure 30:
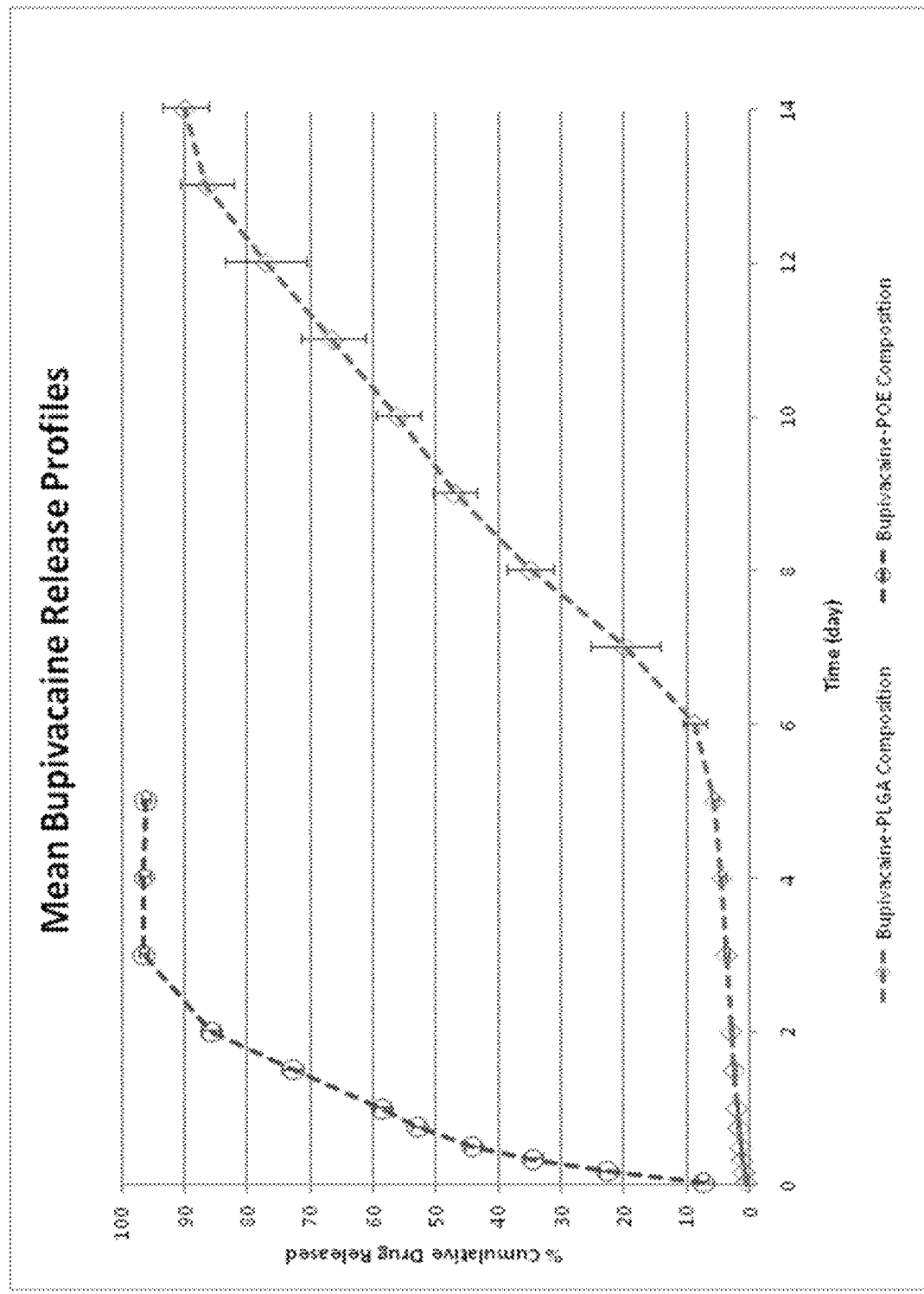
FIG. 30 shows that release from a PLGA composition showed more variability than release from a POE composition as shown by the larger error bars (standard deviation).

In vitro release of bupivacaine from the compositions was assessed according to the methods described below. FIG. 30 shows the mean cumulative release of bupivacaine from the PLGA and POE compositions.

Figure 31:
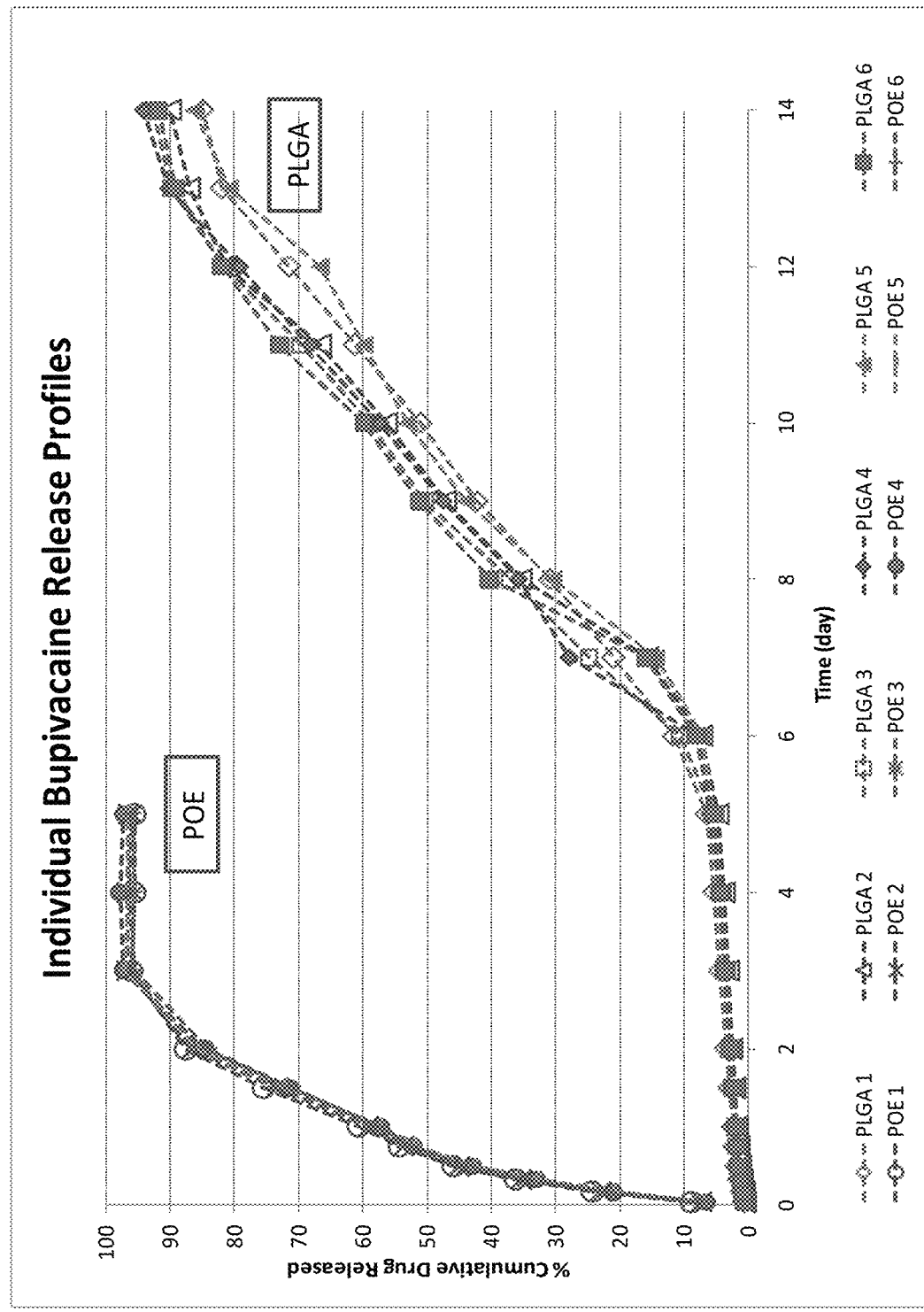
FIG. 31 also shows larger variability in release from a PLGA composition than from a POE composition, which shows the individual release profiles for each of the six replicates of each formulation.

The release from the PLGA composition showed more variability than the release from the POE composition as shown by the larger error bars (standard deviation) in FIG. 30. The larger variability is also apparent in FIG. 31, which shows the individual release profiles for each of the six replicates of each formulation. The six replicates involving the POE composition are POE1 to POE6, and the six replicates involving the PLGA composition are PLGA1 to PLGA6.

Cumulative Release of Bupivacaine In Vitro

The in vitro cumulative release of bupivacaine was determined as follows.

Materials

The bupivacaine-poly(lactide-co-glycolide) (PLGA) composition was prepared as follows. Bupivacaine base was dispersed in triacetin. PLGA (50:50 L:G, $M_w$=16 kDa, $M_n$=8 kDa, initiated with 1-dodecanol) was added to the bupivacaine-triacetin mixture. The resulting mixture was homogenized.

The bupivacaine-polyorthoester (POE) composition was prepared as follows. POE (90:80:20 DETOSU:TEG:TEG-diGL, $M_w$=5 kDa, $M_n$=3 kDa) was mixed with triacetin. The mixture was tumbled for 4.5 hours. Bupivacaine base was added to the triacetin-POE mixture. The resulting mixture was homogenized.

Dissolution Testing

Dissolution was measured using a USP Apparatus II. Approximately 0.5 mL of each formulation was loaded via cannula and syringed into 900 mL of 37±0.5° C. dissolution media (0.025 M sodium phosphate buffer at pH 7.4 with 0.03% sodium dodecyl sulfate). The USP Apparatus II was set at 50 RPM, and samples were collected at 1, 4, 8, 12, 18, 24, 36, 48, and 72 hours and daily afterward. Samples were collected for 5 days and 14 days for the POE and PLGA compositions, respectively. Six replicates were obtained for each composition. The collected samples were assayed for bupivacaine content by HPLC.

The present invention having been thus described, variations and modifications thereof as would be apparent to those of skill in the art will be understood to be within the scope of the appended claims.

What is claimed is:

1. A pharmaceutical composition comprising:
   bupivacaine free base present in the pharmaceutical composition in an amount ranging from 10 wt % to 15 wt %, based on weight of the pharmaceutical composition;
   sucrose acetate isobutyrate present in the pharmaceutical composition in an amount ranging from 63 wt % to 67 wt %, based on weight of the pharmaceutical composition;
   benzyl alcohol present in the pharmaceutical composition in an amount ranging from 20 wt % to 25 wt %, based on weight of the pharmaceutical composition;
   benzyl acetate; and
   2,6-dimethylaniline,
   wherein the benzyl acetate is present in the pharmaceutical composition at a level less than 30 mg/mL,
   wherein the 2,6-dimethylaniline is present in the pharmaceutical composition at a level less than 12 ppm, and
   wherein the pharmaceutical composition is suitable for parenteral use in humans.

2. The pharmaceutical composition of claim 1, wherein the 2,6-dimethylaniline is present in the pharmaceutical composition at a level less than or equal to 10 ppm.

3. The pharmaceutical composition of claim 1, wherein the 2,6-dimethylaniline is present in the pharmaceutical composition at a level ranging from 0.3 ppm to 10 ppm.

4. The pharmaceutical composition of claim 1, wherein the pharmaceutical composition further comprises bupivacaine N-oxide.

5. The pharmaceutical composition of claim 4, wherein the bupivacaine N-oxide is present in the pharmaceutical composition at a level less than 1 wt %, based on weight of the pharmaceutical composition.

6. The pharmaceutical composition of claim 4, wherein the bupivacaine N-oxide is present in the pharmaceutical composition at a level ranging from 0.01 wt % to 1 wt %, based on weight of the pharmaceutical composition.

7. The pharmaceutical composition of claim 1, wherein the benzyl acetate is present in the pharmaceutical composition at a level ranging from 0.1 mg/mL to 20 mg/mL.

8. The pharmaceutical composition of claim 1, wherein the pharmaceutical composition further comprises benzyl isobutyrate.

9. The pharmaceutical composition of claim 8, wherein the benzyl isobutyrate is present in the pharmaceutical composition at a level ranging from 0.1 mg/mL to 40 mg/mL.

10. The pharmaceutical composition of claim 1, wherein the pharmaceutical composition is storage stable such that when the pharmaceutical composition is stored in a sealed, upright, clear glass vial at 25° C./60% RH for 36 months, the 2,6-dimethylaniline is present at a level of less than 12 ppm.

11. The pharmaceutical composition of claim 4, wherein the pharmaceutical composition is storage stable such that when the pharmaceutical composition is stored in a sealed, upright, clear glass vial at 25° C./60% RH for 36 months, the bupivacaine N-oxide is present at a level of less than 1 wt %, based on weight of the pharmaceutical composition.

12. The pharmaceutical composition of claim 1, wherein the pharmaceutical composition is storage stable such that when the pharmaceutical composition is stored in a sealed, upright, clear glass vial at 25° C./60% RH for 36 months, the benzyl acetate is present at a level of less than 30 mg/mL.

13. The pharmaceutical composition of claim 8, wherein the pharmaceutical composition is storage stable such that when the pharmaceutical composition is stored in a sealed, upright, clear glass vial at 25° C./60% RH for 36 months, the benzyl isobutyrate is present at a level of less than 50 mg/mL.

14. A dosage system comprising:
a container comprising a first inert material;
a closure capable of closing the container, the closure comprising a second inert material; and
the pharmaceutical composition of claim 1 contained within the container.

15. The dosage system of claim 14, wherein the second inert material comprises a fluorinated polymer.

16. The dosage system of claim 14, wherein the first inert material comprises glass that does not contain iron.

17. A dosage system comprising:
a first container;
a second container within the first container, the second container comprising a first inert material and the first container reduces ambient visible light from irradiating onto the second container; and
the pharmaceutical composition of claim 1 within the second container.

18. The dosage system of claim 17, wherein the first container comprises a box.

19. A pharmaceutical composition comprising:
bupivacaine free base present in the pharmaceutical composition in an amount ranging from 10 wt % to 15 wt %, based on weight of the pharmaceutical composition;
sucrose acetate isobutyrate present in the pharmaceutical composition in an amount ranging from 63 wt % to 67 wt %, based on weight of the pharmaceutical composition;
benzyl alcohol present in the pharmaceutical composition in an amount ranging from 20 wt % to 25 wt %, based on weight of the pharmaceutical composition;
benzyl acetate; and
2,6-dimethylaniline,
wherein the benzyl acetate is present in the pharmaceutical composition at a level less than 30 mg/mL,
wherein the 2,6-dimethylaniline is present in the pharmaceutical composition at a level less than 12 ppm, and
wherein the pharmaceutical composition is sterile.

20. The pharmaceutical composition of claim 19, wherein the 2,6-dimethylaniline is present in the pharmaceutical composition at a level less than or equal to 10 ppm.

21. The pharmaceutical composition of claim 19, wherein the 2,6-dimethylaniline is present in the pharmaceutical composition at a level ranging from 0.3 ppm to 10 ppm.

22. The pharmaceutical composition of claim 19, wherein the pharmaceutical composition further comprises bupivacaine N-oxide.

23. The pharmaceutical composition of claim 19, wherein the pharmaceutical composition further comprises benzyl isobutyrate.

24. The pharmaceutical composition of claim 19, wherein the pharmaceutical composition is storage stable such that when the pharmaceutical composition is stored in a sealed, upright, clear glass vial at 25° C./60% RH for 36 months, the 2,6-dimethylaniline is present at a level of less than 12 ppm.

25. The pharmaceutical composition of claim 22, wherein the pharmaceutical composition is storage stable such that when the pharmaceutical composition is stored in a sealed, upright, clear glass vial at 25° C./60% RH for 36 months, the bupivacaine N-oxide is present at a level of less than 1 wt %, based on weight of the pharmaceutical composition.

26. The pharmaceutical composition of claim 19, wherein the pharmaceutical composition is storage stable such that when the pharmaceutical composition is stored in a sealed, upright, clear glass vial at 25° C./60% RH for 36 months, the benzyl acetate is present at a level of less than 30 mg/mL.

27. The pharmaceutical composition of claim 23, wherein the pharmaceutical composition is storage stable such that when the pharmaceutical composition is stored in a sealed, upright, clear glass vial at 25° C./60% RH for 36 months, the benzyl isobutyrate is present at a level of less than 50 mg/mL.

\* \* \* \* \*

UNITED STATES PATENT AND TRADEMARK OFFICE
CERTIFICATE OF CORRECTION

PATENT NO. : 11,400,019 B2
APPLICATION NO. : 17/504913
DATED : August 2, 2022
INVENTOR(S) : Andrew R. Miksztal et al.

Page 1 of 1

It is certified that error appears in the above-identified patent and that said Letters Patent is hereby corrected as shown below:

In the Specification

Column 32, Line 45, insert -- VII:

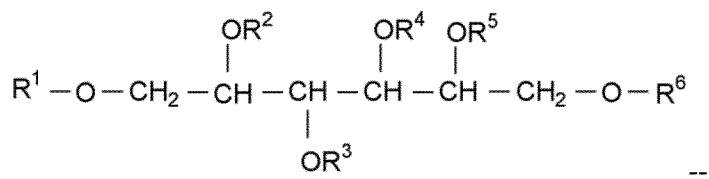

--

Column 52, Line 62, replace "1.20" with --1.2%--

Column 74, Line 22, replace "SA" with --SAIB--

Column 76, Line 28, replace "SAB" with --SAIB--

Column 86, Line 29, replace "P;" with --PI--

Signed and Sealed this
Thirty-first Day of October, 2023

*Katherine Kelly Vidal*
Katherine Kelly Vidal
*Director of the United States Patent and Trademark Office*